(12) United States Patent
Zhao et al.

(10) Patent No.: US 11,091,486 B2
(45) Date of Patent: *Aug. 17, 2021

(54) PROCESS FOR THE PREPARATION OF PYRAZOLO[1,5-A]PYRIMIDINES AND SALTS THEREOF

(71) Applicants: Array BioPharma Inc., Boulder, CO (US); Loxo Oncology, Inc., Stamford, CO (US)

(72) Inventors: Qian Zhao, Boulder, CO (US); Stacey Spencer, Lyons, CO (US); Yutong Jiang, Boulder, CO (US); Julia Haas, Boulder, CO (US); Charles Todd Eary, Longmont, CO (US)

(73) Assignees: Array BioPharma, Inc, Boulder, CO (US); Loxo Oncology, Inc., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/345,571

(22) PCT Filed: Oct. 26, 2017

(86) PCT No.: PCT/US2017/058518
§ 371 (c)(1),
(2) Date: Apr. 26, 2019

(87) PCT Pub. No.: WO2018/081417
PCT Pub. Date: May 3, 2018

(65) Prior Publication Data
US 2020/0216451 A1    Jul. 9, 2020

Related U.S. Application Data

(63) Continuation-in-part of application No. PCT/US2016/058951, filed on Oct. 26, 2016.

(60) Provisional application No. 62/524,801, filed on Jun. 26, 2017.

(51) Int. Cl.
| | |
|---|---|
| A61P 25/00 | (2006.01) |
| A61P 35/00 | (2006.01) |
| A61P 35/02 | (2006.01) |
| A61P 43/00 | (2006.01) |
| C07D 471/22 | (2006.01) |
| A61K 31/519 | (2006.01) |

(52) U.S. Cl.
CPC ........ *C07D 471/22* (2013.01); *C07B 2200/13* (2013.01)

(58) Field of Classification Search
CPC .......... A61P 25/00; A61P 35/00; A61P 35/02; A61P 43/00; C07D 471/22; A61K 31/519
See application file for complete search history.

(56) References Cited

U.S. PATENT DOCUMENTS

| | | |
|---|---|---|
| 5,374,659 A | 12/1994 | Gowan |
| 5,430,021 A | 7/1995 | Rudnic et al. |
| 5,760,068 A | 6/1998 | Talley et al. |
| 5,844,092 A | 12/1998 | Presta et al. |
| 5,877,016 A | 3/1999 | Presta et al. |
| 5,910,574 A | 6/1999 | Presta et al. |
| 6,025,166 A | 2/2000 | Presta et al. |

(Continued)

FOREIGN PATENT DOCUMENTS

| | | |
|---|---|---|
| AU | 2015/101722 | 5/2016 |
| CN | 1938311 | 3/2007 |

(Continued)

OTHER PUBLICATIONS

U.S. Appl. No. 16/044,653, filed Jul. 25, 2018, Allowed.

(Continued)

*Primary Examiner* — Sun Jae Yoo
(74) *Attorney, Agent, or Firm* — Meunier Carlin & Curfman LLC

(57) ABSTRACT

In some embodiments, provided herein are processes for preparing a compound of Formula C or a salt thereof, as disclosed herein. In some embodiments, provided herein is a compound of Formula I or a pharmaceutically acceptable salt, solvate or hydrate thereof. In some embodiments, provided herein is a solid form of the compound, such as a crystalline form of the compound crystalline Form I.

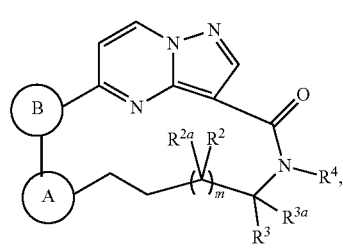

Formula C

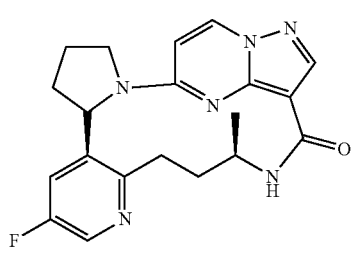

Formula I

11 Claims, 52 Drawing Sheets

Specification includes a Sequence Listing.

(56) References Cited

U.S. PATENT DOCUMENTS

| | | |
|---|---|---|
| 6,027,927 A | 2/2000 | Presta et al. |
| 6,153,189 A | 11/2000 | Presta et al. |
| 6,218,375 B1 | 4/2001 | Raghavan |
| 6,534,085 B1 | 3/2003 | Zeligs |
| 7,384,632 B2 | 6/2008 | Devaux et al. |
| 7,491,794 B2 | 2/2009 | Blatt et al. |
| 7,514,446 B2 | 4/2009 | Davis-Ward et al. |
| 7,550,470 B2 | 6/2009 | Fraley |
| 7,612,067 B2 | 11/2009 | Barbosa et al. |
| 7,615,383 B2 | 11/2009 | Devaux et al. |
| 7,863,289 B2 | 1/2011 | Spevak et al. |
| 8,026,247 B2 | 9/2011 | Bold et al. |
| 8,106,167 B2 | 1/2012 | Wild, Jr. et al. |
| 8,114,989 B2 | 2/2012 | Wang et al. |
| 8,119,592 B2 | 2/2012 | Beigelman et al. |
| 8,148,107 B2 | 4/2012 | Macdonald et al. |
| 8,299,021 B2 | 10/2012 | Blatt et al. |
| 8,299,057 B2 | 10/2012 | Lombardi Borgia et al. |
| 8,338,417 B2 | 12/2012 | Li et al. |
| 8,399,442 B2 | 3/2013 | Berdini et al. |
| 8,450,322 B2 | 5/2013 | Andrews et al. |
| 8,501,756 B2 | 8/2013 | Artman, III et al. |
| 8,513,263 B2 | 8/2013 | Haas et al. |
| 8,552,002 B2 | 10/2013 | Ding et al. |
| 8,568,998 B2 | 10/2013 | Mani |
| 8,637,256 B2 | 1/2014 | Ernst |
| 8,637,516 B2 | 1/2014 | Fan et al. |
| 8,642,035 B2 | 2/2014 | Luehrsen |
| 8,673,347 B2 | 3/2014 | Traversa et al. |
| 8,691,221 B2 | 4/2014 | Pavone et al. |
| 8,791,123 B2 | 7/2014 | Allen et al. |
| 8,815,901 B2 | 8/2014 | Furet et al. |
| 8,865,698 B2 | 10/2014 | Haas et al. |
| 8,911,734 B2 | 12/2014 | Latham et al. |
| 8,912,194 B2 | 12/2014 | Ciomei |
| 8,912,204 B2 | 12/2014 | Ibrahim et al. |
| 8,933,084 B2 | 1/2015 | Andrews |
| 8,937,071 B2 | 1/2015 | Eidam et al. |
| 8,946,226 B2 | 2/2015 | Ciomei et al. |
| 9,006,256 B2 | 4/2015 | Matsui |
| 9,035,063 B2 | 5/2015 | Eidam et al. |
| 9,102,671 B2 | 8/2015 | Molteni et al. |
| 9,127,013 B2 | 9/2015 | Haas et al. |
| 9,187,489 B2 | 11/2015 | Takeda et al. |
| 9,227,975 B2 | 1/2016 | Andrews et al. |
| 9,242,977 B2 | 1/2016 | Takeuchi et al. |
| 9,260,437 B2 | 2/2016 | Ibrahim et al. |
| 9,273,051 B2 | 3/2016 | Chen et al. |
| 9,346,788 B2 | 5/2016 | Wu et al. |
| 9,447,104 B2 | 9/2016 | Haas et al. |
| 9,447,135 B2 | 9/2016 | Rohr et al. |
| 9,469,876 B2 | 10/2016 | Kuslich |
| 9,493,476 B2 | 11/2016 | Andrews et al. |
| 9,511,050 B2 | 12/2016 | Toretsky et al. |
| 9,670,207 B2 | 6/2017 | Sasmal et al. |
| 9,676,783 B2 | 6/2017 | Haas et al. |
| 9,682,979 B2 | 6/2017 | Allen et al. |
| 9,701,681 B2 | 6/2017 | Kim et al. |
| 9,718,822 B2 | 8/2017 | Andrews et al. |
| 9,750,744 B2 | 9/2017 | Andrews et al. |
| 9,782,400 B2 | 10/2017 | Yao et al. |
| 9,782,414 B2 | 10/2017 | Arrigo et al. |
| 9,782,415 B2 | 10/2017 | Allen et al. |
| 9,795,611 B2 | 10/2017 | Andrews et al. |
| 9,796,723 B2 | 10/2017 | Andrews et al. |
| 9,796,724 B2 | 10/2017 | Allen et al. |
| 9,840,519 B2 | 12/2017 | Andrews et al. |
| 9,902,741 B2 | 2/2018 | Andrews et al. |
| 10,005,783 B2 | 6/2018 | Haas et al. |
| 10,011,604 B2 | 7/2018 | Andrews et al. |
| 10,045,991 B2 | 8/2018 | Cox et al. |
| 10,047,097 B2 | 8/2018 | Haas et al. |
| 10,137,127 B2 | 11/2018 | Reynolds et al. |
| 10,172,861 B2 | 1/2019 | Arrigo et al. |
| 10,251,889 B2 | 4/2019 | Shelley et al. |
| 2003/0118654 A1 | 6/2003 | Santos |
| 2003/0229047 A1 | 12/2003 | Joshi-Hangal et al. |
| 2005/0209195 A1 | 9/2005 | Menta et al. |
| 2005/0239840 A1 | 10/2005 | Arbuthnot et al. |
| 2006/0089362 A1 | 4/2006 | Seno et al. |
| 2006/0094699 A1 | 5/2006 | Kampen et al. |
| 2006/0128725 A1 | 6/2006 | Guzi |
| 2006/0211696 A1 | 9/2006 | Hibi et al. |
| 2007/0025540 A1 | 2/2007 | Travis |
| 2007/0042941 A1 | 2/2007 | Hirashima et al. |
| 2007/0082900 A1 | 4/2007 | Guzi et al. |
| 2007/0082902 A1 | 4/2007 | Pamch al. |
| 2007/0184117 A1 | 8/2007 | Gregory et al. |
| 2007/0225270 A1 | 9/2007 | Guzi et al. |
| 2007/0281951 A1 | 12/2007 | Guzi et al. |
| 2008/0226747 A1 | 9/2008 | Bearss et al. |
| 2009/0041717 A1 | 2/2009 | Macdonald et al. |
| 2009/0099167 A1 | 4/2009 | Bold et al. |
| 2009/0130229 A1 | 5/2009 | Lanzi et al. |
| 2009/0227556 A1 | 9/2009 | Obaishi |
| 2009/0275622 A1 | 11/2009 | Linga et al. |
| 2010/0029633 A1 | 2/2010 | Allen et al. |
| 2010/0152219 A1 | 6/2010 | Block et al. |
| 2010/0297115 A1 | 11/2010 | Blaustein |
| 2010/0324065 A1 | 12/2010 | Ibrahim et al. |
| 2011/0053934 A1 | 3/2011 | Angell et al. |
| 2011/0166122 A1 | 7/2011 | Andrews et al. |
| 2011/0195948 A1 | 8/2011 | Haas et al. |
| 2011/0268725 A1 | 11/2011 | Shelton |
| 2011/0301157 A1 | 12/2011 | Bold et al. |
| 2012/0108568 A1 | 5/2012 | Allen et al. |
| 2013/0029925 A1 | 1/2013 | Vandier et al. |
| 2013/0203776 A1 | 8/2013 | Andrews et al. |
| 2013/0217662 A1 | 8/2013 | Andrews et al. |
| 2014/0121239 A1 | 5/2014 | Aftab |
| 2014/0194403 A1 | 7/2014 | Haas et al. |
| 2014/0227287 A1 | 8/2014 | Kamohara et al. |
| 2014/0243332 A1 | 8/2014 | Davare |
| 2014/0315199 A1 | 10/2014 | Rhodes et al. |
| 2014/0336236 A1 | 11/2014 | Cronin et al. |
| 2015/0005499 A1 | 1/2015 | Haas et al. |
| 2015/0018336 A1 | 1/2015 | Chen et al. |
| 2015/0031667 A1 | 1/2015 | Allen et al. |
| 2015/0051222 A1 | 2/2015 | Barbugian et al. |
| 2015/0073036 A1 | 3/2015 | Hawryluk et al. |
| 2015/0166564 A1 | 6/2015 | Allen et al. |
| 2015/0218132 A1 | 8/2015 | Wu |
| 2015/0218652 A1 | 8/2015 | Doebele et al. |
| 2015/0283132 A1 | 10/2015 | Lim et al. |
| 2015/0306086 A1 | 10/2015 | Wilcoxen |
| 2015/0315657 A1 | 11/2015 | Rhodes et al. |
| 2015/0336970 A1 | 11/2015 | Andrews et al. |
| 2016/0000783 A1 | 1/2016 | Takeuchi et al. |
| 2016/0009785 A1 | 1/2016 | Lipson et al. |
| 2016/0010068 A1 | 1/2016 | Bastian |
| 2016/0032396 A1 | 2/2016 | Diehn |
| 2016/0032402 A1 | 2/2016 | Jagani et al. |
| 2016/0032404 A1 | 2/2016 | Schweighofer et al. |
| 2016/0108123 A1 | 4/2016 | Freeman et al. |
| 2016/0108380 A1 | 4/2016 | Iavarone et al. |
| 2016/0137654 A1 | 5/2016 | Arrigo et al. |
| 2016/0145237 A1 | 5/2016 | Hu et al. |
| 2016/0228441 A1 | 8/2016 | Haas et al. |
| 2016/0251357 A1 | 9/2016 | Andrews et al. |
| 2016/0263086 A1 | 9/2016 | Toretsky |
| 2016/0272725 A1 | 9/2016 | Stransky et al. |
| 2016/0305943 A1 | 10/2016 | Takeuchi et al. |
| 2016/0367547 A1 | 12/2016 | Yao et al. |
| 2017/0107232 A1 | 4/2017 | Andrews et al. |
| 2017/0112842 A1 | 4/2017 | Andrews et al. |
| 2017/0112849 A1 | 4/2017 | Andrews et al. |
| 2017/0114059 A1 | 4/2017 | Andrews et al. |
| 2017/0114067 A1 | 4/2017 | Haas et al. |
| 2017/0114068 A1 | 4/2017 | Andrews et al. |
| 2017/0114069 A1 | 4/2017 | Allen et al. |
| 2017/0114415 A1 | 4/2017 | Doebele et al. |
| 2017/0119770 A1 | 5/2017 | Allen et al. |
| 2017/0165267 A1 | 6/2017 | Arrigo et al. |
| 2017/0224662 A1 | 8/2017 | Motheram et al. |

(56) References Cited

U.S. PATENT DOCUMENTS

| | | |
|---|---|---|
| 2017/0260589 A1 | 9/2017 | Nanda et al. |
| 2017/0281632 A1 | 10/2017 | Cox et al. |
| 2017/0283435 A1 | 10/2017 | Andrews et al. |
| 2017/0296544 A1 | 10/2017 | Reynolds et al. |
| 2018/0021342 A1 | 1/2018 | Arrigo et al. |
| 2018/0030548 A1 | 2/2018 | Nanda et al. |
| 2018/0030549 A1 | 2/2018 | Nanda et al. |
| 2018/0119228 A1 | 5/2018 | Nanda et al. |
| 2018/0127427 A1 | 5/2018 | Haas et al. |
| 2018/0133222 A1 | 5/2018 | Cox et al. |
| 2018/0140604 A1 | 5/2018 | Tuch et al. |
| 2018/0142306 A1 | 5/2018 | Nanda et al. |
| 2018/0207162 A1 | 7/2018 | Arrigo et al. |
| 2018/0263984 A1 | 9/2018 | Allen et al. |
| 2019/0031684 A1 | 1/2019 | Andrews |
| 2019/0076436 A1 | 3/2019 | Andrews |
| 2019/0076437 A1 | 3/2019 | Andrews |
| 2019/0151322 A1 | 5/2019 | Andrews |
| 2019/0169193 A1 | 6/2019 | Andrews et al. |
| 2019/0211017 A1 | 7/2019 | Haas et al. |
| 2019/0216814 A1 | 7/2019 | Reynolds et al. |
| 2019/0218222 A1 | 7/2019 | Reynolds et al. |
| 2019/0247398 A1* | 8/2019 | Zhao ................ C07C 59/08 |
| 2019/0365763 A1 | 12/2019 | Allen et al. |
| 2020/0000807 A1 | 1/2020 | Arrigo et al. |
| 2020/0237765 A1 | 7/2020 | Cox et al. |
| 2020/0291026 A1 | 9/2020 | Andrews et al. |
| 2020/0338079 A1 | 10/2020 | Reynolds et al. |
| 2021/0002287 A1 | 1/2021 | Haas et al. |
| 2021/0023086 A1 | 1/2021 | Bilenker et al. |

FOREIGN PATENT DOCUMENTS

| | | |
|---|---|---|
| CN | 101119996 | 2/2008 |
| CN | 101208093 | 6/2008 |
| EA | 009517 | 2/2008 |
| EP | 0810217 | 12/1997 |
| EP | 1873157 | 1/2008 |
| EP | 1948633 | 8/2011 |
| EP | 2986736 | 2/2016 |
| EP | 2558490 | 12/2016 |
| EP | 3266795 | 10/2018 |
| JP | H10120683 A | 5/1998 |
| JP | 2004-087707 | 3/2004 |
| JP | 2004-277337 | 10/2004 |
| JP | 2005-008581 | 1/2005 |
| JP | 2006-518364 | 8/2006 |
| JP | 2007-504276 | 3/2007 |
| JP | 2007-514712 | 6/2007 |
| JP | 2008-523034 | 7/2008 |
| JP | 2008-285464 | 11/2008 |
| JP | 2009-502734 | 1/2009 |
| JP | 2009-511487 | 3/2009 |
| JP | 2009-221199 | 10/2009 |
| JP | 2009-541242 | 11/2009 |
| JP | 2010-508315 | 3/2010 |
| JP | 2011-520887 | 7/2011 |
| JP | 2012-506446 | 3/2012 |
| JP | 2012-507569 | 3/2012 |
| JP | 2013-226108 | 11/2013 |
| JP | 2014-082984 | 5/2014 |
| WO | WO 1998/49167 | 11/1998 |
| WO | 00/59929 | 10/2000 |
| WO | 02/41920 | 5/2002 |
| WO | WO 2003/080064 | 10/2003 |
| WO | WO 2004/022561 | 3/2004 |
| WO | WO 2004/052286 | 6/2004 |
| WO | WO 2004/052315 | 6/2004 |
| WO | WO 2004/074290 | 9/2004 |
| WO | WO 2004/082458 | 9/2004 |
| WO | WO 2004/087707 | 10/2004 |
| WO | WO 2004/089415 | 10/2004 |
| WO | WO 2004/089471 | 10/2004 |
| WO | WO 2005/044835 | 5/2005 |
| WO | WO 2005/049033 | 6/2005 |
| WO | WO 2005/051366 | 6/2005 |
| WO | WO 2005/077954 | 8/2005 |
| WO | WO 2006/052913 | 5/2006 |
| WO | 2006/061417 | 6/2006 |
| WO | WO 2006/087538 | 8/2006 |
| WO | WO 2006/115452 | 11/2006 |
| WO | WO 2006/123113 | 11/2006 |
| WO | WO 2006/131051 | 12/2006 |
| WO | WO 2006/131952 | 12/2006 |
| WO | WO 2007/002325 | 1/2007 |
| WO | WO 2007/002433 | 1/2007 |
| WO | WO 2007/013673 | 2/2007 |
| WO | WO 2007/015824 | 2/2007 |
| WO | WO 2007/022999 | 3/2007 |
| WO | WO 2007/024680 | 3/2007 |
| WO | WO 2007/025090 | 3/2007 |
| WO | WO 2007/025540 | 3/2007 |
| WO | WO 2007/038314 | 4/2007 |
| WO | WO 2007/044410 | 4/2007 |
| WO | WO 2007/044449 | 4/2007 |
| WO | WO 2007/044893 | 4/2007 |
| WO | WO 2007/048066 | 4/2007 |
| WO | WO 2007/057399 | 5/2007 |
| WO | 2007/070504 | 6/2007 |
| WO | WO 2007/062805 | 6/2007 |
| WO | WO 2007/084815 | 7/2007 |
| WO | WO 2007/087245 | 8/2007 |
| WO | WO 2007/102679 | 9/2007 |
| WO | WO 2007/103308 | 9/2007 |
| WO | WO 2007/110344 | 10/2007 |
| WO | WO 2007/113000 | 10/2007 |
| WO | WO 2007/129161 | 11/2007 |
| WO | WO 2007/136103 | 11/2007 |
| WO | 2007/147647 | 12/2007 |
| WO | 2008/016192 | 2/2008 |
| WO | WO 2008/016131 | 2/2008 |
| WO | WO 2008/021924 | 2/2008 |
| WO | WO 2008/030579 | 3/2008 |
| WO | WO 2008/031551 | 3/2008 |
| WO | WO 2008/037477 | 4/2008 |
| WO | WO 2008/052734 | 5/2008 |
| WO | WO 2008/058126 | 5/2008 |
| WO | WO 2008/079903 | 7/2008 |
| WO | WO 2008/079906 | 7/2008 |
| WO | WO 2008/079909 | 7/2008 |
| WO | WO 2008/080001 | 7/2008 |
| WO | WO 2008/080015 | 7/2008 |
| WO | WO 2008/115974 | 9/2008 |
| WO | WO 2008/116898 | 10/2008 |
| WO | WO 2008/155421 | 12/2008 |
| WO | WO 2009/007748 | 1/2009 |
| WO | WO 2009/012283 | 1/2009 |
| WO | WO 2009/013126 | 1/2009 |
| WO | WO 2009/014637 | 1/2009 |
| WO | WO 2009/017838 | 2/2009 |
| WO | WO 2009/052145 | 4/2009 |
| WO | WO 2009/053442 | 4/2009 |
| WO | WO 2009/060197 | 5/2009 |
| WO | WO 2009/070567 | 6/2009 |
| WO | WO 2009/071480 | 6/2009 |
| WO | WO 2009/092049 | 7/2009 |
| WO | WO 2009/118411 | 10/2009 |
| WO | WO 2009/140128 | 11/2009 |
| WO | WO 2009/143018 | 11/2009 |
| WO | WO 2009/143024 | 11/2009 |
| WO | WO 2009/152083 | 12/2009 |
| WO | WO 2010/012733 | 2/2010 |
| WO | WO 2010/031816 | 3/2010 |
| WO | WO 2010/033941 | 4/2010 |
| WO | WO 2010/048314 | 4/2010 |
| WO | WO 2010/051549 | 5/2010 |
| WO | WO 2010/058006 | 5/2010 |
| WO | WO 2010/093928 | 8/2010 |
| WO | WO 2010/111527 | 9/2010 |
| WO | WO 2010/145998 | 12/2010 |
| WO | WO 2011/006074 | 1/2011 |
| WO | WO 2011/092120 | 8/2011 |
| WO | WO 2011/130340 | 10/2011 |
| WO | WO 2011/133637 | 10/2011 |

(56) References Cited

FOREIGN PATENT DOCUMENTS

| | | |
|---|---|---|
| WO | WO 2011/146336 | 11/2011 |
| WO | 2011/156588 | 12/2011 |
| WO | WO 2012/024650 | 2/2012 |
| WO | WO 2012/034091 | 3/2012 |
| WO | WO 2012/034095 | 3/2012 |
| WO | WO 2012/053606 | 4/2012 |
| WO | WO 2012/101029 | 8/2012 |
| WO | WO 2012/101032 | 8/2012 |
| WO | WO 2012/109075 | 8/2012 |
| WO | WO 2012/113774 | 8/2012 |
| WO | WO 2012/116217 | 8/2012 |
| WO | WO 2012/139930 | 10/2012 |
| WO | WO 2012/143248 | 10/2012 |
| WO | WO 2012/152763 | 11/2012 |
| WO | WO 2012/158413 | 11/2012 |
| WO | WO 2013/014039 | 1/2013 |
| WO | WO 2013/050446 | 4/2013 |
| WO | WO 2013/050448 | 4/2013 |
| WO | WO 2013/059740 | 4/2013 |
| WO | WO 2013/074518 | 5/2013 |
| WO | WO 2013/102059 | 7/2013 |
| WO | WO 2013/174876 | 11/2013 |
| WO | WO 2013/183578 | 12/2013 |
| WO | 2014/005021 | 1/2014 |
| WO | 2014/016433 A1 | 1/2014 |
| WO | 2014/018567 | 1/2014 |
| WO | WO 2014/011900 | 1/2014 |
| WO | WO 2014/019908 | 2/2014 |
| WO | WO 2014/036387 | 3/2014 |
| WO | WO 2014/047572 | 3/2014 |
| WO | WO 2014/071358 | 5/2014 |
| WO | WO 2014/072220 | 5/2014 |
| WO | WO 2014/078322 | 5/2014 |
| WO | WO 2014/078323 | 5/2014 |
| WO | WO 2014/078325 | 5/2014 |
| WO | WO 2014/078328 | 5/2014 |
| WO | WO 2014/078331 | 5/2014 |
| WO | WO 2014/078372 | 5/2014 |
| WO | WO 2014/078378 | 5/2014 |
| WO | WO 2014/078408 | 5/2014 |
| WO | WO 2014/078417 | 5/2014 |
| WO | WO 2014/078454 | 5/2014 |
| WO | WO 2014/083567 | 6/2014 |
| WO | WO 2014/130975 | 8/2014 |
| WO | WO 2014/134096 | 9/2014 |
| WO | WO 2014/152777 | 9/2014 |
| WO | WO 2014/160521 | 10/2014 |
| WO | WO 2014/184069 | 11/2014 |
| WO | WO 2014/194127 | 12/2014 |
| WO | WO 2015/017528 | 2/2015 |
| WO | WO 2015/017533 | 2/2015 |
| WO | WO 2015/039006 | 3/2015 |
| WO | WO 2015/057873 | 4/2015 |
| WO | WO 2015/058129 | 4/2015 |
| WO | WO 2015/061572 | 4/2015 |
| WO | WO 2015/064621 | 5/2015 |
| WO | WO 2015/108992 | 7/2015 |
| WO | WO 2015/112806 | 7/2015 |
| WO | WO 2015/124697 | 8/2015 |
| WO | WO 2015/161274 | 10/2015 |
| WO | WO 2015/161277 | 10/2015 |
| WO | WO 2015/175788 | 11/2015 |
| WO | WO 2015/183836 | 12/2015 |
| WO | WO 2015/183837 | 12/2015 |
| WO | WO 2015/184443 | 12/2015 |
| WO | WO 2015/191666 | 12/2015 |
| WO | WO 2015/191667 | 12/2015 |
| WO | WO 2016/011141 | 1/2016 |
| WO | WO 2016/011144 | 1/2016 |
| WO | WO 2016/011147 | 1/2016 |
| WO | WO 2016/022569 | 2/2016 |
| WO | WO 2016/027754 | 2/2016 |
| WO | WO 2016/075224 | 5/2016 |
| WO | WO 2016/077841 | 5/2016 |
| WO | WO 2016/081450 | 5/2016 |
| WO | WO 2016/097869 | 6/2016 |
| WO | WO 2016/187508 | 11/2016 |
| WO | WO 2016/196141 | 12/2016 |
| WO | WO 2016/196671 | 12/2016 |
| WO | WO 2017/001491 | 1/2017 |
| WO | WO 2017/004342 | 1/2017 |
| WO | WO 2017/075107 | 5/2017 |
| WO | WO 2017/155018 | 9/2017 |
| WO | 2017/176744 | 10/2017 |
| WO | 2017/176751 | 10/2017 |
| WO | WO 2017/184597 | 10/2017 |
| WO | WO 2017/201156 | 11/2017 |
| WO | WO 2017/201241 | 11/2017 |
| WO | WO 2018/081417 | 5/2018 |
| WO | WO 2018/170381 | 9/2018 |
| WO | 2019/191659 | 10/2019 |

OTHER PUBLICATIONS

U.S. Appl. No. 14/943,014, filed Nov. 16, 2015, Published.
U.S. Appl. No. 16/366,368, filed Mar. 27, 2019, Pending.
U.S. Appl. No. 15/622,388, filed Apr. 4, 2017, Issued.
U.S. Appl. No. 15/861,017, filed Jan. 3, 2018, Allowed.
U.S. Appl. No. 16/199,739, filed Nov. 26, 2018, Published.
U.S. Appl. No. 15/900,019, filed Feb. 20, 2018, Pending.
U.S. Appl. No. 16/025,281, filed Jul. 2, 2018, Published.
U.S. Appl. No. 15/335,378, filed Oct. 26, 2016, Published.
U.S. Appl. No. 15/785,218, filed Oct. 16, 2017, Published.
U.S. Appl. No. 15/860,789, filed Jan. 3, 2018, Published.
U.S. Appl. No. 16/199,818, filed Nov. 26, 2018, Pending.
U.S. Appl. No. 16/199,875, filed Nov. 26, 2018, Published.
U.S. Appl. No. 16/377,514, filed Apr. 8, 2019, Pending.
Bayer. "A Study to Test the Effect of the Drug Larotrectinib in Adults and Children With NTRK-fusion Positive Solid Tumors (NAVIGATE)." https://clinicaltrials.gov/ct2/show/NCT02576431. First Posted Oct. 15, 2015. Updated Aug. 20, 2020. 19 pages.
PCT International Preliminary Report on Patentability in International Application No. PCT/US2018/039502, dated Jan. 9, 2020, 8 pages.
U.S. Appl. No. 16/366,368, filed Mar. 27, 2019, Published.
U.S. Appl. No. 15/922,388, filed Apr. 4, 2017, Issued.
U.S. Appl. No. 16/739,845, filed Jan. 10, 2020, Pending.
U.S. Appl. No. 16/199,739, filed Nov. 26, 2018, Allowed.
U.S. Appl. No. 15/900,019, filed Feb. 20, 2018, Allowed.
U.S. Appl. No. 16/025,281, filed Jul. 2, 2018, Allowed.
U.S. Appl. No. 15/785,218, filed Oct. 16, 2017, Allowed.
U.S. Appl. No. 15/785,28, filed Oct. 16, 2017, Issued.
U.S. Appl. No. 16/377,514, filed Apr. 8, 2019, Published.
U.S. Appl. No. 16/345,571, filed Oct. 26, 2017, Pending.
Adriaenssens et al., "Nerve Growth Factor Is a Potential Therapeutic Target in Breast Cancer," Cancer Res., 2008, 68(2):346-351.
Agaram et al., "Recurrent NTRK1 gene fusions define a novel subset oflocally aggressive lipofibromatosis-like neural tumors," Am. J. Surg. Pathol., Oct. 2016, 40(10): 1407-1416.
Agaram, et al., "Abstract 33: NTRK1 Associated Gene Fusions in Pediatric Fibroblastic Myofibroglastic Neoplasms: A Molecular Study of 58 Cases," 105th Annual Meeting of the United States and Canadian Academy of Pathology, 2016, 12A.
Aisner et al., "ROS1 and ALK fusions in colorectal cancer, with evidence of intra-tumoral heterogeneity for molecular drivers.", Mal. Cancer Res., 12(1): 111-8, 2014.
Alassiri et al., "ETV6-NTRK3 Is Expressed in a Subset of ALK-Negative Inflammatory Myofibroblastic Tumors," Am J Surg Pathol., Aug. 2016, 40(8): 1051-1061.
Albaugh et al., "Discovery of GNF-5837, a Selective TRK Inhibitor with Efficacy in Rodent Cancer Tumor Models," ACS Medicinal Chemistry Letters, 2012, 3(2):140-145.
Ali et al., "Comprehensive Genomic Profiling Identifies a Subset of Crizotinib-Responsive ALK-Rearranged Non-Small Cell Lung Cancer Not Detected by Fluorescence In Situ Hybridization.", Oncologist, 21(6): 762-70, 2016.
Alvarez-Breckenridge et al., "Clinical and radiographic response following targeting ofBCAN-NTRK1 fusion in glioneuronal tumor," NPJ Precision Oncology, Mar. 2017, 5 pages.

(56) References Cited

OTHER PUBLICATIONS

Amatu et al., "NTRK gene fusions as novel targets of cancer therapy across multiple tumour types", ESMD Open, Jan. 9, 2016.

American Association for Cancer Research, "TRK Inhibitor Shows Early Promise," Cancer Discovery, 6(1), Jan 1, 2016, XP009194480.

American Cancer Society,"Sarcoma: Adult Soft Tissue Cancer," Jun. 2014, retrieved on Apr. 27, 2015, http://www. cancer.org/cancer/sarcoma-adultsofttissuecancer/detailedguide/sarcoma-adult-soft-tissue-cancer-key-statistics, 45 pages.

Andreason et al., "ETV6 Gene Rearrangements Characterize a Morphologically Distinct Subset of Sinonasal Low-grade Non-intestinal-type Adenocarcinoma," Am. J. Surg. Pathol, Nov. 2017, 41(11):1552-1560.

Arce et al., "Secretory carcinoma of the breast containing the ETV6-NTRK3 fusion gene in a male: case report and review of the literature," World J. Sug. Oncol, Jun. 2005, 3:35.

Ardini et al., "The TPM3-NTRK1 rearrangement is a recurring event in colorectal carcinoma and is associated with tumor sensitivity to TRKA kinase inhibition," Mol. Oncol. 8(8): 1495-1507, 2014.

Asaumi et al., "Expression of neurotrophins and their receptors (TRK) during fracture healing," Bone, 2000, 26(6):625-633.

Awad et al., "Acquired resistance to crizotinib from a mutation in CD74-ROS1. ", N Engl. J Med, 368(25): 2395-401, 2013.

Bailey, Justin J., et al. "Tropomyosin receptor kinase inhibitors: an updated patent review for 2010-2016—Part II." Expert opinion on therapeutic patents 27.7 (2017): 831-849.

Bardelli et al., "Mutational Analysis of the Tyrosine Kinome in Colorectal Cancers," Science, May 2003, 300(5621):949.

Bartenstein et al., "Lipofibromatosis-like neural tumor: Case report of a unique infantile presentation," JAAD Case Reports, 4(2):185-188, 2018.

Baughn et al., "Abstract 5115: Whole-Genome Mate Pair Sequencing Reflex Test to Characterize Chromosome Rearrangements in Hematologic Neoplasia," Blood, 2017, 130: 5115.

Bavle et al., "Abstract GENE-04: Pediatric Malignant Epithelioid Glioneuronal Tumor: Pathological, Clinical, and Molecular Characterization of a Rare and Deadly Malignancy," Neuro-Oncology, Jun. 2017, iv18-iv19.

Behrens et al., "Go 6976 is a potent inhibitor of neurotrophin-receptor intrinsic tyrosine kinase," J Neurochem., Mar. 1999, 72(3):919-924.

Beimfohr et al., "NTRK.1 re-arrangement in papillary thyroid carcinomas of children after the Chernobyl reactor accident," Int. J Cancer, Mar. 15, 1999;80(6):842-847.

Bender et al., Abstract H-024: Multiple Novel Fusion Genes with the RTK-RAS-PBK Signalling Axis Highlight its Central Role in the Turmorigenesis of Pediatric Gioblastoma, Neuro-oncology, Jun. 2014, 145.

Bensinger et al., "Transplantation of allogeneic peripheral blood stem cells mobilized by recombinant human granulocyte colony stimulating factor," Stem Cells, Jan. 1996;14(1):90-105.

Bensinger et al., "Transplantation of allogeneic peripheral blood stem cells mobilized by recombinant human granulocyte colony-stimulating factor [see comments].," Blood, Mar. 15, 1995;85(6):1655-8.

Bertrand et al., "The crystal structures of TrkA and TrkB suggest key regions for achieving selective inhibition," Journal of molecular biology, Oct. 26, 2012;423(3):439-53.

Birch et al., "Chromosome 3 anomalies investigated by genome wide SNP analysis of benign, low malignant potential and low grade ovarian serous tumours.", PLoS One, 6(12): e28250, 2011.

Bonanno et al., Journal of Thoracic Oncology, vol. 11, No. 4, Supp. Suppl. 1, pp. S67. Abstract No. 28P; 6th European Lung Cancer Conference, ELCC 2016, Geneva, Switzerland.

Bongarzone et al., "Age-related activation of the tyrosine kinase receptor protooncogenes RET and NTRK.1 in papillary thyroid carcinoma," J Clin. Endocrinol. Metab., May 1996, 81(5):2006-2009.

Bouhana et al., "Abstract #1798: Identification of Pan-Trk Inhibitors for the Treatment of Trk-Driven Cancers," Poster, Presented at Proceedings of the AACR 103rd Annual Meeting, Apr. 15, 2012.

Bourgeois et al., "Molecular Detection of the ETV6-NTRK3 Gene Fusion Differentiates Congenital Fibrosarcoma From Other Childhood Spindle Cell Tumors," Am. J Surg. Pathol., Jul. 2000, 24(7):937-946.

Braga, Dario, et al. "Crystal polymorphism and multiple crystal forms." Struct Bond (2009) 132:25-50. Springer-Verlag Berlin Heidelberg.

Branford, S., et al. "High frequency of point mutations clustered within the adenosine triphosphate-binding region of BCR/ABL in patients with chronic myeloid leukemia or Ph-positive acute lymphoblastic leukemia who develop imatinib (STI571) resistance," Blood, May 2002, 99, 3472-3475.

Brastianos et al., "Abstract OS06.4: Identification of Novel NTRK Fusion in Glioneuronal Tumors and Radiographic Response Following Therapy with an NTRK Inhibitor," Neuro-Oncology, May 2017, iii1 1, 1 page, Meeting Info: 5th Quadrennial Meeting of the World Federation of Neuro-Oncology Societies, WFNOS. Zurich, Switzerland, 2017.

Brenca et al., "Transcriptome sequencing identifies ETV6-NTRK3 as a gene fusion involved in GISTt," J. Pathol. 238(4):543-549, 2016.

Brinner et al., "A rapid and general method for asymmetric synthesis of 2-substituted pyrrolidines using ter-butanesulfinamide," Organic & Biomolecular Chemistry, Jan. 2005, 3(11): 2019.

Brodeur, "Neuroblastoma: biological insights into a clinical enigma," Nat. Rev. Cancer, 2003, 3:203-216.

Bruse et al., "Improvements to Bead Based Oligonucleotide Ligation SNP Genotyping Assays," Biotechniques, Nov. 2008, 45:559-571.

Brzezianska et al., "Rearrangements of NTRK.1 oncogene in papillary thyroid carcinoma," Neuroendocrinology Letters, 2007, 28(3):221-229.

Burris et al., "Pharmacokinetics (PK) of LOXO-101 During the First-in-Human Phase I Study in Patients with Advanced Solid Tumors," Interim Update AACR Annual Meeting, Mar. 2015, Philadelphia, PA., 1 page.

Butti et al., "A sequence analysis of the genomic regions involved in the rearrangements between TPM3 and NTRK1 genes producing TRK oncogenes in papillary thyroid carcinomas," Genomics. 28(1):15-24, 1995.

Caira, "Crystalline Polymorphism of Organic Compounds," Topics in Current Chemistry, Feb. 1999, 198: 163-208.

Cajaiba et al., "Expanding the spectrum of ALK-rearranged renal cell carcinomas in children: Identification of a novel HOOK1-ALK fusion transcript.", Genes Chromosomes Cancer, 55(10): 814-7, 2016.

Calabresi and Chabner, Goodman & Gilnnan's The Pharmacological Basis of Therapeutics, 10th ed., 2001, ne: 1388, para 2, lines 4-5.

Calero et al., "Sunitinib suppress neuroblastoma growth through degradation of MYCN and inhibition of angiogenesis," PLoS One, Apr. 23, 2014;9(4):e95628. doi: 10.1371/iournal.pone.0095628. eCollection 2014.

Camidge, D. Ross, William Pao, and Lecia V. Sequist. "Acquired resistance to TKIs in solid tumours: learning from lung cancer." Nature reviews Clinical oncology 11.8 (2014): 473.

Camoratto et al., "CEP-751 inhibits TRK receptor tyrosine kinase activity in vitro exhibits anti-tumor activity," Int. J Cancer, Aug. 1997, 72:673-679.

Campos et al., "Enantioselective, palladium-catalyzed alpha-arylation ofN-Boc-pyrrolidine," J. Am. Chem Soc., 2006, 128:3538-3539.

Cancer.gov [online]. "National Cancer Institute: Oral TRK Inhibitor LOXO-101 (Larotrectinib) for Treatment of Advanced Pediatric Solid or Primary Central Nervous System Tumors," ClinicalTrials. gov Identifier: NCT02637687, [retrieved on Jul. 17, 2017] Retrieved from the Internet: URL<https://www.cancer.gov/about-cancer/treatment/clinical-trials/search/view?cdrid=781 000>, 5 pages.

Cancer.sanger.ac.uk [online]. "COSMIC, Catalog of Somatic Mutations in Cancer: Cosmic» Mutation» Overview» NTRK.1 p. V321M / c.961G>A," Catalog of Somatic Mutations in Cancer

(56) References Cited

OTHER PUBLICATIONS (COSMIC) database, [retrieved on Jul. 17, 2017] Retrieved from the Internet: URL<cancer.sanger.ac.uk/cosmic/mutation/ overview?id=1259646>, 1 page.
Cancer.sanger.ac.uk [online]. "COSMIC, Catalog of Somatic Mutations in Cancer: Cosmic» Mutation» Overview» NTRK.1 p.D679N / c.2035G>A," Catalog of Somatic Mutations in Cancer (COSMIC) database, [retrieved on Jul. 17, 2017] Retrieved from the Internet: URL<cancer. sanger.ac.uk/cosmic/mutation/overview?id=897427>, 1 page.
Cancer.sanger.ac.uk [online]. "COSMIC, Catalog of Somatic Mutations in Cancer: Cosmic» Mutation» Overview» NTRK.3 p.D537Y / c.1609G>T," Catalog of Somatic Mutations in Cancer (COSMIC) database, [retrieved on Jul. 17, 2017] Retrieved from the Internet: URL<cancer.sanger.ac.uk/cosmic/mutation/ overview?id=966118>, 1 page.
Cancer.sanger.ac.uk [online]. "COSMIC, Catalog of Somatic Mutations in Cancer: Cosmic» Mutation» Overview» NTRK.3 p.D609V / c.1826A>T," Catalog of Somatic Mutations in Cancer (COSMIC) database, [retrieved on Jul. 17, 2017] Retrieved from the Internet: URL:<cancer.sanger.ac.uk/cosmic/mutation/ overview?id=124878>, 1 page.
Cancer.sanger.ac.uk [online]. "COSMIC, Catalog of Somatic Mutations in Cancer: Cosmic» Mutation» Overview» NTRK.3 p.G608S / c.1822G>A," Catalog of Somatic Mutations in Cancer (COSMIC) database, [retrieved on Jul. 17, 2017] Retrieved from the Internet: URL<cancer.sanger.ac.uk/cosmic/mutation/ overview?id=88799>, 1 page.
Cancer.sanger.ac.uk [online]. "COSMIC, Catalog of Somatic Mutations in Cancer: Cosmic» Mutation» Overview» NTRK.3 p.L282M / c.844C>A," Catalog of Somatic Mutations in Cancer (COSMIC) database, [retrieved on Jul. 17, 2017] Retrieved from the Internet: URL<cancer.sanger.ac.uk/cosmic/mutation/ overview?id=401588>, 1 page.
Cancer.sanger.ac.uk [online]. "COSMIC, Catalog of Somatic Mutations in Cancer: Cosmic» Mutation» Overview» NTRK.3 p.V539M I c.1615G>A," Catalog of Somatic Mutations in Cancer (COSMIC) database, [retrieved on Jul. 17, 2017] Retrieved from the Internet: URL<cancer. sanger.ac.uk/cosmic/mutation/ overview?id=1708512>, 1 page.
Capparelli et al., "Stromal neuregulin-1 modulates the response to MEK inhibitors in WT BRAF/WT NRAS (WT/WT) melanomas", Pigment Cell Melanoma Res. vol. 30, No. 5, pp. e61, 2017.
Caria et al., "Cytogenetic and molecular events in adenoma and well-differentiated thyroid follicular-cell neoplasia," Cancer Genet. Cytogenet., 2010, 203:21-29.
Carpinelli et al., "PHA-739358, a potent inhibitor of Aurora kinases with a selective target inhibition profile relevant to cancer," Mol Cancer Ther, Dec. 2007;6(12 Pt 1):3158-3168.
Carvalho et al., Neuro-Oncology 1 7:iii1-iii40, 2015, Abstract No. HG-09, 1 page.
Catalog of Somatic Mutations in Cancer (COSMIC) database, cancer.sanger.ac.uk/cosmic/mutation/overview?id=1517968, downloaded on May 31, 2016, 2 pages.
Catalog of Somatic Mutations in Cancer (COSMIC) database, cancer.sanger.ac.uk/cosmic/mutation/overview?id=1636266, downloaded on May 31, 2016, 2 pages.
Catalog of Somatic Mutations in Cancer (COSMIC) database, cancer.sanger.ac.uk/cosmic/mutation/overview?id=1688778, downloaded on May 31, 2016, 2 pages.
Catalog of Somatic Mutations in Cancer (COSMIC) database, cancer.sanger.ac.uk/cosmic/mutation/overview?id=3711772, downloaded on May 31, 2016, 2 pages.
Catalog of Somatic Mutations in Cancer (COSMIC) database, cancer.sanger.ac.uk/cosmic/mutation/overview?id=471203, downloaded on May 31, 2016, 2 pages.
Catalog of Somatic Mutations in Cancer (COSMIC) database, cancer.sanger.ac.uk/cosmic/mutation/overview?id=48622, downloaded on May 31, 2016, 2 pages.
Catic et al., "A novel cytogenetic and molecular characterization of renal metanephric adenoma, identification of partner genes involved in translocation t(9;15)(p24;q24)," Cancer Genet. 214-215:9-15, doi: 10.1016/j.cancergen.2017.03.001, 2017.
Catic et al., "Abstract 1537: The frequency of a novel KANK1 and NTRK3translocation and BRAFV600E mutation in patients diagnosed with metanephric adenoma utilizing molecular mechanisms," 2017 Annual Meeting of the American Society of Clinical Oncology, 2017, 1 page.
Center for Drug Evaluation and Research: www.accessdata.fda.gov/drugsatfda_docs/nds/2018/210861Origls000_211710Origls000ChemR.pdf , 2017, 64 pages.
Chang-Qi et al., "Brain derived neurotrophic factor (BDNF) contributes to the pain hypersensitivity following surgical incision in the rats," Molecular Pain, 2008, 4:27.
Chaudhuri et al., "Early Detection of Molecular Residual Disease in Localized Lung Cancer by Circulating Tumor DNA Profiling," Cancer Discov, Dec. 2017, 7(12):1394-1403.
Chen et al.,"40: The landscape of kinase fusions in 445 Chinese NSCLC patients," Annals of Oncology, Oct. 2017, 28(7): vii16, 1 page.
Cherry et al., "Recent kinase and kinase inhibitor X-ray structures: mechanisms of inhibition and selectivity insights," Curr Med Chem. Mar. 2004;11(6):663-73.
Chiang et al., "NTRK Fusions Define a Novel Uterine Sarcoma Subtype with Features of Fibrosarcoma," Am. J. Surg. Pathol. doi: 10.1097IPAS.0000000000001055, 2018.
Chintakuntlawar et al., "High-grade transformation of acinic cell carcinoma: an inadequately treated entity?," Oral Surg Oral Med Oral Pathol Oral Radiol, May 2016, 121(5):542-549.
Chmielecki et al., "Abstract LB-178: Genomic profiling of 1239 diverse pediatric cancers identifies novel discoveries across tumors", Cancer Research, vol. 76, No. 14, Supp. Supplement. Abstract No. LB-178. 107th Annual meeting of the American Association for Cancer Research, AACR. New Orleans, LA Apr. 16-20, 2016.
Chmielecki et al., "Genomic Profiling of a Large Set of Diverse Pediatric Cancers Identifies Known and Novel Mutations across Tumor Spectra.", Cancer Research, 77(2): 509-519, 2017.
Cho et al., "Expression of mRNA for brain-derived neurotrophic factor in the dorsal root ganglion following peripheral inflammation," Brain Research, 1997, 749:358-362.
Choi et al., "(R)-2-Phenylpyrrolidine Substituted Irnidazopy ridazines. A New Class of Potent and Selective Pan-TRK Inhibitors," ACS medicinal chemistry letters, Mar. 2015 I 9;6(5):562-7.
Chung et al., "Infantile fibrosarcoma," Cancer, Aug. 1976, 38(2):729-739.
Church et al., "Abstract ST16: A Novel EML4-NTRK3 Translocation in Infantile Fibrosarcoma and Congenital Mesoblastic Nephroma Requires a New Approach to Conventional Diagnostic Algorithms," J Molecular Diag, 2015, 816.
Church et al., "Recurrent EML4-NTRK3 fusions in infantile fibrosarcoma and congenital mesoblastic nephroma suggest a revised testing strategy," Mod. Pathol. 31(3), 463-473, 2018.
Cocce et al., "Identification of ZCCHC8 as fusion partner of ROS1 in a case of congenital glioblastoma multiforme with a t(6;12)(q21;q24.3)", Genes Chromosomes Cancer, 55(9): 677-87, 2016.
Coebergh et al., "Abstract 490: Identification of oncogenic gene fusions in primary colon cancers," Cancer Research, Jul. 2017, DOI: 10.1158/1538-7445.AM2017-490, 2 pages.
Comina-Mendez and Turner, "Predicting Relapse with Circulating Tumor DNA Analysis in Lung Cancer," CancerDiscov, Dec. 2017, 7(12): 1368-1370.
Cook et al., "Somatic chromosomal engineering identifies BCAN-NTRK1 as a potent glioma driver and therapeutic target," Nat. Comm. 8(15987). DOI 10.1038/ncomms15987, 2017.
Creancier et al., "Chromosomal rearrangements involving the NTRK.1 gene in colorectal carcinoma," Cancer Lett., Awmst 2015, 365(1):107-111.
Crescenzo et al., "Convergent mutations and kinase fusions lead to oncogenic STAT3 activation in anaplastic large cell lymphoma.", Cancer Cell., 27(4): 516-32, 2015.
Croucher et al., "TrkB inhibition by GNF-4256 slows growth and enhances chemotherapeutic efficacy in neuroblastoma xenografts,"

(56) References Cited

OTHER PUBLICATIONS

Cancer Chemother Pharmacol. Jan. 2015;75(1):131-41. doi: 10.1007/s00280-014-2627-1. Epub Nov. 14, 2014.
Cruz, "Lung cancer: epidemiology, etiology and prevention," Clinics in Chest Medicine, 2011, 32(4): 1-61.
Cui et al., "Abstract #MA 07.09: ALK/ROS1/inhibitor TPX-0005 Effectively Overcomes Clinical Resistance Solvent Front Mutations," Abstracts, Nov. 2017, p. S1829.
Cui et al., "Use of capture-based next-generation sequencing to detect ALK fusion in plasma cell-free DNA of patients with non-small-cell lung cancer", Oncotarget, 2771-2780, 2016.
Dacie et al., "ALK FISH patterns and the detection of ALK fusions by next generation sequencing in lung adenocarcinoma", Oncotarget, vol. 7, No. 50, pp. 82943-82952, 2016.
Dang et al., "Expression of nerve growth factor receptors is correlated with progression and prognosis of human pancreatic cancer," J. Gastroenterology and Hepatology, 2006, 21(5): 850-858.
Das et al., "Synergistic Effects of Crizotinib and Temozolomide in Experimental FIG-ROS1 Fusion-Positive Glioblastoma.", Cancer Growth Metastasis, 8:51-60, 2015.
Davare et al., "Foretinib is a potent inhibitor of oncogenic ROS1 fusion proteins.", Proc. Natl. Acad Sci. USA., 110(48): 19519-24, 2013.
Davare et al., "Structural insight into selectivity and resistance profiles of ROS1 tyrosine kinase inhibitors.", Proc. Natl. Acad Sci. USA., 112(39): E5381-90, 2015.
Davidson et al., "Expression and activation of the nerve growth factor receptor TrkA in serous ovarian carcinoma," Clin. Cancer Res., 2003, 9(6):2248-2259.
Davies and Dobele, "Molecular pathways: ROS1 fusion proteins in cancer.", Clin. Cancer Res, 19(15): 4040-4045, 2013.
Davies et al., "Identifying and targeting ROS1 gene fusions in non-small cell lung cancer.", Clin Cancer Res 18: 4570-4579, 2012.
Davies et al., "Resistance to ROS1 inhibition mediated by EGFR pathway activation in non-small cell lung cell," PLoS One, 2013, 8(12):e82236, 13 pages.
Davis et al., "Infantile NTRK-associated Mesenchymal Tumors," Pediatr. Dev. Pathol. 21(1):68-78, 2018.
De Smith et al., "Clonal and microclonal mutational heterogeneity in high hyperdiploid acute lymphoblastic leukemia", Oneatarget., 7(45) 72733-72745, 2016.
Deihimi et al., "BRCA2, EGFR, and NTRK mutations in mismatch repair-deficient colorectal cancers with MSH2 or MLH1 mutations," Oncotarget. Jun. 20;8(25):39945-39962, 2017.
Delafoy et al., "Role of nerve growth factor in the trinitrobenzene sulfonic acid-induced colonic hypersensitivity," Pain, 2003, 105:489-497.
Demaria et al., "Development of tumor-infiltrating lymphocytes in breast cancer after neoadjuvant paclitaxel chemotherapy," Clin Cancer Res, Oct. 2001;7(10):3025-30.
Di Mola et al., "Nerve growth factor and Trk high affinity receptor (TrkA) gene expression in inflammatory bowel disease," Gut, 2000, 46(5):670-678.
Diner et al., "Preparation of 3-substituted-1-isopropyl-1H-pyrazolo[3,4-d]pyrimidin-4-amines as RET kinase inhibitors," J. Med. Chem., May 2012, 55 (10), 4872-4876.
Dionne et al., "Cell cycle-independent death of prostate adenocarcinoma is induced by the trk tyrosine kinase inhibitor CEP-751 (KT6587)," Clin. Cancer Research, 1998, 4(8):1887-1898.
Doebele et al., "Abstract 8023: NTRK1 gene fusions as a novel oncogene target in lung cancer," 2013 Annual Meeting of the American Society of Clinical Oncology, Chicago, IL, 2013, 1 page.
Doebele et al., "An oncogenic NTRK fusion in a soft tissue sarcoma patient with response to the tropomyosin-related kinase (TRK) inhibitor LOXO-101," Cancer Discovery, Jul. 2015, 5(10):1049-1057.
Doebele et al., "Phase II Trial of Stereotactic Body Radiation Therapy Combined with Erlotinib for Patients with Limited but Progressive Metastatic Non-Small-Cell Lung Cancer," J. Clin. Oncol., 2014, 32:9 pages.

Dolle et al., "Nerve growth factor-induced migration of endothelial cells," J. Pharmacol Exp Ther, 2005, 315(3):1220-1227.
Dolomanov et al., "OLEX2: a complete structure solution, refinement and analysis program," J Anml. Cryst. 2009, 42, 339-341.
Dou et al., "Increased nerve growth factor and its receptors in atopic dermatitis: an immunohistochemical study," Archives of Dermatological Research, 2006, 298(1):31-37.
Drexler et al., "Pathobiology of NPM-ALK and variant fusion genes in anaplastic large cell lymphoma and other lymphomas," Leukemia, Sep. 2000, 14:1533-1559.
Drilon et al., "A Novel Crizotinib-Resistant Solvent-Front Mutation Responsive to Cabozantinib Therapy in a Patient with ROS1-Rearranged Lung Cancer.", Clin. Cancer Res., 22(10): 2351-8, 2016.
Drilon et al., "A phase 1 study of oral LOXO 292 in adult patients with advanced solid tumors, including RET-fusion non-small cell lung cancer, medullary thyroid cancer and other tumors with increased RET activity," Annals of oncology Developmental Therapeutics, Sep. 2017, 28(5):138.
Drilon et al., "Abstract CT007: Entrectinib, an oral pan-Trk, ROS1, and ALK inhibitor in TKI-naive patients with advanced solid tumors harboring gene rearrangements: Updated phase I results," Cancer research, 76(14), AACR 107th Annual Meeting, Apr. 2016, URL <http://cancerres.aacrjournals.org/content/76/14 Supplement/CT007.short>, 5 pages.
Drilon et al., "Entrectinib, an oral pan-Trk, ROS1, and ALK inhibitor in TK1-naive patients with advanced solid tumors harboring gene rearrangements," Cancer research, vol. 76, No. 14, Supp. Supplement., Abstract No. 15 CT007; Presented at the 107th Annual Meeting of the American Association for Cancer Research, Aacr 2016. New Orleans, LA; Apr. 16-20, 2016, 35 pages.
Drilon et al., "What hides behind the MASC: clinical response and acquired resistance to entrectinib after ETV6-NTRK3 identification in a mammary analogue secretory carcinoma (MASC)," Annals of Oncology., Feb. 15, 2016, 27(5):920-926.
Du et al., "Expression of NGF family and their receptors in gastric carcinoma: a cDNA microarray study," World Journal of Gastroenterology, http://www.wjgnet.com/1007-9327/full/v9/i7/1431.htm, Jul. 2003, 9(7):1431-1434.
Duranti et al., "Homologation of Mexiletine alkyl chain and stereoselective blockade of skeletal muscle sodium channels," Euro. J. Med. Chem., 2000, 35:147-156.
Durham et al. "Diverse and Targetable Kinase Alterations Drive Histiocytic Neoplasms," Blood. 126(23):481, 2015.
Edgren et al., Cancer Res. 75(15 Supplement): 4793, 2015; Abstract only, 3 pages.
Eguchi et al., "Absence of t(12;15) associated ETV6-NTRK3 fusion transcripts in pediatric acute leukemias," Med Pediatr. Oncol., Oct. 2001, 37:417.
Eguchi et al., "Fusion of ETV6 to neurotrophin-3 receptor TRKC in acute myeloid leukemia with t(12;15)(p13;q25)," Blood, 1999, 93(4):1355-1363.
Eisenhauer et al., "New response evaluation criteria in solid tumours: revised RECIST guideline (version 1.1)," Eur J Cancer, Jan. 2009, 45(2):228-247.
Ellison et al., "Abstract 013: Genetic alterations in uncommon low-grade neural tumors—BRAF, FGFR1, and MYB/MYBL1 mutations occur frequently and align with morphology," Neuropathology and Applied Neurobiology, 2016, 42(S1): 18.
Elvin et al., "319: Genomic profiling of uterine leiomyosarcomas reveal frequent alterations in Akt/mammalian target of rapamycin (mTOR) pathway genes and other actionable genomic abnormalities linked to targeted therapies," Poster Session—Molecular Targeted Agents I, Nov. 2014, 1 page.
Endometrial Cancer Gene Database, ecgene.bioinfominzhao.org/gene_mutation.cgi?gene=4915, downloaded on May 31, 2016, 13 pages.
Engman et al., "Syngeneic transplant in mantle cell lymphoma: a rare event and review of the literature," Clin Adv Hematol Oncol. May 2009;7(5):321-3.
Esmo, "TRK Cancer-Causing Mutation Discovered in 1982 Finally Target of Clinical Trials: Matching drugs to long-overlooked oncogene," European Society of Medical Oncology, Jan. 2015, 2 pages.

(56) References Cited

OTHER PUBLICATIONS

Essand et al., "Genetically engineered T cells for the treatment of cancer," J Intern Med. Feb. 2013;273(2):166-81. doi: 10.1111/joim.12020.

Estrada-Bernal et al., "Abstract#: C65: TRK kinase domain mutations that induce resistance to a pan-TRK inhibitor," Poster, Presented at Proceedings of the AACR-NCI-EORTC International Conference: Molecular Targets and Cancer Therapeutics, Boston MA, Nov. 5-9, 2015; Mol Cancer Ther, Dec. 2015, 14(12)(Suppl. 2): 1 page.

Estrada-Bernal et al., "Abstract#: LB-118: Identification of TRKA and TRKB kinase domain mutations that induce resistance to a pan-TRK inhibitor," Poster, Presented at Proceedings of the 107th Annual Meeting of the American Association for Cancer Research, New Orleans LA, Apr. 16-20, 2016; Cancer Res, Jul. 2016, 76(14): 1 page.

Euthus et al., "ETV6-NTRK3—Trk-ing the primary event in human secretory breast cancer," Cancer Cell, 2002, 2(5):347-348.

Evans et al., "Antitumor activity of CEP-751 (KT-6587) on human neuroblastoma and medulloblastomaxenografts," Clin. Cancer Res., Nov. 1999, 5(11):3594-3602.

Extended European Search Report in European Application No. 13197815.7, dated Apr. 1, 2014, 5 pages.

Extended European Search Report in European Application No. 16166461.0, dated Sep. 28, 2016, 5 pages.

Extended European Search Report in European Application No. 17163978.4, dated Jul. 17, 2017, 5 pages.

Extended European Search Report in European Application No. 17199899.0, dated Feb. 26, 2018, 7 pages.

Extended European Search Report in European Application No. 18151233.6, dated Jun. 26, 2018, 6 pages.

Extended European Search Report in European Application No. 18208279.2, dated Jun. 27, 2019, 10 pages.

Facchinetti et al., "Crizotinib-Resistant ROS1 Mutations Reveal a Predictive Kinase Inhibitor Sensitivity Model for ROS1- and ALK-Rearranged Lung Cancers.", Clin. Cancer Res., 22(24): 5983-5991, 2016.

Farago et al., "Abstract MINB0.09: Clinical Response to Entrectinib in a Patient with NTRK1-Rearranged Non-small cell Lung Cancer," J Thoracic Oncol, Sep. 2015, 10(9-S2): S374-S375.

Farago et al., "Durable clinical response to entrectinib in NTRK1-rearranged non-small cell lung cancer," J. Thorac Oncol. 10(12):1670-1674, 2015.

Farhat et al., "Primary benign and malignant thyroid neoplasms with signet ring cells: cytologic, histologic, and molecular features," Am. J. Clin. Pathol., 148(3):251-258, 2017.

Fernandez-Cuesta et al., "Abstract 1531: Cross-entity mutation analysis of lung neuroendocrine tumors sheds light into their molecular origin and identifies new therapeutic targets," AACR Annual Meeting 2014, Apr. 2014, URL <http://cancerres.aacrjournals.org/content/7 4/19 Supplement/1531.short>, 5 pages.

Flannery et al., "Immunomodulation: NK cells activated by interferon-conjugated monoclonal antibody against human osteosarcoma," Eur J Cancer Clin Oncol. Jun. 1984;20(6):791-8.

Forghieri et al., Abstract P137: Chronic Eosinophilic Leukemia with ETV6-NTRK3 Fusion Transcript in an Elderly Patient Affected with Pancreatic Carcinoma, Haemologica, 2010, 95(s3):S125-S126.

Frattini et al., "The integrated landscape of driver genomic alterations in glioblastoma," Nature Genet., 2013, 45:1141-1149.

Freund-Michel and Frossard, "The nerve growth factor and its receptors in airway inflammatory diseases," Pharmacology & Therapeutics, 2008, 117(1):52-76.

Frey et al., "7-Aminopyrazolo[1,5-a]pyrimidines as potent multitargeted receptor tyrosine kinase inhibitors," J. Med. Chem, Jul. 2008, 51(13):3777-3787.

Fu et al., "The Frequency and Clinical Implication of ROS1 and RET Rearrangements in Resected Stage IIIA-N2 Non-Small Cell Lung Cancer Patients.", PLoS One, 10(4):e0124354, 2015.

Fuse et al., "Mechanisms of Resistance to NTRK Inhibitors and Therapeutic Strategies in NTRK1-Rearranged Cancers," Mol. Cancer Ther., Oct. 2017; 16(10); 2130-43.

Gainor et al., "Patterns of Metastatic Spread and Mechanisms of Resistance to Crizotinib in ROS1-Positive Non-Small-Cell Lung Cancer", JCO Precis Oneal. 10.1200/PO. 1 7.00063, 2017.

Gang et al., "The landscape of fusion transcripts in spitzoid melanoma and biologically indeterminate spitzoid tumors by RNA sequencing.", Mod Pathol., 29(4): 359-69, 2016.

Gao et al., "Driver fusions and their implications in the development and treatment of human cancers," Cell Rep. 23(1):227-238.e3, 2018.

Gatalica et al., "Abstract A047: Molecular characterization of the malignancies with targetable NTRK gene fusions," American Association for Cancer Research, Jan. 2018, 2 pages.

Gaudet et al., "Allele-specific PCR in SNP genotyping," Methods Mol Biol. 2009;578:415-24. doi: 10.1007/978-1-60327-411-126.

Gavrin et al., "Synthesis of Pyrazolo[1,5-[alpha]]pyrimidoinone Regioisomers," J Org Chem, Feb. 2007, 72(3): 1043-1046.

Geiger et al., "Functional Characterization of Human Cancer-Derived TRKB Mutations," PLoS ONE, Feb. 17, 2011, 6(2):e16871.

Geiger et al., "The neurotrophic receptor TrkB in anoikis resistance and metastasis: a perspective," J Cancer Res., Aug. 2005, 65(16):7033-7036.

GenBank Accession No. AAB33109.1, "trkB [*Homo sapiens*]," Jul. 27, 1995, 1 page.

GenBank Accession No. AAB33111.1 "trkC [*Homo sapiens*]," Jul. 27, 1995, 1 page.

GenBank Accession No. NM_ 002529, "high affinity nerve growth factor receptor isoform 2 precursor [*Homo sapiens*]," May 11, 2014, 4 pages.

GenBank Accession No. NM_001007792 "*Homo sapiens* neurotrophic tyrosine kinase, receptor, type 1 (NTRK1), transcript variant 3, mRNA," May 10, 2014, 5 pages.

GenBank Accession No. NM_001012338, "*Homo sapiens* neurotrophic tyrosine kinase, receptor, type 3 (NTRK3), transcript variant 1, mRNA," May 10, 2014, 6 pages.

GenBank Accession No. NM_006180, "*Homo sapiens* neurotrophic tyrosine kinase, receptor, type 2 (NTRK2), transcript variant a, mRNA," May 12, 2014, 9 pages.

GenBank Accession No. NP 001007793, "high affinity nerve growth factor receptor isoform 3 [*Homo sapiens*]," May 10, 2014, 3 pages.

GenBank Accession No. NP_ 002520 "high affinity nerve growth factor receptor isoform 2 precursor [*Homo sapiens*]," May 11, 2014, 4 pages.

GenBank Accession No. NP_001007157, "NT-3 growth factor receptor isoform c precursor [*Homo sapiens*]," May 10, 2014, 3 pages.

GenBank Accession No. NP_001012331.1, "high affinity nerve growth factor receptor isoform 1 precursor [*Homo sapiens*]," May 10, 2014, 4 pages.

GenBank Accession No. NP_001012338, "NT-3 growth factor receptor isoform a precursor [*Homo sapiens*]," May 10, 2014, 3 pages.

GenBank Accession No. NP_006171, "BDNF/NT-3 growth factors receptor isoform a precursor [*Homo sapiens*]," May 12, 2014, 4 pages.

GenBank Accession No. S76473.1, "trkB [human, brain, mRNA, 3194 nt]," Jul. 27, 1995, 2 pages.

GenBank Accession No. S76475.1, "trkC [human, brain, mRNA, 2715 nt]," Jul. 27, 1995, 2 pages.

Genevois et al., "Dependence receptor TrkC is a putative colon cancer tumor suppressor," Proc. Nat. Acad. Sci. U.S.A. Feb. 19, 2013, 110(8):3017-3022.

Giacomini et al., "Breakpoint Analysis of Transcriptional and Genomic Profiles Uncovers Novel Gene Fusions Spanning Multiple Human Cancer Types", PLoS Gene.t, 9(4): e1003464, 2013.

Gimm et al., "Mutation analysis ofNTRK.2 and NTRK.3, encoding 2 tyrosine kinase receptors, in sporadic human medullary thyroid carcinoma reveals novel sequence variants," International Journal of Cancer, Apr. 1, 2001, 92(1):70-74.

(56) References Cited

OTHER PUBLICATIONS

Greco et al., "Chromosome I rearrangements involving the genes TPR and NTRK1 produce structurally different thyroid-specific TRK oncogenes," Genes Chromosomes Cancer. 19(2):112-23, 1997.
Greco et al., "Rearrangements of NTRK1 gene in papillary thyroid carcinoma," Molecular and Cellular Endocrinology, 2010, 321(1):44-49.
Greco et al., "The DNA rearrangement that generates the TRK-T3 oncogene involves a novel gene on chromosome 3 whose product has a potential coiled-coil domain," Mol. Cell. Biol. 15(11):6118-6127, 1995.
Greco et al., "TRK-T1 is a novel oncogene formed by the fusion of TPR and TRK genes in human papillary thyroid carcinomas," Oncogene. 7(2):237-42, 1992.
Green & Wuts, eds, "Protective Groups in Organic Synthesis," John Wiley & Sons Inc, May 8, 1999.
Groisberg et al., "Clinical next-generation sequencing in sarcomas", Journal of Clinical Oncology, vol. 34, Supp. Supplement 15; Abstract No. 11046; 2016 Annual Meeting of the American Society of Clinical Oncology, ASCO 2016, Chicago, IL. Jun. 3-7, 2016.
Gruber-Olipitz et al., "Neurotrophin 3/TrkC-regulated proteins in the human medulloblastoma cell line DAOY," J. Proteome Research, 2008, 7(5):1932-1944.
Gu et al., "Lung adenocarcinoma harboring concomitant SPTBN1-ALK fusion, c-Met overexpression, and HER-2 amplification with inherent resistance to crizotinib, chemotherapy, and radiotherapy.", J Hematol Oneal, 9(1): 66, 2016.
Gwak et al., "Attenuation of mechanical hyperalgesia following spinal cord injury by administration of antibodies to nerve growth factor in the rat." Neurosci. Lett., 2003, 336:117-120.
Hainsworth et al., "Lung Adenocarcinoma with Anaplastic Lymphoma Kinase (ALK) Rearrangement Presenting as Carcinoma of Unknown Primary Site: Recognition and Treatment Implications.", Drugs Real World Outcomes, 3:115-120, 2016.
Hakimi et al., "Minimally invasive approaches to prostate cancer: a review of the current literature.", Urol. J., 4: 130-137, 2007.
Hallberg and Palmer, "The role of the ALK receptor in cancer biology.", Ann. Oncology, 27 (Suppl 3):iii4-iii15. doi: 10.1093/annonc/mdw301, 2016.
Haller et al., "Paediatric and adult soft tissue sarcomas with NTRK.1 gene fusions: a subset of spindle cell sarcomas unified by a prominent myopericytic/haemangiopericytic pattern," J Pathol, Apr. 2016, 238(5):700-710.
Hamdouchi et al "Imidazo[1,2-b]pyridazines, novel nucleus with potent and broad spectrum activity against human picornavimses: design, synthesis, and biological evaluation" J Med Chem., Sep. 25, 2003;46(20):4333-4341.
Hansen et al., "Autophagic cell death induced by TrkA receptor activation in human glioblastoma cells," J. of Neurochemistry, 2007, 103:259-275.
Harada et al., "Role and Relevance of TrkB Mutations and Expression in Non-Small Cell Lung Cancer," Clinical Cancer Research, Jan. 17, 2011, 17(9):2638-2645.
Harris et al., "Multicenter Feasibility Study of Tumor Molecular Profiling to Inform Therapeutic Decisions in Advanced Pediatric Solid Tumors: The Individualized Cancer Therapy (iCat) Study," JAMA Oncol, Jan. 2016; 10.1001/jamaoncol.2015.5689, 8 pages.
Harwood et al., "Experimental organic chemistry—Principles and practice," Experimental Chemistry—Organic Chemistry and Reaction, Jan. 1, 1989, 127-132.
Hayashi et al., "Crizotinib treatment for refractory pediatric acute myeloid leukemia with RAN-binding protein 2-anaplastic lymphoma kinase fusion gene.", Blood Cancer J, 6(8): e456, 2016.
Hechtman et al., "Identification of targetable kinase alterations in patients with colorectal carcinoma that are preferentially associated with wild-type RAS/RAF," Mol. Cancer Res. 14(3):296-301, 2016.
Hechtman et al., Abstract 1837: Pan-TRK IHC Is an Efficient and Reliable Screening Assay for Targetable NTRK Fusions, Annual Meeting Abstracts, 2017, 457A.
Herzberg et al., "NGF involvement in pain induced by chronic constriction injury of the rat sciatic nerve," Neuroreport, 1997, 8:1613-1618.
Hilfiker, Rolf, Fritz Blatter, and Markus von Raumer. "Relevance of solid-state properties for pharmaceutical products." Polymorphism in the pharmaceutical industry (2006): 1-19.
Hinrichs et al., "Exploiting the curative potential of adoptive T-cell therapy for cancer," Immunol Rev. Jan. 2014;257(1):56-71. doi: 10.1111/imr.12132.
Hobbs et al., "Effects of T-Cell Depletion on Allogeneic Hematopoietic Stem Cell Transplantation Outcomes in AML Patients," J Clin Med. Mar. 19, 2015;4(3):488-503. doi: 10.3390/jcm4030488.
Hotta et al., "ALK: a tyrosine kinase target for cancer therapy", Cold Spring Harb Mol Case Study, 3(1):a001115. doi: 10.1101/mcs.a001115, 20 pages, 2017.
Hong et al., "Clinical Safety and activity from a Phase 1 study of LOXO-101, a selective TRKA/B/C inhibitor, in solid-tumor patients with NTRK gene fusions," 2016 AACR Annual Meeting, Apr. 17, 2016, 32 pages.
Hong et al., Abstract PR13: Clinical safety and activity from a phase 1 study of LOXO-101, a selective TRKA/B/C inhibitor, in solid-tumor patients with NTRK gene fusions, Molecular Cancer Therapeutics 2015:14(12 Supplement 2):PR13.; Abstract only, 4 pages.
Hornick et al., "Expression of ROSI predicts ROSI gene rearrangement in inflammatory myofibroblastic tumors.", Mod Pathol., 28(5): 732-9, 2015.
Hover et al., "Abstract TMOD-07: NTRK3 Gene Fusions Drive Tumorigenesis in Novel Models of Pediatric HighGrade Glioma," Neuro-Oncology, Jun. 2017, iv49.
Howell et al., "Dynamic allele-specific hybridization. A new method for scoring single nucleotide polymorphisms," Nat Biotechnol. Jan. 1999;17(1):87-8.
Hu et al., "Decrease in bladder overactivity with REN1820 in rats with cyclophosphamide induced cystitis," J. Urology, 2005, 173(3):1016-1021.
Hu et al., "Identification of brain-derived neurotrophic factor as a novel angiogenic protein in multiple myeloma" Cancer Genetics and Cytogenetics, 2007, 178:1-10.
Huehls et al., "Bispecific T-cell engagers for cancer immunotherapy," Immunol Cell Biol. Mar. 2015;93(3):290-6. doi: 10.1038/icb.2014.93. Epub Nov. 4, 2014.
Hyrcza et al., "Abstract OFP-06-007: Comparison of ultrastructural features between pediatric Mammary Analogue Secretory Carcinoma (MASC) of the salivary glands and Pediatric Secretory Breast Carcinoma (SBC) reveals similar pathological features," Virchows Arch, Sep. 2016, 469(S1): S17.
Hyrcza et al., vol. 469, Supp. Supplement 1, pp. S17. Abstract No. OFP-1997-7; 31st International Congress of the International Academy of Pathology and the 28th Congress of the European Society of Pathology, Cologne, Germany. Sep. 25-29, 2016.
Igaz et al., "Biological and clinical significance of the JAK-STAT pathway; lessons from knockout mice," Inflamm Res., 2001, 50:435-441.
Ihle et al., "The Roles of Jaks and Stats in Cytokine Signaling," Cane. J. Sci. Am., 1998, 4(1):84-91.
Ihuegbu et al., "Non-invasive detection of crizotinib resistance in ALK-rearranged lung adenocarcinoma directs treatment with next-generation ALK inhibitors", J Clin. Oncology, vol. 34, Supp. Supplement 15, Abstract No. e20643, 2016 Annual Meeting of the American Society of Clinical Oncology, Chicago, IL, 2016.
Ikeda et al., "Basic Science", Annals of Oncology. vol. 28 (suppl_10): xl x6.10.1093/annonc/mdx652, 2017.
Imamura et al., "Allogeneic hematopoietic stem cell transplantation in adult acute lymphoblastic leukemia: potential benefit of medium-dose etoposide conditioning," Exp Hematol Oncol, Jul. 16, 2015;4:20. doi: 10.1186/s40164-015-0015-0. eCollection 2015.
Iniguez-Ariza et al., "Abstract 6087: NTRK.1-3-point mutations in poor prognosis thyroid cancers," J Clinical Oncology, May 2017, 35(15): 6087.
Isdori et al., "Advancement in high dose therapy and autologous stem cell rescue in lymphoma," World J Stem Cells, Aug. 2015, 7(7):1039-1046.

(56) References Cited

OTHER PUBLICATIONS

Iyama et al., "Identification of Three Novel Fusion Oncogenes, SQSTM1/NTRK3, AFAP1L2/RET, and PPFIBP2/RET, in Thyroid Cancers of Young Patients in Fukushima," Thyroid. 27(6):811-818, 2017.
Iyer et al., "AZ64 inhibits TrkB and enhances the efficacy of chemotherapy and local radiation in neuroblastoma xenografts," Cancer Chemother Pharmacol. Sep. 2012;70(3):477-86. doi: 10.1007/s00280-012-1879-x. Epub May 24, 2012.
Iyer, R., "Entrectinib is a potent inhibitor of Trk-driven neuroblastomas in a xenograft mouse model." Cancer letters 372.2 (2016): 179-186. (Year: 2016).
Jaggar et al., "Inflammation of the rat urinary bladder is associated with a referred thermal hyperalgesia which is nerve growth factor dependent," Br. J. Anaesth, 1999, 83:442-448.
Jencks and Regenstein, "Ionization Constants of Acids and Bases," Handbook of Biochemistry and Molecular Biology, 3rd ed., G.D. Fassman, CRC Press, 1976, 1: 305-347.
Jin et al., "TrkC plays an essential role in breast tumor growth and metastasis," Carcinogenesis, 2010, 31(11):1939-1947.
Johnson et al., "Comprehensive Genomic Profiling of 282 Pediatric Low- and High-Grade Gliomas Reveals Genomic Drivers, Tumor Mutational Burden, and Hypermutation Signatures.", Oncologist. 22(12): 1478-1490, 2017.
Jones et al., "Recurrent somatic alterations of FGFR1 and NTRK.2 in pilocytic astrocytoma," Nature Genetics, 2013, 45:927-932.
Kao et al., "Recurrent BRAF Gene Fusions in a Subset of Pediatric Spindle Cell Sarcomas," Am. J. Surg. Pathol. 42(1):28-38, 2018.
Karachialiou et al., "Real-time liquid biopsies become a reality in cancer treatment", Ann. Transl. Med, 3(3):36, 2016.
Katayama et al., "Cabozantinib Overcomes Crizotinib Resistance in ROS1 Fusion-Positive Cancer", Clin. Cancer Res., 21 (I): 166-7 4, 2015.
Katayama et al., "Mechanisms of Acquired Crizotinib Resistance in ALK Rearranged Lung Cancers," Sci Transl Med, Feb. 2012, 4(120): 120ra17.
Katayama et al., "Therapeutic targeting of anaplastic lymphoma kinase in lung cancer: a paradigm for precision cancer medicine.", Clin Cancer Res, 21(10): 2227-35, 2015.
Keysar et al., "A patient tumor transplant model of Squamous cell cancer identifies PBK inhibitors as candidate therapeutics in defined molecular bins," Molecular Oncology, 2013, 7(4):776-790.
Kim et al., "Mammaglobin-A is a target for breast cancer vaccination", OncoImmunology 5(2): e1069940, 2016.
Kim et al., "NTRK.1 fusion in glioblastoma multiforme," PloS ONE, 2014, 9(3): e91940.
Kim et al., "SEC31A-ALK Fusion Gene in Lung Adenocarcinoma", Cancer Res Treat, 48(1): 398-402,2016.
Klijn et al., "A comprehensive transcriptional portrait of human cancer cell lines," Nat Biotechnol., 2015, 33(3):306-312.
Knezevich et al., "A novel ETV6-NTRK.3 gene fusion in congenital fibrosarcoma," Nat Genet, Feb. 1998:18(2):184-187.
Knezevich et al., "ETV6-NTRK3 gene fusions and trisomy 11 establish a histogenetic link between mesoblastic nephroma and congenital fibrosarcoma," Cancer Res, Nov. 1998:58(22):5046-5048.
Koboldt et al., "The next-generation sequencing revolution and its impact on genomics," Cell, Sep. 26, 2013;155(1):27-38. doi: 10.1016/j.cell.2013.09.006.
Kohsaka et al., Pediatric soft tissue tumor of the upper arm with LMNA-NTRK1 fusion, Hum. Pathol. 72:167-173, 2017.
Kolokythas et al., "Nerve growth factor and tyrosine kinase A receptor in oral squamous cell carcinoma: is there an association with perineural invasion?" J. Oral Maxillofacial Surgery, 2010, 68(6):1290-1295.
Konicek et al., Cancer research, vol. 76, No. 14, Supp. Supplement. Abstract No. 2647; 107th Annual Meeting of the American Association for Cancer Research, AACR 2016. New Orleans, LA; Apr. 16-20, 2016; Abstract only, 3 pages.
Kralik et al., "Characterization of a newly identified ETV6-NTRK3 fusion transcript in acute myeloid leukemia," Diagn. Pathol. 6:19, 2011.
Kremer et al., "The safety and efficacy of a JAK inhibitor in patients with active rheumatoid arthritis: Results of a double-blind, placebo-controlled phase IIa trial of three dosage levels of CP-690,550 versus placebo," Arth. & Rheum., 2009, 60:1895-1905.
Kruttgen et al., "The dark side of the NGF family: neurotrophins in neoplasias," Brain Pathology, 2006, 16:304-310.
Kubler et al., "Self-adjuvanted mRNA vaccination in advanced prostate cancer patients: a first-in-man phase I/IIa study.", J. Immunother Cancer 3 :26, 2015.
Kusano et al., "Two Cases of Renal Cell Carcinoma Harboring a Novel STRN-ALK Fusion Gene.", Am J SurgPathol. 40(6): 761-9, 2016.
Lamb et al., "Nerve growth factor and gastric hyperalgesia in the rat," Neurogastrenterol. Motil., 2003, 15:355-361.
Lannon et al., "ETV6-NTRK3: a chimeric protein tyrosine kinase with transformation activity in multiple cell lineages," Semin Cancer Biol, Jun. 2005:15(3):215-223.
Lansky et al., "The measurement of performance in childhood cancer patients," Cancer, 1987, 60(7):1651-1651.
Lecht et al., "Angiostatic effects ofK252a, a TRK inhibitor, in murine brain capillary endothelial cells," Mol Cell Biochem, Jun. 2010;339(1-2):201-13. doi: 10.1007/s11010-010-0386-9. Epub Feb. 11, 2010.
Lee et al., "Identification of ROS1 rearrangement in gastric adenocarcinoma.", Cancer, 119(9): 1627-1635, 2013.
Leeman-Neill et al., "ETV6-NTRK3 is a common chromosomal rearrangement in radiation-associated thyroid cancer," Cancer, 2014, 120(6):799-807.
Leukemia, Wikipedia the Free Encyclopedia, Dec. 8, 2001, https://en.wikipedia.org/wiki/Leukemia, 15 pages.
Leyvraz et al., Abstract No. 897. Meeting Info: 33. Deutscher Krebskongress, DKK. Berlin, Germany, 2018.
Lezcano et al., "Regular transfusion lowers plasma free hemoglobin in children with sickle-cell disease at risk for stroke," Am. J. Surg. Pathol. doi: 10.1097/P AS.0000000000001070, 2018.
Li et al., "Brain derived neurotrophic factor (BDNF) contributes to the pain hypersensitivity following surgical incision in the rats," Molecular Pain, 2008, 4(28):1-11.
Li et al., "Combinational Analysis of FISH and Immunohistochemistry Reveals Rare Genomic Events in ALK Fusion Patterns in NSCLC that Responds to Crizotinib Treatment", J Thorac. Oneal., 12(1):94-101. doi: 10.1016/i .itho.2016.08.145, 2017.
Li et al., "Correlation of expressions of GFAP, NT-3, TRK and NCAM with neurotropic molecular mechanism and clinical factors in adenoid cystic carcinoma of salivary gland," Chinese Journal of Cancer Prevention and Treatment, 2009, 16(6): 428-430 (with English abstract).
Li et al., "In vivo sensitized and in vitro activated B cells mediate tumor regression in cancer adoptive immunotherapy," J Immunol, Sep. 1, 2009;183(5):3195-203. doi: 10.4049/jimmunol.0803773. Epub Aug. 10, 2009.
Li et al., "Lumbar 5 ventral root transection-induced upregulation of nerve growth factor in sensory neurons and their target tissues: a mechanism in neuropathic pain," Mol. Cell. Neurosci., 2003, 23:232-250.
Li et al., "Trk inhibitor attenuates the BDNF/TrkB-induced protection of neuroblastoma cells from etoposide in vitro and in vivo," Cancer Biol. Ther., Feb. 2015, 16(3):477-483.
Lin et al., "HG-48. Integrated sequencing of pediatric pilocytic Astrocytoma with anaplasia reveals molecular features of both Lowand high-grade glial tumors", Neuro-Oneol, vol. 18, Supp. Supplement 3, pp. iii58, Abstract No. HG-48; 17th International Symposium on Pediatric Neuro-Oncology, ISPNO 2016. Liverpool, UK, Jun. 12, 2016-Jun. 15, 2016.
Lin et al., Neuro-Oncol, vol. 18, Supp. Supplement 3, pp. iii58, Abstract No. HG-48; 17th International Symposium on Pediatric Neuro-Oncology, ISPNO 2016. Liverpool, UK, Jun. 12, 2016-Jun. 15, 2016.

(56) References Cited

OTHER PUBLICATIONS

Linch et al., "Systemic treatment of soft-tissue sarcoma [mdash] gold standard and novel therapies," Nature Reviews Clinical Oncology, 2014, 11(4):187-202.
Loh et al., "Treatment of infantile fibrosarcoma with chemotherapy and surgery: results from the Dana-Farber Cancer Institute and Children's Hospital, Boston," J Pediatr Hematol Oncol, Dec. 2002:24(9):722-726.
Lorigan et al., "Phase III trial of two investigational schedules of ifosfamide compared with standard-dose doxombicin in advanced or metastatic soft tissue sarcoma: a European Organisation for Research and Treatment of Cancer Soft Tissue and Bone Sarcoma Group Study," J. Clin Oncol., 2007, 25(21):3144-3150.
Lovly et al., "Inflammatory myofibroblastic tumors harbor multiple potentially actionable kinase fusions," Cancer Discov., 2014, 4(8):889-895.
Lu et al., "Targeted next generation sequencing identifies somatic mutations and gene fusions in papillary thyroid carcinoma," Oncotarget. 8(28):45784-45792, 2017.
Ma and Woolf, "The progressive tactile hyperalgesia induced by peripheral inflammation is nerve growth factor dependent," Neuroreport, 1997, 8:807-810.
Ma et al., "Responses to crizotinib in patients with ALK-positive lung adenocarcinoma who tested immunohistochemistry (IHC)-positive and fluorescence in situ hybridization (FISH)-negative", Oncotarget, 7(39), 64410-64420, 2016.
Macleod, et al., "Abstract 0294: Gene Targets ofETV6-NTRK3 Fusion," Haematologica, 14th Congress of the European Hematology Association,2009, 94(s2): 116.
Majweskaetal., CancerResearch, vol. 76, No. 14, Supp. Supplement. Abstract No. 3190. 107th Annual meeting ofthe American Association for Cancer Research, AACR. New Orleans, LA Apr. 16-20, 2016.
Makretsov et al., "A fluorescence in situ hybridization study ofETV6-NTRK3 fusion gene in secretory breast carcinoma," Genes, Chromosomes and Cancer, Jun. 2004:40(2):152-157.
Marchetti et al., "Frequent mutations in the neurotrophic tyrosine receptor kinase gene family in large cell neuroendocrine carcinoma of the lung," Human Mutation, 2008, 29(5):609-616.
Marras et al., "Genotyping SNPs with molecular beacons," Methods Mol Biol, 2003;212:111-28.
Marras et al., Single Nucleotide Polymorphism: Methods and Protocols. Methods in Molecular Biology, Kwok, P.-Y., Ed., Totowa, NJ, Humana Press, vol. 212, pp. 111-128, 2003.
Martin-Zanca et al., "A human oncogene formed by the fusion of truncated tropomyosin and protein tyrosine kinase sequences," Nature, 1986, 319:743-748.
Matayoshi, "Actions of brain-derived neurotrophic factor on spinal nociceptive transmission during inflammation in the rat," J. Physiol., 2005, 569:685-695.
McCahon et al., "Non-Resectable Congenital Tumors with the ETV6-NTRK3 Gene Fusion Are Highly Responsive to Chemotherapy," Med. Pediatr. Oncol., May 2003, 40(5):288-292.
McCarthy et al., "Tropomyosin receptor kinase inhibitors: a patent update 2009-2013," Expert Opin TherPat. Jul. 2014;24(7):731-44. doi: 10.1517/13543776.2014.910195. Epub May 8, 2014.
McMahon et al., "The biological effects of endogenous nerve growth factor on adult sensory neurons revealed by a trkA-lgG fusion molecule," Nat. Med., 1995, 1:774-780.
McMahon., "VEGF Receptor Signaling in Tumor Angiogenesis," The Oncologist, 2000, 5(1): 3-10.
Mekinist, Highlights of Prescribing Information, Initial Approval 2013, revised Nov. 2015, Novartis Pharmaceuticals Com., 27 pages.
Melo-Jorge et al., The Chagas' disease parasite Trypanosoma cmzi exploits nerve growth factor receptor TrkA to infect mammalian hosts Cell Host & Microbe, 2007, 1(4):251-261.
Meyer et al., "Remarkable leukemogenic potency and quality of a constitutively active neurotrophin receptor, delta TrkA," Leukemia, 2007, 21:2171-2180.

Milione et al., "Identification and characterization of a novel SCYL3-NTRK1 rearrangement in a colorectal cancer patient," Oncotarget, 8(33):55353-55360, 2017.
Miranda et al., "Functional characterization of NTRK1 mutations Identified in melanoma," Genes Chromosomes & Cancer, Jun. 26, 2014, 53(10):875-880.
Montagnoli et al., "Anti-proliferative effects of GW441756, a novel inhibitor of NGF receptor tyrosine kinase a (TRKA), in human sarcoma," Italian Journal of Anatomy and Embryology, Nov. 11, 2010, 115:117.
Montalli et al., "Mammaglobin and DOG-1 expression in polymorphous low-grade adenocarcinoma: an appraisal of its origin and morphology," J Oral Pathol Med., Mar. 2017, 46(3):182-187.
Morissette et al., "High-throughput crystallization: polymorphs, salts, co-crystals and solvates of pharmaceutical solids," Adv. Drug Deliv Rev, 2004, 56: 375-300.
Mulligan, "RET revisited: expanding the oncogenic portfolio.", Nature Reviews Cancer, 14, 173-186,2014.
Murakami et al., "Integrated molecular profiling of juvenile myelomonocytic leukemia", Blood, blood-2017-07-798157; DOI: 10.1182/blood-2017-07-798157, 2018.
Myers, "Synthesis of Chiral Amines by Asymmetric Additions to tert-Butylsulfinimines (Ellman Auxiliary)," Chem 115, retrieved on May 18, 2016, retrieved from the Internet. URL: <faculty.chemistry.harvard.edu/files/myers/files/15-ellman auxiliarv.pelf>, 6 pages.
Nagasubmamanian et al., "Brief Report: Infantile Fibrosarcoma With NTRK3-ETV6 Fusion Successfully Treated with the Tropomyosin-Related Kinase Inhibitor LOXO-101," Pediatric Blood & Cancer, 2016, DOI 10.1002, 3 pages.
Nakagawara, "Trk receptor tyrosine kinases: a bridge between cancer and neural development," Cancer Letters, 2001, 169(2):107-114.
Nakano et al., "Novel Oncogenic KLC1-ROS1 Fusion in Pediatric Low Grade Glioma", Pediatr Blood Cancer. vol. 64, S54-S55 Suppe. 4. 013-1-7, 2017.
Narayanan et al., "Discovery and preclinical characterization of novel small molecule TRK and ROS1 tyrosine kinase inhibitors for the treatment of cancer and inflammation," PLoS One, Dec. 26, 2013;8(12):e83380. doi: 10.1371/iournal.pone.0083380. eCollection 2013.
National Cancer Institute at the National Institutes of Health, posted on or before Jan. 5, 2000,n retrieved on Jan. 13, 2015, http://www.cancer.gov/, 2 pages.
National Comprehensive Cancer Network, posted on or before Dec. 3, 1998, retrieved on Jan. 13, 2015, http://www.nccn.org/, 1 page.
NCT02050919, "Sorafenib Tosylate, Combination Chemotherapy, Radiation Therapy, and Surgery in Treating Patients with High-Risk Stage IIB-IV Soft Tissue Sarcoma," ClinicalTrials.gov, Last Updated Dec. 16, 2015, https://www.clinicaltrials.gov/ct2/show/NCT02050919, 5 pages.
NCT02122913, "Oral TRL Inhibitor LOXO-101 for Treatment of Advanced Adult Solid Tumors," ClinicalTrials.gov, Last Updated Dec. 7, 2015, https://clinicaltrials.gov/ct2/show/NCT02122913.
Ni et al., "siRNA interference with a proliferation-inducing ligand gene in the Sgr-7901 gastric carcinoma cell line," Asian Pacific Journal of Cancer Prevention, 2012, 13:1511-1514.
Ni et al., "Tyrosine receptor kinase Bis a drug target in astrocytomas," Neuro Oncol., Jan. 2017, 19(1):22-30.
NIH National Cancer Institute [online], "progression (pm-GREH-shun)," NCI Dictionary of Cancer Terms, retrieved on Sep. 17, 2018, URL: <https://www.cancer.gov/publications/dictionaries/cancer-terms/def/progression>, 1 page.
NIH National Cancer Institute [online], "recurrence (ree-KER-ents)," NCI Dictionary of Cancer Terms, retrieved on Sep. 21, 2018, URL: <https://www.cancer.gov/publications/dictionaries/cancer-terms/def/recurrence>, 1 page.
NIH National Cancer Institute [online], "relapse (REE-laps)," NCI Dictionary of Cancer Terms, retrieved on Sep. 17, 2018, URL: <https://www.cancer.gov/publications/dictionaries/cancer-terms/def/relapse>, 1 page.
NIH, "List of Cancer-causing Agents Grows," National Institute of Environmental Health Sciences, https://www.niehs.nih.gov/news/newsroom/releases/2005/january31/index.cfm, 4 pages.

(56) References Cited

OTHER PUBLICATIONS

Nikiforova et al., Abstract No. 5. Meeting Info: 84th Annual Meeting of the American Thyroid Association. Coronado, CA, United States, 2014.
Nollau et al., "Methods for detection of point mutations: performance and quality assessment. IFCC Scientific Division, Committee on Molecular Biology Techniques," Clin Chem. Jul. 1997;43(7):1114-28.
Obianyo et al., "Novel small molecule activators of the Trk family of receptor tyrosine kinases. BiochimBiophys Acta, 1834:2214-2218," BiochimBiophys Acta, Oct. 2013, 1834(10):2213-2218.
Ocgene.bioinfo-minzhao org [online]. "Ovarian Cancer Gene Database, Gene ID: 4914," [retrieved on Jul. 17, 2017] Retrieved from the Internet: URL<ocgene.bioinfominzhao.org/gene mutation/cgi?gene=4914>, 13 pages.
Oken et al., "Toxicity and response criteria of the Eastern Cooperative Oncology Group," Am J Clin Oncol, 1982, 5:649-655.
Olivier, "The Invader assay for SNP genotyping," Mutat Res, Jun. 3, 2005;573(1-2): 103-10.
Orbach et al., "Conservative strategy in infantile fibrosarcoma is possible: The European paediatric Soft tissue sarcoma Study Group experience," Eur J Cancer, Apr. 2016, 57:1-9.
Orbach et al., "Infantile fibrosarcoma: management based on the European experience," J Clin Oncol, Jan. 2010, 28(2):318-323.
O'Shea, "Jaks, STATs, cytokine signal transduction, and immunoregulation: are we there yet?" Immunity, 1997, 7:1-11.
Otsubo et al., "Sporadic pediatric papillary thyroid carcinoma harboring the ETV6/NTRK3 fusion in oncogene in a 7-year-old Japanese girl: a case report and review of literature," J. Pediatr. Endocrinol. Metab. 28;31(4):461-467, 201.
Ott et al., "An immunogenic personal neoantigen vaccine for patients with melanoma.", Nature 547: 217-221, 2017.
Ou et al., "Emergence of novel and dominant acquired EGFR solvent-front mutations at Gly796 (G796S/R) together with C797S/R and L792F/H mutations in one EGFR (L858R/T790M) NSCLC patient who progressed on osimertinib," Lung Cancer, 2017, 108: 228-231.
Ou et al., "Identification of a novel TMEM106B-ROS1 fusion variant in lung adenocarcinoma by comprehensive genomic profiling.", Lung Cancer, 88(3):352-4, 2015.
Ou et al., "Next-Generation Sequencing Reveals a Novel NSCLC ALK Fl 174V Mutation and Confirms ALK G1202R Mutation Confers High-Level Resistance to Alectinib (CH5424802/RO5424802) in ALK-Rearranged NSCLC Patients Who Progressed on Crizotinib," Journal of Thoracic Oncology, Apr. 2014, 9: 549-553.
Ovarian Cancer Gene Database, ocgene.bioinfo-minzhao.org/gene_mutation.cgi?gene=49 1 4, downloaded on May 31, 2016, 14 pages.
Ovarian Cancer Gene Database, ocgene.bioinfo-minzhao.org/gene_mutation.cgi?gene=4916, downloaded on May 31, 2016, 21 pages.
Pan et al., Laboratory Investigation, vol. 96, Supp. Suppl. 1, pp. 367A, Abstract No. 1450, 105th Annual Meeting of the United States and Canadian Academy of Pathology, Seattle, WA, 2016.
Panagopoulos et al., "Recurrent fusion of the genes FN1 and ALK in gastrointestinal leiomyomas", Modem Pathology 29: 1415-1423, 2016.
Pao, W., et al. "Acquired resistance of lung adenocarcinomas to gefitinib or erlotinib is associated with a second mutation in the EGFR kinase domain," PLoS Med, Feb. 2005, 2(3), e73.
Papatsoris et al., "Manipulation of the nerve growth factor network in prostate cancer," Exper Opin Invest Drugs, 2007, 16(3):303-309.
Park et al., "Genomic alterations in BCL2L1 and DLC1 contribute to drug sensitivity in gastric cancer," Proc. Natl. Acad. Sci. U.S.A., Oct. 2015, 112(40):12492-12497.
Park et al., "NTRK1 fusions for the therapeutic intervention of Korean patients with colon cancer," Oncotarget. 7(7):8399-412, 2016.
Patani et al., "Bioisosterism: A rational approach in Drug Design," Chem Rev., Dec. 1996, 96(8):3147-3176.
Patapoutian et al., "Trk receptors: mediators of neurotrophin action," Current Opinion in Neurobiology, 2001, 11:272-280.
Pavlick et al., "Identification of NTRK fusions in pediatric mesenchymal tumors," Pediatr Blood Cancer, Aug. 2017, 64(8). doi: 10.1002/pbc.26433. Epub Jan. 18, 2017.
PCT International Preliminary Report on Patentability in International Application No. PCT/US2009/057729, dated Mar. 22, 2011, 7 pages.
PCT International Preliminary Report on Patentability in International Application No. PCT/US2009/061519, dated Apr. 26, 2011, 6 pages.
PCT International Preliminary Report on Patentability in International Application No. PCT/US2010/041538, dated Jan. 10, 2012, 7 pages.
PCT International Preliminary Report on Patentability in International Application No. PCT/US201 1/036452, dated Nov. 29, 2012, 6 pages.
PCT International Preliminary Report on Patentability in International Application No. PCT/US2015/060953, dated May 16, 2017, 7 pages.
PCT International Preliminary Report on Patentability in International Application No. PCT/US2016/035327, dated Dec. 14, 2017, 9 pages.
PCT International Preliminary Report on Patentability in International Application No. PCT/US2016/058951, dated May 11, 2018, 11 pages.
PCT International Preliminary Report on Patentability in International Application No. PCT/US2017/033257, dated Nov. 20, 2018, 8 pages.
PCT International Preliminary Report on Patentability in International Application. No. PCT/US2017/058518, dated Apr. 30, 2019, 8 pages.
PCT International Preliminary Report on Patentability in International Application No. PCT/US2018/022833, dated Sep. 26, 2019, 8 pages.
PCT International Search Report and Written Opinion in International Application No. PCT/US2009/0161519, dated Feb. 2, 2010, 8 pages.
PCT International Search Report and Written Opinion in International Application No. PCT/US2009/057729, dated Feb. 4, 2010, 10 pages.
PCT International Search Report and Written Opinion in International Application No. PCT/US2010/041538, dated Oct. 1, 2010, 10 pages.
PCT International Search Report and Written Opinion in International Application No. PCT/US2011/036452, dated Aug. 18, 2011, 9 pages.
PCT International Search Report and Written Opinion in International Application No. PCT/US2015/060953, dated Feb. 8, 2016, 12 pages.
PCT International Search Report and Written Opinion for International Application No. PCT/US2016/035327, dated Aug. 18, 2016, 15 pages.
PCT International Search Report and Written Opinion in International Application No. PCT/US2016/058951, dated Feb. 7, 2017, 20 pages.
PCT International Search Report and Written Opinion in International Application No. PCT/US2017/025932, dated May 31, 2017, 16 pages.
PCT International Search Report and Written Opinion in International Application No. PCT/US2017/025939, dated May 31, 2017, 16 pages.
PCT International Search Report and Written Opinion in International Application No. PCT/US2017/033257, dated Jul. 24, 2017, 13 pages.
PCT International Search Report and Written Opinion in International Application No. PCT/US2017/058518, dated May 2, 2018, 17 pages.
PCT International Search Report and Written Opinion in International Application No. PCT/US2018/022833, dated Aug. 13, 2018.
PCT International Search Report and Written Opinion in International Application No. PCT/US2018/039502, dated Apr. 16, 2018, 16 pages.

(56) References Cited

OTHER PUBLICATIONS

PCT International Search Report and Written Opinion in International Application No. PCT/US2018/057542, dated Mar. 6, 2019, 19 pages.
PCT International Search Report and Written Opinion in International Application No. PCT/US2019/024961, dated Jul. 23, 2019, 13 pages.
Pediatric Cancer Gene Database, pedican.bioinfominzhao.org/gene_mutation.cgi?gene=4914, downloaded on May 31, 2016, 6 pages.
Pediatric Cancer Gene Database, pedican.bioinfominzhao org/gene_mutation.cgi?gene=4915, downloaded on May 31, 2016, 5 pages.
Pediatric Cancer Gene Database, pedican.bioinfominzhao.org/gene_mutation.cgi?gene=4916, downloaded on May 31, 2016, 9 pages.
Perales et al., "Fast Cars and No Brakes: Autologous Stem Cell Transplantation as a Platform for Novel Immunotherapies," Biol Blood Marrow Transplant, Jan. 2016;22(1):17-22. doi: 10.1016/j.bbmt.2015.10.014. Epub Oct. 17, 2015.
Perez-Pinera et al., "The Trk tyrosine kinase inhibitor K252a regulates growth of lung adenocarcinomas," Molecular and Cellular Biochemistry, 2007, 295(1&2):19-26.
Perrault et al., "The Synthesis ofN-Aryl-5(S)-aminomethyl-2-oxazolidinone Antibacterials and Derivatives in One Step from Aryl Carbamates," Org. Process Res. Dev., 2003, 7:533-546.
Peus et al., "Appraisal of the Karnofsky Performance Status and proposal of simple algorithmic system for its evaluation," BMC Med Inform and Decision Making, 2013, 13:72.
Picarsic et al., "Molecular characterization of sporadic pediatric thyroid carcinoma with the DNA/RNA ThyroSeq v2 next-generation sequencing assay," Pediatr. Dev. Pathol, Mar. 2016, 19(2):115-122.
Pierottia and Greco, "Oncogenic rearrangements of the NTRK1/NGF receptor," Cancer Letters, 2006, 232:90-98.
Pinedo et al., "Translational Research: The Role of VEGF in Tumor Angiogenesis," The Oncologist, 2000, 5(1): 1-2.
Pinski et al., "Trk receptor inhibition induces apoptosis of proliferating but not quiescent human osteoblasts," Cancer Res, 2002, 62:986-989.
Plosker, "Sipuleucel-T: in metastatic castration-resistant prostate cancer.", Drugs 71(1): 101-108, 2011.
Ponsaerts et al., "Cancer immunotherapy using RNA-loaded dendritic cells," Clin. Exp. Immunol., Dec. 2003, 134:378-384.
Prabhakaran et al., "Novel TLE4-NTRK2 fusion in a ganglioglioma identified by array-CGH and confirmed by NGS: Potential for a gene targeted therapy," Neuropathology, Mar. 2018, doi:10.1111/neup.12458.
Prasad et al., "NTRK fusion oncogenes in pediatric papillary thyroid carcinoma in northeast United States," Cancer, Apr. 2016, 122(7):1097-1107.
PubChem, "Larotrectinib," https://pubchem.ncbi.nlm.nih.gov/compound/46188928, retrived on Apr. 29, 2019, 20 pages.
Pulciani et al., "Oncogenes in solid human tumours," Nature, 1982, 300(5892):539-542.
Qaddoumi et al., "Genetic alterations in uncommon low-grade neuroepithelial tumors: BRAF, FGFR1, and MYB mutations occur at high frequency and align with morphology," Acta Neuropathol, Jun. 2016, 131(6):833-845.
Qiu et al., "Next generation sequencing (NGS) in wild type GISTs", J Clin. Oneal. 35: 15 _suppl, e22507-e22507,2017.
Ramer and Bisby, "Adrenergic innervation of rat sensory ganglia following proximal or distal painful sciatic neuropathy: distinct mechanisms revealed by anti-NFD treatment," Eur. J. Neurosci., 1999, 11:837-846.
Rausch et al., "mRNA vaccine CV9103 and CV9104 for the treatment of prostate cancer.", Human Vaccinimmunother 10(11): 3146-52, 2014.
Raychaudhuri et al., K252a, a high-affinity nerve growth factor receptor blocker, improves psoriasis: an in vivo study using the severe combined immunodeficient mouse-human skin model, J. Investigative Dermatology, 2004, 122(3):812-819.

Reshmi et al., "Abstract 477: Genomic and Outcome Analyses of Philadelphia Chromosome like (Ph-like) NCI Standard Risk B-Acute Lymphoblastic Leukemia (SR B-ALL) Patients Treated on Children's Oncology Group (COF) AALL0331," Blood, 2017, 130(SI): 477.
Reungwetwattana et al., "Targeted therapies in development for non-small cell lung cancer," J Carcinog, Dec. 2013, 12:22, doi: 10.4103/1477-3163.123972. eCollection 2013.
Reuther et al., "Identification and characterization of an activating TrkA deletion mutation in acute myeloid leukemia," Mol. Cell. Biol. 2000, 20:8655-8666.
Ricarte-Filho et al., "Identification of kinase fusion oncogenes in post-Chernobyl radiation-induced thyroid cancers," J. Clin. Invest, Nov. 2013, 123(11): 4935-4944.
Ricci et al., Neurotrophins and neurotrophin receptors in human lung cancer, Am. J. Respiratory Cell and Molecular Biology, Oct. 2001, 25(4): 439-446.
Richard et al., "Syngeneic stem cell transplant for spent-phase polycythaemia vera: eradication of myelofibrosis and restoration of normal haematopoiesis," Br. J Haematol., Apr. 2002, 117(1):245-246.
Rimkunas et al., "Analysis of receptor tyrosine kinase ROSI-positive tumors in non-small cell lung cancer: identification of a FIG-ROSI fusion.", Clin. Cancer Res., 18: 4449-58, 2012.
Ritterhouse et al., "ROSI Rearrangement in Thyroid Cancer.", Thyroid, 26(6): 794-7, 2016.
Ro et al., "Effect of NGF and anti-NGF on neuropathic pain in rats following chronic constriction iniury of the sciatic nerve," Pain, 1999, 79:265-274.
Roberts et al., "Targetable kinase-activating lesions in Ph-like acute lymphoblastic leukemia," N Engl J Med, Sep. 2014, 371(11):1005-1015.
Roberts et al., Blood, vol. 128, No. 22. Abstract No. 278, 58th Annual Meeting of the American Society of Hematology, ASH 2016. San Diego, CA, United States. Dec. 3, 2016-Dec. 6, 2016, 2 pages.
Roblin et al., "Topical TrkA Kinase Inhibitor CT327 is an Effective, Novel Therapy for the Treatment of Pmritus due to Psoriasis: Results from Experimental Studies, and Efficacy and Safety of CT327 in a Phase 2b Clinical Trial in Patients with Psoriasis," Acta Denn. Venereal., 2015, 95:542-548.
Rosenbaum et al., "Next Generation Sequencing Reveals Genomic Heterogenity of ALK Fusion Breakpoints in Non-Small Cell Lung Cancer", Laboratory Investigation, vol. 96, Supp. Suppl. 1, pp. 481A-482A, Abstract No. 1914, 105th Annual Meeting of the United States and Canadian Academy of Pathology, Seattle, WA, 2016.
Roskoski, Jr. et al., "Classification of small molecule protein kinase inhibitors based upon the structures of their drug-enzyme complexes," Pharmacological Research, 2016, 103: 26-48.
Ross et al., "New routes to targeted therapy of intrahepatic cholangiocarcinomas revealed by next-generation sequencing," Oncologist, 2014, 19:235-242.
Rossi et al., "Abstract 84: RNA-Sequencing Identifies ETV6-NTRAK3 as a Gene Fusion Involved in Gastrointestinal Stromal Tumors," Meeting Info: 105th Annual Meeting of the United States and Canadian Academy of Pathology, Seattle, WA, Annual Meeting Abstracts, 24A.
Rubin et al., "Congenital mesoblastic nephroma t(12;15) is associated with ETV6-NTRK3 gene fusion: cytogenetic and molecular relationship to congenital (infantile) fibrosarcoma," Am. J. Pathol, Nov. 1998, 153(5):1451-1458.
Rubin et al., "Growth, survival and migration: the Trk to cancer," Cancer Treat Res, 2003, 115:1-18.
Russo et al., "Acquired Resistance to the Trk Inhibitor Entrectinib in Colorectal Cancer," Cancer Discovery, Jan. 1, 2016, 6(1):36-44.
Rutkowski et al., "Treatment of advanced dermatofibrosarcoma protuberans with imatinib mesylate with or without surgical resection," J. Eur. Acad. Dermatol. Venereol., 2011, 25:264-270.
Sahin et al., "Personalized RNA mutanome vaccines mobilize poly-specific therapeutic immunity against cancer.", Nature 547: 222-226, 2017.

(56) References Cited

OTHER PUBLICATIONS

Saborowski et al., "Mouse model of intrahepatic cholangiocarcinoma validates FIG-ROS as a potent fusion oncogene and therapeutic target.", Proc. Natl. Acad Sci. USA, 110(48): 19513-19518, 2013.
Santoro et al., "Doxombicin versus CYVADIC versus doxombicin plus ifosfamide in first-line treatment of advanced soft tissue sarcomas: a randomized study of the European Organization for Research and Treatment of Cancer Soft Tissue and Bone Sarcoma Group," J. Clin Oncol., 1995, 13(7):1537-1545.
Saragovi et al., "A TrkA-selective, fast internalizing nerve growth factor-antibody complex induces trophic but not neuritogenic signals," J Biol Chem, Dec. 25, 1998 25;273(52):34933-34940.
Sartore-Bianchi et al., "Sensitivity to Entrectinib Associated With a Novel LMNA-NTRK1 Gene Fusion in Metastatic Colorectal Cancer," J. Natl. Cancer Inst, Nov. 2015, 108(1). doi: 10.1093/inci/div306.
Sassolas et al., "Oncogenic alterations in papillary thyroid cancers of young patients," Thyroid Jan. 2012, 22(1):17-26.
Scaruffi et al., "Detection of DNA polymorphisms and point mutations of high-affinity nerve growth factor receptor (TrkA) in human neuroblastoma," Int. J. Oneal., May 1999, 14:935-938.
Schmidt et al., "Heilmittelchemische untersuchungen in der Heterocyclischen Rihe. Pyrazolo-(3,4-D)-Pyrimidine (Medicinal chemical studies in the heterocyclic series. Pyrazolo-(3,4-D)-Pyrimidine)," Helvetica Chimica, Verlag Helvetica Chimica Acta, Jan. 1956, 39: 986-991 (with English Abstract).
Schmidt, Charles. "Combinations on trial." Nature 552.7685 (Dec. 21, 2017): S67-S69.
Schram et al., "Abstract LB-302: Potential role of larotrectinib (LOXO-101), a selective pan-TRK inhibitor, in NTRX fusion-positive recurrent glioblastoma, "Cancer Research, Jul. 2017, DOI: 10.1158/1538-7445.AM2017-LB-302, 2 pages.
Schrock et al., "Gastrointestinal tumours, non-colorectal", Annals of Oncology. vol. 27, Suppl 6, 6130, 2016.
Shah et al., "Cardiac metastasis and hypertrophic osteoarthropathy in recurrent infantile fibrosarcoma," Pediatr. Blood Cancer, Jul. 2012, 59(1):179-181.
Shaver et al., "Diverse, Biologically Relevant, and Targetable Gene Rearrangements in Triple-Negative Breast Cancer and Other Malignancies.", Cancer Res, 76(16): 4850-60, 2016.
Shaw et al., "Ceritinib in ALK-rearranged non-small-cell lung cancer," N Engl J Med, Mar. 27, 2014;370(13):1189-97. doi: 10.1056/NEJMoal311 107.
Shaw et al., "Crizotinib in ROSI-rearranged non-small-cell lung cancer," N Engl J Med, Nov. 20, 2014;371(21):1963-71. doi: 10.1056/NEJMoal406766. Epub Sep. 27, 2014.
Shaw et al., "Tyrosine kinase gene rearrangements in epithelial malignancies," Nat Rev Cancer, Nov. 2013, 13(11):772-787.
Sheldrick, "A short history of SHELX," Acta Crystallogr A, Jan. 2008, 64(Pt1): 112-122.
Shelton et al., "Nerve growth factor mediates hyperalgesia and cachexia in auto-immune arthritis," Pain, 2005, 116:8-16.
Sheng et al., "Congenital-infantile fibrosarcoma. A clinicopathologic study of 10 cases and molecular detection of the ETV6-NTRK3 fusion transcripts using paraffin-embedded tissues," Am. J Clin. Pathol., Mar. 2001, 115:348-355.
Sigal, et al., "Activity of Entrectinib in a Patient with the First Reported NTRK Fusion in Neuroendocrine Cancer," J. Natl. Compr. Cane. Netw, Nov. 2017, 15(11): 1317-1322.
Silverman, The Organic Chemistry of Drug Design and Drug Action, Second Edition, 2007, 20-21.
Sims et al., Abstract P280: Profiling abscopal regression in a pediatric fibrosarcoma with a novel EML4-NTRK3 fusion using immunogenomics and high-dimensional histopathology, J mmunotherapy of Cancer, Nov. 2016, 4(S1): 73.
Skalova et al., "Mammary Analogue Secretory Carcinoma of Salivary Glands: Molecular Analysis of 25 ETV6 Gene Rearranged Tumors with Lack of Detection of Classical ETV6-NTRK3 Fusion Transcript by Standard RT-PCR: Report of 4 Cases Harboring ETV6-X Gene Fusion," Am. J. Surg. Pathol, Jan. 2016, 40(1):3-13.
Skalova et al., "Molecular Profiling of Mammary Analog Secretory Carcinoma Revealed a Subset of Tumors Harboring a Novel ETV6-RET Translocation: Report of 10 Cases," Am. J. Surg. Pathol, Feb. 2018, 42(2):234-246.
Skalova et al., "Newly described salivary gland tumors," Modem Pathology, Jan. 2017, 30, S27-S43.
Sleijfer et al., "Prognastic and predictive factors for outcome to firs-line ifosfamide-containing chemotherapy for adult patients with advanced soft tissue sarcomas: an exploratory, retrospective analysis on large series from the European Organization for Research and Treatment of Cancer-Soft Tissue and Bone Sarcoma Group," Eur J. Cancer, 2010, 46(1):72-83.
Sleijfer et al., "Using single-agent therapy in adult patients with advanced soft tissue sarcoma can still be considered standard care," Oncologist, 2005, 10(10):833-841.
Smith et al., "Annotation of human cancers with EGFR signaling-associated protein complexes using proximity ligation assays," Sci Signal, 2015, 8(359):ra4, 12 pages.
Sohrabji et al., "Estrogen-BDNF interactions: implications for neurodegenerative diseases," Frontiers in Neuroendocrinology, 2006, 27(4):404-414.
Song et al., "Molecular Changes Associated with Acquired Resistance to Crizotinib in ROS1-Rearranged Non-Small Cell Lung Cancer.", Clin. Cancer Res., 21(10): 2379-87, 2015.
Stephens et al., "Trk receptors use redundant signal transduction pathways involving SHC and PLC-gamma 1 to mediate NGF responses," Neuron, Mar. 1994, 12(3):691-705.
Stransky et al., "The landscape of kinase fusions in cancer," Nature comm., 2014, 5:4846.
Subramaniam et al., Abstract 2019: RNA-Seq analysis of glioma tumors to reveal targetable gene fusions, 2017 Annual Meeting of the American Society of Clinical Oncology,2017, 1 page.
Sun et al., "P-loop conformation governed crizotinib resistance in G2032R-mutated ROSI tyrosine kinase: clues from free energy landscape," PLoS computational biology, Jul. 17, 2014, 10(7): e1003729.
Tacconelli et al., "TrkA alternative splicing: a regulated tumor-promoting switch in human neuroblastoma," Cancer Cell, 2004, 6:347-360.
Tafinlar, Highlights of Prescribing Information, GlaxoSmithKline, Jan. 2014, 41 pages.
Tahira et al., "dbQSNP: a database of SNPs in human promoter regions with allele frequency information determined by single-strand conformation polymorphism-based methods," Hum Mutat, Aug. 2005;26(2):69-77.
Taipale et al., "Chaperones as thermodynamic sensors of drug-target interactions reveal kinase inhibitor specificities in living cells," Nat Biotech, 2013, 31(7):630-637.
Tan et al., "Genetic landscape of ALK+ non-small cell lung cancer (NSCLC) patients (pts) and response to ceritinib in ASCEND-I", J. Clin. Oncology, vol. 34, Supp. Supplement 15, Abstract No. 9064, 2015 Annual Meeting of the American Society of Clinical Oncology, Chicago, IL, 2016.
Tanaka et al., "Brain-derived neurotrophic factor (BDNF)-induced tropomyosin-related kinase B (Trk B) signaling is a potential threapeutic target for peritoneal carcinomatosis arising from colorectal cancer," PLoS One May 6, 2014, 9(5):e96410.
Tannenbaum, et al., "Abstract 749: Characterization of a Novel Fusion Gene, EML4-NTRK3, in Infantile Fivrosarcoma," Pediatr Blood Cancer, DOI 10.1002/pbc, 1 page.
Tannenbaum-Dvir et al., "Characterizatio of a novel fusion gene EML4-NTRK3 in a case of recurrent congenital fibrosarcoma," Cold Spring Harb. Mol. Case Stud., Oct. 1, 2015(1):a00471.
Tarate et al., "Oral Solid Self-Emulsifying Formulatins: A Patent Review," Recent Patents on Drug Delivery & Formulation, 2014, 8(2):126-143.
Taylor et al., "Abstract 794: Characterization of NTRK fusions and Therpeutic Response to NTRK Inhibition in Hematologic Malignancies," Blood, 2017, 130: 794.
The Cancer Genome Atlas Netowrk, "Comprehensive Molecular Characterizaito of Human colon and Rectal Cancer," Nature, Jan. 2013, 487(7407): 330-337.

(56) References Cited

OTHER PUBLICATIONS

Theodosiou et al., "Hyperalgesia due to nerve damage: role of Nerve growth factor," Pain, 1999, 81:245-255.
Thiele, "On Trk—the TrkB signal transduction pathway is an increasingly importang target in cancer biology," Clinical Cancer Research, 2009, 105(19):5962-5967.
Thompson et al., "Brain-derived neurotrophic factor is an endogenous modulator of nociceptive responses iin the spinal cord," Proc. Natl. Acad. Sci. USA, 1999, 96:7714-7718.
Thress et al., "Identification and preclinical characterization of AZ-23, a novel, selective, and orally bioavailable inhibitor of the Trk kinase pathway," Mol Cancer Ther, Jul. 2009;8(7):1818-27. doi: 10.1158/1535-7163.MCT-09-0036. Epub Jun. 9, 2009.
Truzzi et al., "Neurotrophins and their receptors stimulate malanoma cell proliferation and migration," J. Investigative Dermatology, 2008, 128(3):2031-2040.
Truzzi et al., "Neurotrophins in healthy and diseased skin," Dermato-Endocrinology, 2008, 3(1):32-36.
Tognon et al., "Expression of the ETV6-NTRK3 gene fusion as a primary event in human secretory breast carcinoma," Cancer Cell, Nov. 2002, 2(5):367-376.
Turtle et al., "Artificial antigen-presenting cells for use in adoptive immunotherapy," Cancer J, Jul.-Aug. 2010;16(4):374-51. doi: 10.1097/PPO.0b013e3181eb33a6.
UniProtKB/Swiss-Prot: P04629.4, "RecName: Full=High affinity nerve growth factor receptor; AltName: Full=Neurotrophic tyrosine kinase receptor type 1; AltName: Full=TRK.1-transforming tyrosine kinase protein; AltName: Full=Tropomyosin-related kinase A; AltName: Full=Tyrosine kinase receptor; AltName: Full=Tyrosine kinase receptor A; Short=Trk-A; AltName: Full=gp140trk; AltName: Full=p140-TrkA; Flags: Precursor," May 14, 2014, 28 pages, available at URL<https://www.ncbi.nlm.nih.gov/protein/94730402?sat=18&satkey=12407077>.
UniProtKB/Swiss-Prot: Q16288.2, "RecName: Full=NT-3 growth factor receptor; AltName: Full=GP145-TrkC; Short=Trk-C; AltName: Full=Neurotrophic tyrosine kinase receptor type 3; AltName: Full=TrkC tyrosine kinase; Flags: Precursor," May 14, 2014, 13 pages, available at URL<www.ncbi.nlm.nih.gov/protein/134035335?report=genbank&log$=protalign&blast_rank=O&RID=0>.
UniProtKB/Swiss-Prot: Q16620.1, "RecName: Full=BDNF/NT-3 growth factors receptor; AltName: Full=GP145-TrkB; Short=Trk-B; AltName: Full=Neurotrophic tyrosine kinase receptor type 2; AltName: Full=TrkB tyrosine kinase; AltName: Full=Tropomyosin-related kinase B; Flags: Precursor," May 14, 2014, 17 pages, available at URL<www.ncbi.nlm.nih.gov/protein/2497560?report=genbank&log$=protalign&blast_rank=O&RID=0>.
Vaishnavi et al., "Oncogenic and drug-sensitive NTRK1 rearrangements in lung cancer.", Nature Med 19: 1469-1472, 2013.
Vaishnavi et al., "TRK.ing Down an Old Oncogene in a New Era of Targeted Therapy," Cancer Discovery, Jan. 2015, 5(1):25-34.
Van Gurp et al., "Phase 1 dose-escalation study of CP-690 550 in stable renal allograft recipients: preliminary findings of safety, tolerability, effects on lymphocyte subsets and pharmacokinetics," Am. J. Transpl., 2008, 8:1711-1718.
Van Noesel et al., "Pediatric neuroblastomas: genetic and epigenetic 'danse macabre'," Gene, 2004, 325:1-15.
Vanden et al., "endocrine and neuroendocrine tumours", Annals of Oncology, vol. 27, Supp. Supplement 6. Abstract No. 427PD 4pt European Society for Medical Oncology Congress, ESMO 2016; Copenhagen, Denmark; Oct. 7-11, 2016.
Vippagunta et al., "Crystalline Solids" Advanced Drug Delivery Rev., 2001, 48(1): 3-26.
Vogelstein and Kinzler, The Genetic Basis of Human Cancer, 2nd ed., 2002, ng 3, col. 1, para 2.
Wadhwa et al., "Expression of the neurotrophin receptors Trk A and Trk B in adult human astrocytoma and glioblastoma," Journal of Biosciences, 2003, 28(2):181-188.
Walch et al., "Role of neurotrophins and neurotrophins receptors in the in vitro invasion and heparanase production of human prostate cancer cells," Clin. Exp. Metastasis, 1999, 17:307-314.

Walther et al., "Cytogenetic and single nucleotide polymorphism array findings in soft tissue tumors in infants," Cancer Genet, Jul.-Aug. 2013, 206(7-8): 299-303.
Wang et al., "Design, synthesis and biological evaluation of novel 4-arylaminopyrimidine derivatives possessing a hydrazone moiety as dual inhibitors of L1196M ALK and ROS1.", Eur. J Med Chem., 123, 80-99, 2016.
Wang et al., "Identification of 4-aminopyrazolylpyrimidines as potent inhibitors of Trk kinases," J Med Chem, Aug. 14, 2008;51(15):4672-84. doi: 10.1021/jm800343j. Epub Jul. 23, 2008.
Wang et al., "Identification of NTRK3 fusions in childhood melanocytic neoplasms," J. Mol. Diagn, May 2017, 19(3):387-396.
Wang et al., "T cells sensitized with breast tumor progenitor cell vaccine have therapeutic activity against spontaneous HER2/neu tumors," Breast Cancer Res Treat, Jul. 2012;134(1):61-70. doi: 10.1007/s10549-011-1912-5. Epub Dec. 16, 2011.
Wang et al., "Trk kinase inhibitors as new treatments for cancer and pain," Expert Opin. Ther Patents, Mar. 2009, 19(3):305-319.
Wang, "Pan-cancer analysis of ROSI genomic aberrations", University of Hong Kong, Pokfulam, Hong Kong SAR (Thesis), 44 pages, 2015.
Watanbe et al., "Cryptic t(12;15)(p13;q26) producing the ETV6-NTRK3 fusion gene and no loss of IGF2 imprinting in congenital mesoblastic nephroma with trisomy 11: fluorescence in situ hybridization and IGF2 allelic expression analysis," Cancer Genet. Cytogenet, Jul. 2002, 136(1):10-16.
Wei et al., "Abstract #2136: Entrectinib is Effective Against the Gatekeeper and Other Emerging Resistance Mutations in NTRK-, ROSI- and Alk-Rearranged Cancers," Poster, Presented at Proceedings of the 107th Annual Meeting of the American Association for Cancer Research, New Orleans LA, Apr. 16-20, 2016; Cancer Res, Jul. 2016, 76(14): 1 page.
Wei et al., "Abstract 78: Entrectinib, a highly potent pan-Trk, and ALK inhibitor, has broad-spectrum, histology-agnostic anti-tumor activity in molecularly defined cancers," 28thEORTC-NCI-AACR Symposium on Molecular Targets and Cancer Therapeutics, Munich, Germany, 2016, 1 page.
Weinstein, "Cancer. Addiction to oncogenes—the Achilles heal of cancer," Science, Jul. 2002, 297(5578):63-64.
Wen et al, "Updated response assessment criteria for high-grade gliomas: response assessment in neuro-oncology working group," J Clin Oncol, Apr. 2010, 28(11): 1963-1972.
Wiesner et al., "Kinase fusions are frequent in Spitz tumours and spitzoid melanomas," Nature Comm., 2014, 5:3116.
Winski et al., "LOXO-101, a pan-TRJ inhibitor, for the treatment of TRK-driven cancers," 26th EORTC-NCI-AACR Symposium on Molecular Targets and Cancer Therapeutics, Barcelona, Spain, 2014, 175.
Wittwer et al., "High-resolution genotyping by amplicon melting analysis using LCGreen," Clin Chem, Jun. 2003;49(6 Pt 1):853-60.
Wlodarska et al., "ALK-Positive Anaplastic Large Cell Lymphoma with the Variant EEF1G-, RNF213- and Atic-ALK Fusions Is Featured by Copy Number Gain of the Rearranged ALK Gene", Blood, vol. 126(23): 3654, 57th Annual Meeting of the American Society of Hematology, San Diego, CA, 2015.
Won et al., "Post-crizotinib management of effective ceritinib therapy in a patient with ALK-positive non-small cell lung cancer", BMC Cancer, 16: 568, 2016.
Wong et al., "Evaluation of a Congenital Infantile Fibrosarcoma by Comprehensive Genomic Profiling Reveals an LMNA-NTRK.1 Gene Fusion Responsive to Crizotinib," J Natl Cancer Inst, Nov. 2016, 108(1) pii: div307.
Woodward, "Bi-allelic SNP genotyping using the TaqMan® assay," Methods Mol Biol., 2014;1145:67-74. doi: 10.1007/978-1-4939-0446-4 6.
Woolf et al., "Letter to Neuroscience: Nerve Growth Factor Contributes to the Generation of Inflammatory Sensory Hypersensitivity," Neuroscience, 1994, 62:327-331.
Wu et al., "The genomic landscape of diffuse intrinsic pontine glioma and pediatric non-brainstem high-grade glioma," Nature Genetics, 2014, 444-450.

(56) References Cited

OTHER PUBLICATIONS

Wu et al., "The landscape of fusion transcripts in spitzoid melanoma and biologically indeterminate spitzoid tumors by RNA sequencing," Modern Pathol., Apr. 2016, 29(4):359-369.
Xalkori, Highlights of Prescribing Information, Pfizer Labs, Initial approval 2011, revised Mar. 2016, 20 pages.
Yakirevich et al., "Colorectal Adenocarcinoma with ALK Rearrangement: Clinicopathologic and Molecular Characteristics", Laboratory Investigation, vol. 96, Supp. Suppl. 1, pp. 209A, Abstract No. 827, 105th Annual Meeting of the United States and Canadian Academy of Pathology, Seattle, WA, 2016.
Yakirevich et al., "Oncogenic ALK Fusion in Rare and Aggressive Subtype of Colorectal Adenocarcinoma as a Potential Therapeutic Target.", Clin Cancer Res, 22(15): 3831-40, 2016.
Yamamoto et al., "ALK, ROS1 and NTRK3 gene rearrangements in inflammatory myofibroblastic tumours.", Histopathology, 69(1): 72-83, 2016.
Yamamoto et al., "Anaplastic lymphoma kinase-positive squamous cell carcinoma of the lung: A case report.", Mal Clin. Oneal. 5(1): 61-63, 2016.
Yanai et al., "A rare case of bilateral stage IV adrenal neuroblastoma with multiple skin metastases in a neonate: diagnosis, management, and outcome," J Pediatr. Surg., Dec. 2004, 39(12):1782-1783.
Yeh et al., "NTRK.3 kinase fusions in Spitz tumours," J Pathol., Nov. 2016, 240(3): 282-290.
Yilmaz et al., "Theraputic targeting of Trk supresses tumor proliferation and enhances cisplatin activity inHNSCC," Cancer Biology and Therapy, 2010, 10(6):644-653.
Ying et al., "Atypical negative ALK FISH accompanied by immunohistochemistry positivity harbored various ALK rearrangements in NSCLC patients and respond to targeted therapy.", J Clin. Oncology, vol. 34, Supp. Supplement 15, Abstract No. e20506, 2016 Annual Meeting of the American Society of Clinical Oncology, Chicago, IL, 2016.
Yu et al., "Denaturing high performance liquid chromatography: high throughput mutation screening in familial hypertrophic cardiomyopathy and SNP genotyping in motor neurone disease," J Clin Pathol, May 2005;58(5):479-85.
Yu et al., "Detection of ALK rearrangements in lung cancer patients using a homebrew PCR assay", Oncotarget, 8(5): 7722-7728, 2016.
Yuzugullu et al., "NTRK.2 activation cooperates with PTEN deficiency in T-ALL through activation of both the PBK-AKT and JAK-STAT3 pathways," Cell Discov., Sep. 2016, 2: 16030.
Zage et al., "The selective Trk inhibitor AZ623 inhibits brain-derived neurotrophic factor-mediated neuroblastoma cell proliferation and signaling and is synergistic with topotecan," Cancer, Mar. 2011, 117(6): 1321-1391.
Zahn et al., "Effect of blockade of nerve growth factor and tumor necrosis factor on pain behaviors after plantar incision," J. Pain, 2004, 5:157-163.
Zehir et al., "Mutational landscape of metastatic cancer revealed from prospective clinical sequencing of 10,000 patients," Nat. Med, Jun. 2017, 23(6):703-713.
Zelboraf, Highlights of Prescribing Information, Genentech USA, Initial Approval 2011, revised Aug. 2015, 18 pages.
Zhang et al., "A novel multiplex tetra-primer ARMS-PCR for the simultaneous genotyping of six single nucleotide polymorphisms associated with female cancers," PLoS One, Apr. 17, 2013;8(4):e62126. doi: 10.1371/iournal.pone.0062126. Print 2013.
Zhang et al., "Expression of nerve growth factor receptors and their prognostic value in human pancreatic cancer," Oncology Reports, 2005, 14:161-171.
Zhang et al., "Novel Phenotypic and Genetic Analysis ofT-Cell Prolymphocytic Leukemia (T-PLL)," Blood, 2014, 124(21):1682.
Zhang et al., "Whole-genome sequencing identifies genetic alterations in pediatric low-grade gliomas," Nat. Genet., Jun. 2013, 45(6): 602-612.
Zheng et al., "Anchored multiplex PCR for targeted next-generation sequencing," Nature Med., Dec. 2014, 20(12):1479-1486.
Zhu et al., "TPD52L1-ROS1, a new ROSI fusion variant in lung adenosquamous cell carcinoma.identified by comprehensive genomic profiling", Lung Cancer, 97:48-50, doi: 10.1016/j.lungcan.2016.04.013, 2012.
Ziemiecki et al., "Oncogenic activation of the human trk proto-oncogene by recombination with the ribosomal large subunit protein L7a," EMBO J, Jan. 1990, 9(1):191-196.
Zou et al., "PF-06463922 is a potent and selective next-generation ROS1/ALK inhibitor capable of blocking crizotinib-resistant ROS1 mutations.", Proc. Natl. Acad Sci. USA., 112(11): 3493-8, 2015.
U.S. Appl. No. 14/575,633, filed Dec. 18, 2014, Issued.
U.S. Appl. No. 15/41,839, filed Jan. 9, 2017, Issued.
Byrn, Stephen, et al. "Pharmaceutical solids: a strategic approach to regulatory considerations." Pharmaceutical research 12.7 (1995): 945-954.
Ghilardi, Joseph R., et al. "Administration of a tropomyosin receptor kinase inhibitor attenuates sarcoma-induced nerve sprouting, neuroma formation and bone cancer pain." Molecular pain 6 (2010). doi: 10.1186/1744-8069-6-87. 12 pages.
Lipska, Beata S., et al. "c. 1810C> T Polymorphism of NTRK1 Gene is associated with reduced Survival in Neuroblastoma Patients." BMC cancer 9.1 (2009): 436.
PCT International Preliminary Report on Patentability in International Application No. PCT/US2018/057542, dated May 7, 2020. 12 pages.
Perrigo Compounding Information for ORA-Blend® SF (Year: 2015). "ORA-BLEND® SF Flavoured Sugar-Free Oral Suspending Vehicle." 4 pages.
Spectrum Pharmacy Products (2015) "Suggested Formula." 3 pages.
Wood, Laura D., et al. "Somatic mutations of GUCY2F, EPHA3, and NTRK3 in human cancers." Human mutation 27.10 (2006): 1060-1061.
Loftsson, Thorsteinn, and Marcus E. Brewster. "Pharmaceutical applications of cyclodextrins. 1. Drug solubilization and stabilization." Journal of pharmaceutical sciences 85.10 (1996): 1017-1025.
Nagasubramanian et al., "Infantile Fibrosarcoma With NTRK3-ETV6 Fusion Successfully Treated With the Tropomyosin-Related Kinase Inhibitor LOXO-101," Pediatr Blood Cancer., Aug. 2016, 63(8):1468-70.
PCT International Preliminary Report on Patentability in International Application No. PCT/US2019/024961, dated Oct. 8, 2020. 8 pages.
U.S. Appl. No. 13/125,263, filed Oct. 21, 2009, Issued.
U.S. Appl. No. 13/943,590, filed Jul. 16, 2013, Issued.
U.S. Appl. No. 14/490,460, filed Sep. 18, 2014, Issued.
U.S. Appl. No. 14/596,611, filed Jan. 14, 2015, Issued.
U.S. Appl. No. 14/846,166, filed Sep. 4, 2015, Issued.
U.S. Appl. No. 15/399,389, filed Jan. 5, 2017, Issued.
U.S. Appl. No. 15/860,948, filed Jan. 3, 2018, Issued.
U.S. Appl. No. 16/044,653, filed Jul. 25, 2018, Issued.
U.S. Appl. No. 17/020,461, filed Sep. 14, 2020, Published.
U.S. Appl. No. 14/943,014, filed Nov. 16, 2015, Issued.
U.S. Appl. No. 15/399,207, filed Jan. 5, 2017, Issued.
U.S. Appl. No. 15/706,062, filed Sep. 15, 2017, Issued.
U.S. Appl. No. 15/872,769, filed Jan. 16, 2018, Issued.
U.S. Appl. No. 16/366,368, filed Mar. 27, 2019, Issued.
U.S. Appl. No. 16/302,312, filed May 18, 2017, Published.
U.S. Appl. No. 15/579,007, filed Jun. 1, 2016, Published.
U.S. Appl. No. 15/6922,388, filed Apr. 4, 2017, Issued.
U.S. Appl. No. 15/861,017, filed Jan. 3, 2018, Issued.
U.S. Appl. No. 16/739,845, filed Jan. 10, 2020, Published.
U.S. Appl. No. 15/622,544, filed Apr. 4, 2017, Issued.
U.S. Appl. No. 16/199,739, filed Nov. 26, 2018, Issued.
U.S. Appl. No. 16/859,275, filed Apr. 27, 2020, Published.
U.S. Appl. No. 17/043,134, filed Sep. 29, 2020, Published.
U.S. Appl. No. 13/698,922, filed May 13, 2011, Issued.
U.S. Appl. No. 14/575,663, filed Dec. 18, 2014, Issued.
U.S. Appl. No. 15/350,888, filed Nov. 14, 2016, Issued.
U.S. Appl. No. 15/401,839, filed Jan. 9, 2017, Issued.
U.S. Appl. No. 15/632,187, filed Jun. 23, 2017, Issued.
U.S. Appl. No. 15/900,019, filed Feb. 20, 2018, Issued.
U.S. Appl. No. 15/401,952, filed Jan. 9, 2017, Issued.
U.S. Appl. No. 16/818,125, filed Mar. 13, 2020, Published.

(56) References Cited

OTHER PUBLICATIONS

U.S. Appl. No. 13/063,894, filed Sep. 21, 2009, Issued.
U.S. Appl. No. 13/614,968, filed Sep. 13, 2012, Issued.
U.S. Appl. No. 14/984,353, filed Dec. 30, 2015, Issued.
U.S. Appl. No. 15/401,792, filed Jan. 9, 2017, Issued.
U.S. Appl. No. 15/401,969, filed Jan. 9, 2017, Issued.
U.S. Appl. No. 16/025,281, filed Jul. 2, 2018, Issued.
U.S. Appl. No. 16/170,976, filed Oct. 25, 2018, Published.
U.S. Appl. No. 17/078,508, filed Oct. 23, 2020, Pending.
U.S. Appl. No. 15/335,378, filed Oct. 26, 2016, Issued.
U.S. Appl. No. 15/785,174, filed Oct. 16, 2017, Issued.
U.S. Appl. No. 15/785,218, filed Oct. 16, 2017, Issued.
U.S. Appl. No. 15/860,789, filed Jan. 3, 2018, Allowed.
U.S. Appl. No. 15/785,228, filed Oct. 16, 2017, Issued.
U.S. Appl. No. 17/163,930, filed Feb. 1, 2021, Pending.
U.S. Appl. No. 16/199,818, filed Nov. 26, 2018, Allowed.
U.S. Appl. No. 16/199,867, filed Nov. 26, 2018, Published.
U.S. Appl. No. 16/199,875, filed Nov. 26, 2018, Issued.
U.S. Appl. No. 17/074,746, filed Oct. 20, 2020, Pending.
U.S. Appl. No. 13/382,858, filed Jul. 9, 2010, Issued.
U.S. Appl. No. 14/321,246, filed Jul. 1, 2014, Issued.
U.S. Appl. No. 15/401,895, filed Jan. 9, 2017, Issued.
U.S. Appl. No. 15/401,913, filed Jan. 9, 2017, Issued.
U.S. Appl. No. 15/724,601, filed Oct. 4, 2017, Issued.
U.S. Appl. No. 16/377,514, filed Apr. 8, 2019, Issued.

\* cited by examiner

FIG. 50

Met Leu Arg Gly Gly Arg Arg Gly Gln Leu Gly Trp His Ser Trp Ala
Ala Gly Pro Gly Ser Leu Leu Ala Trp Leu Ile Leu Ala Ser Ala Gly
Ala Ala Pro Cys Pro Asp Ala Cys Cys Pro His Gly Ser Ser Gly Leu
Arg Cys Thr Arg Asp Gly Ala Leu Asp Ser Leu His His Leu Pro Gly
Ala Glu Asn Leu Thr Glu Leu Tyr Ile Glu Asn Gln Gln His Leu Gln
His Leu Glu Leu Arg Asp Leu Arg Gly Leu Gly Glu Leu Arg Asn Leu
Thr Ile Val Lys Ser Gly Leu Arg Phe Val Ala Pro Asp Ala Phe His
Phe Thr Pro Arg Leu Ser Arg Leu Asn Leu Ser Phe Asn Ala Leu Glu
Ser Leu Ser Trp Lys Thr Val Gln Gly Leu Ser Leu Gln Glu Leu Val
Leu Ser Gly Asn Pro Leu His Cys Ser Cys Ala Leu Arg Trp Leu Gln
Arg Trp Glu Glu Glu Gly Leu Gly Gly Val Pro Glu Gln Lys Leu Gln
Cys His Gly Gln Gly Pro Leu Ala His Met Pro Asn Ala Ser Cys Gly
Val Pro Thr Leu Lys Val Gln Val Pro Asn Ala Ser Val Asp Val Gly
Asp Asp Val Leu Leu Arg Cys Gln Val Glu Gly Arg Gly Leu Glu Gln
Ala Gly Trp Ile Leu Thr Glu Leu Glu Gln Ser Ala Thr Val Met Lys
Ser Gly Gly Leu Pro Ser Leu Gly Leu Thr Leu Ala Asn Val Thr Ser
Asp Leu Asn Arg Lys Asn Val Thr Cys Trp Ala Glu Asn Asp Val Gly
Arg Ala Glu Val Ser Val Gln Val Asn Val Ser Phe Pro Ala Ser Val
Gln Leu His Thr Ala Val Glu Met His His Trp Cys Ile Pro Phe Ser
Val Asp Gly Gln Pro Ala Pro Ser Leu Arg Trp Leu Phe Asn Gly Ser
Val Leu Asn Glu Thr Ser Phe Ile Phe Thr Glu Phe Leu Glu Pro Ala
Ala Asn Glu Thr Val Arg His Gly Cys Leu Arg Leu Asn Gln Pro Thr
His Val Asn Asn Gly Asn Tyr Thr Leu Leu Ala Ala Asn Pro Phe Gly
Gln Ala Ser Ala Ser Ile Met Ala Ala Phe Met Asp Asn Pro Phe Glu
Phe Asn Pro Glu Asp Pro Ile Pro Val Ser Phe Ser Pro Val Asp Thr

FIG. 50 (cont'd)

Asn Ser Thr Ser Gly Asp Pro Val Glu Lys Lys Asp Glu Thr Pro Phe
Gly Val Ser Val Ala Val Gly Leu Ala Val Phe Ala Cys Leu Phe Leu
Ser Thr Leu Leu Leu Val Leu Asn Lys Cys Gly Arg Arg Asn Lys Phe
Gly Ile Asn Arg Pro Ala Val Leu Ala Pro Glu Asp Gly Leu Ala Met
Ser Leu His Phe Met Thr Leu Gly Gly Ser Ser Leu Ser Pro Thr Glu
Gly Lys Gly Ser Gly Leu Gln Gly His Ile Ile Glu Asn Pro Gln Tyr
Phe Ser Asp Ala Cys Val His His Ile Lys Arg Arg Asp Ile Val Leu
Lys Trp Glu Leu Gly Glu Gly Ala Phe Gly Lys Val Phe Leu Ala Glu
Cys His Asn Leu Leu Pro Glu Gln Asp Lys Met Leu Val Ala Val Lys
Ala Leu Lys Glu Ala Ser Glu Ser Ala Arg Gln Asp Phe Gln Arg Glu
Ala Glu Leu Leu Thr Met Leu Gln His Gln His Ile Val Arg Phe Phe
Gly Val Cys Thr Glu Gly Arg Pro Leu Leu Met Val Phe Glu Tyr Met
Arg His Gly Asp Leu Asn Arg Phe Leu Arg Ser His Gly Pro Asp Ala
Lys Leu Leu Ala Gly Gly Glu Asp Val Ala Pro Gly Pro Leu Gly Leu
Gly Gln Leu Leu Ala Val Ala Ser Gln Val Ala Ala Gly Met Val Tyr
Leu Ala Gly Leu His Phe Val His Arg Asp Leu Ala Thr Arg Asn Cys
Leu Val Gly Gln Gly Leu Val Val Lys Ile Gly Asp Phe Gly Met Ser
Arg Asp Ile Tyr Ser Thr Asp Tyr Tyr Arg Val Gly Gly Arg Thr Met
Leu Pro Ile Arg Trp Met Pro Pro Glu Ser Ile Leu Tyr Arg Lys Phe
Thr Thr Glu Ser Asp Val Trp Ser Phe Gly Val Val Leu Trp Glu Ile
Phe Thr Tyr Gly Lys Gln Pro Trp Tyr Gln Leu Ser Asn Thr Glu Ala
Ile Asp Cys Ile Thr Gln Gly Arg Glu Leu Glu Arg Pro Arg Ala Cys
Pro Pro Glu Val Tyr Ala Ile Met Arg Gly Cys Trp Gln Arg Glu Pro
Gln Gln Arg His Ser Ile Lys Asp Val His Ala Arg Leu Gln Ala Leu
Ala Gln Ala Pro Pro Val Tyr Leu Asp Val Leu Gly

FIG. 51

Met Ser Ser Trp Ile Arg Trp His Gly Pro Ala Met Ala Arg Leu Trp
Gly Phe Cys Trp Leu Val Val Gly Phe Trp Arg Ala Ala Phe Ala Cys
Pro Thr Ser Cys Lys Cys Ser Ala Ser Arg Ile Trp Cys Ser Asp Pro
Ser Pro Gly Ile Val Ala Phe Pro Arg Leu Glu Pro Asn Ser Val Asp
Pro Glu Asn Ile Thr Glu Ile Phe Ile Ala Asn Gln Lys Arg Leu Glu
Ile Ile Asn Glu Asp Asp Val Glu Ala Tyr Val Gly Leu Arg Asn Leu
Thr Ile Val Asp Ser Gly Leu Lys Phe Val Ala His Lys Ala Phe Leu
Lys Asn Ser Asn Leu Gln His Ile Asn Phe Thr Arg Asn Lys Leu Thr
Ser Leu Ser Arg Lys His Phe Arg His Leu Asp Leu Ser Glu Leu Ile
Leu Val Gly Asn Pro Phe Thr Cys Ser Cys Asp Ile Met Trp Ile Lys
Thr Leu Gln Glu Ala Lys Ser Ser Pro Asp Thr Gln Asp Leu Tyr Cys
Leu Asn Glu Ser Ser Lys Asn Ile Pro Leu Ala Asn Leu Gln Ile Pro
Asn Cys Gly Leu Pro Ser Ala Asn Leu Ala Ala Pro Asn Leu Thr Val
Glu Glu Gly Lys Ser Ile Thr Leu Ser Cys Ser Val Ala Gly Asp Pro
Val Pro Asn Met Tyr Trp Asp Val Gly Asn Leu Val Ser Lys His Met
Asn Glu Thr Ser His Thr Gln Gly Ser Leu Arg Ile Thr Asn Ile Ser
Ser Asp Asp Ser Gly Lys Gln Ile Ser Cys Val Ala Glu Asn Leu Val
Gly Glu Asp Gln Asp Ser Val Asn Leu Thr Val His Phe Ala Pro Thr
Ile Thr Phe Leu Glu Ser Pro Thr Ser Asp His His Trp Cys Ile Pro
Phe Thr Val Lys Gly Asn Pro Lys Pro Ala Leu Gln Trp Phe Tyr Asn
Gly Ala Ile Leu Asn Glu Ser Lys Tyr Ile Cys Thr Lys Ile His Val
Thr Asn His Thr Glu Tyr His Gly Cys Leu Gln Leu Asp Asn Pro Thr
His Met Asn Asn Gly Asp Tyr Thr Leu Ile Ala Lys Asn Glu Tyr Gly
Lys Asp Glu Lys Gln Ile Ser Ala His Phe Met Gly Trp Pro Gly Ile
Asp Asp Gly Ala Asn Pro Asn Tyr Pro Asp Val Ile Tyr Glu Asp Tyr
Gly Thr Ala Ala Asn Asp Ile Gly Asp Thr Thr Asn Arg Ser Asn Glu
Ile Pro Ser Thr Asp Val Thr Asp Lys Thr Gly Arg Glu His Leu Ser
Val Tyr Ala Val Val Val Ile Ala Ser Val Val Gly Phe Cys Leu Leu

FIG. 51 (con'td)

Val Met Leu Phe Leu Leu Lys Leu Ala Arg His Ser Lys Phe Gly Met
Lys Gly Pro Ala Ser Val Ile Ser Asn Asp Asp Asp Ser Ala Ser Pro
Leu His His Ile Ser Asn Gly Ser Asn Thr Pro Ser Ser Ser Glu Gly
Gly Pro Asp Ala Val Ile Ile Gly Met Thr Lys Ile Pro Val Ile Glu
Asn Pro Gln Tyr Phe Gly Ile Thr Asn Ser Gln Leu Lys Pro Asp Thr
Phe Val Gln His Ile Lys Arg His Asn Ile Val Leu Lys Arg Glu Leu
Gly Glu Gly Ala Phe Gly Lys Val Phe Leu Ala Glu Cys Tyr Asn Leu
Cys Pro Glu Gln Asp Lys Ile Leu Val Ala Val Lys Thr Leu Lys Asp
Ala Ser Asp Asn Ala Arg Lys Asp Phe His Arg Glu Ala Glu Leu Leu
Thr Asn Leu Gln His Glu His Ile Val Lys Phe Tyr Gly Val Cys Val
Glu Gly Asp Pro Leu Ile Met Val Phe Glu Tyr Met Lys His Gly Asp
Leu Asn Lys Phe Leu Arg Ala His Gly Pro Asp Ala Val Leu Met Ala
Glu Gly Asn Pro Pro Thr Glu Leu Thr Gln Ser Gln Met Leu His Ile
Ala Gln Gln Ile Ala Ala Gly Met Val Tyr Leu Ala Ser Gln His Phe
Val His Arg Asp Leu Ala Thr Arg Asn Cys Leu Val Gly Glu Asn Leu
Leu Val Lys Ile Gly Asp Phe Gly Met Ser Arg Asp Val Tyr Ser Thr
Asp Tyr Tyr Arg Val Gly Gly His Thr Met Leu Pro Ile Arg Trp Met
Pro Pro Glu Ser Ile Met Tyr Arg Lys Phe Thr Thr Glu Ser Asp Val
Trp Ser Leu Gly Val Val Leu Trp Glu Ile Phe Thr Tyr Gly Lys Gln
Pro Trp Tyr Gln Leu Ser Asn Asn Glu Val Ile Glu Cys Ile Thr Gln
Gly Arg Val Leu Gln Arg Pro Arg Thr Cys Pro Gln Glu Val Tyr Glu
Leu Met Leu Gly Cys Trp Gln Arg Glu Pro His Met Arg Lys Asn Ile
Lys Gly Ile His Thr Leu Leu Gln Asn Leu Ala Lys Ala Ser Pro Val
Tyr Leu Asp Ile Leu Gly

FIG. 52

Met Asp Val Ser Leu Cys Pro Ala Lys Cys Ser Phe Trp Arg Ile Phe
Leu Leu Gly Ser Val Trp Leu Asp Tyr Val Gly Ser Val Leu Ala Cys
Pro Ala Asn Cys Val Cys Ser Lys Thr Glu Ile Asn Cys Arg Arg Pro
Asp Asp Gly Asn Leu Phe Pro Leu Leu Glu Gly Gln Asp Ser Gly Asn
Ser Asn Gly Asn Ala Ser Ile Asn Ile Thr Asp Ile Ser Arg Asn Ile
Thr Ser Ile His Ile Glu Asn Trp Arg Ser Leu His Thr Leu Asn Ala
Val Asp Met Glu Leu Tyr Thr Gly Leu Gln Lys Leu Thr Ile Lys Asn
Ser Gly Leu Arg Ser Ile Gln Pro Arg Ala Phe Ala Lys Asn Pro His
Leu Arg Tyr Ile Asn Leu Ser Ser Asn Arg Leu Thr Thr Leu Ser Trp
Gln Leu Phe Gln Thr Leu Ser Leu Arg Glu Leu Gln Leu Glu Gln Asn
Phe Phe Asn Cys Ser Cys Asp Ile Arg Trp Met Gln Leu Trp Gln Glu
Gln Gly Glu Ala Lys Leu Asn Ser Gln Asn Leu Tyr Cys Ile Asn Ala
Asp Gly Ser Gln Leu Pro Leu Phe Arg Met Asn Ile Ser Gln Cys Asp
Leu Pro Glu Ile Ser Val Ser His Val Asn Leu Thr Val Arg Glu Gly
Asp Asn Ala Val Ile Thr Cys Asn Gly Ser Gly Ser Pro Leu Pro Asp
Val Asp Trp Ile Val Thr Gly Leu Gln Ser Ile Asn Thr His Gln Thr
Asn Leu Asn Trp Thr Asn Val His Ala Ile Asn Leu Thr Leu Val Asn
Val Thr Ser Glu Asp Asn Gly Phe Thr Leu Thr Cys Ile Ala Glu Asn
Val Val Gly Met Ser Asn Ala Ser Val Ala Leu Thr Val Tyr Tyr Pro
Pro Arg Val Val Ser Leu Glu Glu Pro Glu Leu Arg Leu Glu His Cys
Ile Glu Phe Val Val Arg Gly Asn Pro Pro Pro Thr Leu His Trp Leu
His Asn Gly Gln Pro Leu Arg Glu Ser Lys Ile Ile His Val Glu Tyr
Tyr Gln Glu Gly Glu Ile Ser Glu Gly Cys Leu Leu Phe Asn Lys Pro
Thr His Tyr Asn Asn Gly Asn Tyr Thr Leu Ile Ala Lys Asn Pro Leu
Gly Thr Ala Asn Gln Thr Ile Asn Gly His Phe Leu Lys Glu Pro Phe
Pro Glu Ser Thr Asp Asn Phe Ile Leu Phe Asp Glu Val Ser Pro Thr
Pro Pro Ile Thr Val Thr His Lys Pro Glu Glu Asp Thr Phe Gly Val

FIG. 52 (cont'd)

Ser Ile Ala Val Gly Leu Ala Ala Phe Ala Cys Val Leu Leu Val Val

Leu Phe Val Met Ile Asn Lys Tyr Gly Arg Arg Ser Lys Phe Gly Met

Lys Gly Pro Val Ala Val Ile Ser Gly Glu Glu Asp Ser Ala Ser Pro

Leu His His Ile Asn His Gly Ile Thr Thr Pro Ser Ser Leu Asp Ala

Gly Pro Asp Thr Val Val Ile Gly Met Thr Arg Ile Pro Val Ile Glu

Asn Pro Gln Tyr Phe Arg Gln Gly His Asn Cys His Lys Pro Asp Thr

Tyr Val Gln His Ile Lys Arg Arg Asp Ile Val Leu Lys Arg Glu Leu

Gly Glu Gly Ala Phe Gly Lys Val Phe Leu Ala Glu Cys Tyr Asn Leu

Ser Pro Thr Lys Asp Lys Met Leu Val Ala Val Lys Ala Leu Lys Asp

Pro Thr Leu Ala Ala Arg Lys Asp Phe Gln Arg Glu Ala Glu Leu Leu

Thr Asn Leu Gln His Glu His Ile Val Lys Phe Tyr Gly Val Cys Gly

Asp Gly Asp Pro Leu Ile Met Val Phe Glu Tyr Met Lys His Gly Asp

Leu Asn Lys Phe Leu Arg Ala His Gly Pro Asp Ala Met Ile Leu Val

Asp Gly Gln Pro Arg Gln Ala Lys Gly Glu Leu Gly Leu Ser Gln Met

Leu His Ile Ala Ser Gln Ile Ala Ser Gly Met Val Tyr Leu Ala Ser

Gln His Phe Val His Arg Asp Leu Ala Thr Arg Asn Cys Leu Val Gly

Ala Asn Leu Leu Val Lys Ile Gly Asp Phe Gly Met Ser Arg Asp Val

Tyr Ser Thr Asp Tyr Tyr Arg Leu Phe Asn Pro Ser Gly Asn Asp Phe

Cys Ile Trp Cys Glu Val Gly Gly His Thr Met Leu Pro Ile Arg Trp

Met Pro Pro Glu Ser Ile Met Tyr Arg Lys Phe Thr Thr Glu Ser Asp

Val Trp Ser Phe Gly Val Ile Leu Trp Glu Ile Phe Thr Tyr Gly Lys

Gln Pro Trp Phe Gln Leu Ser Asn Thr Glu Val Ile Glu Cys Ile Thr

Gln Gly Arg Val Leu Glu Arg Pro Arg Val Cys Pro Lys Glu Val Tyr

Asp Val Met Leu Gly Cys Trp Gln Arg Glu Pro Gln Gln Arg Leu Asn

Ile Lys Glu Ile Tyr Lys Ile Leu His Ala Leu Gly Lys Ala Thr Pro

Ile Tyr Leu Asp Ile Leu Gly

PROCESS FOR THE PREPARATION OF PYRAZOLO[1,5-A]PYRIMIDINES AND SALTS THEREOF

This application is a National Stage application under 35 U.S.C. § 371 of International Application No. PCT/US2017/058518, filed Oct. 26, 2017, which claims priority to U.S. Provisional Application No. 62/524,801, filed Jun. 26, 2017 and International Application No. PCT/US2016/058951, filed Oct. 26, 2016, which are herein incorporated by reference in their entirety.

FIELD OF THE INVENTION

Provided herein are processes and intermediates useful for the preparation of a compound of Formula C:

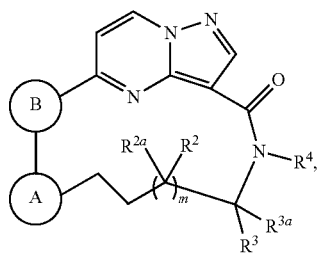

Formula C or a salt thereof.

Provided also herein is (6R,15R)-9-fluoro-15-methyl-2, 11,16,20,21,24-hexaazapentacyclo[16.5.2.0$^{2,6}$.0$^{7,12}$.0$^{21,25}$]pentacosa-1(24),7,9,11,18(25),19,22-heptaen-17-one:

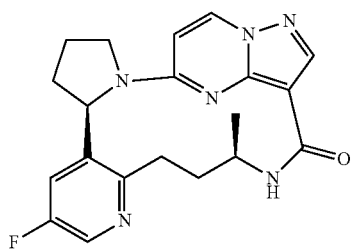

Formula I or a pharmaceutically acceptable salt, solvate or hydrate thereof. The compound of Formula I is also referred to herein as "Compound 1".

Provided also herein are crystalline forms of (6R,15R)-9-fluoro-15-methyl-2,11,16,20,21,24-hexaazapentacyclo[16.5.2.0$^{2,6}$.0$^{7,12}$.0$^{21,25}$]pentacosa-1(24),7,9,11,18(25),19,22-heptaen-17-one, salt forms thereof, and crystalline forms of these salts, including methods of preparation thereof. (6R,15R)-9-fluoro-15-methyl-2,11,16,20,21,24-hexaazapentacyclo[16.5.2.0$^{2,6}$.0$^{7,12}$.0$^{21,25}$]pentacosa-1(24),7,9,11,18(25),19,22-heptaen-17-one and its forms are useful in the treatment of the Trk-associated disorders such as cancer, pain, inflammation, neurodegenerative diseases and certain infectious diseases.

BACKGROUND

Trk's are high affinity receptor tyrosine kinases activated by a group of soluble growth factors called neurotrophins (NT). The Trk receptor family has three members: TrkA, TrkB and TrkC. Among the neurotrophins are (i) nerve growth factor (NGF) which activates TrkA, (ii) brain-derived neurotrophic factor (BDNF) and neurotrophin-4/5 which activate TrkB and (iii) neurotrophin-3 which activates TrkC. Inhibitors of the Trk/neurotrophin pathway have been demonstrated to be effective in numerous pre-clinical animal models of pain. Overexpression, activation, amplification and/or mutation of Trk kinases are associated with many cancers including neuroblastoma, ovarian and colorectal cancer, melanoma, head and neck cancer, gastric carcinoma, lung carcinoma, breast cancer, glioblastoma, medulloblastoma, secretory breast cancer, salivary gland cancer, papillary thyroid carcinoma, and adult myeloid leukemia. The neurotrophin/Trk pathway has been implicated in inflammatory diseases including asthma, interstitial cystitis, inflammatory bowel diseases including ulcerative colitis and Crohn's disease, and inflammatory skin diseases such as atopic dermatitis, eczema and psoriasis. The neurotrophin/Trk pathway has also been implicated in the etiology of neurodegenerative diseases including multiple sclerosis, Parkinson's disease and Alzheimer's Disease. The TrkA receptor is also involved the disease process in the parasitic infection of Trypanosoma cruzi (Chagas disease) in human hosts. As such, inhibition of Trk kinases will be useful to provide therapeutic benefit to patients suffering from the aforementioned conditions.

New forms of macrocyclic pyrazolo[1,5-a]pyrimidines can be useful in the preparation of pharmaceutical formulations and dosage forms. Furthermore, a need exists for alternative synthetic procedures for the preparation of such pyrazolo[1,5-a]pyrimidines. Such alternative synthetic procedures are provided herein.

SUMMARY

Provided herein in some embodiments is a process for preparing a compound of Formula C:

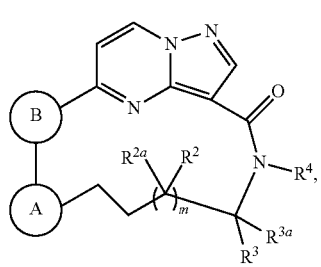

Formula C or a salt thereof. In some embodiments, the process comprises:

a) treating a compound of formula C-I

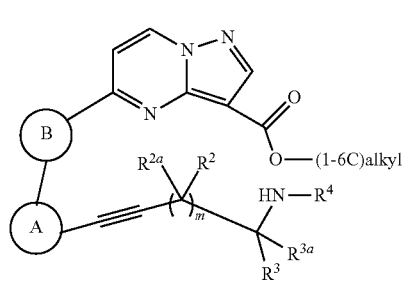

formula C-I or a salt thereof, with a hydrogenation system to form a compound of formula C-II

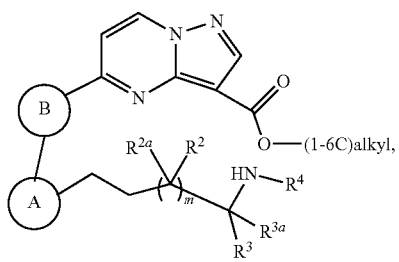

formula C-II or a salt thereof;
b) treating the compound of formula C-II or a salt thereof with a first strong base to form a compound of formula C-III

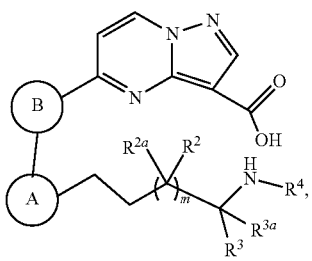

formula C-III or a salt thereof; and
c) cyclizing the compound of formula C-III or a salt thereof with a coupling agent to form the compound of Formula C or a salt thereof;
wherein:
ring A is selected from rings A-1 and A-3 having the structures:

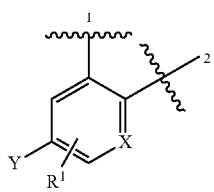

A-1

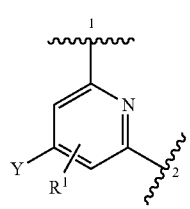

A-3 wherein the wavy line labeled 1 indicates the point of attachment of ring A to ring B and the wavy line labeled 2 indicates the point of attachment of ring A to the carbon atom of the ethylene linker in formulae C, C-II or C-III, or to the carbon atom of the alkyne linker in formula C-I;

X is N or CH;
Y is H or F;
$R^1$ is H, (1-6C)alkyl, (1-3C)alkoxy or halogen;
ring B is selected from rings B-1 and B-2 having the structures:

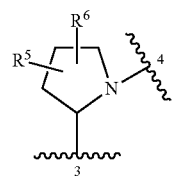

B-1

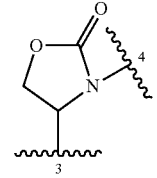

B-2 wherein the wavy line labeled 3 indicates the point of attachment to ring A and the wavy line labeled 4 indicates the point of attachment to the pyrazolo[1,5-a]pyrimidine ring;

$R^2$ and $R^{2a}$ are independently H, F, (1-3 C)alkyl or OH, provided that $R^2$ and $R^{2a}$ are not both OH;

m is 0, 1 or 2;

$R^3$ and $R^{3a}$ are independently H, (1-3 C)alkyl or hydroxy (1-3 C)alkyl;

$R^4$ is H, (1-6C)alkyl, fluoro(1-6C)alkyl, difluoro(1-6C)alkyl, trifluoro(1-6C)alkyl, hydroxy(1-6C alkyl) or dihydroxy(2-6C alkyl); and $R^5$ and $R^6$ are independently H, halogen, OH, (1-6C)alkyl or hydroxy(1-6C)alkyl.

Provided herein in some embodiments is a process for preparing a compound of Formula I

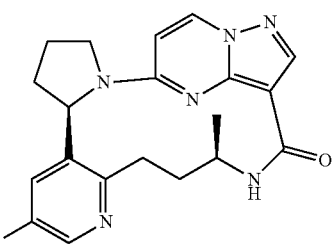

Formula I or a salt thereof, comprising:
a) treating a compound of formula 13

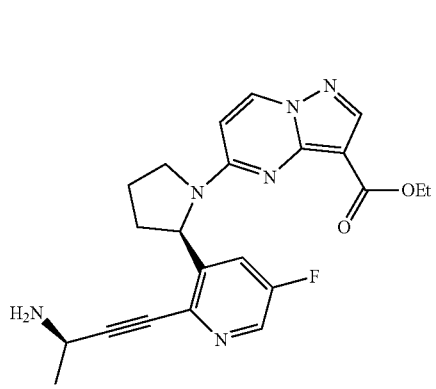
13 or a salt thereof with a hydrogenation system to form a compound of formula 14

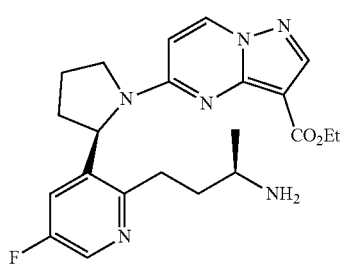
14 or a salt thereof;
b) treating the compound of formula 14 or a salt thereof with a first strong base to form a compound of formula 15

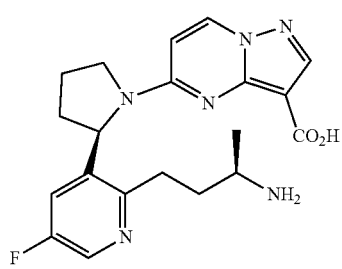
15 or a salt thereof; and
c) cyclizing the compound of formula 15 or a salt thereof with a coupling agent to form the compound of Formula I or a salt thereof.

Provided herein in some embodiments is a process for preparing a compound of Formula II:

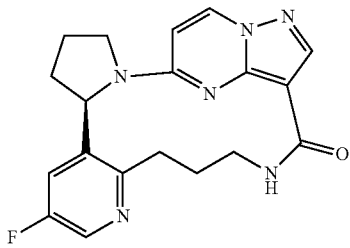
formula II or a salt thereof, comprising:
a) treating a compound of formula 16

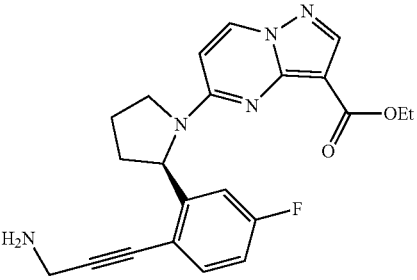
16 or a salt thereof with a hydrogenation system to form a compound of formula 17

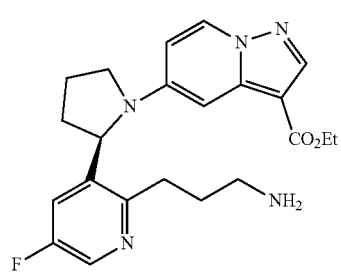
17 or a salt thereof;
b) treating the compound of formula 17 or a salt thereof with a first strong base to form a compound of formula 18

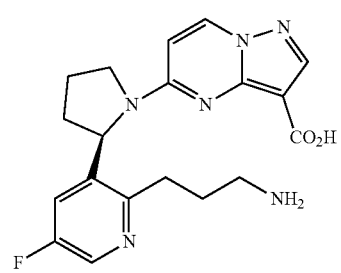
18 or a salt thereof; and
c) cyclizing the compound of formula 18 or a salt thereof with a coupling agent to form the compound of Formula II or a salt thereof.

Provided herein in some embodiments is a process for preparing a compound of Formula III:

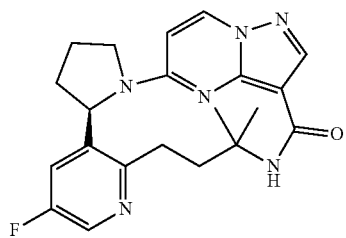

formula III or a salt thereof, comprising:
a) treating a compound of formula 20

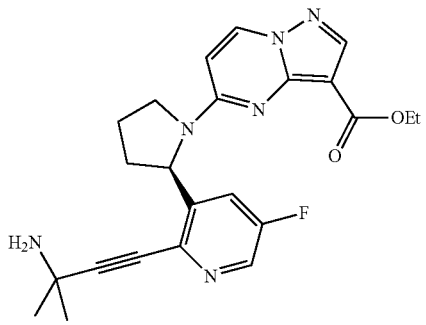

20 or a salt thereof with a hydrogenation system to form a compound of formula 21

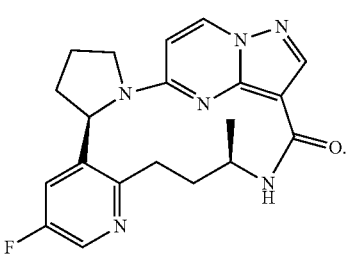

21 or a salt thereof;
b) treating the compound of formula 21 or a salt thereof with a first strong base to form a compound of formula 22

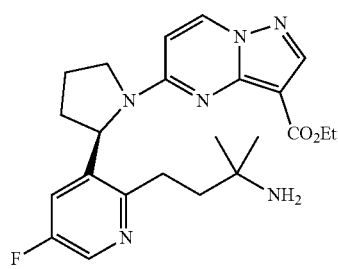

22 or a salt thereof; and
c) cyclizing the compound of formula 22 or a salt thereof with a coupling agent to form the compound of Formula III or a salt thereof.

Provided herein in some embodiments is a compound of Formula I

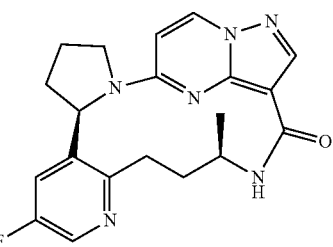

Formula I or a pharmaceutically acceptable salt, solvate or hydrate thereof.

The present disclosure in one embodiment is directed to a solid form of (6R,15R)-9-fluoro-15-methyl-2,11,16,20,21, 24-hexaazapentacyclo[16.5.2.0$^{2,6}$.0$^{7,12}$.0$^{21,25}$]pentacosa-1 (24),7,9,11,18(25),19,22-heptaen-17-one having the following structural formula:

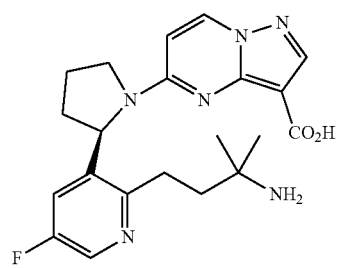

(Compound 1)

The present disclosure is further directed to a crystalline form of Compound 1, such as a crystalline form of Compound 1 having Form I. In some embodiments, Form I has the XRPD peaks, in terms of 2-theta (2θ), at about 9.1, about 20.2 and about 24.9. In some embodiments, Form I has the XRPD peaks, in terms of 2-theta, at about 9.1, about 11.2, about 20.2 and about 24.9. In some embodiments, Form I has the XRPD peaks, in terms of 2-theta, at about 9.1, about 11.2, about 13.4, about 14.8, about 20.2, and about 29.4. In some embodiments, Form I has the XRPD peaks, in terms of 2-theta, at about 9.1, about 11.2, about 13.4, about 14.8, about 18.3, about 18.6, about 20.2, about 23.6, about 24.9, and about 29.4. As used herein, the term "about" in conjunction with XRPD peaks refers to a variation of ±0.2. Thus, for example, a 2-theta value of "about 9.1" means a 2-theta value of 9.1±0.2.

The present disclosure is further directed to salts of Compound 1.

The present disclosure is further directed to crystalline forms of benzenesulfonic acid salt, citric acid salt, methanesulfonic acid salt, 1,2-ethane disulfonic acid salt, p-toluene sulfonic acid salt, oxalic acid salt, fumaric acid salt, L-malic acid salt, and succinic acid salt of Compound 1.

In one aspect, the present disclosure is directed to a crystalline form of Compound 1 besylate. In some embodiments, the crystalline Compound 1 besylate has XRPD peaks, in terms of 2-theta, at about 8.1, about 13.4, and about 21.2. In some embodiments, the crystalline Compound 1 besylate has XRPD peaks, in terms of 2-theta, at about 8.1, about 12.0, about 13.4, and about 21.2. In some embodiments, the crystalline Compound 1 besylate has XRPD peaks, in terms of 2-theta, at about 8.1, about 12.0, about 13.4, about 19.0, about 19.4, and about 21.2. In some embodiments, the crystalline Compound 1 besylate has XRPD peaks, in terms of 2-theta, at about 8.1, about 12.0, about 13.4, about 19.0, about 19.4, about 19.9, about 20.1, about 21.2, about 25.5, and about 32.7.

In another aspect, the present disclosure is directed to a crystalline form of Compound 1 citrate, such as crystalline Compound 1 citrate Form A. In some embodiments, Compound 1 citrate Form A has XRPD peaks, in terms of 2-theta, at about 20.7, about 21.6, and about 24.8. In some embodiments, Compound 1 citrate Form A has XRPD peaks, in terms of 2-theta, at about 8.9. 20.7, about 21.6, and about 24.8. In some embodiments, Compound 1 citrate Form A has XRPD peaks, in terms of 2-theta, at about 8.9, about 11.1, about 14.4, about 15.4, about 20.7, about 21.6, and about 24.8. In some embodiments, Compound 1 citrate Form A has XRPD peaks, in terms of 2-theta, at about 8.9, about 11.1, about 13.9, about 14.4, about 15.4, about 19.2, about 20.7, about 21.6, about 24.8, and about 25.6.

The present disclosure is further directed to the hydrochloric acid salt, sulfuric acid salt, naphthalene-2-sulphonic acid salt, 2-hydroxy ethanesulfonic acid salt, L-aspartic acid salt, maleic acid salt, phosphoric acid salt, ethanesulfonic acid salt, L-glutamic acid salt, L-tartaric acid salt, D-glucuronic acid salt, hippuric acid salt, D-gluconic acid salt, DL-lactic acid salt, L-ascorbic acid salt, benzoic acid salt, benzenesulfonic acid salt, citric acid salt, methanesulfonic acid salt, 1,2-ethane disulfonic acid salt, p-toluene sulfonic acid salt, oxalic acid salt, fumaric acid salt, L-malic acid salt, and succinic acid salt of Compound 1.

The present disclosure is further directed to a hydrate or a solvate of Compound 1, or any one of the salts of Compound 1 described herein. In some aspects, the hydrate or the solvate is crystalline.

The present disclosure is further directed to processes for preparing any one of the crystalline forms, solid forms, solvates, hydrates, or salts described herein.

The present disclosure is further directed to pharmaceutical compositions comprising any one of the crystalline forms, solid forms, solvates, hydrates, or salts described herein, and at least one pharmaceutically acceptable carrier.

The present disclosure is further directed to therapeutic methods of using any one of the crystalline forms, solid forms, solvates, hydrates, or salts described herein.

Unless otherwise defined, all technical and scientific terms used herein have the same meaning as commonly understood by one of ordinary skill in the art to which the present application belongs. Materials are described herein for use in the present application; other, suitable materials known in the art can also be used. The materials and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DESCRIPTION OF DRAWINGS

FIG. 50 is a sequence listing for an exemplary wildtype TrkA polypeptide (SEQ ID NO: 1).

FIG. 51 is a sequence listing for an exemplary wildtype TrkB polypeptide (SEQ ID NO: 2).

FIG. 52 is a sequence listing for an exemplary wildtype TrkC polypeptide (SEQ ID NO: 3).

DETAILED DESCRIPTION

Definitions

Figure 1:
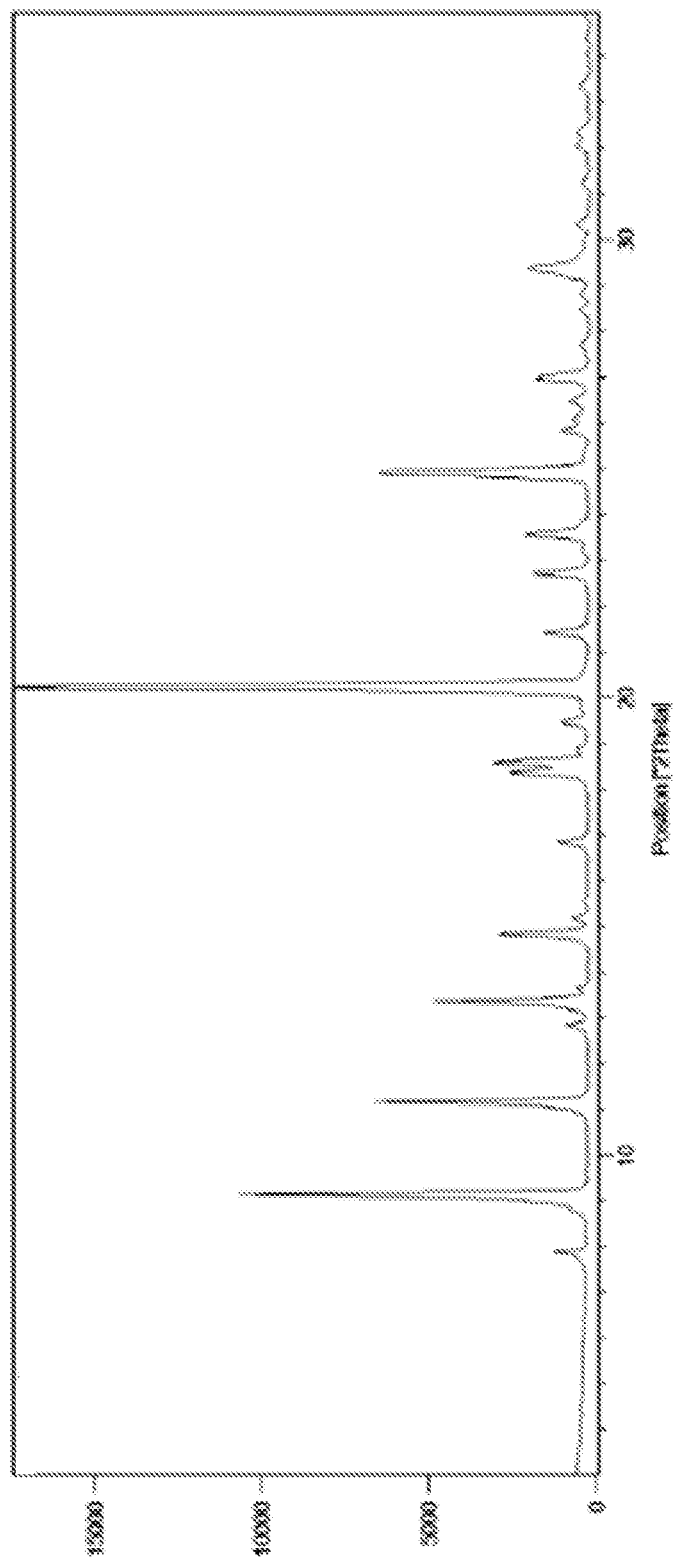
FIG. 1 is a XRPD diffractogram of Compound 1 (Form I).

Unless defined otherwise, all technical and scientific terms used herein have the same meaning as is commonly understood by one of skill in the art to which the invention(s) belong. All patents, patent applications, published applications, and publications, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, the term "alkyl" refers to a hydrocarbon chain that can be a straight chain or branched chain, containing the indicated number of carbon atoms. For example, $C_{1-6}$ indicates that the group can have from 1 to 6 (inclusive) carbon atoms in it. As used herein, recitations such as "$C_{1-6}$ alkyl", "(1-6C)alkyl" or "(1-6C alkyl)" are used interchangeably herein to indicate a straight or branched chain alkyl group having from one to six carbon atoms. Examples of such alkyl groups include methyl, ethyl, iso-propyl, tert-butyl, and n-hexyl.

As used herein, "hydrogenation system" refers to a compound or complex capable of catalyzing a hydrogenation reaction, i.e., the reaction of the hydrogen with a hydrogen reactive group, such as a benzyl group or a carbon-carbon double/triple bond. The hydrogenation system includes hydrogen gas at atmospheric or higher pressure and a catalyst. Catalysts useful for hydrogenation include, but are not limited to, metals, such as palladium, platinum, and rhodium and their oxides or hydroxides, preferably supported on a material such as carbon or alumina.

"Coupling agent," as used herein, refers to a reagent that forms amide or ester bonds, such as by coupling acids and amines or alcohols, respectively. Suitable coupling agents are well known to a person of skill in the art and are commercially available. Coupling agents include, but are not limited to, dicyclohexylcarbodiimide (DCC), N,N'-diisopropylcarbodiimide (DIC), N-(3-dimethylaminopropyl)-N'-ethylcarbodiimide (EDCI). or carbonyl diimidazole (CDI). In some embodiments, one or more than one coupling agent can be used at the same time. A coupling agent may be used in conjunction with a catalyst.

As used herein, "strong base" refers to a basic chemical compound that is able to deprotonate weak acids in an acid-base reaction. A strong base is also able to hydrolyze an ester compound in a hydrolysis reaction to produce the corresponding carboxylic acid compound. Examples of strong bases include, but are not limited to, hydroxides, alkoxides, and ammonia. Common examples of strong bases are the hydroxides of alkali metals and alkaline earth metals, e.g., NaOH. Certain strong bases are even able to deprotonate very weakly acidic C—H groups in the absence of water. Strong bases include, but are not limited to, sodium hydroxide, potassium hydroxide, barium hydroxide, cesium hydroxide, strontium hydroxide, lithium hydroxide and rubidium hydroxide. In certain embodiments, NaOH is used as the strong base.

As used herein, the term "weak base" refers to inorganic and organic bases that are only partially ionized in aqueous solution. Weak bases typically have a pKa of between about 6 and about 11. A large number of such weak bases are known and are exemplified by those listed in the *Handbook of Biochemistry and Molecular Biology*, Vol. 1, 3rd ed., G. D. Fassman, CRC Press, 1976, pp. 305-347. The weak base may be soluble or insoluble in water. Suitable weak bases include, but are not limited to, alkali metal carbonates and bicarbonates, such as lithium carbonate, sodium carbonate, potassium carbonate, and sodium bicarbonate; ammonia; primary amines; secondary amines; and tertiary amines, such as the trialkylamines, e.g., triethylamine, tripropylamine and tributylamine, benzyldiethylamine, pyridine, quinoline, N-methylmorpholine, and the like.

"Non-nucleophilic base," as used herein, refers to a base that will not act as a nucleophile, i.e., a base that will not donate an electron pair to an electrophile to form a chemical bond in relation to a reaction. Typically, non-nucleophilic bases are bulky and sterically hindered, such that protons can attach to the basic center, but alkylation and complexation are prevented. Examples of non-nucleophilic bases include, but are not limited to, amines and nitrogen heterocycles, such as triethylamine and pyridine, lithium compounds, and phsophazenes.

The terms "hydrogen" and "H" are used interchangeably herein.

The terms "halogen" or "halo" refer to fluorine (F), chlorine (Cl), bromine (Br), or iodine (I).

As used herein, the term "alkylamine" refers to an amine that contains one or more alkyl groups. An alkylamine can be a primary amine, a secondary amine or a tertiary amine. For example, a secondary alkylamine is an amine that contains two alkyl groups. An example includes diisopropylethylamine.

As used herein, the singular forms "a," "an," and "the" include plural referents unless the context clearly dictates otherwise.

As used herein, ranges and amounts can be expressed as "about" a particular value or range. About also includes the exact amount. Hence, "about 5 grams" means "about 5 grams" and also "5 grams." It also is understood that ranges expressed herein include whole numbers within the ranges and fractions thereof. For example, a range of between 5 grams and 20 grams includes whole number values such as 5, 6, 7, 8, 9, 10, 11, 12, 13, 14, 15, 16, 17, 18, 19 and 20 grams, and fractions within the range including, but not limited to, 5.25, 6.5, 8.75 and 11.95 grams.

As used herein, "optional" or "optionally" means that the subsequently described event or circumstance does or does not occur and that the description includes instances where said event or circumstance occurs and instances where it does not. For example, a reaction mixture that "optionally includes a catalyst" means that the reaction mixture contains a catalyst or it does not contain a catalyst.

The compounds disclosed herein include compounds having a sulfoxide group, as shown, by way of example, in the structure of compound 2, below:

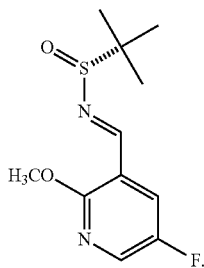

The sulfur-oxygen bond can also be rendered pictorially as being in ionic form. Thus, for example, compound 2 can also be rendered as shown in the structure below:

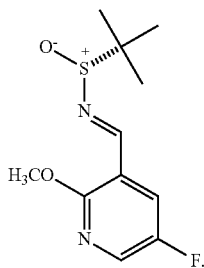

It is intended throughout this disclosure that the recitation of a given structure for a compound having a sulfoxide group encompasses all representations of the compound, whether the sulfur-oxygen bond is rendered as being an ionic bond, a covalent bond, a dative bond, or in any form that can be envisioned by the skilled artisan.

The term "compound," as used herein, is meant to include all stereoisomers, geometric isomers, tautomers, and isotopes of the structures depicted. Compounds herein identified by name or structure as one particular tautomeric form are intended to include other tautomeric forms unless otherwise specified. Compounds herein identified by name or structure without specifying the particular configuration of a stereocenter are meant to encompass all the possible configurations at the stereocenter. For example, if a particular stereocenter in a compound of the invention could be R or S, but the name or structure of the compound does not designate which it is, then the stereocenter can be either R or S. The compounds described herein can be asymmetric (e.g., having one or more stereocenters). Compounds of the present application that contain an asymmetrically substituted carbon atom can be isolated in optically active or racemic forms. Methods on how to prepare optically active forms from optically inactive starting materials are known in the art, such as by resolution of racemic mixtures or by stereoselective synthesis. In some embodiments, an asymmetrically substituted carbon atom has the (R)-configuration according to Cahn-Ingold-Prelog nomenclature. In some embodiments, an asymmetrically substituted carbon atom has the (S)-configuration according to Cahn-Ingold-Prelog nomenclature.

"Protecting group", as used herein, refers to any convenient functional group that allows to obtain chemoselectivity in a subsequent chemical reaction. Protecting groups are described, for example, in Greene & Wuts, eds., "Protecting Groups in Organic Synthesis", 2nd ed. New York; John Wiley & Sons, Inc., 1991. For a particular compound and/or a particular chemical reaction, a person skilled in the art knows how to select and implement appropriate protecting groups and synthetic methods. Examples of amine protecting groups include acyl and alkoxycarbonyl groups, such as t-butoxycarbonyl (BOC), and [2-(trimethylsilyl)ethoxy]methyl (SEM). Examples of carboxyl protecting groups include (1-6C)alkyl groups, such as methyl, ethyl and t-butyl. Examples of alcohol protecting groups include benzyl, trityl, silyl ethers, and the like.

"Leaving group", as used herein, refers to a molecule or a molecular fragment (e.g., an anion) that is displaced in a chemical reaction as stable species taking with it the bonding electrons. Examples of leaving groups include arylsulfonyloxy group or an alkylsulfonyloxy group, such as a mesylate or a tosylate group. Common anionic leaving groups also include halides such as Cl—, Br—, and I—.

A salt can form from a compound in any manner familiar to the skilled artisan. Accordingly, the recitation "to form a compound or salt thereof" includes embodiments where a compound is formed and the salt is subsequently formed from the compound in a manner familiar to the skilled artisan.

As used herein, the phrase "solid form" refers to Compound 1 or a salt of Compound 1 in either an amorphous state or a crystalline state ("crystalline form" or "crystalline solid"), whereby a compound in a crystalline state may optionally include solvent or water within the crystalline lattice, for example, to form a solvated or hydrated crystalline form.

The term "hydrated," as used herein, is meant to refer to a crystalline form that includes water molecules in the crystalline lattice.

Different crystalline forms of compounds can be characterized by X-ray powder diffraction (XRPD), differential scanning calorimetry (DSC), differential thermal analysis (DTA), and/or thermogravimetric analysis (TGA). An X-ray powder diffraction (XRPD) pattern of reflections (peaks) is typically considered a fingerprint of a particular crystalline form. It is well known that the relative intensities of the XRPD peaks can widely vary depending on the sample preparation technique, crystal size distribution, various filters used, the sample mounting procedure, and the particular instrument employed. In some instances, new peaks may be observed or existing peaks may disappear depending on the type of instrument or the settings (for example, whether a Ni filter is used or not).

As used herein, the term "peak" refers to a reflection having a relative height/intensity of at least about 5% of the maximum peak height/intensity in the XPRD. Peak assignments, such as those reported herein, can vary by plus or minus 0.2° (2-theta), and the term "substantially" or "about" as used in the context of XRPD herein is meant to refer to the above-mentioned variations. Thus, for example, a 2-theta value of "about 9.1" means a 2-theta value of 9.1±0.2.

As described herein, temperature readings in connection with DSC, TGA, or other thermal experiments can vary by ±4° C. depending on the instrument, particular settings, sample preparation, etc. Accordingly, a crystalline form reported herein having a DSC thermogram "substantially" as shown in any of the Figures is understood to accommodate such variation. An endothermal or exothermic event at "about" a certain temperature is also understood to accommodate this variation.

As used herein, the term "melting point" refers to an endothermal event or endothermal event observed in, e.g., a DSC thermogram. An endothermal event is a process or reaction in which a sample absorbs energy from its surroundings in the form of e.g., heat as in a DSC experiment. An exothermic event is a process or reaction in which a sample releases energy. The process of heat absorption and release can be detected by DSC. In some embodiments, the term "melting point" is used to describe the major endothermal event on a DSC thermogram.

The term "room temperature" or "ambient temperature" as used herein, is understood in the art, and refers generally to a temperature, e.g., a reaction temperature, that is about the temperature of the room in which the reaction is carried out, for example, a temperature from about 20° C. to about 30° C.

In some embodiments, the compounds, salts, and forms described herein are substantially isolated. By "substantially isolated" is meant that the compound, salt, or form is at least partially or substantially separated from the environment in which it was formed or detected. Partial separation can include, e.g., a composition enriched in the compound, salt or form. Substantial separation can include compositions containing at least about 50%, at least about 60%, at least about 70%, at least about 80%, at least about 90%, at least about 95%, at least about 97%, or at least about 99% by weight of the compound, salt or form.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

In one embodiment, the term "preventing" as used herein means the prevention of the onset, recurrence or spread, in whole or in part, of the disease or condition as described herein (e.g., multiple types of pain including inflammatory pain, neuropathic pain, and pain associated with cancer, surgery, and bone fracture), or a symptom thereof.

The terms "effective amount" and "therapeutically effective amount" refer to an amount of compound that, when administered to a mammal in need of such treatment, is sufficient to (i) treat or prevent a particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a Compound 1, or salt thereof, that will correspond to such an amount will vary depending upon factors such as the particular compound, disease condition and its severity, the identity (e.g., weight) of the mammal in need of treatment, but can nevertheless be routinely determined by one skilled in the art.

The terms "individual" or "patient," used interchangeably, refer to any animal, including mammals, and most preferably humans. As used herein, the term "mammal" refers to a warm-blooded animal that has or is at risk of developing a disease described herein and includes, but is not limited to, guinea pigs, dogs, cats, rats, mice, hamsters, primates, and humans.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

All combinations of the embodiments pertaining to the aspects described herein are specifically embraced by the present invention just as if each and every combination was individually explicitly recited, to the extent that such combinations embrace possible aspects. In addition, all sub-combinations of the embodiments contained within the aspects described herein, as well as all sub-combinations of the embodiments contained within all other aspects described herein, are also specifically embraced by the present invention just as if each and every sub-combination of all embodiments are explicitly recited herein.

Examples of Embodiments

The present application provides, inter alia, a process for preparing a compound of Formula C, or a salt thereof, as set out, for example, in Scheme 1:

Scheme 1

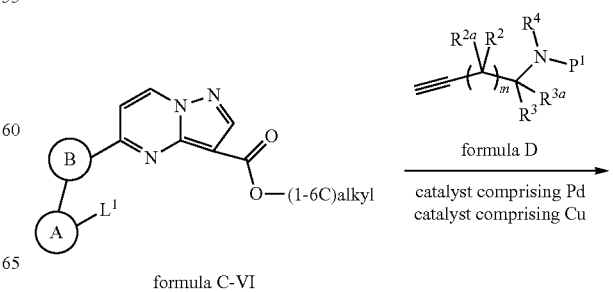

-continued

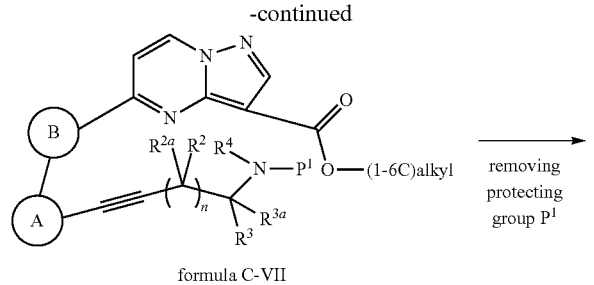

formula C-VII

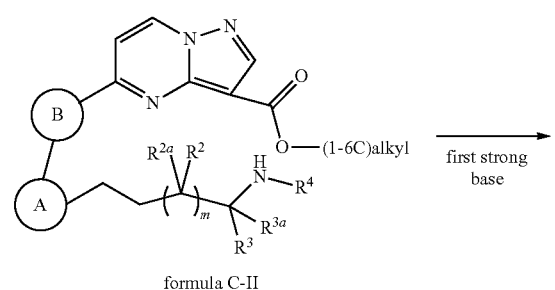

formula C-I

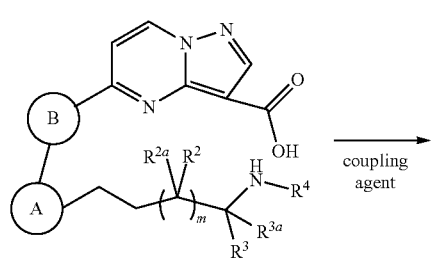

formula C-II

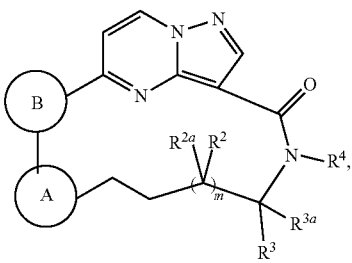

Formula C or a salt thereof, comprising:
a) treating a compound of formula C-I

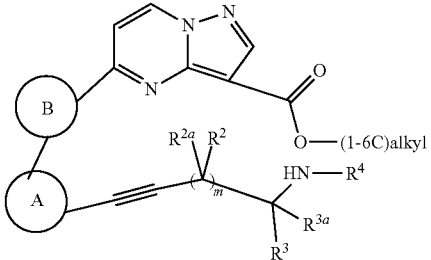

formula C-I or a salt thereof, with a hydrogenation system to form a compound of formula C-II

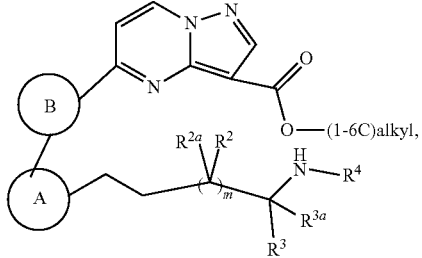

formula C-II or a salt thereof;
b) treating the compound of formula C-II or a salt thereof with a first strong base to form a compound of formula C-III formula C-III

[structure]

Formula C

In some embodiments, provided herein is a process for preparing a compound of Formula C or a salt thereof; and
c) cyclizing the compound of formula C-III or a salt thereof with a coupling agent to form the compound of Formula C or a salt thereof;

wherein:
ring A is selected from rings A-1 and A-3 having the structures:

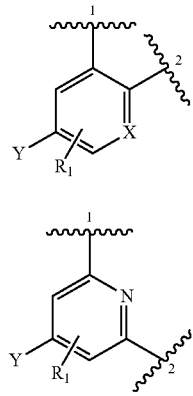

A-1

A-3 wherein the wavy line labeled 1 indicates the point of attachment of ring A to ring B and the wavy line labeled 2 indicates the point of attachment of ring A to the carbon atom of the ethylene linker in formulae C, C-II or C-III, or to the carbon atom of the alkyne linker in formula C-I;
X is N or CH;
Y is H or F;
$R^1$ is H, (1-3C)alkyl, (1-3C)alkoxy or halogen;
ring B is selected from rings B-1 and B-2 having the structures:

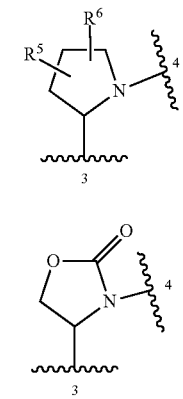

B-1

B-2 wherein the wavy line labeled 3 indicates the point of attachment to ring A and the wavy line labeled 4 indicates the point of attachment to the pyrazolo[1,5-a]pyrimidine ring;
$R^2$ and $R^{2a}$ are independently H, F, (1-3 C)alkyl or OH, provided that $R^2$ and $R^{2a}$ are not both OH;
m is 0, 1 or 2;
$R^3$ and $R^{3a}$ are independently H, (1-3 C)alkyl or hydroxy (1-3 C)alkyl; $R^4$ is H, (1-6C)alkyl, fluoro(1-6C)alkyl, difluoro(1-6C)alkyl, trifluoro(1-6C)alkyl, hydroxy(1-6C alkyl) or dihydroxy(2-6C alkyl); and
$R^5$ and $R^6$ are independently H, halogen, OH, (1-6C)alkyl or hydroxy(1-6C)alkyl. In some embodiments, provided herein is a process for preparing a compound of Formula C, or a salt thereof, comprising cyclizing the compound of formula C-III, or a salt thereof, with a coupling agent to form the compound of Formula C, or a salt thereof.

In some embodiments, provided herein is a process for preparing a compound of formula C-III, or a salt thereof, comprising treating the compound of formula C-II, or a salt thereof, with a first strong base to form a compound of formula C-III, or a salt thereof.

In some embodiments, provided herein is a process for preparing a compound of formula C-II, or a salt thereof, comprising treating a compound of formula C-I, or a salt thereof, with a hydrogenation system to form a compound of formula C-II, or a salt thereof.

In some embodiments, the process for preparing a compound of formula C, or a salt thereof, further comprises preparing the compound of formula C-I

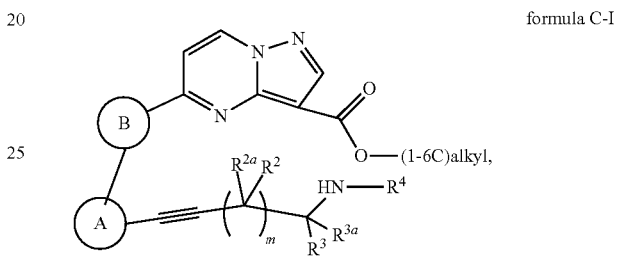

formula C-I or a salt thereof, by a process comprising:
a) coupling the compound of formula C-VI

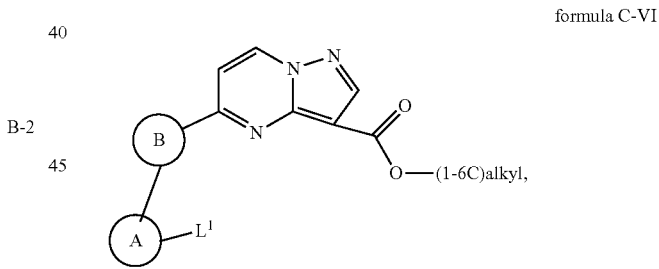

formula C-VI or a salt thereof;
with a compound of formula D

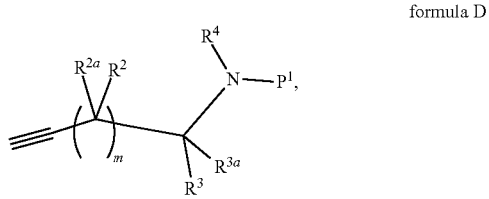

formula D or a salt thereof, in the presence of a catalyst comprising palladium and a catalyst comprising copper to form the compound of formula C-VII formula C-VII

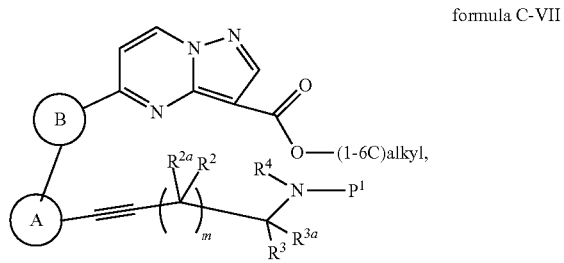

or a salt thereof; and
b) deprotecting the compound of formula C-VII to obtain the compound of formula C-I or a salt thereof;
wherein:
P¹ is an amino-protecting group; and
L¹ is a leaving group.

In some embodiments, provided herein is a process for preparing a compound of formula C-I, or a salt thereof, comprising deprotecting the compound of formula C-VII, or a salt thereof, to form a compound of formula C-I, or a salt thereof.

In some embodiments, provided herein is a process for preparing a compound of formula C-VII, or a salt thereof, comprising coupling a compound of formula C-VI, or a salt thereof, with a compound of formula D or a salt thereof, in the presence of a catalyst comprising palladium and a catalyst comprising copper to form the compound of formula C-VII, or a salt thereof.

In some embodiments, the compound of formula C-VI, or salt thereof, may be prepared as set out in Scheme 1a:

Scheme 1a

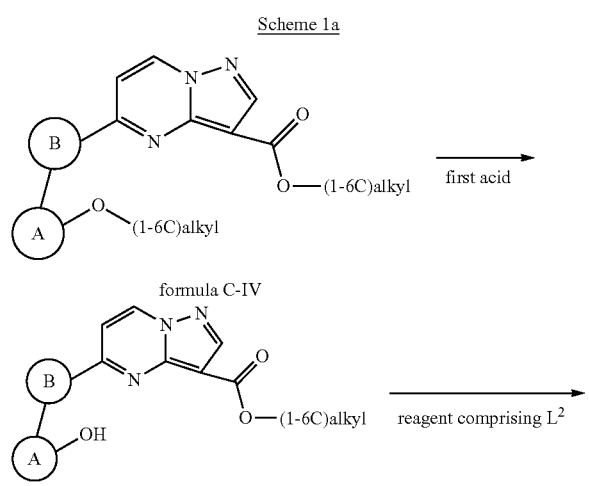

In some embodiments, provided herein is a process for preparing a compound of formula C-VI

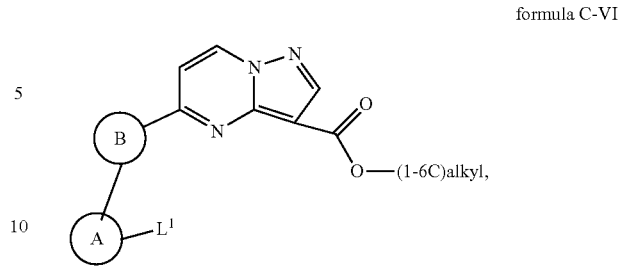

or a salt thereof, comprising treating the compound of formula C-V

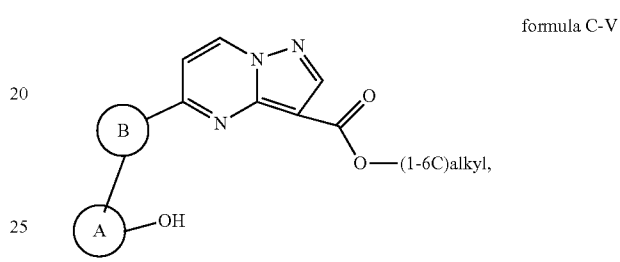

or a salt thereof, with a reagent comprising a group L² to form a compound of formula C-VI, wherein L² is a group that, when bonded to an oxygen atom, forms a leaving group L¹.

For example, when the leaving group L¹ is trifluoromethanesulfonate (triflate), the group L² is trifluoromethanesulfonyl (triflyl); when the leaving group L¹ is tosylate, the group L² is tosyl; when the leaving group L¹ is mesylate, the group L² is mesyl; or when the leaving group L¹ is nosylate, the group L² is nosyl. In some more particular embodiments, the reagent comprising a group L² has a formula L²-Hal, wherein Hal is a halogen (e.g., Cl, Br or I). In some more particular embodiments, the reagent comprising a group L² has a formula L²-O-L². In some embodiments, the reagent comprising a group L² is a reagent comprising a —S(O₂)LG moiety, wherein LG is a leaving group such as a halogen or a OS(O₂)-alkyl or OS(O₂)-aryl group. In some embodiments, the reagent comprising a group L² is a sulfonic anhydride, such as trifluoromethanesulfonic anhydride, trifluoromethanesulfonyl chloride, tosyl chloride, mesyl chloride or nosyl chloride. In some embodiments, the reagent comprising a group L² is a sulfonimide, such as N-Phenyl-bis(trifluoromethanesulfonimide).

In some embodiments, provided herein is a process for preparing a compound of formula C-V

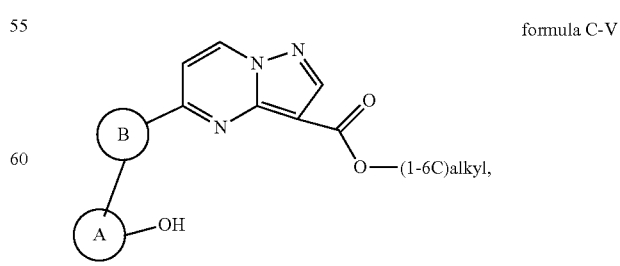

or a salt thereof, comprising treating a compound of formula C-IV formula C-IV

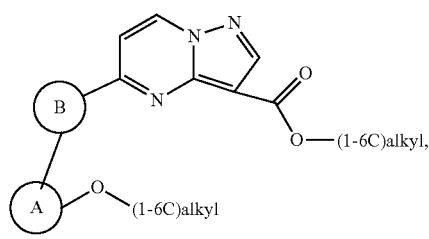

or a salt thereof, with a first acid to form a compound of formula C-V.

In some embodiments, the compound of Formula C has formula Ca:

formula Ca

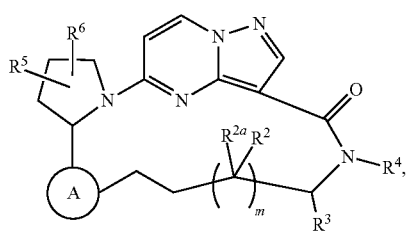

or a salt thereof;

the compound of formula C-I has formula C-Ia formula C-Ia

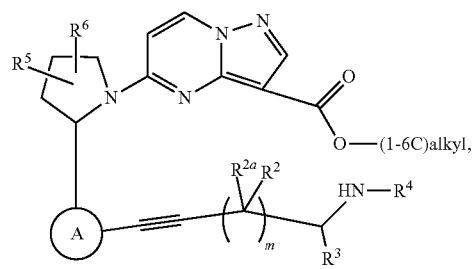

or a salt thereof;

the compound of formula C-II has formula C-IIa formula C-IIa

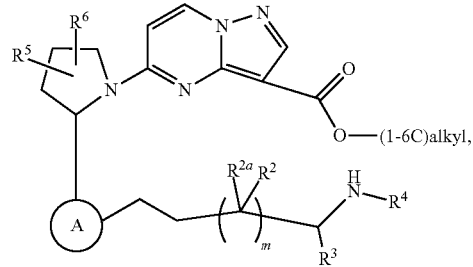

or a salt thereof; and the compound of formula C-III has formula C-IIIa:

formula C-IIIa

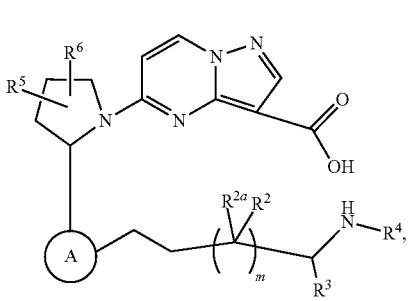

or a salt thereof.

In some embodiments, the compound of formula C-VI has formula C-VIa formula C-VIa

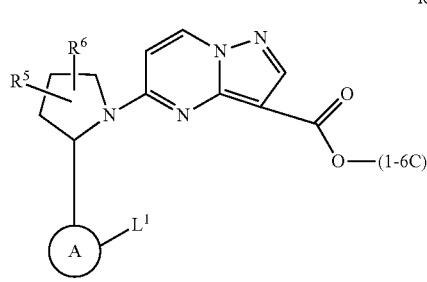

or a salt thereof;

the compound of formula D has formula D-1 formula D-1

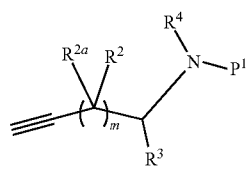

the compound of formula C-VII has formula C-VIIa formula C-VIIa

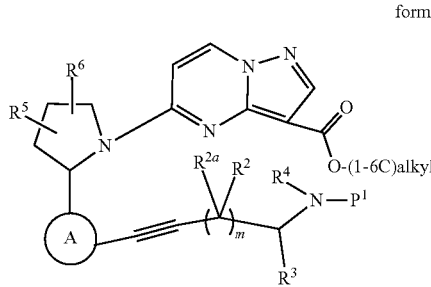

or a salt thereof.

In some embodiments, the compound of formula C-IV has formula C-IVa formula C-IVa

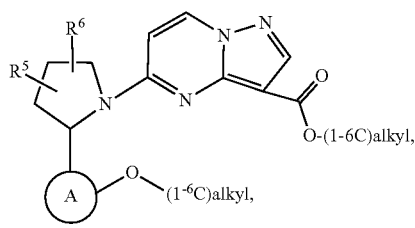

or a salt thereof; and
the compound of formula C-V has formula C-Va formula C-Va

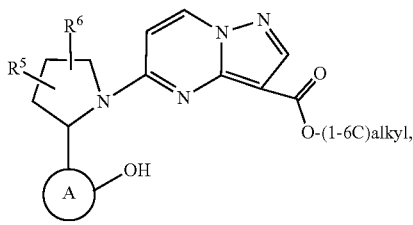

or a salt thereof;

In some embodiments, the compound of formula C has formula Cb formula Cb

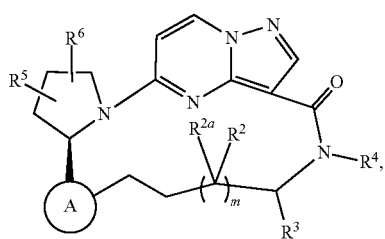

In some embodiments, the compound of formula C has formula Cc formula Cc

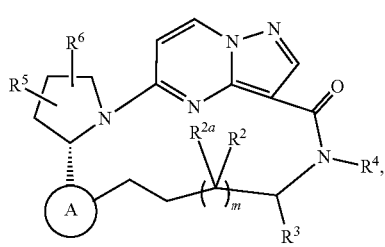

or a salt thereof.

In some embodiments, the compound of formula C has formula Cd formula Cd

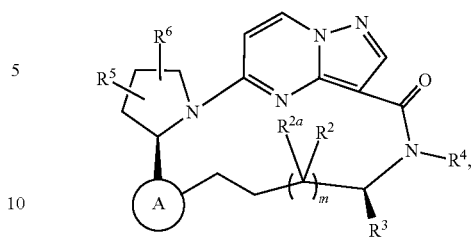

or a salt thereof.

In some embodiments, the compound of formula C has formula Ce formula Ce

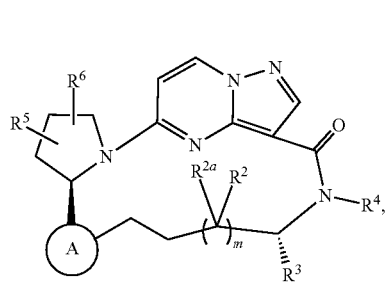

or a salt thereof.

In some embodiments, the compound of formula C has formula Cf formula Cf

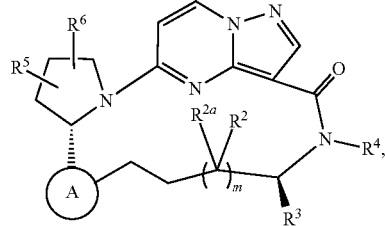

or a salt thereof.

In some embodiments, the compound of formula C has formula Cg formula Cg

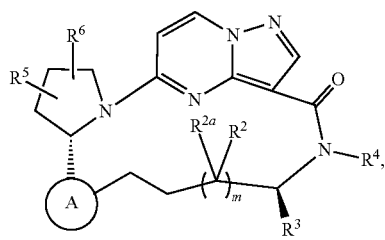

or a salt thereof.

In some embodiments, the compound of formula C has formula Ch

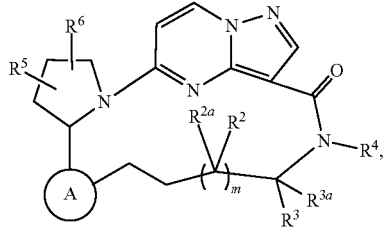

formula Ch or a salt thereof.

In some embodiments, the compound of formula C has formula Ci

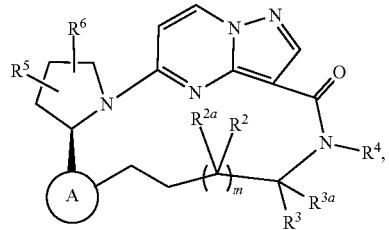

formula Ci or a salt thereof.

In some embodiments, the compound of formula C has formula Cj

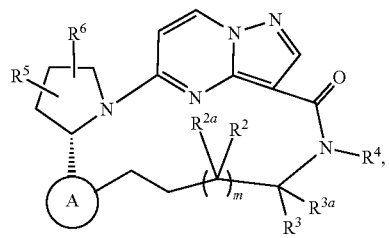

formula Cj or a salt thereof.

In some embodiments, the compound of formula C-I has formula C-Ib

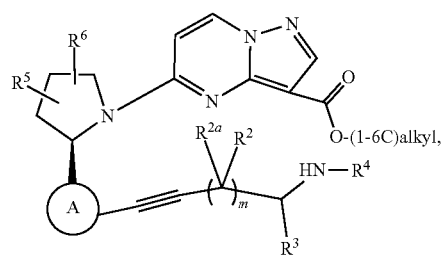

formula C-Ib or a salt thereof.

In some embodiments, the compound of formula C-I has formula C-Ic

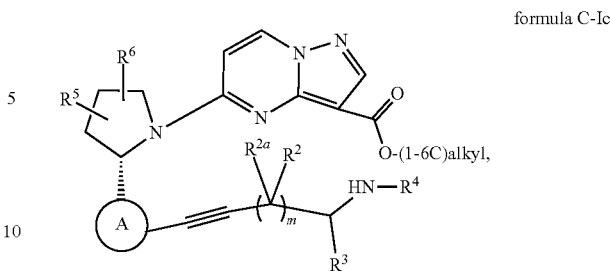

formula C-Ic or a salt thereof.

In some embodiments, the compound of formula C-I has formula C-Id

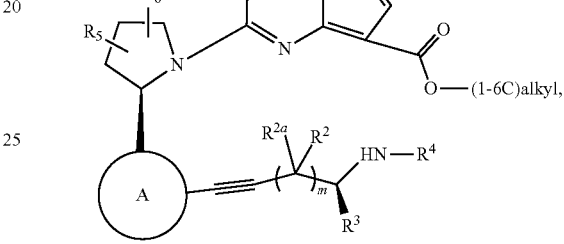

formula C-Id or a salt thereof.

In some embodiments, the compound of formula C-I has formula C-Ie

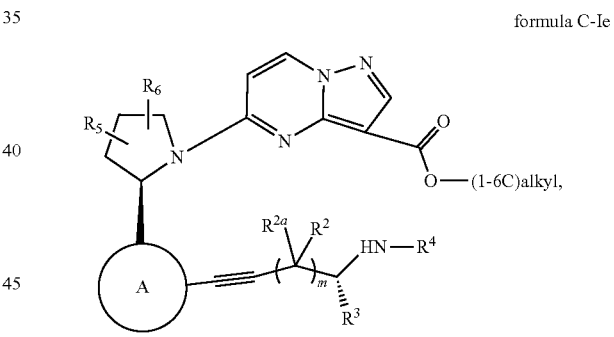

formula C-Ie or a salt thereof.

In some embodiments, the compound of formula C-I has formula C-If

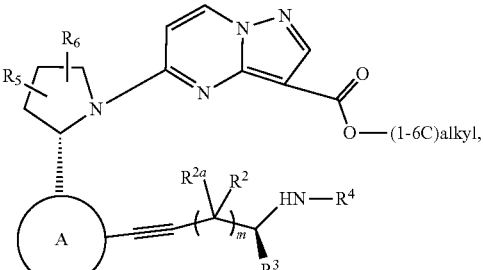

formula C-If or a salt thereof.

In some embodiments, the compound of formula C-I has formula C-Ig formula C-Ig

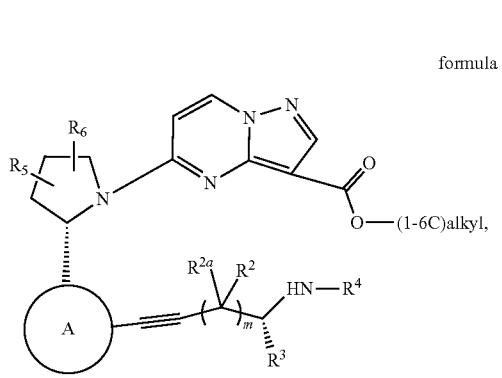

or a salt thereof.

In some embodiments, the compound of formula C-I has formula C-Ih formula C-Ih

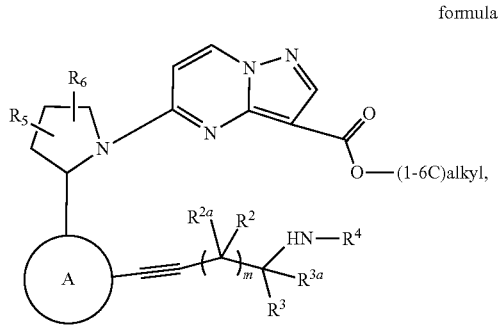

or a salt thereof.

In some embodiments, the compound of formula C-I has formula C-Ii formula C-Ii

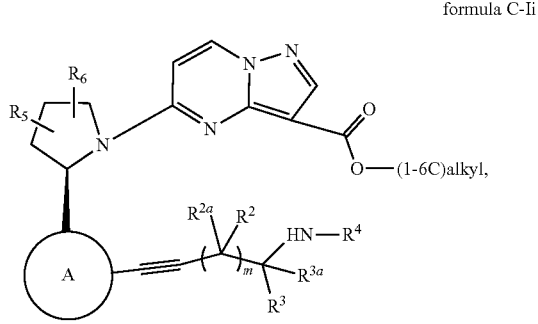

or a salt thereof.

In some embodiments, the compound of formula C-I has formula C-Ij formula C-Ij

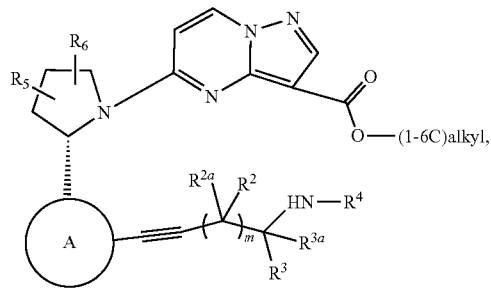

or a salt thereof.

In some embodiments, compound of formula C-II has formula C-IIb formula C-IIb

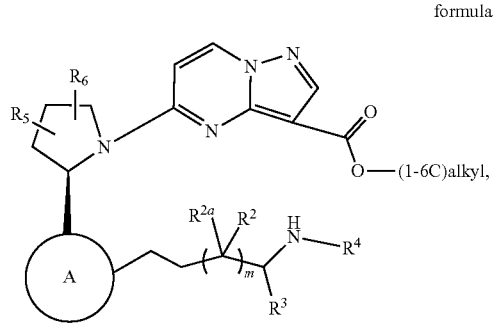

or a salt thereof.

In some embodiments, compound of formula C-II has formula C-IIc formula C-IIc

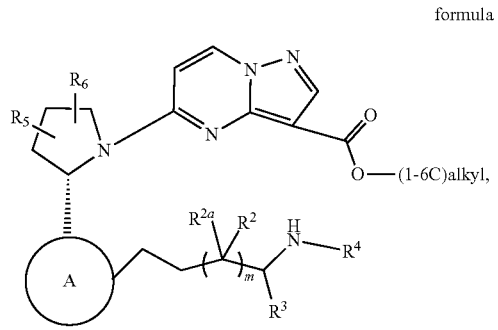

or a salt thereof.

In some embodiments, compound of formula C-II has formula C-IId formula C-IId

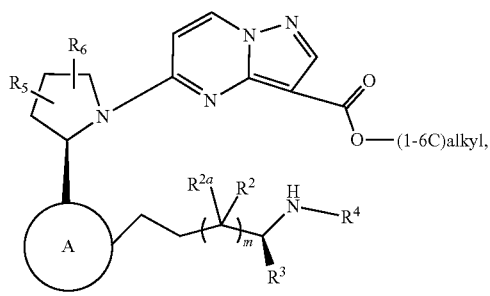

or a salt thereof.

In some embodiments, compound of formula C-II has formula C-IIe formula C-IIe

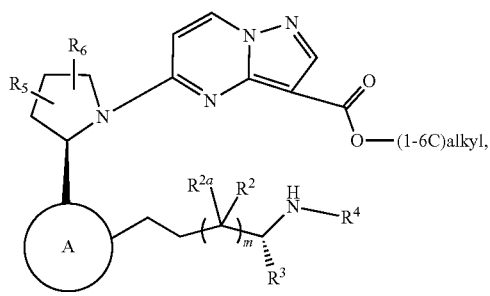

or a salt thereof.

In some embodiments, compound of formula C-II has formula C-IIf formula C-IIf

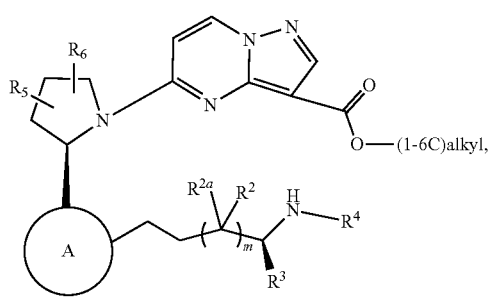

or a salt thereof.

In some embodiments, compound of formula C-II has formula C-IIg formula C-IIg

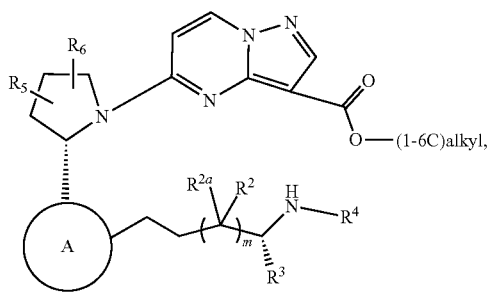

or a salt thereof.

In some embodiments, compound of formula C-II has formula C-IIh formula C-IIh

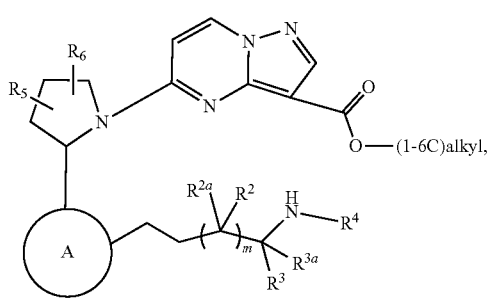

or a salt thereof.

In some embodiments, compound of formula C-II has formula C-IIi formula C-IIi

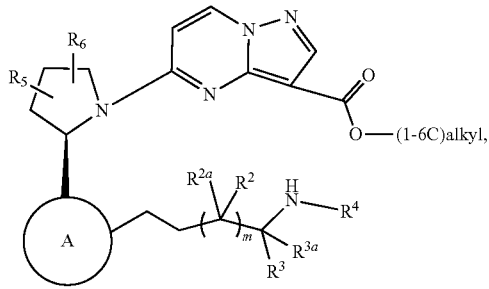

or a salt thereof.

In some embodiments, compound of formula C-II has formula C-IIj formula C-IIj

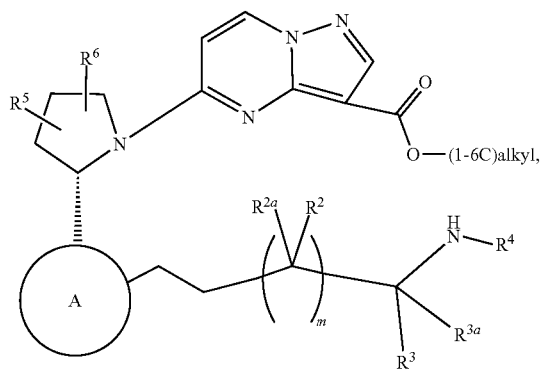

or a salt thereof.

In some embodiments, the compound of formula C-III has formula C-IIIb:

formula C-IIIb

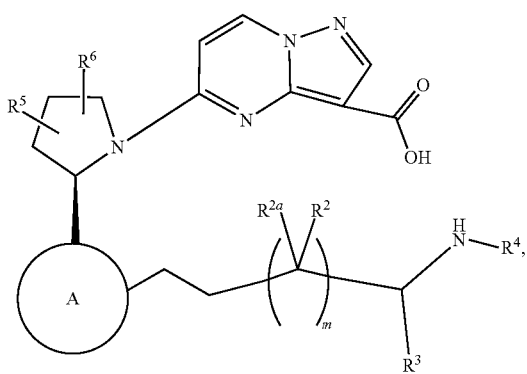

or a salt thereof.

In some embodiments, the compound of formula C-III has formula C-IIIc:

formula C-IIIc

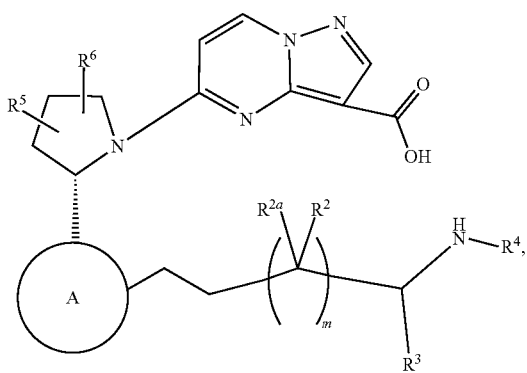

or a salt thereof.

In some embodiments, the compound of formula C-III has formula C-IIId:

formula C-IIId

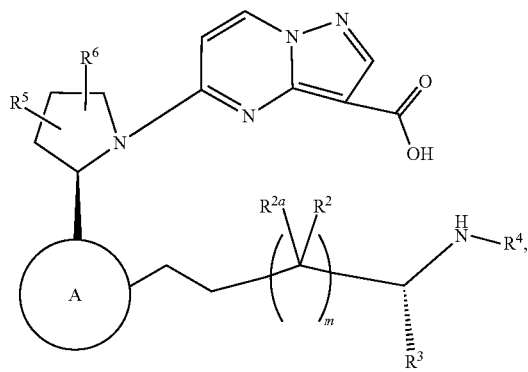

or a salt thereof.

In some embodiments, the compound of formula C-III has formula C-IIIe:

formula IIIe

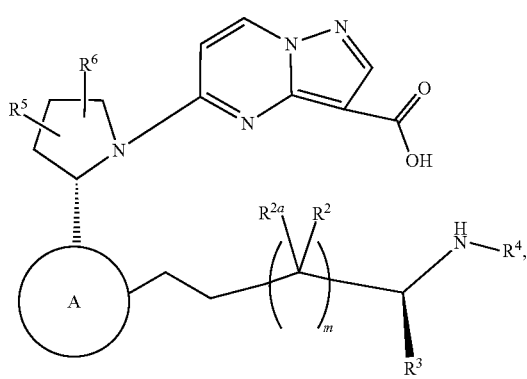

or a salt thereof.

In some embodiments, the compound of formula C-III has formula C-IIIf:

formula C-IIIf

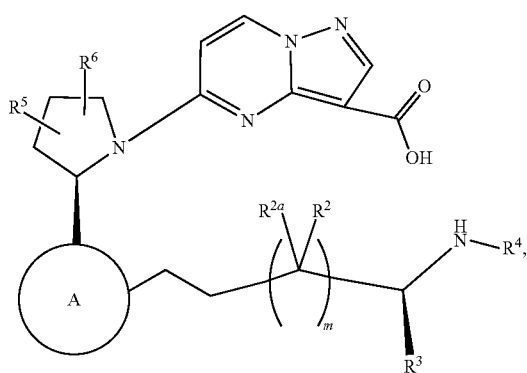

or a salt thereof.

In some embodiments, the compound of formula C-III has formula C-IIIg:

formula C-IIIg

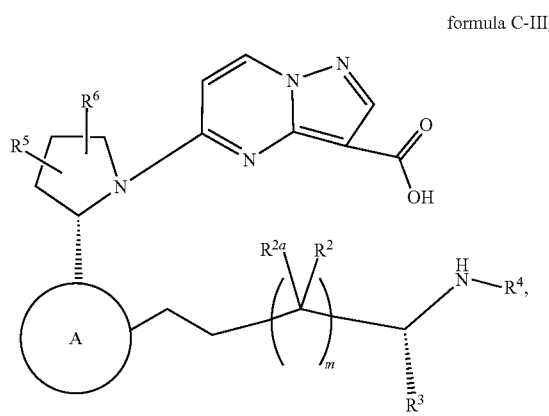

or a salt thereof.

In some embodiments, the compound of formula C-III has formula C-IIIh:

formula C-IIIh

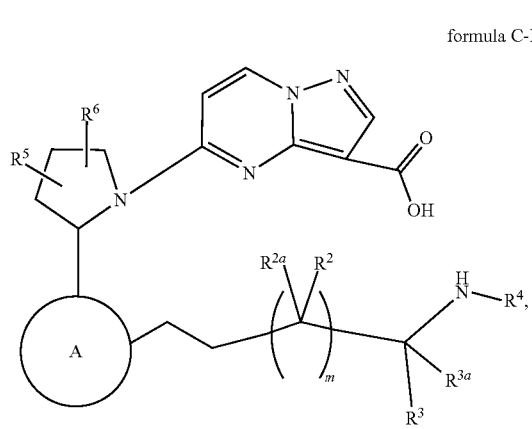

or a salt thereof.

In some embodiments, the compound of formula C-III has formula C-IIIi:

formula IIIi

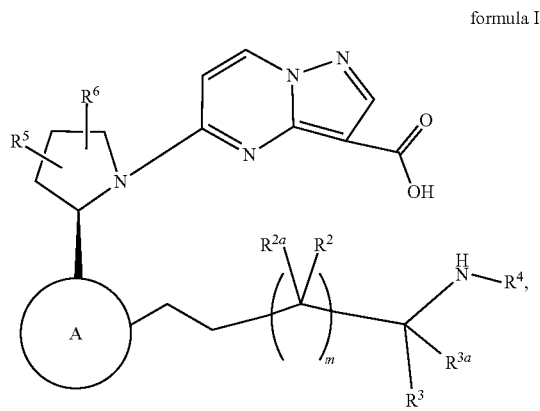

or a salt thereof.

In some embodiments, the compound of formula C-III has formula C-IIIj:

formula C-IIIj

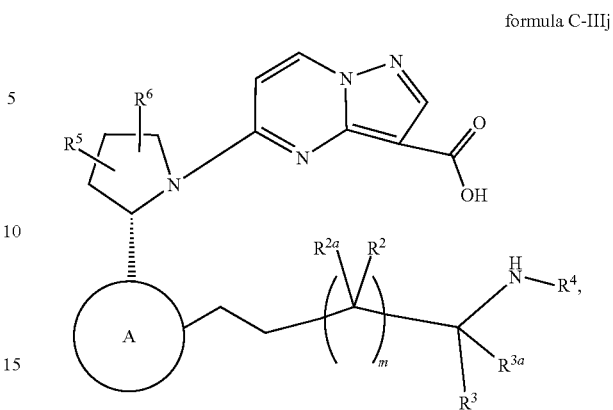

or a salt thereof.

In some embodiments, the compound of formula C-IV has formula C-IVa formula C-IVa

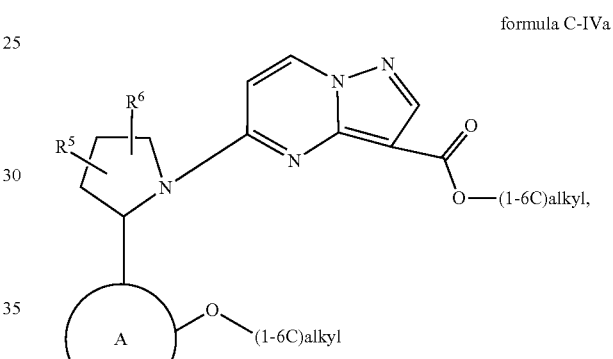

or a salt thereof.

In some embodiments, the compound of formula C-IV has formula C-IVb formula C-IVb

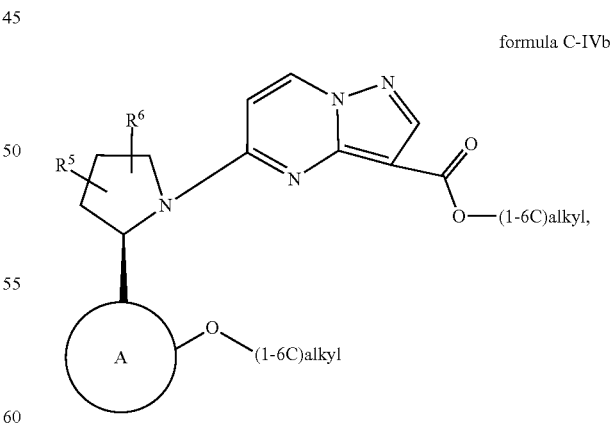

or a salt thereof.

In some embodiments, the compound of formula C-IV has formula C-IVc formula C-IVc

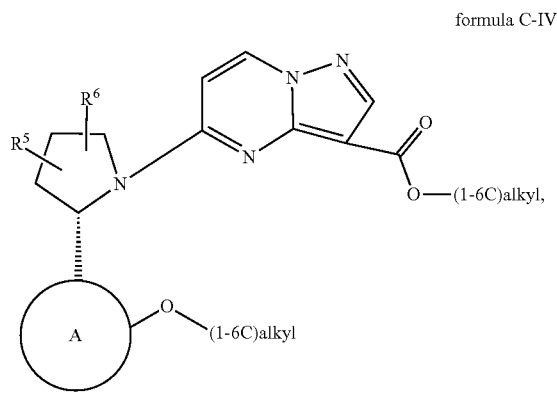

or a salt thereof.

In some embodiments, the compound of formula C-V has formula C-Va formula C-Va

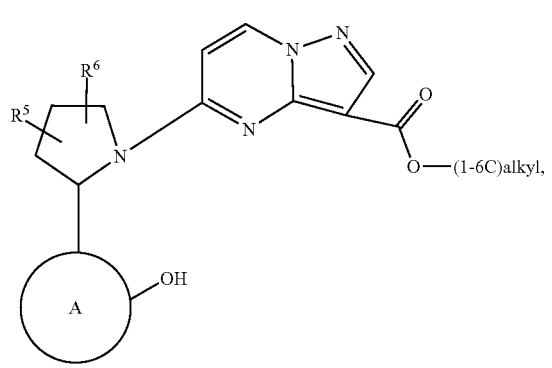

or a salt thereof.

In some embodiments, the compound of formula C-V has formula C-Vb formula C-Vb

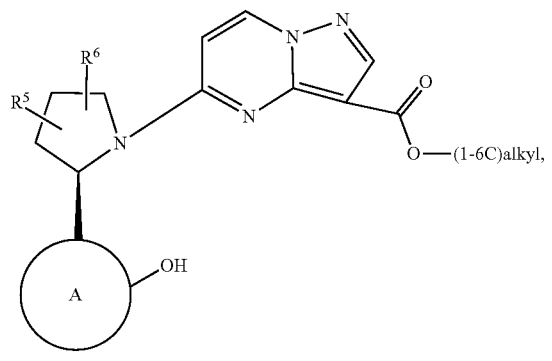

or a salt thereof.

In some embodiments, the compound of formula C-V has formula C-Vc formula C-Vc

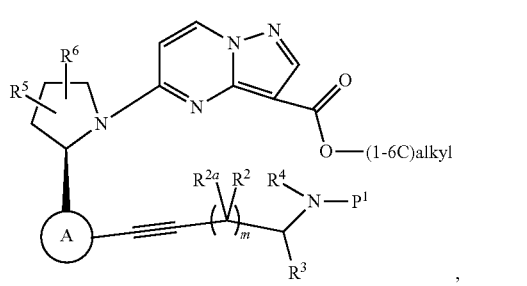

or a salt thereof.

In some embodiments, the compound of formula C-VI has formula C-VIb formula C-VIb or a salt thereof.

In some embodiments, the compound of formula C-VI has formula C-VIc formula C-VIc or a salt thereof.

In some embodiments, the compound of formula C-VII has formula C-VIIb formula C-VIIb or a salt thereof.

In some embodiments, the compound of formula C-VII has formula C-VIIc formula C-VIIc

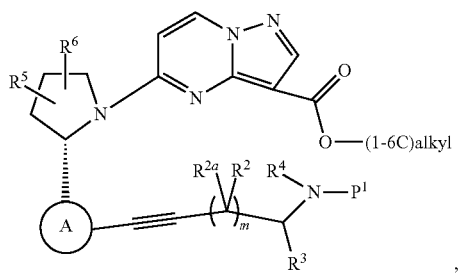

or a salt thereof.

In some embodiments, the compound of formula C-VII has formula C-VIId formula C-VIId

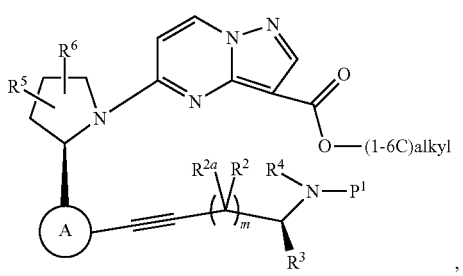

or a salt thereof.

In some embodiments, the compound of formula C-VII has formula C-VIIe formula C-VIIe

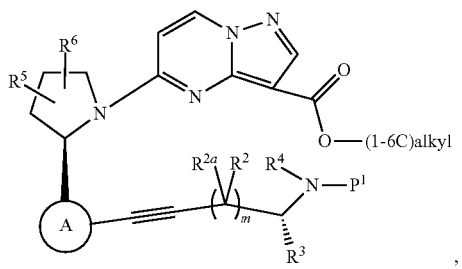

or a salt thereof.

In some embodiments, the compound of formula C-VII has formula C-VIIf formula C-VIIf

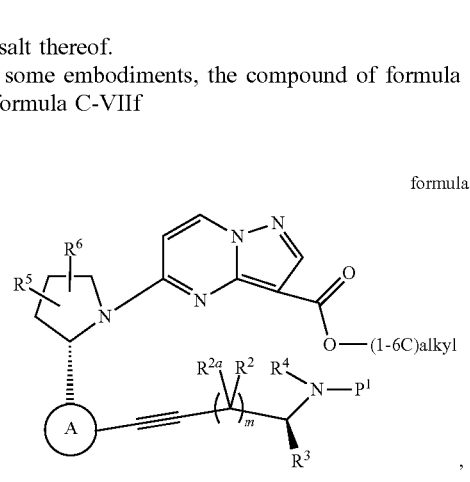

or a salt thereof.

In some embodiments, the compound of formula C-VII has formula C-VIIg formula C-VIIg

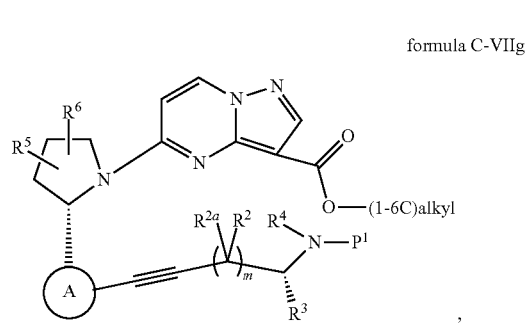

or a salt thereof.

In some embodiments, the compound of formula C-VII has formula C-VIIh formula C-VIIh

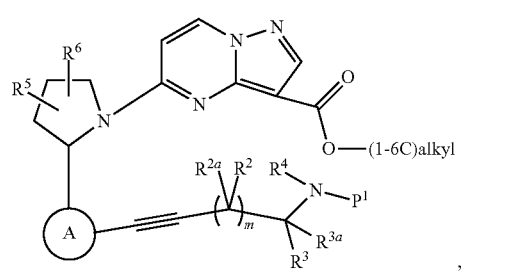

or a salt thereof.

In some embodiments, the compound of formula C-VII has formula C-VIIi formula C-VIIi

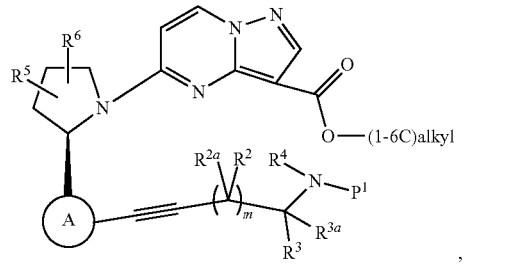

or a salt thereof.

In some embodiments, the compound of formula C-VII has formula C-VIIj formula C-VIIj

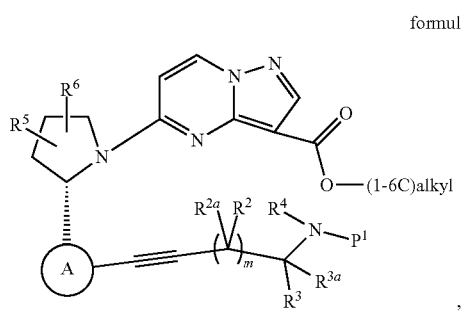

or a salt thereof.

In some embodiments, the compound of formula D-1 has formula D-1a formula D-1a

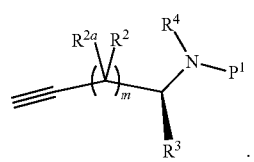

In some embodiments, the compound of formula D-1 has formula D-1b formula D-1b

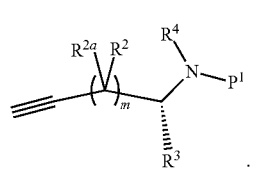

In some embodiments, the compound of formula D has formula D-2 formula D-2

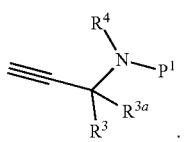

In some embodiments, the compound of formula D-2 has formula D-2a formula D-2a

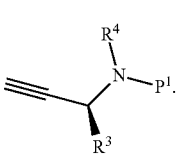

In some embodiments, the compound of formula D-2 has formula D-2b formula D-2b

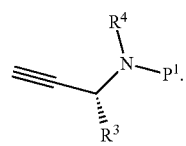

In some embodiments, the compound of formula D has formula D-3 formula D-3

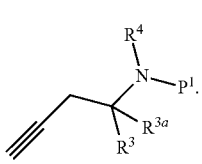

In some embodiments, the compound of formula D-3 has formula D-3a formula D-3a

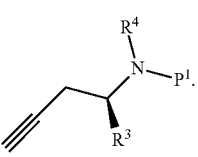

In some embodiments, the compound of formula D-3 has formula D-3b formula D-3b

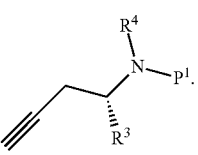

In some embodiments, the compound of formula D-3 has formula D-3c formula D-3c

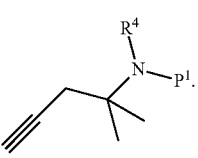

In any one of the formulae disclosed herein, ring A is selected from rings A-1 and A-3 having the structures:

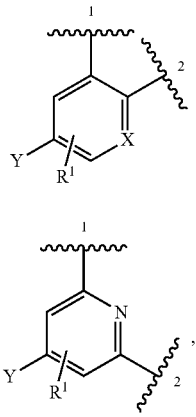

wherein in the ring of formulae A-1 or A-3 the wavy line labeled 1 indicates the point of attachment of ring A to ring B (e.g., the pyrrolidine ring), and the wavy line labeled 2 indicates the point of attachment of ring A to either i) the aliphatic chain connecting ring A to the $NR^4$ nitrogen, ii) OH, iii) O-(1-6C) alkyl, iv) $L^1$, or v) $OL^2$.

In some embodiments, ring A is ring A-1 having the structure

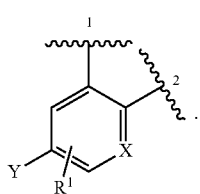

In some embodiments, X is CH. In other embodiments, X is N. In particular embodiments, ring A when represented by structure A-1 include the structures:

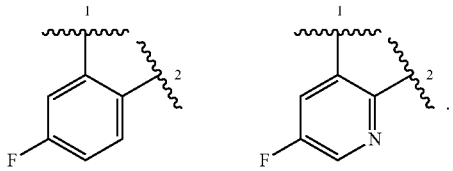

In some embodiments, ring A is ring A-3 having the structure

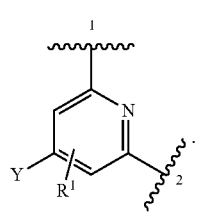

In any one of the embodiments of ring A, Y is H. In some embodiments, Y is halogen. For example, Y is Cl, F or Br. In some embodiments, Y is F. In any one of the embodiments of ring A, $R^1$ is H. In some embodiments, $R^1$ is (1-3C)alkyl or (1-3C)alkoxy. In one embodiment, $R^1$ is (1-3C)alkoxy. A particular example is methoxy. In one embodiment, $R^1$ is (1-3C)alkyl. A particular example is methyl. In some embodiments, $R^1$ is halogen. In one embodiment, $R^1$ is F.

In some embodiments of any one of the formulae disclosed herein, $R^4$ is H. In some embodiments, $R^4$ is (1-6C)alkyl, fluoro(1-6C)alkyl, difluoro(1-6C)alkyl, trifluoro(1-6C)alkyl, hydroxy(1-6C alkyl) or dihydroxy(2-6C alkyl). In one embodiments, $R^4$ is (1-6C)alkyl. Examples include methyl, ethyl, propyl, isopropyl, butyl, and isobutyl. In one embodiment, $R^4$ is fluoro(1-6C)alkyl. Examples include fluoromethyl and 2-fluoroethyl. In one embodiment, $R^4$ is difluoro(1-6C)alkyl. Example include difluoromethyl and 2,2-difluoroethyl. In one embodiment, $R^4$ is trifluoro(1-6C)alkyl. Examples include trifluoromethyl and 2,2,2-trifluoroethyl. In one embodiment, $R^4$ is hydroxy(1-6C alkyl). Examples include hydroxymethyl, 2-hydroxyethyl, 2-hydroxypropyl and 3-hydroxypropyl. In one embodiment, $R^4$ is dihydroxy(2-6C alkyl). An example includes 2,3-dihydroxypropyl. In one embodiments, $R^4$ is H or (1-6C)alkyl. In one embodiment, $R^4$ is H or methyl.

In some embodiments of any one of the formulae disclosed herein, $R^2$ and $R^{2a}$ are independently H, F, methyl or OH, provided that $R^2$ and $R^{2a}$ are not both OH. In some embodiments, $R^2$ and $R^{2a}$ are each hydrogen. In some embodiments, $R^2$ and $R^{2a}$ are each fluoro. In some embodiments, $R^2$ is hydrogen and $R^{2a}$ is fluoro. In some embodiments, $R^2$ is hydrogen and $R^{2a}$ is OH. In some embodiments, $R^2$ is H and $R^{2a}$ is (1-6C)alkyl. In some embodiments, $R^2$ is H and $R^{2a}$ is methyl. In some embodiments, $R^2$ and $R^{2a}$ are both (1-6 C) alkyl. In some embodiments, $R^2$ and $R^{2a}$ are both methyl.

In some embodiments of any one of the formulae disclosed herein, $R^3$ and $R^{3a}$ are independently H, (1-3C)alkyl or hydroxy(1-3 C)alkyl. In one embodiment, $R^{3a}$ is H. In one embodiment, $R^3$ is H. In some embodiments, $R^{3a}$ is H and $R^3$ is H. In one embodiment, $R^{3a}$ is (1-3C)alkyl. Examples include methyl, ethyl, propyl and isopropyl. In one embodiment, $R^3$ is (1-3C)alkyl. Examples include methyl, ethyl, propyl and isopropyl. In some embodiments, $R^{3a}$ is H, and $R^3$ is (1-3 C)alkyl or hydroxy(1-3 C)alkyl. In one embodiment, $R^{3a}$ is (1-3C)alkyl and $R^3$ is H. In one embodiment, $R^{3a}$ is methyl and $R^3$ is H. In one embodiment, $R^3$ is hydroxy(1-3C)alkyl. Examples include hydroxymethyl, 2-hydroxyethyl, 2-hydroxypropyl, and 3-hydroxypropyl. In one embodiment, $R^3$ is hydroxymethyl, 2-hydroxyethyl, 2-hydroxypropyl, or 3-hydroxypropyl and $R^{3a}$ is H. In some embodiments, $R^{3a}$ is H and $R^3$ is (1-3 C)alkyl. In some embodiments, $R^{3a}$ is H and $R^3$ is methyl. In one embodiment, $R^{3a}$ is (1-3C)alkyl and $R^3$ is H. In one embodiment, $R^{3a}$ is methyl and $R^3$ is H. In some embodiments, $R^{3a}$ and $R^3$ are both (1-3 C)alkyl. In some embodiments, $R^3$ and $R^{3a}$ are both methyl.

In some embodiments, $R^3$ and $R^{3a}$ are different, and the configuration of the carbon atom to which $R^3$ and $R^{3a}$ are attached is (S). In other embodiments, $R^3$ and $R^{3a}$ are different, and the configuration of the carbon atom to which $R^3$ and $R^{3a}$ are attached is (R). In some aspects of these embodiments, when $R^{3a}$ is hydrogen, $R^3$ is other than hydrogen and the configuration of the carbon atom to which $R^3$ is attached is (S). In other aspects of these embodiments, when $R^{3a}$ is hydrogen, $R^3$ is other than hydrogen and the configuration of the carbon atom to which $R^3$ is attached is (R).

In some embodiments of any one of the formulae disclosed herein, $R^5$ and $R^6$ are independently H, halogen, OH, (1-6C)alkyl or hydroxy(1-6C)alkyl. In one embodiment, $R^5$ and $R^6$ are independently H, F, OH, (1-6C)alkyl or hydroxy (1-6C)alkyl. In one embodiment, $R^5$ is H and $R^6$ is H, F, OH, (1-6C)alkyl or hydroxy(1-6C)alkyl. In some embodiments, $R^5$ and $R^6$ are independently H, F, OH, methyl, ethyl, $HOCH_2$— or $HOCH_2CH_2$—. In one embodiment, $R^5$ and $R^6$ are independently H, F, OH, (1-3C)alkyl or hydroxy(1-3C)alkyl. In one embodiment, $R^5$ is hydrogen and $R^6$ is H, F, OH, (1-3C)alkyl or hydroxy(1-3C)alkyl. In one embodiment, $R^5$ and $R^6$ are independently H, F, OH, methyl, ethyl, $HOCH_2$— or $HOCH_2CH_2$—. In one embodiment, $R^5$ is hydrogen and $R^6$ is H, F, OH, methyl, ethyl, $HOCH_2$— or $HOCH_2CH_2$—. In one embodiment, $R^5$ and $R^6$ are independently H, F, or methyl. In one embodiment, $R^5$ is H and $R^6$ is H, F, or methyl. In one embodiment, $R^5$ is H and $R^6$ is F. In one embodiment, $R^5$ is H and $R^6$ is methyl. In one embodiment, $R^5$ and $R^6$ are both H. In one embodiment, $R^5$ and $R^6$ are both F. In one embodiment, $R^5$ and $R^6$ are both methyl. In some embodiments, $R^5$ is hydrogen. In some embodiments, $R^6$ is hydrogen.

In some embodiments of formulae C, C-I, C-II, C-IV, C-V, C-VI and C-VII, ring B when represented by ring B-1 includes the structures:

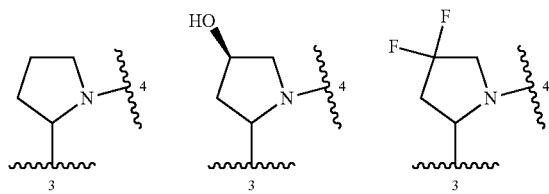 [SMILES: *C1CCCN1* ; *C1C[C@@H](O)CN1* ; *C1CC(F)(F)CN1*]

wherein the wavy line labeled 3 indicates the point of attachment to ring A and the wavy line labeled 4 indicates the point of attachment to the pyrazolo[1,5-a]pyrimidine ring.

In some embodiments of formulae C, C-I, C-II, C-IV, C-V, C-VI and C-VII, ring B is ring B-2 having the formula:

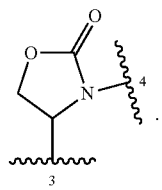

B-2

In some embodiments of any one of the formulae disclosed herein, m is 0, 1 or 2. In one embodiment, m is 0. In one embodiment, m is 1. In one embodiment, m is 2.

In some embodiments, one or more of C-VII, C-I, C-II and C-III are isolated after forming and prior to the respective following step in the process. In some embodiments, one or more of C-VII, C-I, C-II and C-III are not isolated after forming and prior to the respective following step in the process. In some embodiments, C-VII is not isolated after forming and prior to the following step in the process. In some embodiments, C-I is not isolated after forming and prior to the following step in the process. In some embodiments, C-II is not isolated after forming and prior to the following step in the process. In some embodiments, C-III is not isolated after forming after forming and prior to the following step in the process. In some embodiments, C-III is isolated after forming and prior to the following step in the process.

In some embodiments of any one of the formulae disclosed herein, $L^1$ is a leaving group selected from triflate, tosylate, mesylate, nosylate and a halogen. In some aspects of these embodiments, halogen is Cl, Br or I. In some embodiments, $L^1$ is a leaving group selected from triflate, tosylate, mesylate, and a halogen. In some embodiments, $L^1$ is triflate or mesylate. In one embodiment, $L^1$ is triflate. In some embodiments, $L^1$ is Cl or Br. In one embodiment, $L^1$ is Cl.

In some embodiments of any one of the formulae disclosed herein, $P^1$ is an amino-protecting group selected from methoxymethyl, methylthiomethyl, p-methoxybenzyloxymethyl, p-nitrobenzyloxymethyl, t-butoxymethyl, 2-methoxyethoxymethyl, 1-ethoxyethyl, allyl, p-methoxybenzyloxycarbonyl (Moz), p-nitrobenzyloxycarbonyl (PNZ), trimethylsilyl, diethylisopropylsilyl, triphenylsilyl, formyl, chloroacetyl, methanesulfonyl, tosyl, benzyl sulfonyl, methoxymethylcarbonyl, benzyloxycarbonyl, carboxybenzyl (Cbz), t-butyloxycarbonyl (BOC), 9-fluorenylmethylcarbonyl, N-phenylcarbamoyl, and 4,4'-dimethoxytrityl.

In some embodiments, $P^1$ is an amino-protecting group selected from p-methoxybenzyloxymethyl, p-methoxybenzyloxycarbonyl, trimethylsilyl, diethylisopropylsilyl, triphenylsilyl, methanesulfonyl, tosyl, benzyloxycarbonyl, t-butyloxycarbonyl (BOC), 9-fluorenylmethylcarbonyl and 4,4'-dimethoxytrityl.

In some embodiments, $P^1$ is an amino-protecting group selected from p-methoxybenzyloxycarbonyl, trimethylsilyl, benzyloxycarbonyl and t-butyloxycarbonyl (BOC).

In one embodiment, $P^1$ is t-butyloxycarbonyl (BOC).

In some embodiments, in any one of the formulae disclosed herein, ring A is selected from rings A-1 and A-3 having the structures:

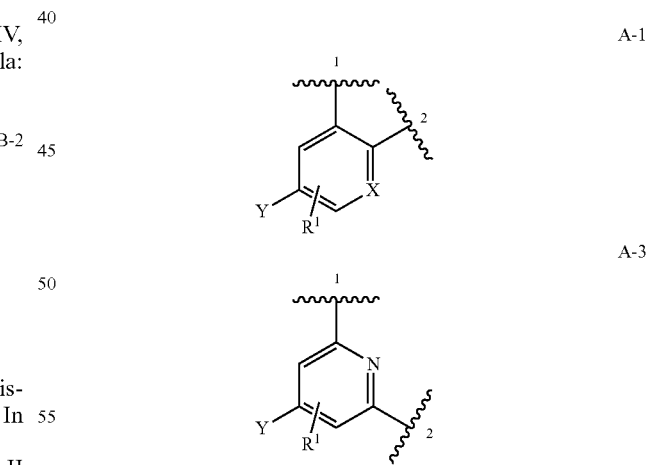

wherein in the ring of formulae A-1 or A-3 the wavy line labeled 1 indicates the point of attachment of ring A to ring B (e.g., the pyrrolidine ring), and the wavy line labeled 2 indicates the point of attachment of ring A to either i) the aliphatic chain connecting ring A to the $NR^4$ nitrogen, ii) OH, iii) O-(1-6C) alkyl, iv) $L^1$, or v) $OL^2$;

X is N or CH;

Y is H or F;

$R^1$ is H, (1-6C)alkyl, (1-3C)alkoxy or halogen;

m is 0, 1 or 2;

R² and R²ᵃ are independently H, F, or OH, provided that R² and R²ᵃ are not both OH;

R³ is H, (1-3 C)alkyl or hydroxy(1-3 C)alkyl;

R³ᵃ (when present) is H, (1-3 C)alkyl or hydroxy(1-3 C)alkyl;

R⁴ is H, (1-6C)alkyl, fluoro(1-6C)alkyl, difluoro(1-6C)alkyl, trifluoro(1-6C)alkyl, hydroxy(1-6C alkyl) or dihydroxy(2-6C alkyl);

R⁵ and R⁶ are independently H, halogen, OH, (1-6C)alkyl or hydroxy(1-6C)alkyl;

L¹ (when present) is a leaving group selected from triflate, tosylate, mesylate, and a halogen; and P¹ (when present) is an amino-protecting group selected from methoxybenzyloxymethyl, p-methoxybenzyloxycarbonyl, trimethylsilyl, diethylisopropylsilyl, triphenylsilyl, methanesulfonyl, tosyl, benzyloxycarbonyl, t-butyloxycarbonyl (BOC), 9-fluorenylmethylcarbonyl and 4,4'-dimethoxytrityl.

In some embodiments, in any one of the formulae disclosed herein, ring A is ring A-1 represented by the structure

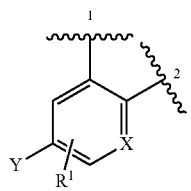

A-1 wherein in the ring of formulae A-1 the wavy line labeled 1 indicates the point of attachment of ring A to ring B (e.g., the pyrrolidine ring), and the wavy line labeled 2 indicates the point of attachment of ring A to either i) the aliphatic chain connecting ring A to the NR⁴ nitrogen, ii) OH, iii) O-(1-6C) alkyl, iv) L¹, or v) OL²;

X is N or CH;

Y is H or F;

R¹ is H, (1-6C)alkyl, (1-3C)alkoxy or halogen;

m is 0, 1 or 2;

R² and R²ᵃ are independently H, F, or OH, provided that R² and R²ᵃ are not both OH;

R³ is H, (1-3 C)alkyl or hydroxy(1-3 C)alkyl;

R³ᵃ (when present) is H, (1-3 C)alkyl or hydroxy(1-3 C)alkyl;

R⁴ is H, (1-6C)alkyl, fluoro(1-6C)alkyl, difluoro(1-6C)alkyl, trifluoro(1-6C)alkyl, hydroxy(1-6C alkyl) or dihydroxy(2-6C alkyl);

R⁵ and R⁶ are independently H, halogen, OH, (1-6C)alkyl or hydroxy(1-6C)alkyl;

L¹ (when present) is a leaving group selected from triflate, tosylate, mesylate, and a halogen; and P¹ (when present) is an amino-protecting group selected from methoxybenzyloxymethyl, p-methoxybenzyloxycarbonyl, trimethylsilyl, diethylisopropylsilyl, triphenylsilyl, methanesulfonyl, tosyl, benzyloxycarbonyl, t-butyloxycarbonyl (BOC), 9-fluorenylmethylcarbonyl and 4,4'-dimethoxytrityl.

In some embodiments, in any one of the formulae disclosed herein, ring A is ring A-3 represented by the structure

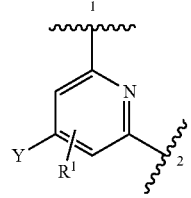

A-3 wherein in the ring of formulae A-3 the wavy line labeled 1 indicates the point of attachment of ring A to ring B (e.g., the pyrrolidine ring), and the wavy line labeled 2 indicates the point of attachment of ring A to either i) the aliphatic chain connecting ring A to the NR⁴ nitrogen, ii) OH, iii) O-(1-6C) alkyl, iv) L¹, or v) OL²;

Y is H or F;

R¹ is H, (1-6C)alkyl, (1-3C)alkoxy or halogen;

R² and R²ᵃ are independently H, F, or OH, provided that R² and R²ᵃ are not both OH;

R³ is H, (1-3 C)alkyl or hydroxy(1-3 C)alkyl;

R³ᵃ (when present) is H, (1-3 C)alkyl or hydroxy(1-3 C)alkyl;

R⁴ is H, (1-6C)alkyl, fluoro(1-6C)alkyl, difluoro(1-6C)alkyl, trifluoro(1-6C)alkyl, hydroxy(1-6C alkyl) or dihydroxy(2-6C alkyl);

R⁵ and R⁶ are independently H, halogen, OH, (1-6C)alkyl or hydroxy(1-6C)alkyl;

L¹ (when present) is a leaving group selected from triflate, tosylate, mesylate, and a halogen; and P¹ (when present) is an amino-protecting group selected from methoxybenzyloxymethyl, p-methoxybenzyloxycarbonyl, trimethylsilyl, diethylisopropylsilyl, triphenylsilyl, methanesulfonyl, tosyl, benzyloxycarbonyl, t-butyloxycarbonyl (BOC), 9-fluorenylmethylcarbonyl and 4,4'-dimethoxytrityl.

In some embodiments, in any one of the formulae disclosed herein, ring A is ring A-1 having the structure

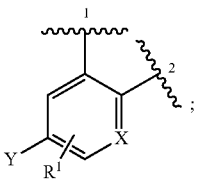

A-1

X is N;

Y is H or F;

R¹ is H or (1-6C)alkyl;

R⁴ is H or (1-6C)alkyl;

m is 0;

R³ᵃ (when present) is H and R³ is H;

R⁵ and R⁶ are each independently H or (1-6C)alkyl;

L¹ (when present) is a triflate leaving group; and

P¹ (when present) is a t-butyloxycarbonyl (BOC) amino-protecting group.

In some embodiments, in any one of the formulae disclosed herein, ring A is ring A-1 having the structure

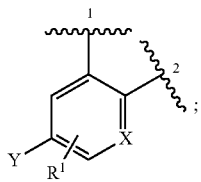

X is CH or N;
Y is H or F;
$R^1$ is H or (1-6C)alkyl;
$R^4$ is H or (1-6C)alkyl;
m is 0;
$R^{3a}$ (when present) is H and $R^3$ is (1-3 C)alkyl;
$R^5$ and $R^6$ are each independently H or (1-6C)alkyl;
$L^1$ (when present) is a triflate leaving group; and
$P^1$ (when present) is a t-butyloxycarbonyl (BOC) amino-protecting group.

In some embodiments, in any one of the formulae disclosed herein, ring A is ring A-1 having the structure

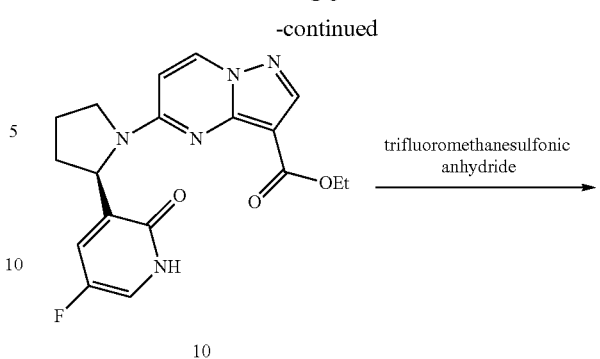

X is CH or N;
Y is H or F;
$R^1$ is H or (1-6C)alkyl;
$R^4$ is H or (1-6C)alkyl;
m is 0;
$R^{3a}$ is present, and $R^{3a}$ and $R^3$ are each (1-3 C)alkyl;
$R^5$ and $R^6$ are each independently H or (1-6C)alkyl;
$L^1$ (when present) is a triflate leaving group; and
$P^1$ (when present) is a t-butyloxycarbonyl (BOC) amino-protecting group.

The present application also provides, inter alia, a process for preparing a compound of Formula I, or a salt thereof, as set out, for example, in Scheme 2:

Scheme 2

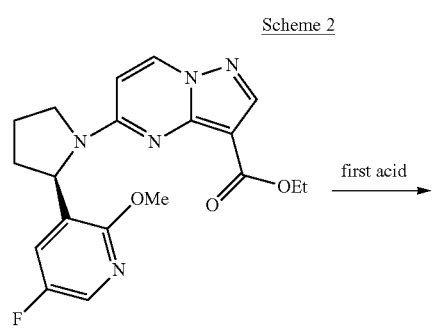

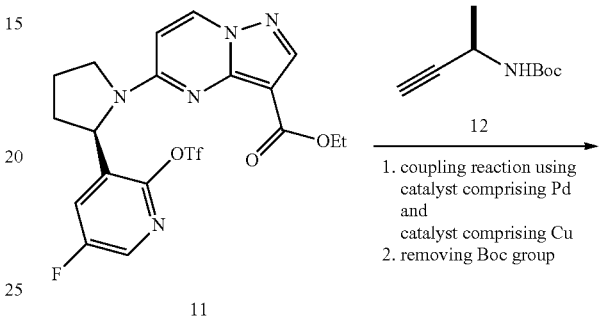

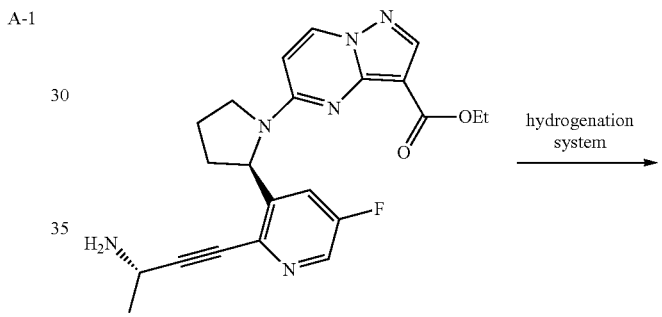

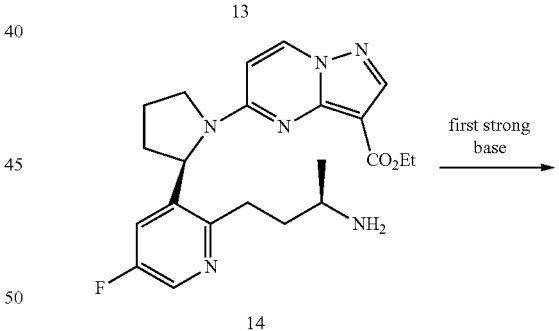

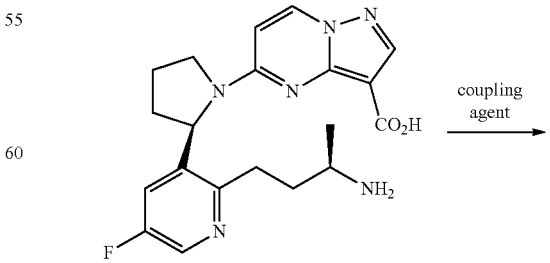

-continued

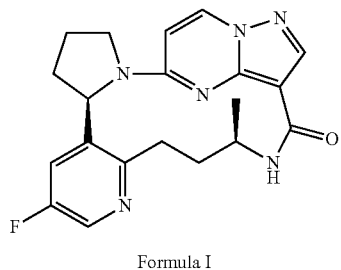

Formula I

In some embodiments, provided herein is a process for preparing a compound of Formula I

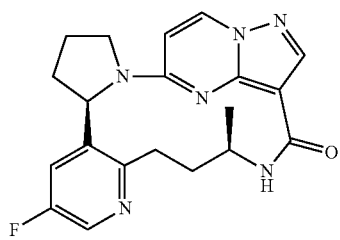

Formula I or a salt thereof, comprising:

a) treating a compound of formula 13

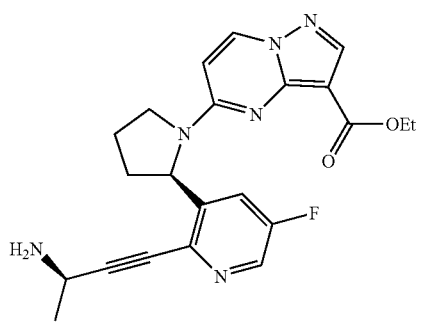

13 or a salt thereof with a hydrogenation system to form a compound of formula 14

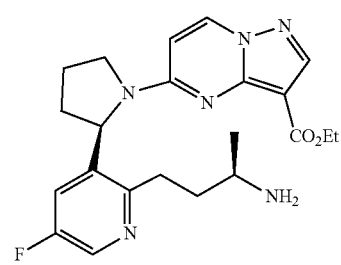

14 or a salt thereof;

b) treating the compound of formula 14 or a salt thereof with a first strong base to form a compound of formula 15

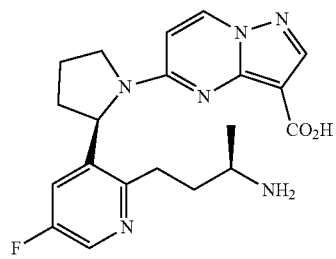

15 or a salt thereof; and c) cyclizing the compound of formula 15 or a salt thereof with a coupling agent to form the compound of Formula I or a salt thereof.

In some embodiments, provided herein is a process for preparing a compound of formula 14

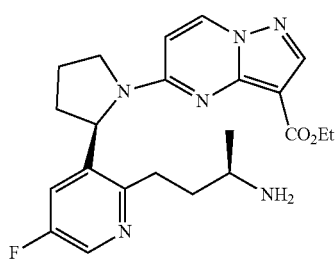

14 or a salt thereof, comprising treating a compound of formula 13

13 or a salt thereof, with a hydrogenation system to form the compound of formula 14 or a salt thereof.

In some embodiments, the process further comprises treating the compound of formula 14 or a salt thereof with a first strong base to form a compound of formula 15

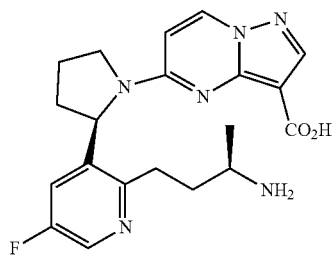

15 or a salt thereof.

In some embodiments, the process further comprises cyclizing the compound of formula 15 or a salt thereof with a coupling agent to form a compound of Formula I

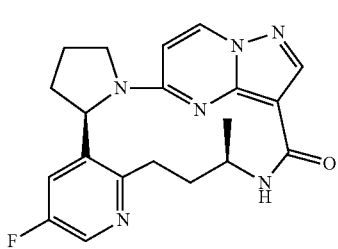

Formula I or a salt thereof.

In some embodiments, provided herein is a process for preparing a compound of formula 15

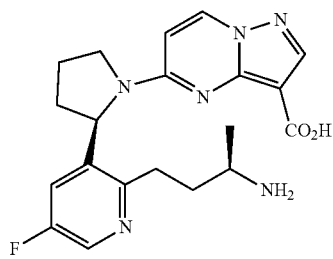

15 or a salt thereof, comprising treating a compound of formula 14

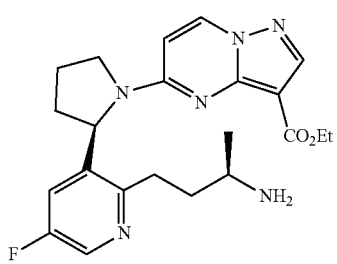

14 or a salt thereof, with a first strong base to form the compound of formula 15.

In some embodiments, the process further comprises cyclizing the compound of formula 15 or a salt thereof with a coupling agent to form a compound of Formula I

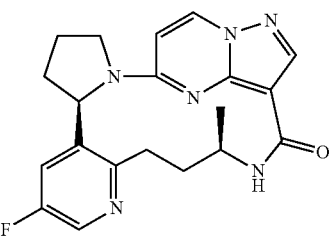

Formula I or a salt thereof.

In some embodiments, the process for preparing the compound of Formula I further comprises preparing the compound of formula 13

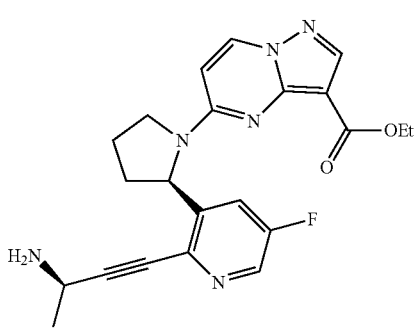

13 or a salt thereof, by a process comprising:
a) treating a compound of formula 9

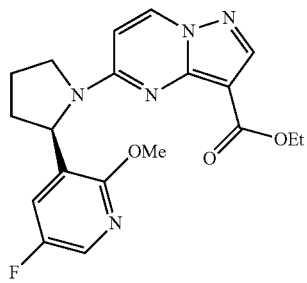

9 or a salt thereof with a first acid to form a compound of formula 10

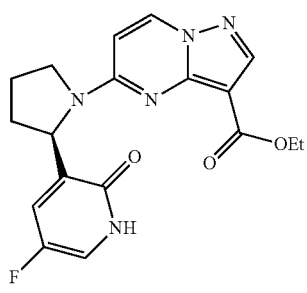

10 or a salt thereof;

b) treating the compound of formula 10 or a salt thereof with a reagent comprising a —S(O₂)LG moiety, such as a sulfonic anhydride, such as trifluoromethanesulfonic anhydride to form a compound of formula 11

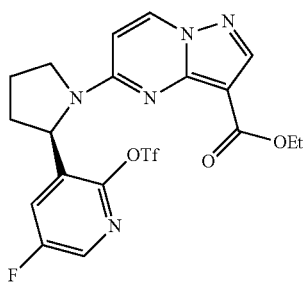

11 or a salt thereof; and c) coupling the compound of formula 11 or a salt thereof with a compound of formula 12

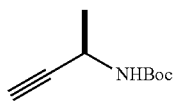

12 in the presence of a catalyst comprising palladium and a catalyst comprising copper; and d) deprotecting the product of the coupling of compound 11 and compound 12 to form the compound of formula 13 or a salt thereof.

In some embodiments step b) is replaced by a step comprising treating the compound of formula 10 or a salt thereof with a sulfonimide, such as N-Phenyl-bis(trifluoromethanesulfonimide), to form a compound of formula 11 or a salt thereof.

In some embodiments, provided herein is a process for preparing a compound of formula 10

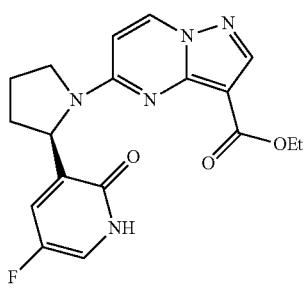

10 or a salt thereof, comprising treating a compound of formula 9

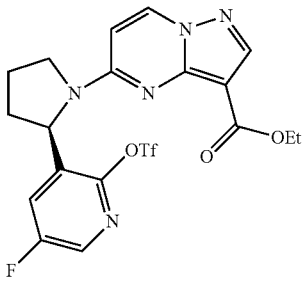

9 or a salt thereof with a first acid to form the compound of formula 10 or a salt thereof.

In some embodiments, the process further comprises treating the compound of formula 10 or a salt thereof with a reagent comprising a —S(O₂)LG moiety, such as a sulfonic anhydride, such as trifluoromethanesulfonic anhydride to form a compound of formula 11

11 or a salt thereof. In some embodiments, the process further comprises treating the compound of formula 10 or a salt thereof with a sulfonimide, such as N-Phenyl-bis(trifluoromethanesulfonimide), to form a compound of formula 11 or a salt thereof.

In some embodiments, the process further comprises coupling the compound of formula 11 or a salt thereof with a compound of formula 12

12 in the presence of a catalyst comprising palladium and a catalyst comprising copper; deprotecting the product of the coupling of compound 11 and compound 12 to form the compound of formula 13

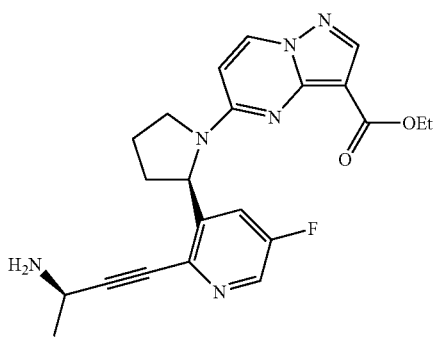

or a salt thereof.

In some embodiments, provided herein is a process for preparing a compound of formula 11

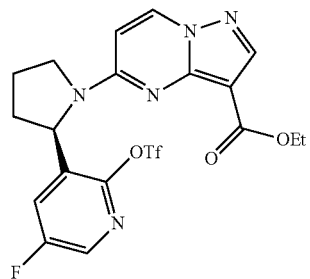

or a salt thereof, comprising treating a compound of formula 10

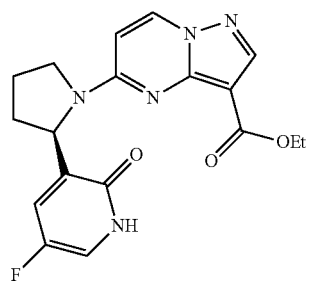

or a salt thereof with a reagent comprising a —S(O₂)LG moiety, such as a sulfonic anhydride, such as trifluoromethanesulfonic anhydride to form the compound of formula 11 or a salt thereof.

In some embodiments, provided herein is a process for preparing a compound of formula 11

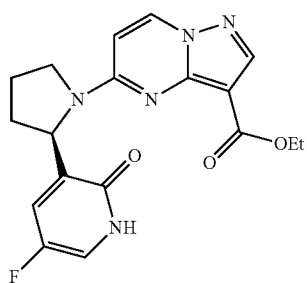

or a salt thereof, comprising treating a compound of formula 10

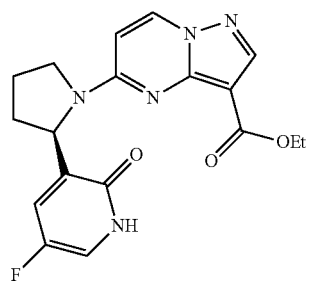

or a salt thereof with a sulfonimide, such as N-Phenyl-bis(trifluoromethanesulfonimide), to form a compound of formula 11 or a salt thereof.

In some embodiments, the process further comprises coupling the compound of formula 11 or a salt thereof with a compound of formula 12

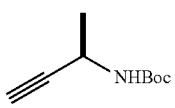

in the presence of a catalyst comprising palladium and a catalyst comprising copper; deprotecting the product of the coupling of compound 11 and compound 12 to form the compound of formula 13

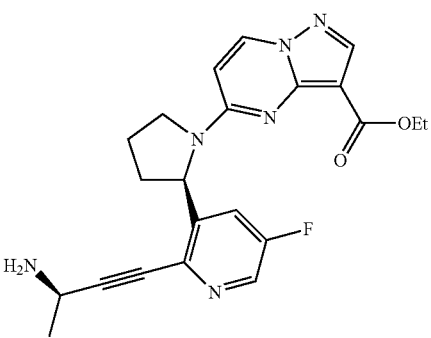

or a salt thereof.

In some embodiments, provided herein is a process for preparing a compound of formula 13

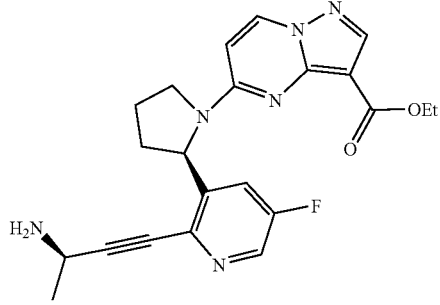

13 or a salt thereof, comprising coupling a compound of formula 11

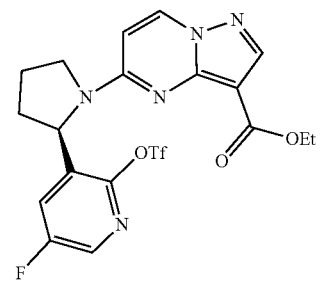

11 or a salt thereof with a compound of formula 12

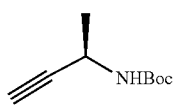

12 in the presence of a catalyst comprising palladium and a catalyst comprising copper; and deprotecting the product of the coupling of compound 11 and compound 12 to form the compound of formula 13 or a salt thereof.

The present application also provides, inter alia, a process for preparing a compound of Formula II, or a salt thereof, as set out, for example, in Scheme 3:

Scheme 3

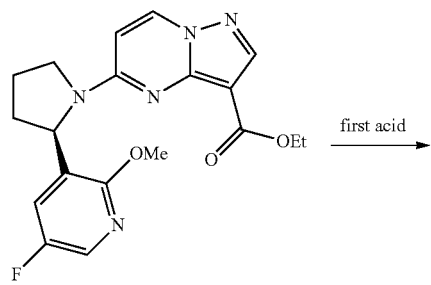

9

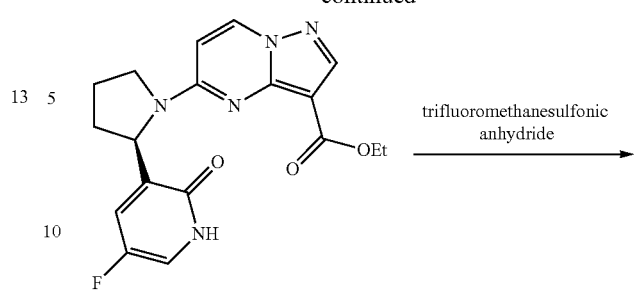

10 trifluoromethanesulfonic anhydride →

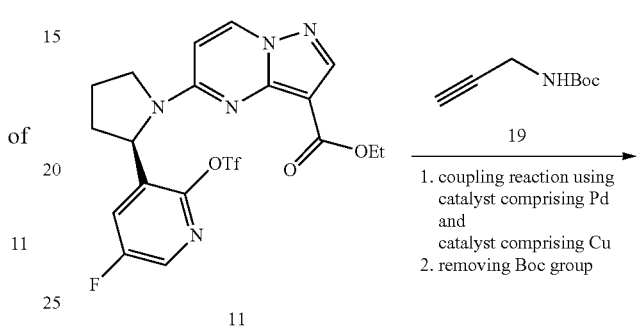

11

19
1. coupling reaction using catalyst comprising Pd and catalyst comprising Cu
2. removing Boc group
→

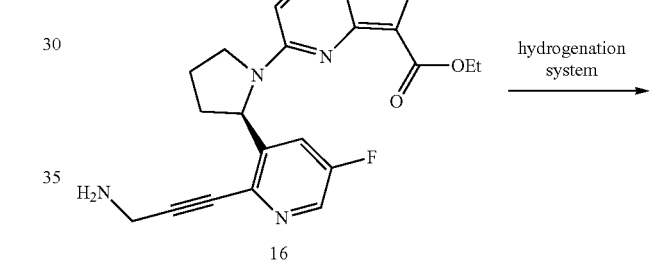

16 hydrogenation system →

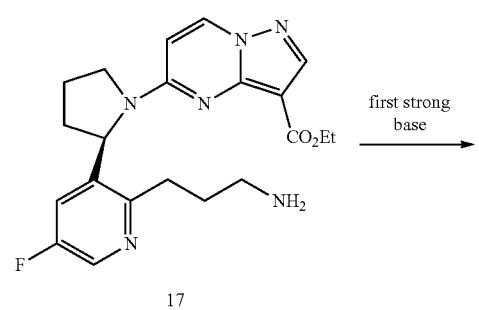

17 first strong base →

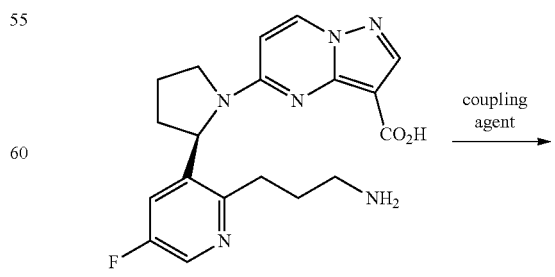

18 coupling agent →

-continued

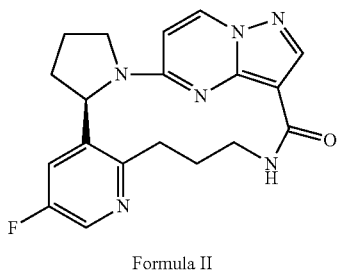

Formula II

In some embodiments, one or more of 10, 11, 16, 17 and 18 are isolated after forming and prior to the respective following step in the process. In some embodiments, one or more of 10, 11, 16, 17 and 18 are not isolated after forming and prior to the respective following step in the process. In some embodiments, 10 is not isolated after forming and prior to the following step in the process. In some embodiments, 11 is not isolated after forming and prior to the following step in the process. In some embodiments, 16 is not isolated after forming and prior to the following step in the process. In some embodiments, 17 is not isolated after forming and prior to the following step in the process. In some embodiments, 18 is not isolated after forming after forming and prior to the following step in the process. In some embodiments, 18 is isolated after forming after forming and prior to the following step in the process.

In some embodiments, provided herein is a process for preparing a compound of Formula II formula II

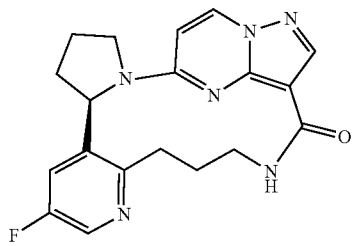

or a salt thereof, comprising:
a) treating a compound of formula 16

16

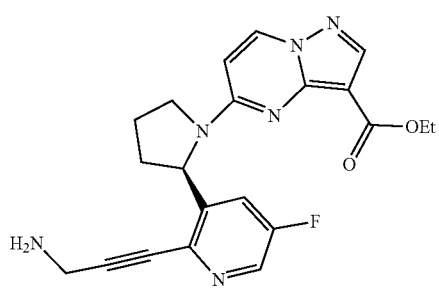

or a salt thereof with a hydrogenation system to form a compound of formula 17

17

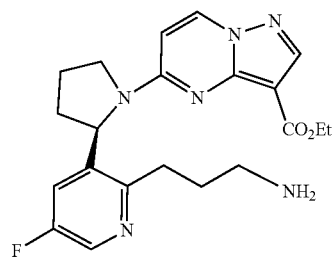

or a salt thereof;
b) treating the compound of formula 17 or a salt thereof with a first strong base to form a compound of formula 18

18

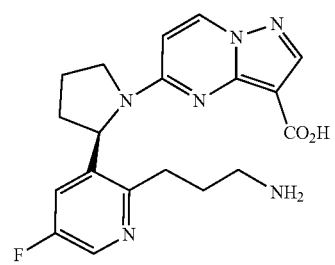 [SMILES: NCCCc1ncc(F)cc1[C@H]1CCCN1c1ccn2ncc(C(=O)O)c2n1]

or a salt thereof; and
c) cyclizing the compound of formula 18 or a salt thereof with a coupling agent to form the compound of Formula II or a salt thereof.

In some embodiments, provided herein is a process for preparing a compound of formula 17

17

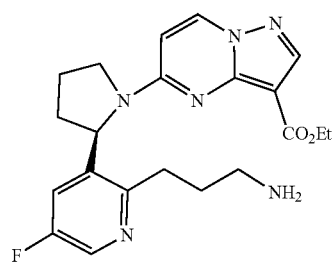

or a salt thereof, comprising treating a compound of formula 16

16

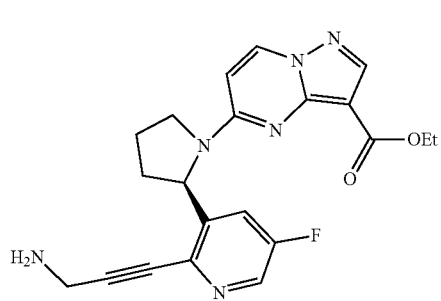

or a salt thereof, with a hydrogenation system to form the compound of formula 17 or a salt thereof.

In some embodiments, the process further comprises treating the compound of formula 17 or a salt thereof with a first strong base to form a compound of formula 18

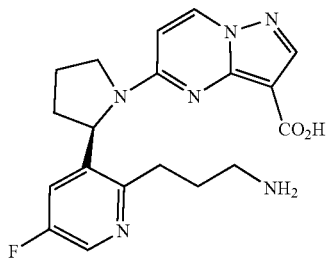

or a salt thereof.

In some embodiments, the process further comprises cyclizing the compound of formula 18 or a salt thereof with a coupling agent to form a compound of Formula II Formula II

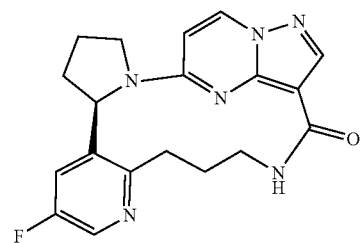

or a salt thereof.

In some embodiments, provided herein is a process for preparing a compound of formula 18

18

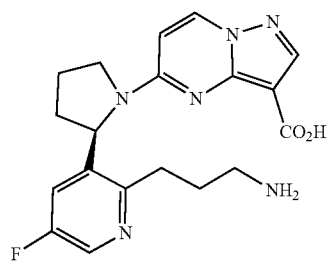

or a salt thereof, comprising treating a compound of formula 17

17

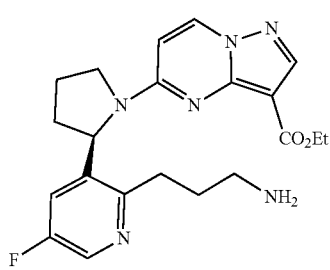

or a salt thereof, with a first strong base to form the compound of formula 18.

In some embodiments, the process further comprises cyclizing the compound of formula 18 or a salt thereof with a coupling agent to form a compound of Formula II Formula II

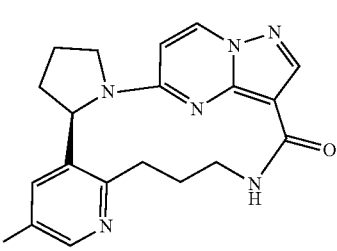

In some embodiments, the process for preparing the compound of Formula II further comprises preparing the compound of formula 16 or a salt thereof by a process comprising:

a) treating a compound of formula 9

9

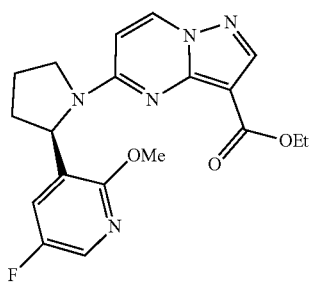

or a salt thereof with a first acid to form a compound of formula 10

10

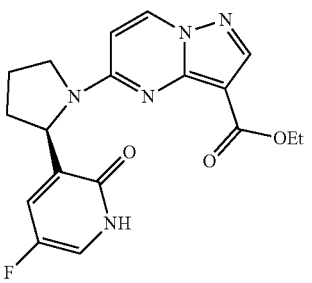

or a salt thereof;

b) treating the compound of formula 10 or a salt thereof with a reagent comprising a —S(O$_2$)LG moiety, such as a sulfonic anhydride, such as trifluoromethanesulfonic anhydride to form a compound of formula 11

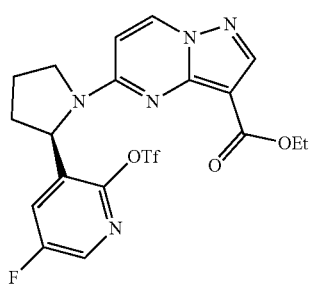

or a salt thereof;
c) coupling the compound of formula 11 with a compound of formula 19

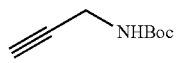

in the presence of a catalyst comprising palladium and a catalyst comprising copper; and
d) deprotecting the product of the coupling of compound 11 and compound 19 to form the compound of formula 16 or a salt thereof.

In some embodiments step b) is replaced by a step comprising treating the compound of formula 10 or a salt thereof with a sulfonimide, such as N-Phenyl-bis(trifluoromethanesulfonimide), to form a compound of formula 11 or a salt thereof.

In some embodiments, provided herein is a process for preparing a compound of formula 10

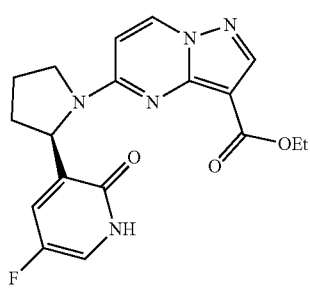

or a salt thereof, comprising treating a compound of formula 9

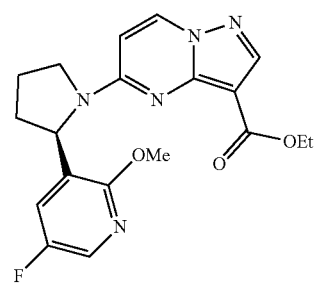

or a salt thereof with a first acid to form the compound of formula 10 or a salt thereof.

In some embodiments, the process further comprises treating the compound of formula 10 or a salt thereof with a reagent comprising a —S(O$_2$)LG moiety, such as a sulfonic anhydride, such as trifluoromethanesulfonic anhydride to form a compound of formula 11

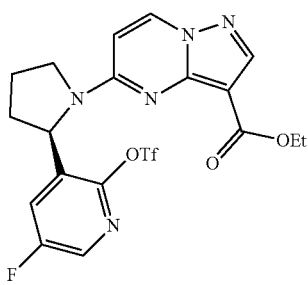

or a salt thereof.

In some embodiments, the process further comprises treating the compound of formula 10 or a salt thereof with a sulfonimide, such as N-Phenyl-bis(trifluoromethanesulfonimide), to form a compound of formula 11 or a salt thereof.

In some embodiments, the process further comprises coupling the compound of formula 11 or a salt thereof with a compound of formula 19

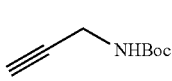

in the presence of a catalyst comprising palladium and a catalyst comprising copper; and deprotecting the product of the coupling of compound 11 and compound 19 to form a compound of formula 16

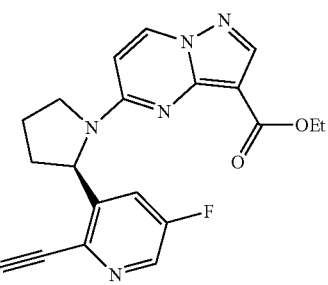

or a salt thereof.

In some embodiments, provided herein is a process for preparing a compound of formula 11

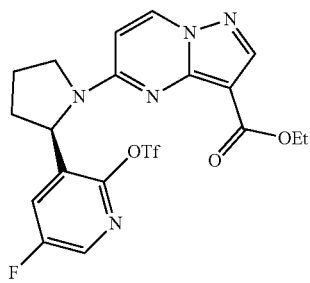

or a salt thereof, comprising treating a compound of formula 10

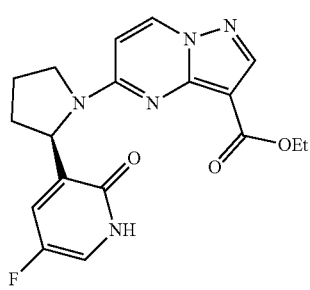

or a salt thereof with a reagent comprising a —S(O$_2$)LG moiety, such as a sulfonic anhydride, such as trifluoromethanesulfonic anhydride to form the compound of formula 11 or a salt thereof.

In some embodiments, provided herein is a process for preparing a compound of formula 11

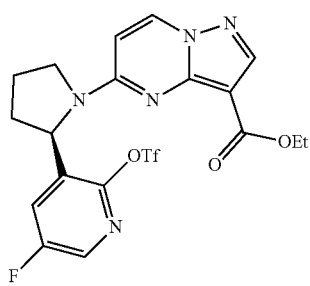

or a salt thereof, comprising treating a compound of formula 10

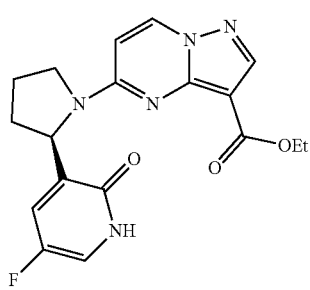

or a salt thereof with sulfonimide, such as N-Phenyl-bis(trifluoromethanesulfonimide), to form a compound of formula 11 or a salt thereof.

In some embodiments, the process further comprises coupling the compound of formula 11 or a salt thereof with a compound of formula 19

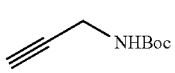

in the presence of a catalyst comprising palladium and a catalyst comprising copper; and deprotecting the product of the coupling of compound 11 and compound 19 to form a compound of formula 16

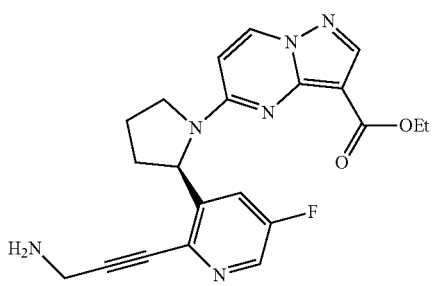

or a salt thereof.

In some embodiments, provided herein is a process for preparing a compound of formula 16

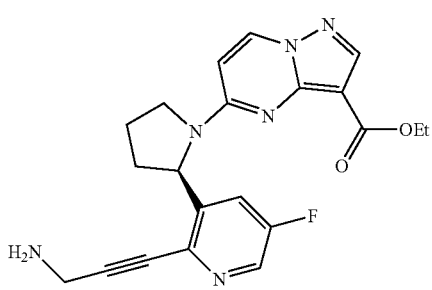

or a salt thereof, comprising coupling a compound of formula 11

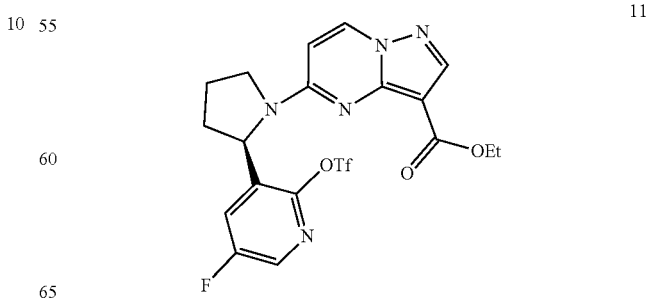

or a salt thereof with a compound of formula 19

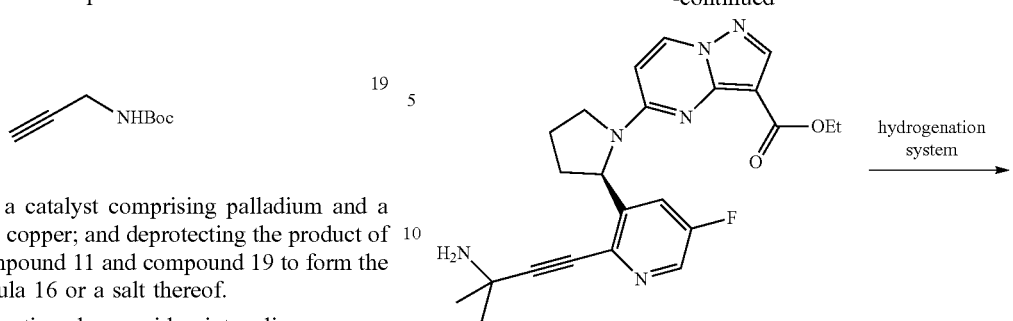

in the presence of a catalyst comprising palladium and a catalyst comprising copper; and deprotecting the product of the coupling of compound 11 and compound 19 to form the compound of formula 16 or a salt thereof.

The present application also provides, inter alia, a process for preparing a compound of Formula III, or a salt thereof, as set out, for example, in Scheme 4:

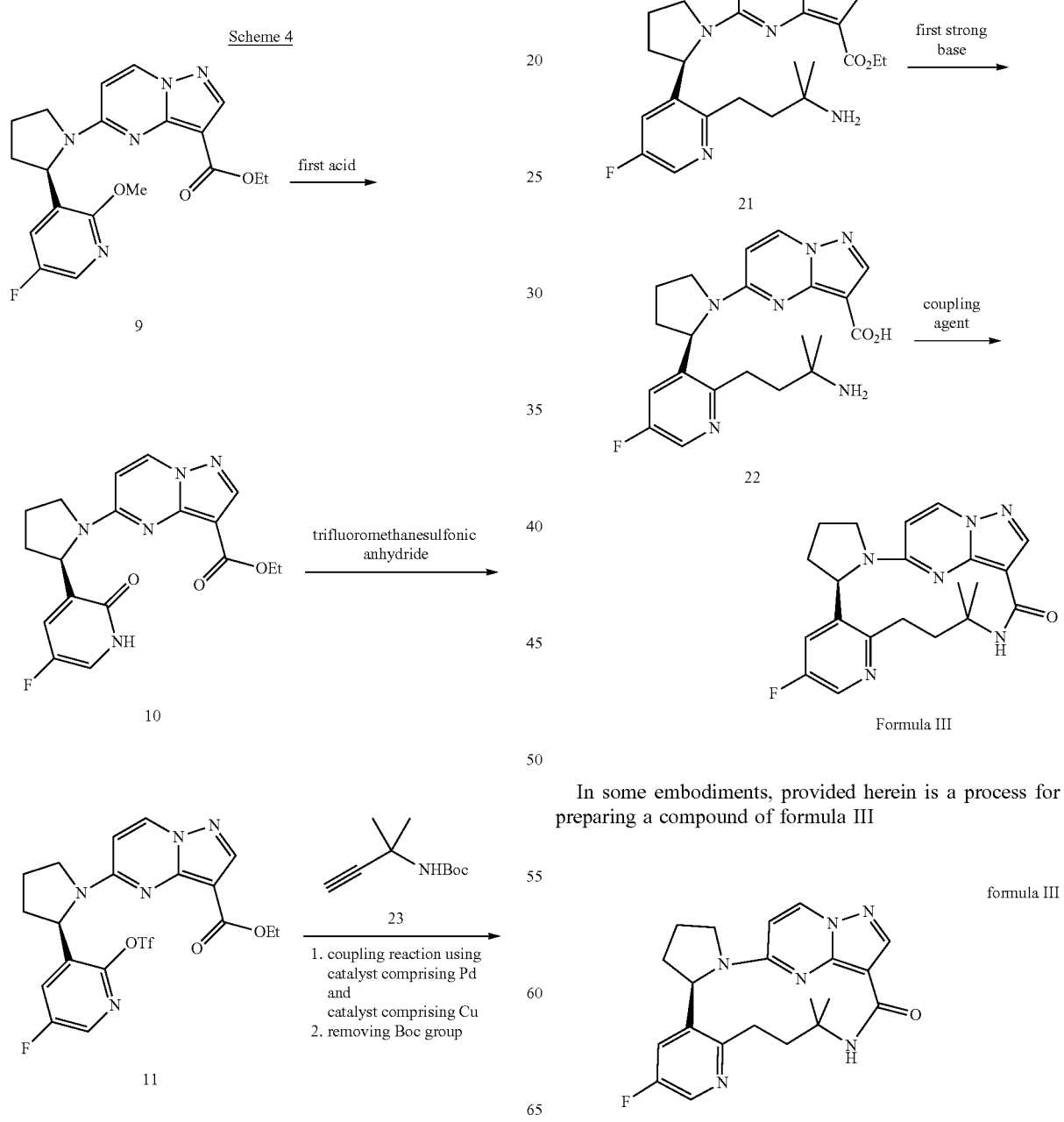

In some embodiments, provided herein is a process for preparing a compound of formula III or a salt thereof, comprising:

a) treating a compound of formula 20

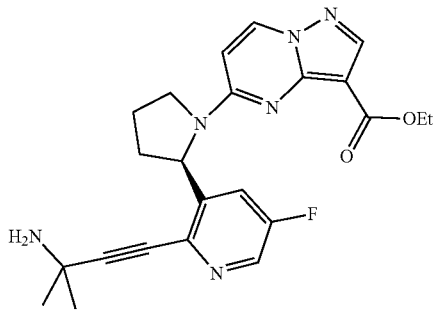

20 or a salt thereof with a hydrogenation system to form a compound of formula 21

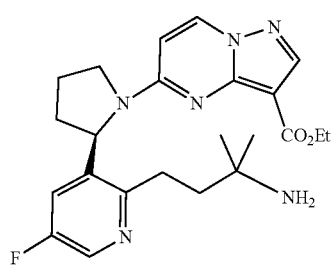

21 or a salt thereof;

b) treating the compound of formula 21 or a salt thereof with a first strong base to form a compound of formula 22

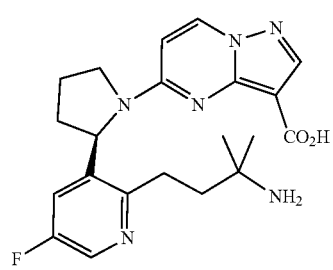

22 or a salt thereof; and c) cyclizing the compound of formula 22 or a salt thereof with a coupling agent to form the compound of Formula III or a salt thereof.

In some embodiments, provided herein is a process for preparing a compound of formula 22

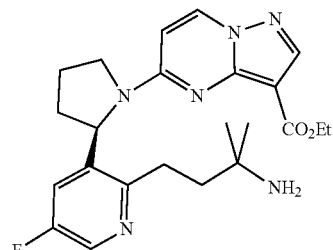

21 or a salt thereof, comprising treating a compound of formula 20

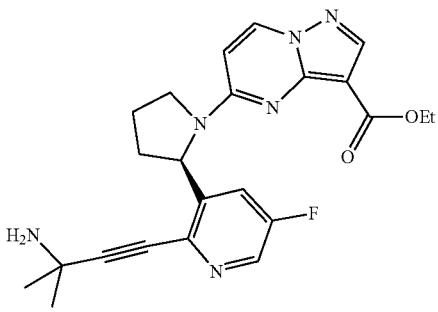

20 or a salt thereof, with a hydrogenation system to form the compound of formula 21 or a salt thereof.

In some embodiments, the process further comprises treating the compound of formula 21 or a salt thereof with a first strong base to form a compound of formula 22

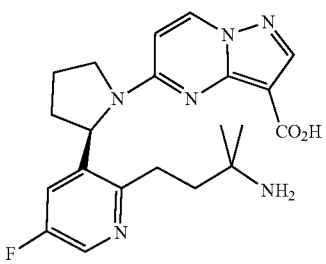

22 or a salt thereof.

In some embodiments, the process further comprises cyclizing the compound of formula 22 or a salt thereof with a coupling agent to form a compound of Formula III Formmula III

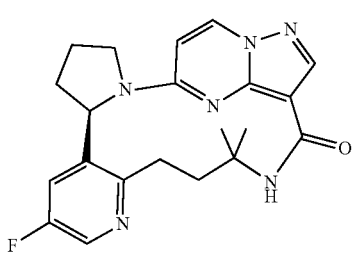

or a salt thereof.

In some embodiments, provided herein is a process for preparing a compound of formula 22

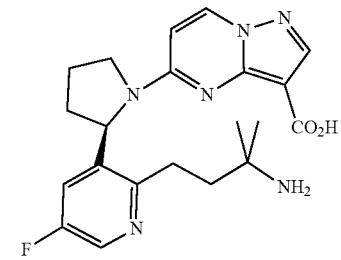
22 or a salt thereof, comprising treating a compound of formula 21

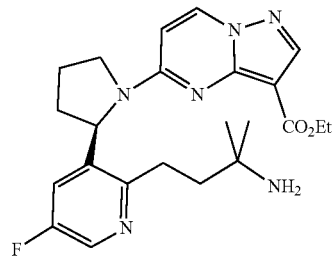
21 or a salt thereof, with a first strong base to form the compound of formula 22.

In some embodiments, the process further comprises cyclizing the compound of formula 22 or a salt thereof with a coupling agent to form a compound of Formula III Formula III

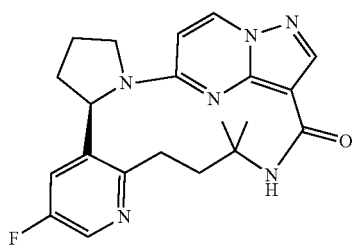

In some embodiments, the process for preparing the compound of Formula III further comprises preparing the compound of formula 20 or a salt thereof by a process comprising:

a) treating a compound of formula 9

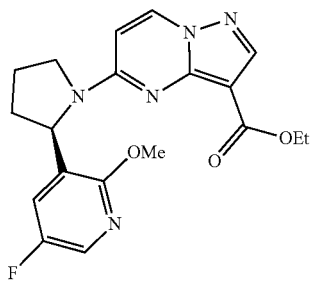
9 or a salt thereof with a first acid to form a compound of formula 10

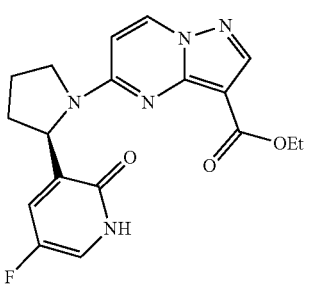
10 or a salt thereof;

b) treating the compound of formula 10 or a salt thereof with a reagent comprising a —S(O$_2$)LG moiety, such as a sulfonic anhydride, such as trifluoromethanesulfonic anhydride to form a compound of formula 11

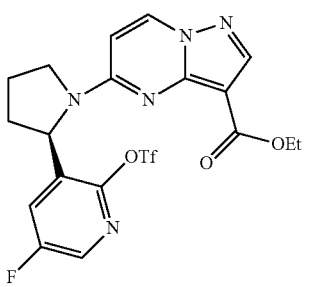
11 or a salt thereof;

c) coupling the compound of formula 11 with a compound of formula 23

23 in the presence of a catalyst comprising palladium and a catalyst comprising copper; and d) deprotecting the product of the coupling of compound 11 and compound 23 to form the compound of formula 20 or a salt thereof.

In some embodiments step b) is replaced by a step comprising treating the compound of formula 10 or a salt thereof with a sulfonimide, such as N-Phenyl-bis(trifluoromethanesulfonimide), to form a compound of formula 11 or a salt thereof.

In some embodiments, provided herein is a process for preparing a compound of formula 10

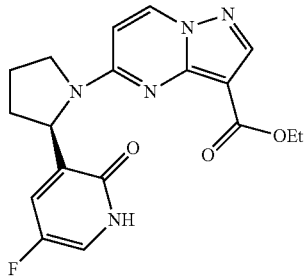

10 or a salt thereof, comprising treating a compound of formula 9

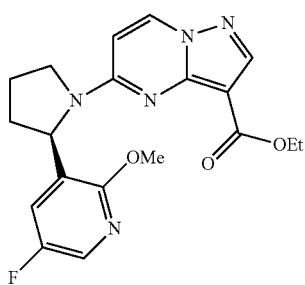

9 or a salt thereof with a first acid to form the compound of formula 10 or a salt thereof.

In some embodiments, the process further comprises treating the compound of formula 10 or a salt thereof with a reagent comprising a —S(O₂)LG moiety, such as a sulfonic anhydride, such as trifluoromethanesulfonic anhydride to form a compound of formula 11

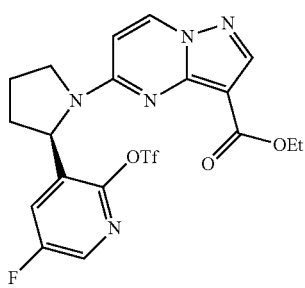

11 or a salt thereof.

In some embodiments, the process further comprises treating the compound of formula 10 or a salt thereof with a sulfonimide, such as N-Phenyl-bis(trifluoromethanesulfonimide), to form a compound of formula 11 or a salt thereof.

In some embodiments, the process further comprises coupling the compound of formula 11 or a salt thereof with a compound of formula 23

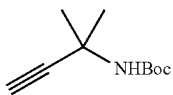

23 in the presence of a catalyst comprising palladium and a catalyst comprising copper; and deprotecting the product of the coupling of compound 11 and compound 23 to form a compound of formula 20

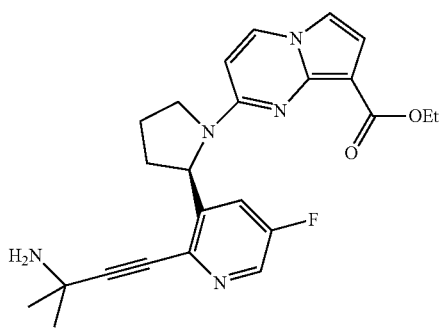

20 or a salt thereof.

In some embodiments, provided herein is a process for preparing a compound of formula 11

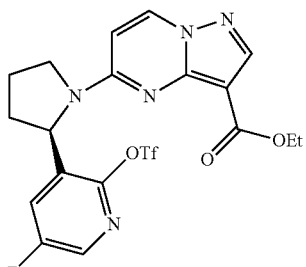

11 or a salt thereof, comprising treating a compound of formula 10

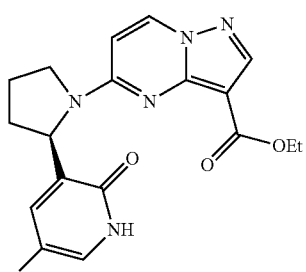

10 or a salt thereof with a reagent comprising a —S(O₂)LG moiety, such as a sulfonic anhydride, such as trifluoromethanesulfonic anhydride to form the compound of formula 11 or a salt thereof.

In some embodiments, the process further comprises coupling the compound of formula 11 or a salt thereof with a compound of formula 23

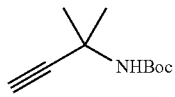

in the presence of a catalyst comprising palladium and a catalyst comprising copper; and deprotecting the product of the coupling of compound 11 and compound 23 to form a compound of formula 20

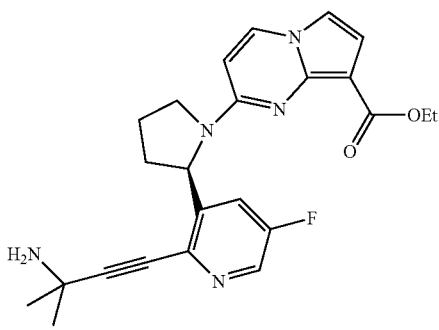

or a salt thereof.

In some embodiments, provided herein is a process for preparing a compound of formula 20

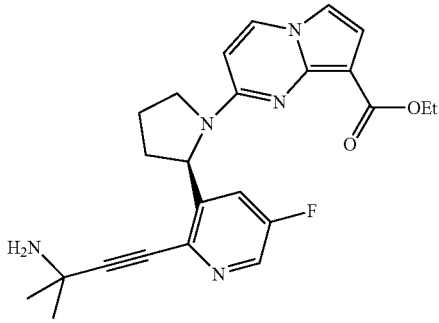

or a salt thereof, comprising coupling a compound of formula 11 or a salt thereof with a compound of formula 23

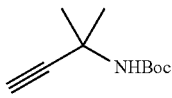

in the presence of a catalyst comprising palladium and a catalyst comprising copper; and deprotecting the product of the coupling of compound 11 and compound 23 to form the compound of formula 20 or a salt thereof.

In some embodiments, provided herein is a process for the preparation of the compound of formula C, wherein the process does not comprise a chromatographic purification step following the formation of the compound of formula C.

In some embodiments, provided herein is a process for the preparation of the compound of Formula I, wherein the process does not comprise a chromatographic purification step following the formation of the compound of Formula I.

In some embodiments, provided herein is a process for the preparation of the compound of Formula II, wherein the process does not comprise a chromatographic purification step following the formation of the compound of Formula II.

In some embodiments, provided herein is a process for the preparation of the compound of Formula III, wherein the process does not comprise a chromatographic purification step following the formation of the compound of Formula III.

In some embodiments, provided herein is a compound of formula C-I

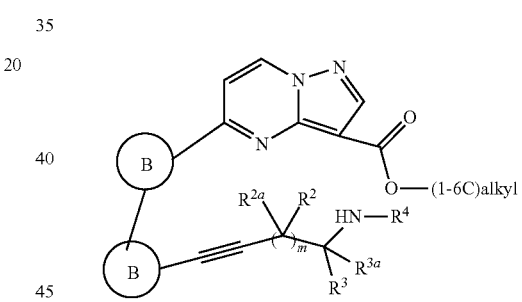

or a salt thereof.

In some embodiments, provided herein is a compound of formula C-II

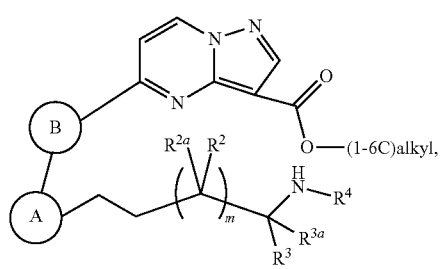

or a salt thereof.

In some embodiments, provided herein is a compound of formula C-III formula C-III

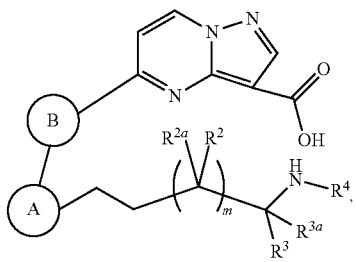

or a salt thereof.

In some embodiments, provided herein is a compound of formula 13

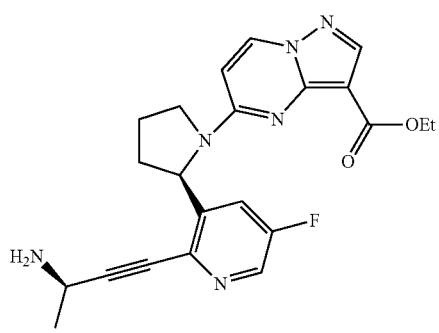

or a salt thereof.

In some embodiments, provided herein is a compound of formula 14

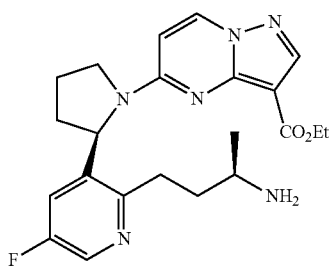

or a salt thereof.

In some embodiments, provided herein is a compound of formula 15

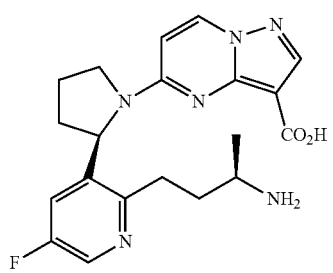

or a salt thereof.

In some embodiments, provided herein is a compound of formula 16

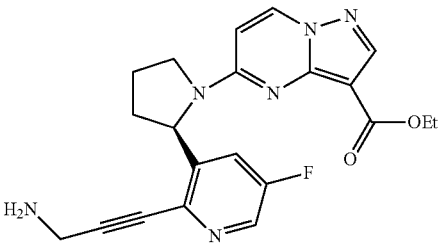

or a salt thereof.

In some embodiments, provided herein is a compound of formula 17

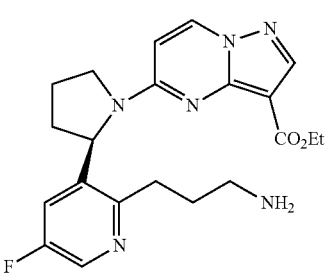

or a salt thereof.

In some embodiments, provided herein is a compound of formula 18

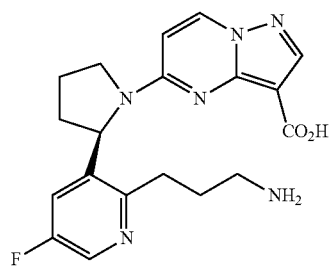

or a salt thereof.

In some embodiments, provided herein is a compound of formula 20

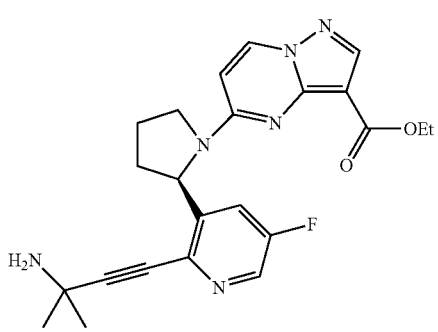

or a salt thereof.

In some embodiments, provided herein is a compound of formula 21

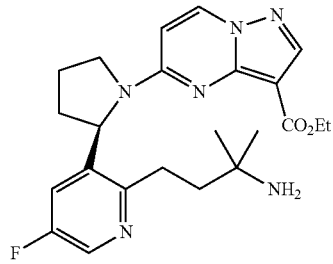

21 or a salt thereof.

In some embodiments, provided herein is a compound of formula 22

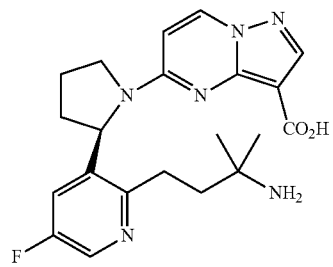

22 or a salt thereof.

In some embodiments, the following compounds are prepared in a manner analogous to the ones disclosed above for compounds of Formulae I-III using suitable starting materials:

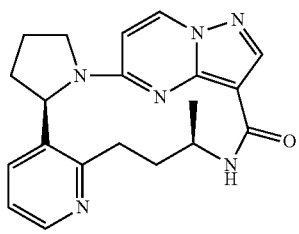

Formula IV

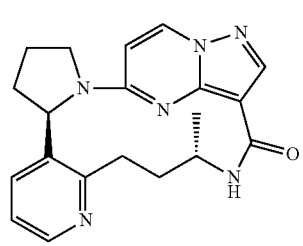

Formula V

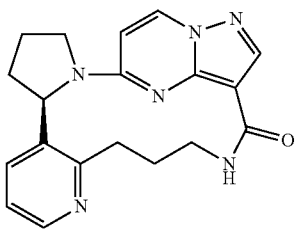

Formula VI

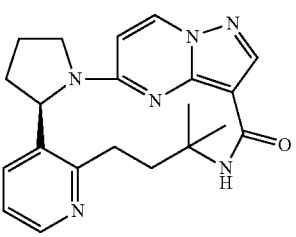

Formula VII

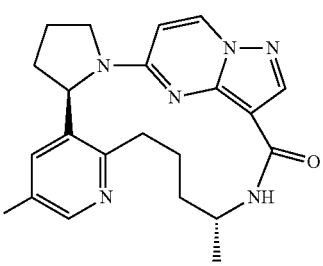

Formula VIII

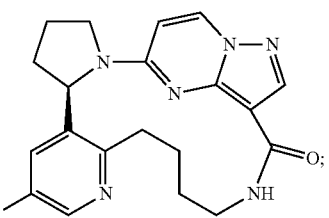

Formula IX

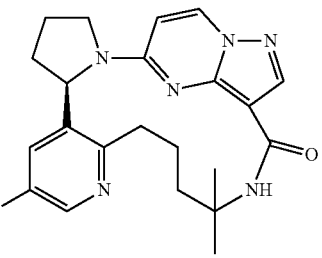

Formula X

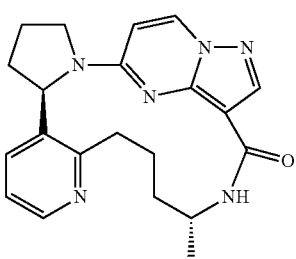

Formula XI

Formula XII
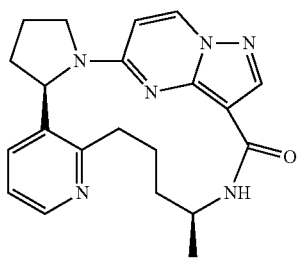
Formula XIII
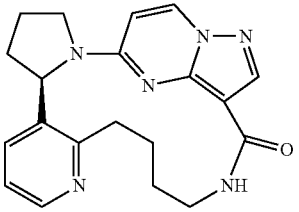
Formula XIV
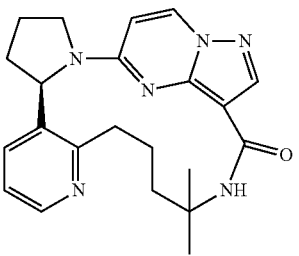
In some embodiments, the following compounds of formulae XVa-XVp are prepared in a manner analogous to the ones disclosed above for compounds of Formulae I-III using suitable starting materials:
Formula XVa
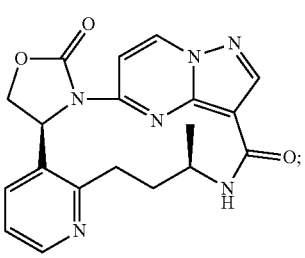
Formula XVb
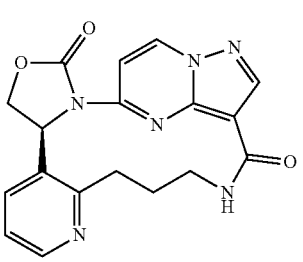
Formula XVc
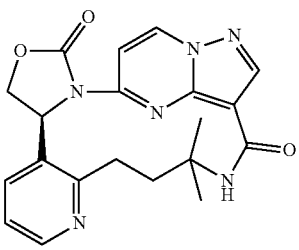
Formula XVd
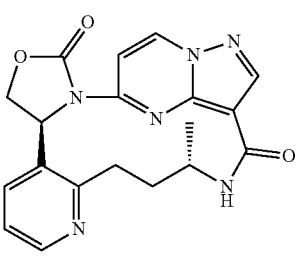
Formula XVe
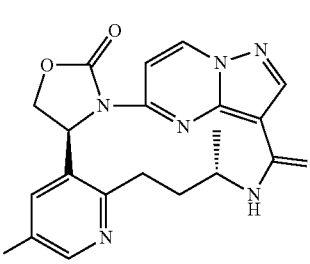
Formula XVf
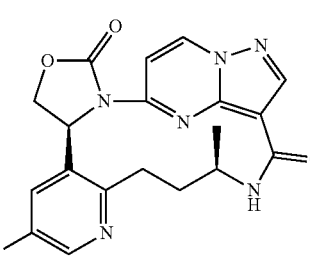
Formula XVg
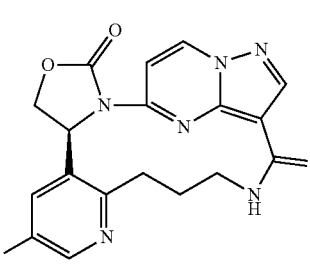
Formula XVh
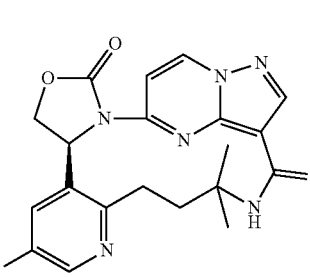

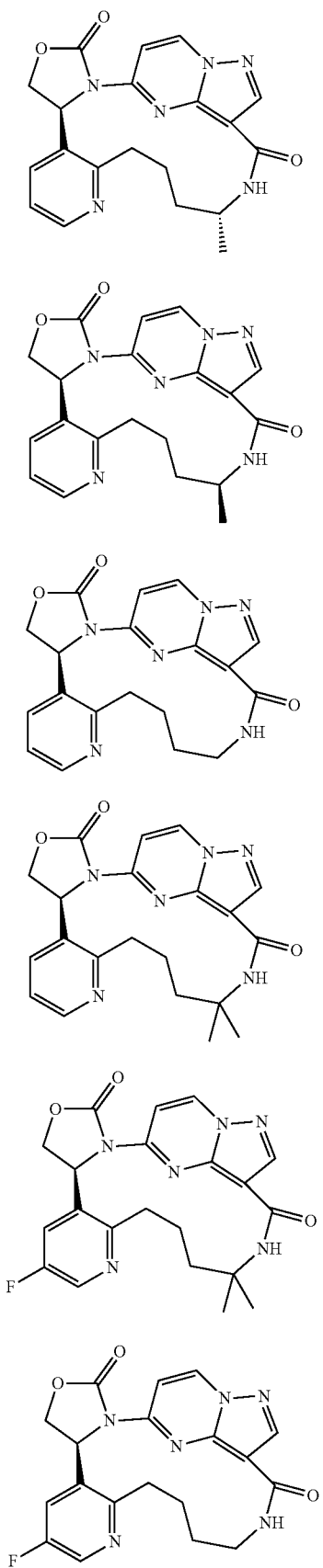
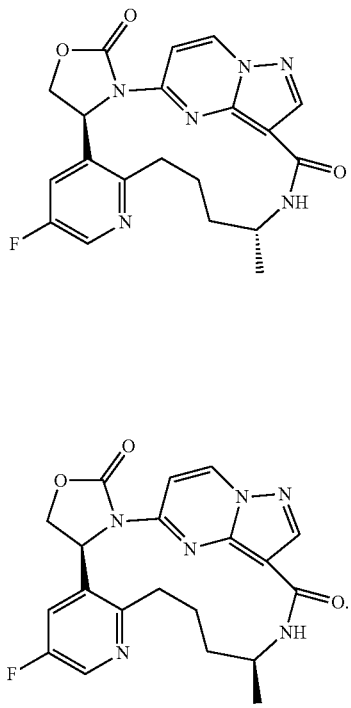
In some embodiments, the following compounds of formulae XVIa-XVIp are prepared in a manner analogous to the ones disclosed above for compounds of Formulae I-III using suitable starting materials:
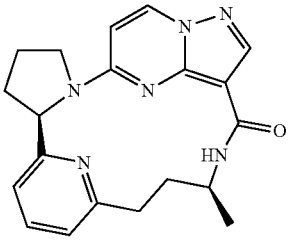
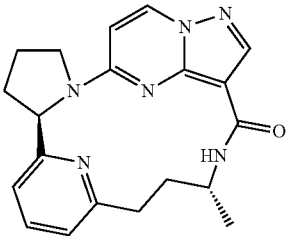
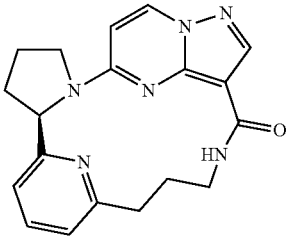

Formula XVId
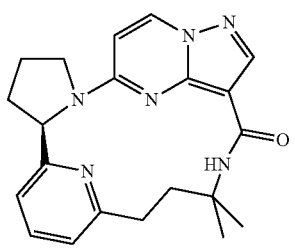
Formula XVIe
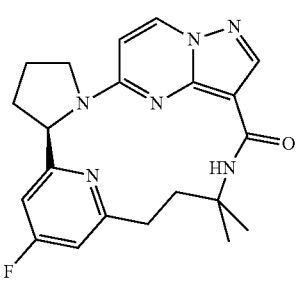
Formula XVIf
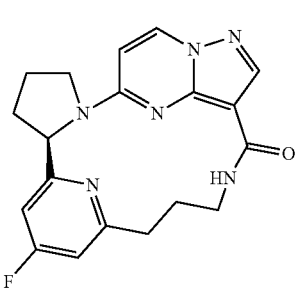
Formula XVIg
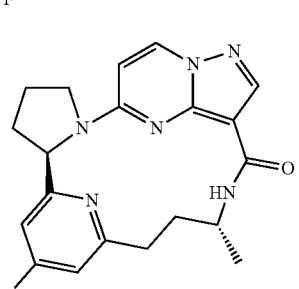
Formula XVIh
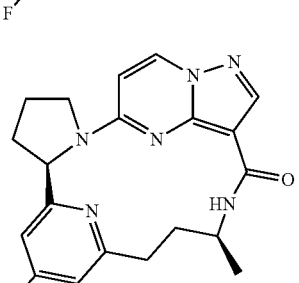
Formula XVIi
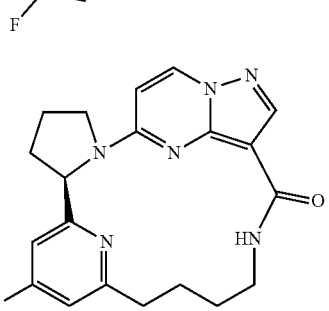
Formula XVIj
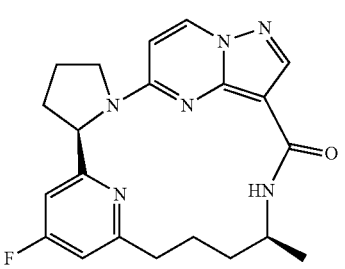
Formula XVIk
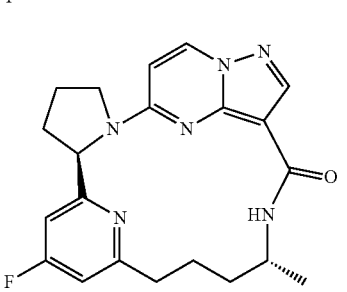
Formula XVIl
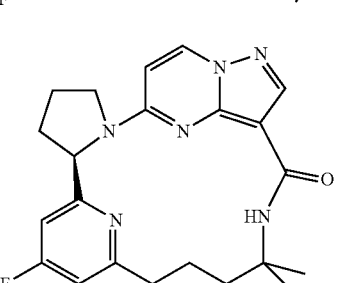
Formula XVIm
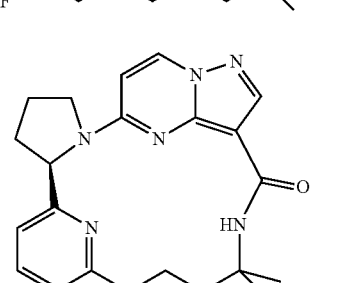
Formula XVIn
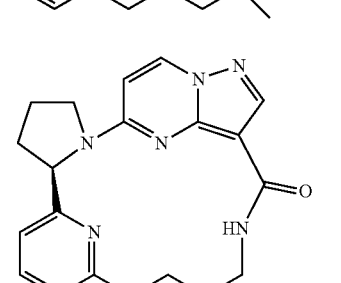
Formula XVIo
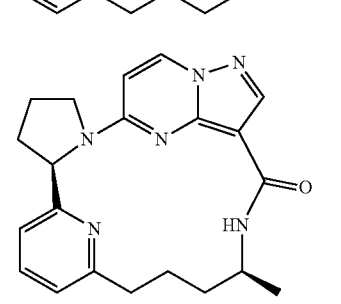

Formula XVIp
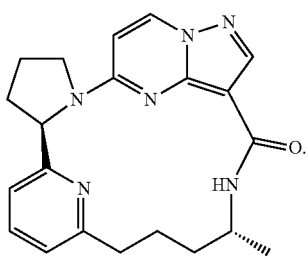
In some embodiments, the following compounds of formulae XVIIa-XVIIp are prepared in a manner analogous to the ones disclosed above for compounds of Formulae I-III using suitable starting materials:
Formula XVIIa
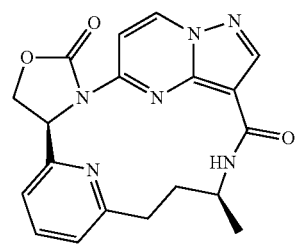
Formula XVIIb
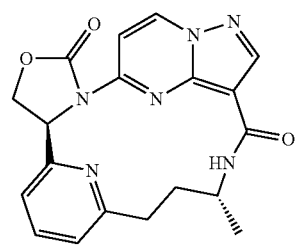
Formula XVIIc
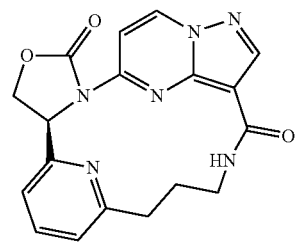
Formula XVIId
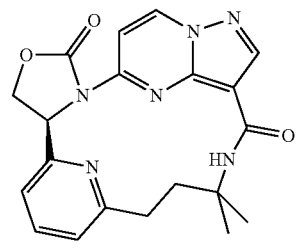
Formula XVIIe
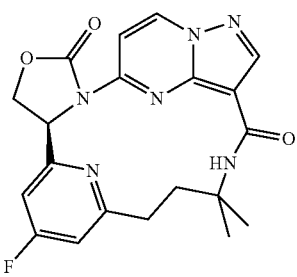
Formula XVIIf
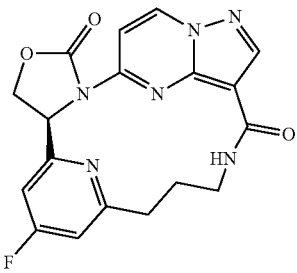
Formula XVIIg
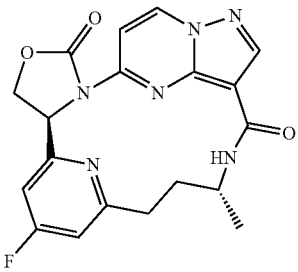
Formula XVIIh
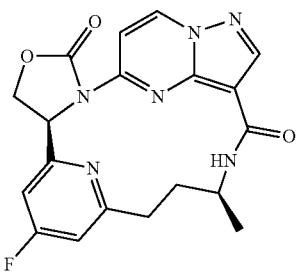
Formula XVIIi
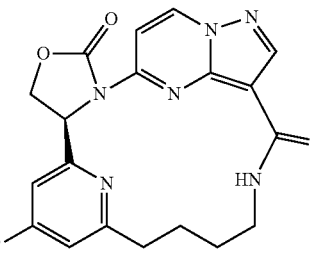
Formula XVIIj
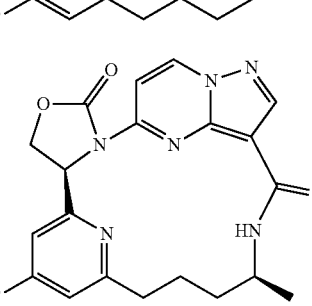

Formula XVIIk
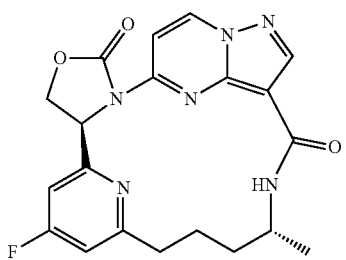

Formula XVIII
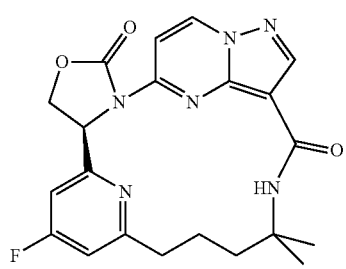

Formula XVIIm
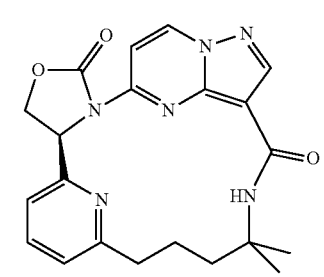

Formula XVIIn
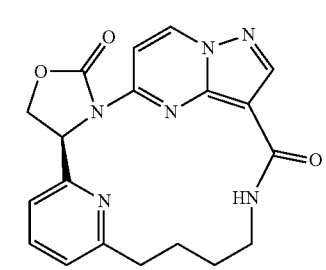

Formula XVIIo
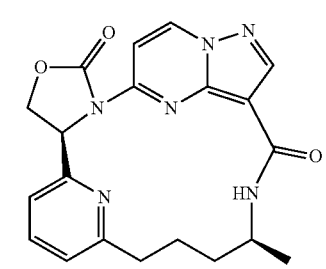

Formula XVIIp
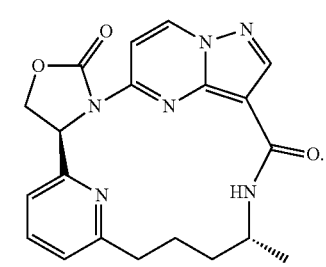

Parameters of Processes for Preparation of any one of Formulae Disclosed herein

In some embodiments of any one the processes provided herein, the hydrogenation system comprises hydrogen ($H_2$) and a catalyst that comprises a metal. In some embodiments, the catalyst comprises a metal selected from gold, ruthenium, sodium, indium, nickel, palladium, and platinum. In some embodiments, the catalyst is selected from gold, ruthenium, sodium sulfide, indium, nickel, palladium, and platinum. In some embodiments, the catalyst comprises a metal selected from nickel, palladium, and platinum. In some embodiments, the metal is palladium. In some embodiments, the catalyst is palladium on carbon (Pd/C). In some embodiments, the hydrogenation system comprises hydrogen ($H_2$) and palladium on carbon (Pd/C).

In some embodiments of any one of the processes provided herein, the first strong base is selected from sodium hydroxide, lithium hydroxide, potassium hydroxide and calcium hydroxide. In some embodiments, the first strong base is sodium hydroxide.

In some embodiments of any one of the processes provided herein, the cyclizing is performed with a coupling agent that comprises one or more of a carbodiimide, an additive, a phosphonium reagent, an aminium/uranium-imonium reagent, and miscellaneous reagents. In some embodiments, the carbodiimide is selected from dicyclohexylcarbodiimide (DCC), diisopropylcarbodiimide (DIC), and N-(3-dimethylaminopropyl)-N'-ethylcarbodiimide (EDCI). In some embodiments, the carbodiimide is dicyclohexylcarbodiimide (DCC). In some embodiments, the carbodiimide is diisopropylcarbodiimide (DIC). In some embodiments, the carbodiimide is N-(3-dimethylaminopropyl)-N'-ethylcarbodiimide (EDCI). In some embodiments, the additive is selected from 1-hydroxybenzotriazole (HOBt), hydroxy-3,4-dihydro-4-oxo-1,2,3-benzotriazine (HOOBt), N-hydroxysuccinimide (HOSu), 1-hydroxy-7-aza-1H-benzotriazole (HOAt), 4-(N,N-dimethylamino)pyridine (DMAP), and ethyl-2-cyano-2-(hydroxyimino)acetate. In some embodiments, the phosphonium reagent is selected from benzotriazol-1-yloxy-tris(dimethylamino)-phosphonium hexafluorophosphate (BOP), benzotriazol-1-yloxy-tripyrrolidino-phosphonium hexafluorophosphate (PyBOP), bromotripyrrolidino-phosphonium hexafluorophosphate (PYBrOP), 7-aza-benzotriazol-1-yloxy-tripyrrolidino-phosphonium hexafluorophosphate (PyAOP), ethyl cyano(hydroxyimino)acetate-$O_2$-tri-(1-pyrrolidinyl)-phosphonium hexafluorophosphate (PyOxim), and 3-(diethoxy-phosphoryloxy)-1,2,3-benzo[d]triazin-4(3H)-one (DEPBT). In some embodiments, the aminium/uranium-imonium reagent is selected from 2-(1H-benzotriazol-1-yl)-N,N,N',N'-tetramethylaminium tetrafluoroborate (TBTU), 2-(1H-benzotriazol-1-yl)-N,N,N',N'-tetramethylaminium hexafluorophosphate (HBTU), 2-(6-chloro-1H-benzotriazol-1-yl)-N,N,N'N'-tetramethylaminium hexafluorophosphate (HCTU), N-[(5-chloro-1H-benzotriazol-1-yl)-dimethylamino-morpholino]-uronium hexafluorophosphate N-oxide (HDMC), 2-(7-aza-1H-benzotriazol-1-yl)-N,N,N'N'-tetramethylaminium hexafluorophosphate (HATU), 1-[1-(cyano-2-ethoxy-2-oxoethylideneaminooxy)-dimethylamino-morpholino]-uronium hexafluorophosphate (COMU), 2-(1-oxy-pyridin-2-yl)-1,1,3,3-tetramethylisothiouronium tetrafluoroborate (TOTT), and tetramethylfluoroformamidinium hexafluorophosphate (TFFH). In some embodiments, the miscellaneous reagent is selected from N-ethoxycarbonyl-2-ethoxy-1,2-dihydroquinoiline (EEDQ), 2-propanephosphonic acid anhydride (T3P), 4-(4,6-dimethoxy-1,3,5-triazin-2-yl)-4-methylmorpholinium (DMTMM) salts, bis-trichloromethylcarbonate (BTC; phosgene), and 1,1'-carbonyldiimidazole (CTI). In some embodiments, the coupling agent comprises EDCI and DMAP.

In some embodiments of any one of the processes provided herein, the first acid is selected from sulfuric acid and hydrochloric acid. In some embodiments, the first acid is hydrochloric acid (HCl).

In some embodiments of any one of the processes provided herein, treatment of a compound with a first acid is conducted in the presence of a solvent. In some embodiments, the solvent is a non-protic solvent. In some embodiments, the solvent is dioxane. In some embodiments, the solvent is a protic solvent. In some embodiments, the solvent is an aliphatic alcohol.

In some embodiments, the deprotecting, or removing the protecting group $P^1$ is conducted using any convenient synthetic method known in the art. The chemistry of protecting groups is described, for example, in in Greene & Wuts, eds., "Protecting Groups in Organic Synthesis", 2n$^d$ ed. New York; John Wiley & Sons, Inc., 1991. For example, when the protecting group $P^1$ is a t-butoxycarbonyl (BOC), the deprotecting is carried out using an acid such as trifluoroacetic acid or hydrochloric acid. In some embodiments, the deprotecting is conducted at room temperature.

In some embodiments, the catalyst comprising palladium is a zerovalent palladium complex selected from Pd(PPh$_3$)$_2$Cl$_2$, Pd(dppe)Cl, Pd(dppp)Cl$_2$, and Pd(dppf)Cl$_2$. In some embodiments, the catalyst comprising palladium is Pd(PPh$_3$)$_2$Cl$_2$.

In some embodiments, the catalyst comprising copper is a halide salt of copper(I) selected from copper iodide, copper bromide, and copper chloride. In some embodiments, the catalyst comprising copper is copper iodide (CuI).

In some embodiments, the catalyst comprising palladium is Pd(PPh$_3$)$_2$Cl$_2$ and the catalyst comprising copper is CuI.

In some embodiments, in any one of the processes provided herein the coupling is performed in the presence of a base. In some embodiments, the base is an alkylamine. In some embodiments, the alkylamine is diisopropylamine (DIA).

In some embodiments, in any one of the processes provided herein the coupling is followed by treating with a second acid. In some embodiments, the second acid is selected from hydrochloric acid, trifluoroacetic acid and sulfuric acid. In some embodiments, the second acid is sulfuric acid (H$_2$SO$_4$).

Compound 12 (CAS 118080-82-3), Compound 19 (tert-butyl prop-2-ynylcarbamate, or N-Boc-propargylamine, CAS Registry No. 92136-39-5), and compound 23 (tert-butyl 2-methylbut-3-yn-2-ylcarbamate, N-boc-2-amino-2-methylbut-3-yne, CAS Registry No. 113486-06-9) are commercially available from numerous commercial suppliers. Similarly to 12, 19 and 23, suitably substituted alkynes that may be used in the preparation of any of formulae IV-XVIII above are commercially available and/or readily prepared using routine procedures.

The present application also provides a method of preparing a compound 9 as set out, for example, in Scheme 6

Scheme 6

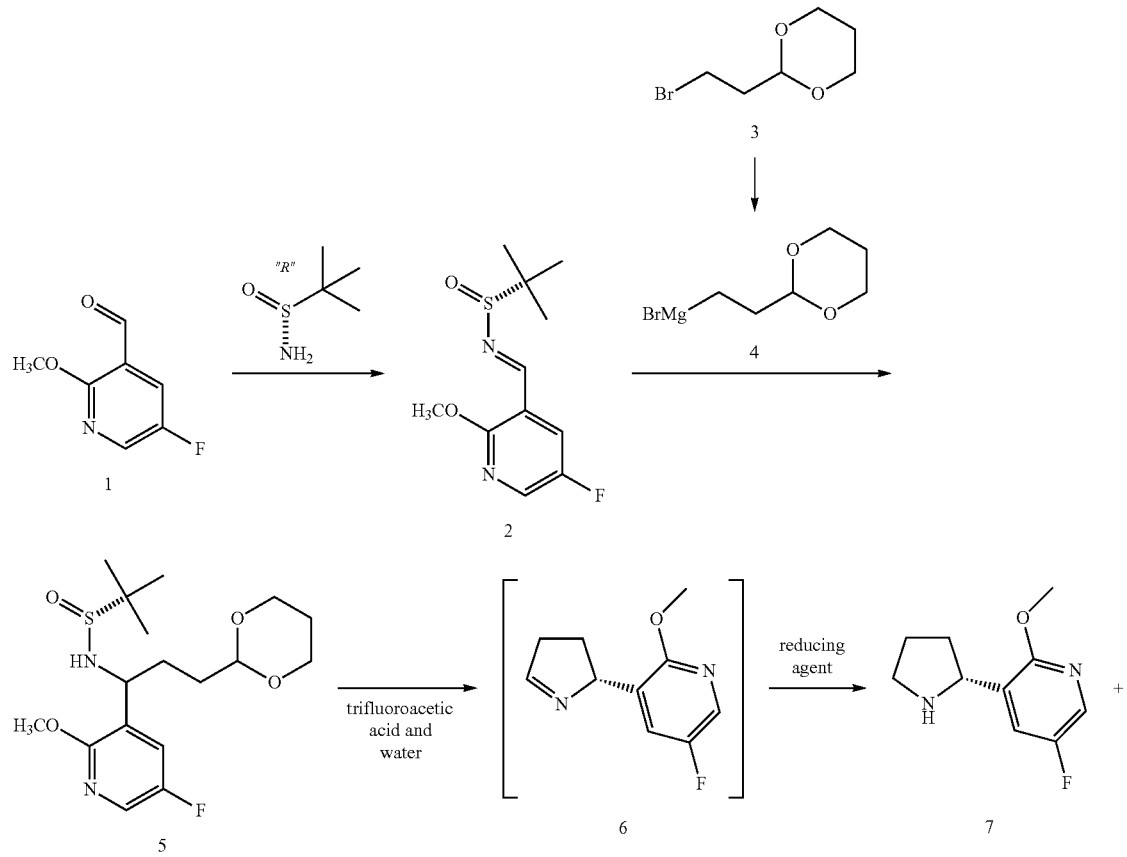

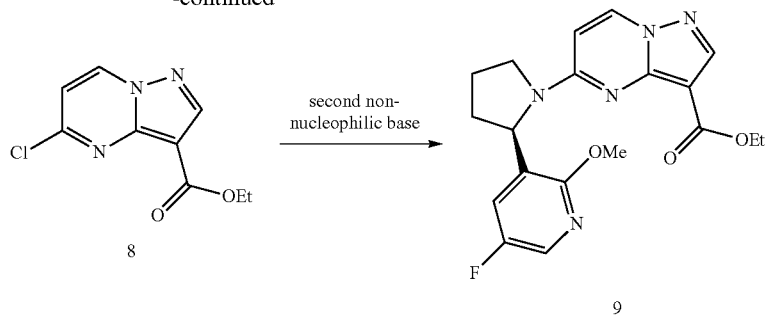

In some embodiments, the process for preparing the compound of any one of Formulae I, II or III further comprises preparing the compound of formula 9

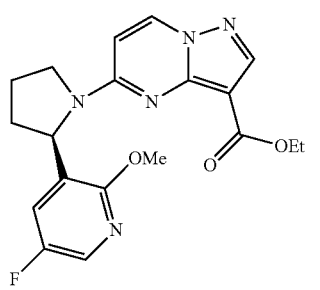

or a salt thereof, by a process comprising reacting a compound of formula 7

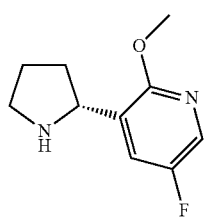

or a salt thereof, with a compound of formula 8

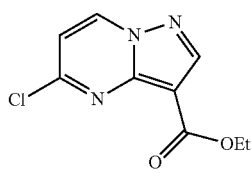

or a salt thereof, in the presence of a second non-nucleophilic base, to form a compound of formula 9.

In some embodiments, the process for preparing the compound of any one of Formulae I, II or III further comprises preparing the compound of formula 8

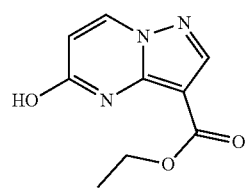

or a salt thereof, by a process comprising reacting

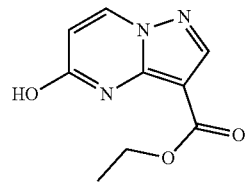

or a salt thereof with POCl$_3$ in an organic solvent to form a compound of formula 8. In some embodiments, the organic solvent is acetonitrile.

In some embodiments, the process for preparing the compound of any one of Formulae I, II or III further comprises preparing or a salt thereof, by a process comprising reacting with

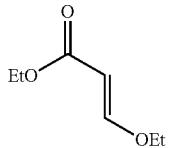

in the presence of a phosphate salt to form

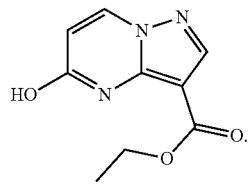

In some embodiments, the phosphate salt is potassium phosphate.

In some embodiments, the second non-nucleophilic base is selected from triethylamine and diisopropylethylamine. In some embodiments, the second non-nucleophilic base is triethylamine.

In some embodiments, the process for preparing the compound of any one of Formulae I, II or III further comprises preparing the compound of formula 7

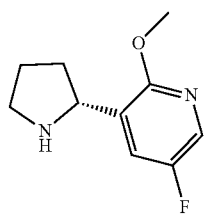

7 or a salt thereof, by a process comprising:

a) treating a compound of formula 1

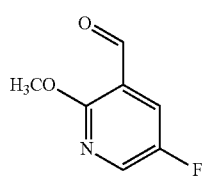

1 or a salt thereof, with (R)-2-methylpropane-2-sulfinamide to form a compound of formula 2

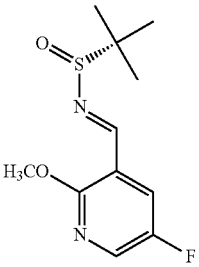

2 or a salt thereof;

b) reacting the compound of formula 2 or a salt thereof with a compound of formula 4

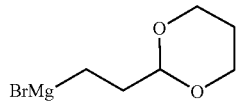

4 to form a compound of formula 5

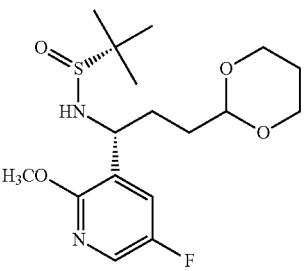

5 or a salt thereof;

c) treating the compound of formula 5 with a first mixture comprising an acid such as trifluoroacetic acid and water to form a second mixture; and d) treating the second mixture with a reducing agent, to form the compound of formula 7 or a salt thereof.

In some embodiments, the compound of formula 1 or a salt thereof, is treated with (R)-2-methylpropane-2-sulfinamide in the presence of an activating agent. In some embodiments, the activating agent is selected from cesium carbonate, $CuSO_4$, $Ti(OEt)_4$, other Ti(IV) compounds, sodium carbonate and lithium carbonate. In some embodiments, the activating agent is selected from cesium carbonate, $CuSO_4$, $Ti(OEt)_4$, and other Ti(IV) compounds. In some embodiments, the activating agent is cesium carbonate.

In some embodiments, the reducing agent is a silane. In some embodiments, the reducing agent is triethylsilane.

In some embodiments, the compound of formula 4

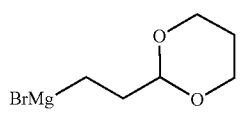

4 is prepared by a process comprising treating a compound of formula 3

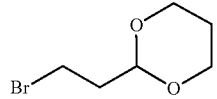

with magnesium.

In some embodiments, the first mixture comprising an acid such as trifluoroacetic acid and water comprises 4:1 trifluoroacetic acid:water.

In some embodiments, the second mixture comprises a compound of formula 6

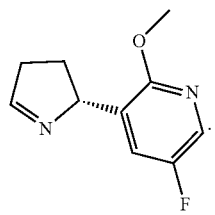

In some embodiments, the process comprises isolating the compound of formula 6 from the second mixture.

In some embodiments, the compound of formula 7 or a salt thereof is prepared by a process comprising:

a) treating a compound of formula 1 or a salt thereof with (R)-2-methylpropane-2-sulfinamide to form a compound of formula 2 or a salt thereof;

b) reacting the compound of formula 2 or a salt thereof with a compound of formula 4 to form a compound of formula 5 or a salt thereof;

c) treating the compound of formula 5 with a first mixture comprising an acid such as trifluoroacetic acid and water to form a compound of formula 6;

d) isolating the compound of formula 6; and e) treating the compound of formula 6 with triethylsilane, to form the compound of formula 7 or a salt thereof.

In some embodiments, the compound of formula 1 or a salt thereof, is treated with (R)-2-methylpropane-2-sulfinamide in the presence of an activating agent. In some embodiments, the activating agent is selected from cesium carbonate, CuSO$_4$, Ti(OEt)$_4$, other Ti(IV) compounds, sodium carbonate and lithium carbonate. In some embodiments, the activating agent is selected from cesium carbonate, CuSO$_4$, Ti(OEt)$_4$, and other Ti(IV) compounds. In some embodiments, the activating agent is cesium carbonate.

In some embodiments, the compound of formula 4 is prepared by a process comprising treating a compound of formula 3 with magnesium.

In some embodiments, the first mixture comprising an acid such as trifluoroacetic acid and water comprises 4:1 trifluoroacetic acid:water.

Provided herein in some embodiments is a compound of Formula I

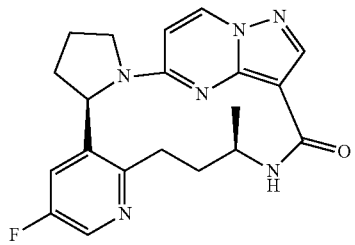

or a pharmaceutically acceptable salt, solvate or hydrate thereof.

Provided herein in some embodiments is a pharmaceutical composition comprising a compound of Formula I or a pharmaceutically acceptable salt, solvate or hydrate thereof, and a pharmaceutically acceptable carrier.

Provided herein in some embodiments is a method of treating a disease in which one or more Trk kinases (e.g., TrkA, TrkB, and/or TrkC) is activated, e.g., by a soluble growth factor such as a neurotrophin (NT), such as a disease disclosed herein, comprising administering to a subject an effective amount of the compound of Formula I or a pharmaceutically acceptable salt, solvate or hydrate thereof.

In some embodiments of the compound of Formula I, a pharmaceutical composition comprising the compound of Formula I, or a method of treating a disease comprising administering to a subject an effective amount of the compound of Formula I, the compound of Formula I is present in a diastereomeric excess (d.e.) of at least 80% relative to the diastereomeric compound of formula I':

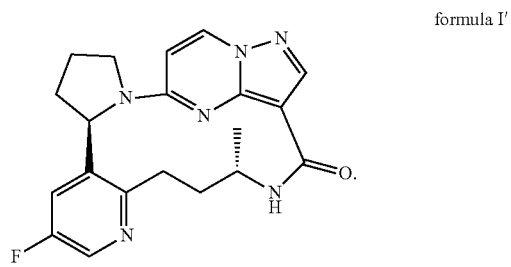 [SMILES: C[C@H]1CCc2ncc(F)cc2[C@H]2CCCN2c2ccn3ncc(c3n2)C(=O)N1]

In some embodiments, the compound of Formula I is present in a d.e. of at least 90% relative to the compound of formula I'. In some embodiments, the compound of Formula I is present in a d.e. of at least 92% relative to the compound of formula I'. In some embodiments, the compound of Formula I is present in a d.e. of at least 94% relative to the compound of formula I'. In some embodiments, the compound of Formula I is present in a d.e. of at least 96% relative to the compound of formula I'. In some embodiments, the compound of Formula I is present in a d.e. of at least 98% relative to the compound of formula I'.

In some embodiments, the compound of Formula I is prepared from a mixture of the compound of Formula I and the compound of formula I' by separating the two compounds. In some embodiments, the two compounds are separated by chromatography.

Table 54 provides exemplary properties of the compound of Formula I and of formula I':

TABLE 54

| Compound | formula I' | Formula I |
|---|---|---|
| Aqueous solubility, pH 6.5 buffer (µg/mL) | 43 | 111 |
| Human Microsome Clearance (% ER) | 92 | 79 |
| Rat Microsome Clearance (% ER) | 77 | 51 |
| Human Hepatocyte Clearance (% ER) | 74 | 48 |
| Rat Hepatocyte Clearance (% ER) | 83 | 64 |
| MDR1 efflux ratio | 5 | 14 |
| hERG IC$_{50}$ (µM) | 9 | 27 |

Referring to the Table 54, the solubility measurement protocol is disclosed in Example 33 hereinbelow. The Microsome and hepatocyte clearance measurement protocol is disclosed in Example 34 hereinbelow. The MDR1 efflux protocol is disclosed in Example 35 hereinbelow. The hERG IC$_{50}$ values were measured using the ChanTest Fast Patch assay, available from Charles River Laboratories International, Inc. (http://www.criver.com/products-services/drug-discovery/cap abilities/ion-channel/selectivity-profiling).

In one general aspect, the present disclosure is directed to forms of (6R,15R)-9-fluoro-15-methyl-2, 11,16,20,21,24-hexaazapentacyclo[16.5.2.0$^{2,6}$.0$^{7,12}$.0$^{21,25}$]pentacosa-1(24), 7,9,11,18(25),19,22-heptaen-17-one (Compound 1), the structure of which is shown below:

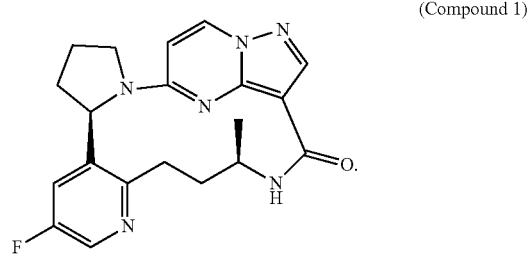 [SMILES: C[C@@H]1CCc2ncc(F)cc2[C@H]2CCCN2c2ccn3ncc(c3n2)C(=O)N1]

(Compound 1)

Compound 1 is an inhibitor of Trk kinase useful in the treatment of diseases in which one or more Trk kinases (e.g., TrkA, TrkB, and/or TrkC) is activated, e.g., by a soluble growth factor such as a neurotrophin (NT). Compound 1 may be referred to herein as "Compound 1 free base". In some embodiments, Compound 1 provided herein is a solid form. In some embodiments, the solid form is crystalline (e.g., Form I). In another general aspect, the present disclosure is directed to salts of Compound 1. In some embodiments, the salt of the present disclosure is a benzenesulfonic acid salt of Compound 1, which is referred to herein as "Compound 1 besylate". In some embodiments, Compound 1 besylate has the following structure:

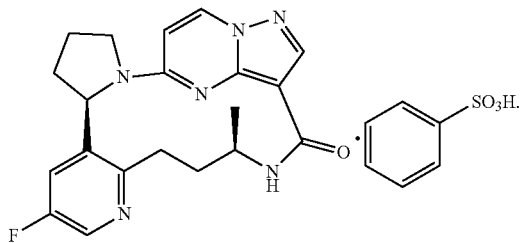

In some embodiments, the salt of the present disclosure is a citric acid salt of Compound 1, which is referred to herein as "Compound 1 citrate". In some embodiments, the Compound 1 citrate has the following structure:

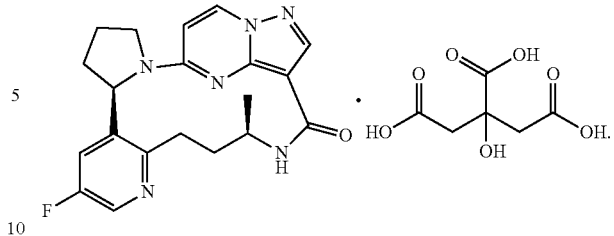

In some embodiments, the salt of the present disclosure is a methanesulfonic acid salt of Compound 1, which is referred to herein as "Compound 1 mesylate". In some embodiments, the Compound 1 mesylate has the following structure:

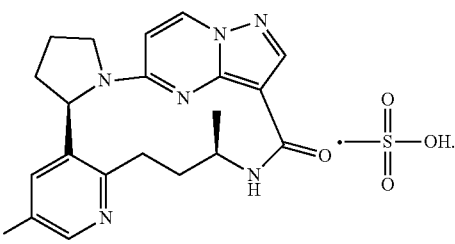

In some embodiments, the salt of the present disclosure is a 1,2-ethane disulfonic acid salt of Compound 1, which is referred to herein as "Compound 1 edisylate". In some embodiments, the Compound 1 edisylate has the following structure:

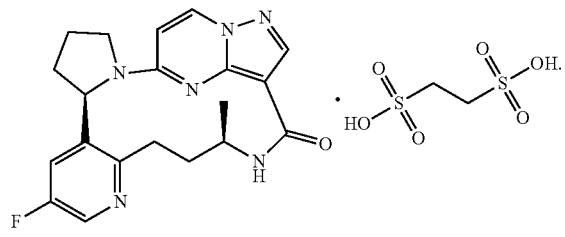

In some embodiments, the salt of the present disclosure is a p-toluene sulfonic acid salt of Compound 1, which is referred to herein as "Compound 1 tosylate". In some embodiments, the Compound 1 tosylate has the following structure:

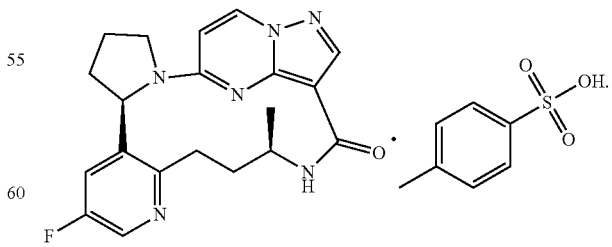

In some embodiments, the salt of the present disclosure is an oxalic acid salt of Compound 1, which is referred to herein as "Compound 1 oxalate". In some embodiments, the Compound 1 oxalate has the following structure:

103

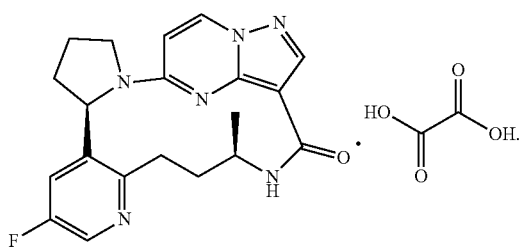 [SMILES: C[C@@H]1CCc2ncc(F)cc2[C@H]2CCCN2c2ccn3ncc(c3n2)C(=O)N1 ; O=C(O)C(=O)O]

In some embodiments, the salt of the present disclosure is a fumaric acid salt of Compound 1, which is referred to herein as "Compound 1 fumarate". In some embodiments, the Compound 1 fumarate has the following structure:

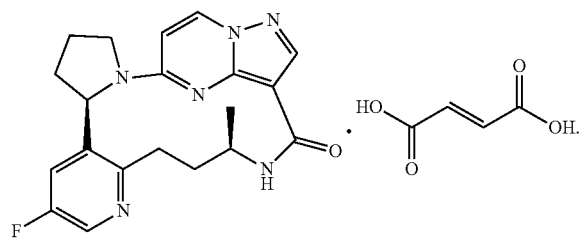 [SMILES: C[C@@H]1CCc2ncc(F)cc2[C@H]2CCCN2c2ccn3ncc(c3n2)C(=O)N1 ; O=C(O)/C=C/C(=O)O]

In some embodiments, the salt of the present disclosure is a L-malic acid salt of Compound 1, which is referred to herein as "Compound 1 L-malate". In some embodiments, the Compound 1 L-malate has the following structure:

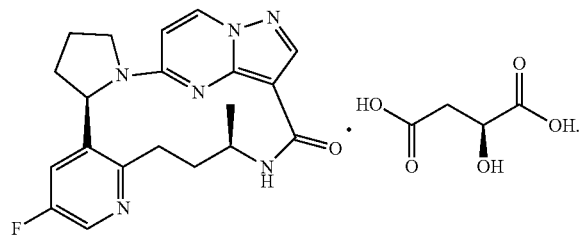 [SMILES: C[C@@H]1CCc2ncc(F)cc2[C@H]2CCCN2c2ccn3ncc(c3n2)C(=O)N1 ; O=C(O)C[C@H](O)C(=O)O]

In some embodiments, the salt of the present disclosure is a succinic acid salt of Compound 1, which is referred to herein as "Compound 1 succinate". In some embodiments, the Compound 1 succinate has the following structure:

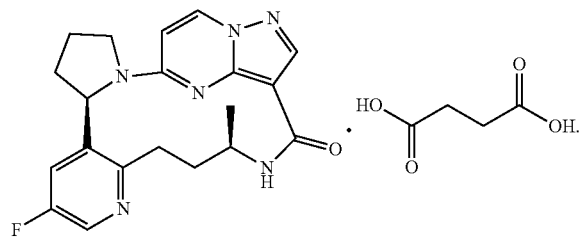 [SMILES: C[C@@H]1CCc2ncc(F)cc2[C@H]2CCCN2c2ccn3ncc(c3n2)C(=O)N1 ; O=C(O)CCC(=O)O]

In some embodiments, the salt of the present disclosure is a hydrochloric acid salt of Compound 1, which is referred to herein as "Compound 1 hydrochloride". In some embodiments, the Compound 1 hydrochloride has the following structure:

104

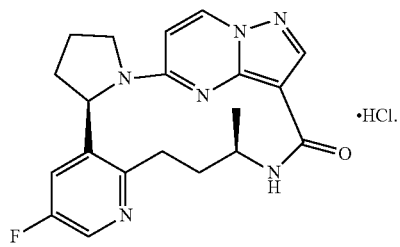 [SMILES: C[C@@H]1CCc2ncc(F)cc2[C@H]2CCCN2c2ccn3ncc(c3n2)C(=O)N1]

In some embodiments, the salt of the present disclosure is a sulfuric acid salt of Compound 1, which is referred to herein as "Compound 1 sulfate". In some embodiments, the Compound 1 sulfate has the following structure:

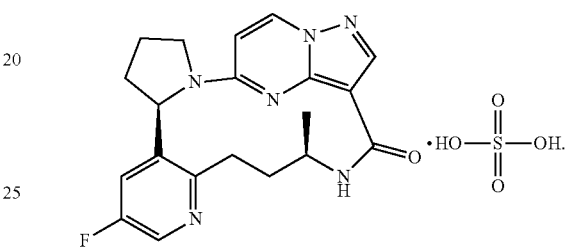

In some embodiments, the salt of the present disclosure is a naphthalene-2-sulphonic acid salt of Compound 1, which is referred to herein as "Compound 1 2-naphthalenesulfonate". In some embodiments, the Compound 1 2-naphthalenesulfonate has the following structure:

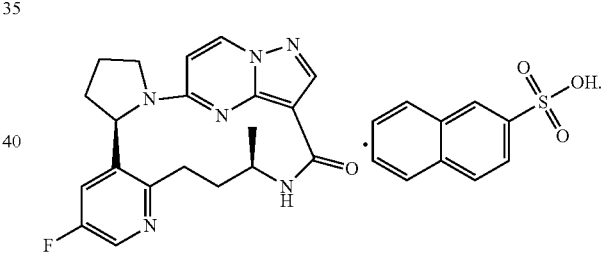

In some embodiments, the salt of the present disclosure is a 2-hydroxy ethanesulfonic acid salt of Compound 1, which is referred to herein as "Compound 1 isethionate". In some embodiments, the Compound 1 isethionate has the following structure:

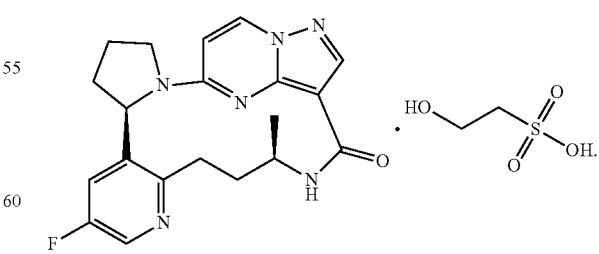

In some embodiments, the salt of the present disclosure is a L-aspartic salt of Compound 1, which is referred to herein as "Compound 1 L-aspartate". In some embodiments, the Compound 1 L-aspartate has the following structure:

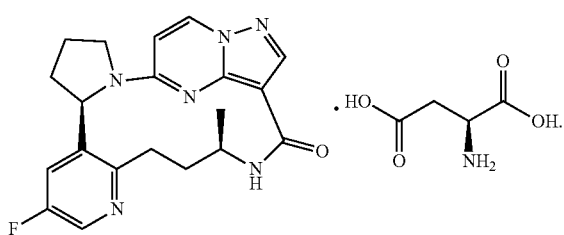 [SMILES: C[C@@H]1CCc2ncc(F)cc2[C@H]2CCCN2c2ccn3ncc(c3n2)C(=O)N1 ; N[C@@H](CC(=O)O)C(=O)O]

In some embodiments, the salt of the present disclosure is a maleic acid salt of Compound 1, which is referred to herein as "Compound 1 maleate". In some embodiments, the Compound 1 maleate has the following structure:

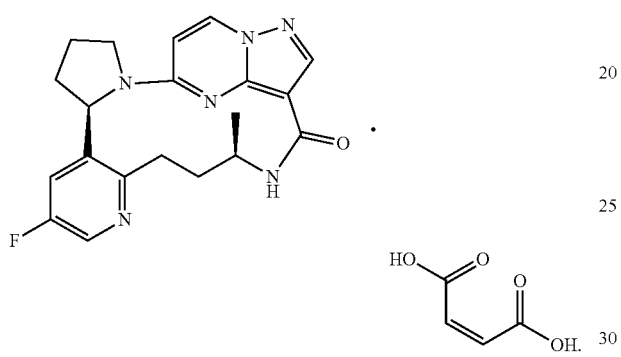

In some embodiments, the salt of the present disclosure is a phosphoric acid salt of Compound 1, which is referred to herein as "Compound 1 phosphate". In some embodiments, the Compound 1 phosphate has the following structure:

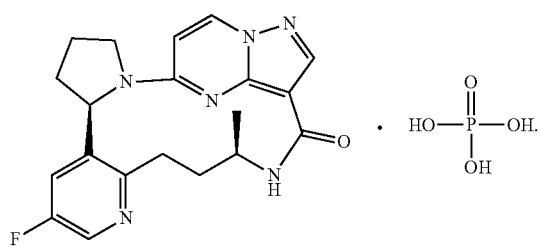 [SMILES: C[C@@H]1CCc2ncc(F)cc2[C@H]2CCCN2c2ccn3ncc(c3n2)C(=O)N1 ; O=P(O)(O)O]

In some embodiments, the salt of the present disclosure is a ethanesulfonic acid salt of Compound 1, which is referred to herein as "Compound 1 esylate". In some embodiments, the Compound 1 esylate has the following structure:

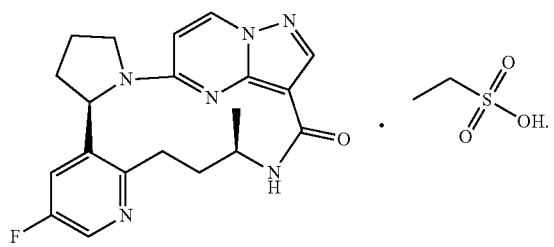

In some embodiments, the salt of the present disclosure is a L-glutamic acid salt of Compound 1, which is referred to herein as "Compound 1 L-glutamate". In some embodiments, the Compound 1 L-glutamate has the following structure:

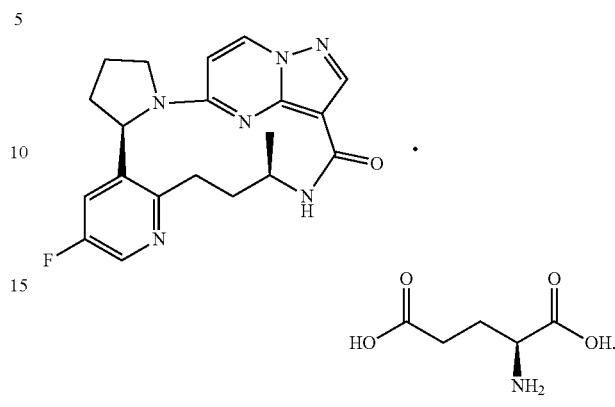

In some embodiments, the salt of the present disclosure is a L-tartaric acid salt of Compound 1, which is referred to herein as "Compound 1 L-tartrate". In some embodiments, the Compound 1 L-tartrate has the following structure:

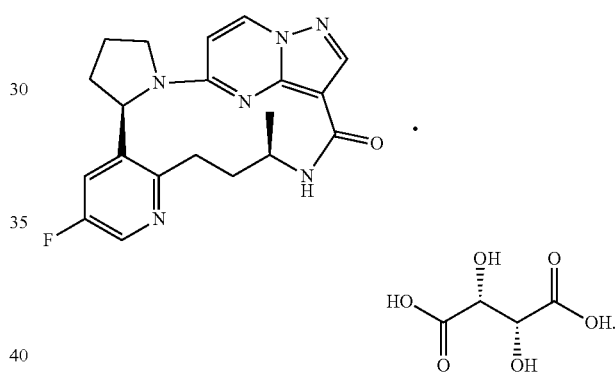

In some embodiments, the salt of the present disclosure is a D-glucuronic acid salt of Compound 1, which is referred to herein as "Compound 1 D-glucuronate". In some embodiments, the Compound 1 D-glucuronate has the following structure:

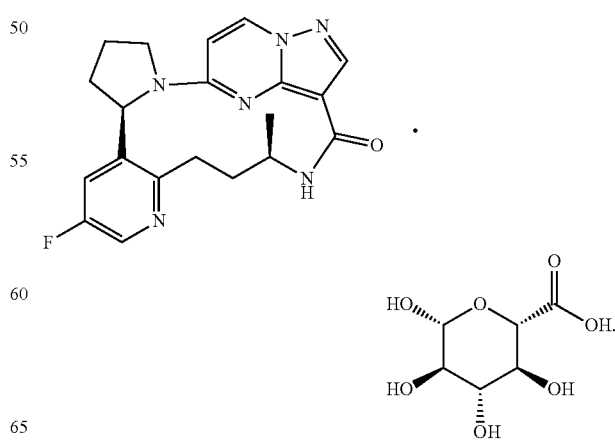

In some embodiments, the salt of the present disclosure is a hippuric acid salt of Compound 1, which is referred to herein as "Compound 1 hippurate". In some embodiments, the Compound 1 hippurate has the following structure:

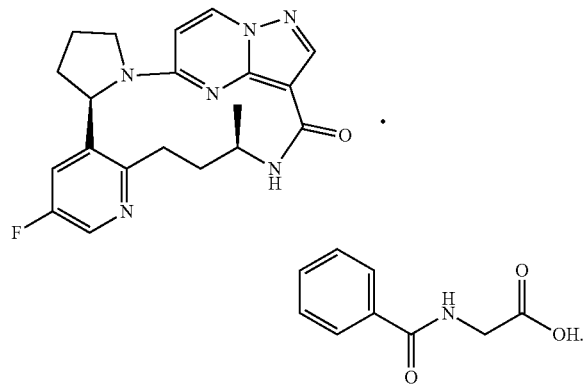

In some embodiments, the salt of the present disclosure is a D-gluconic acid salt of Compound 1, which is referred to herein as "Compound 1 D-gluconate". In some embodiments, the Compound 1 D-gluconate has the following structure:

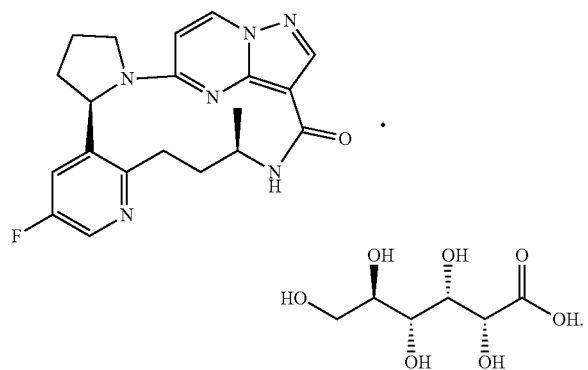

In some embodiments, the salt of the present disclosure is a DL-lactic acid salt of Compound 1, which is referred to herein as "Compound 1 lactate". In some embodiments, the Compound 1 lactate has the following structure:

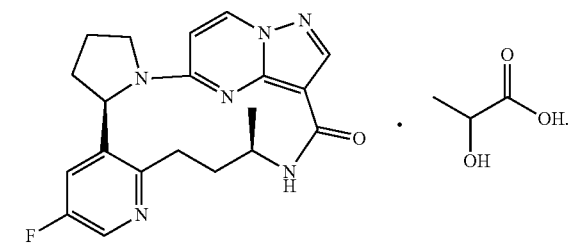

In some embodiments, the salt of the present disclosure is a L-ascorbic acid salt of Compound 1, which is referred to herein as "Compound 1 L-ascorbate". In some embodiments, the Compound 1 L-ascorbate has the following structure:

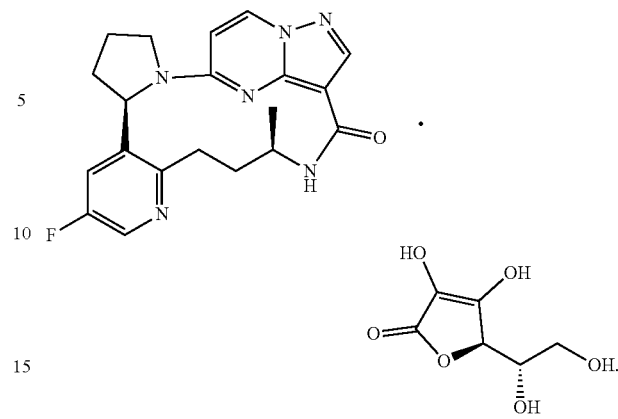

In some embodiments, the salt of the present disclosure is a benzoic acid salt of Compound 1, which is referred to herein as "Compound 1 benzoate". In some embodiments, the Compound 1 benzoate has the following structure:

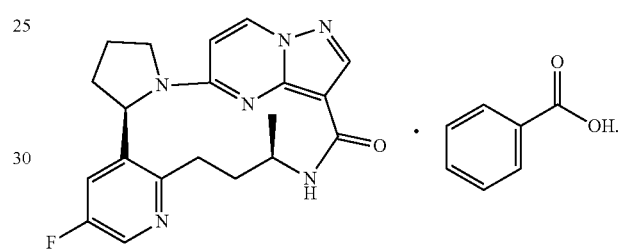

The salts of the present application can be isolated as one or more solid forms. The solid forms, crystalline forms, solvated forms, hydrated forms of the Compound 1 and the salts of Compound 1 are described below, along with the methods of making the same and using the same for therapeutic purposes.

Compound 1 Free Base

In some embodiments, Compound 1 is in the form of the crystalline free base. In some embodiments, Compound 1 is at least 50%, at least 60%, at least 70%, at least 80%, at least 90%, or at least 99% crystalline.

In some embodiments, Form I is substantially free of other forms of Compound 1. In some embodiments, Form I contains less than 10%, such as less than 5%, such as less than 3%, such as less than 1% of other forms of Compound 1. In some embodiments, Form I is substantially free of the amorphous form of Compound 1. In some embodiments, Form I contains less than 10%, such as less than 5%, such as less than 3%, such as less than 1%, of the amorphous form of Compound 1.

In some embodiments, Form I is substantially free of other stereoisomers of Compound 1. In some embodiments, Form I contains less than 10%, such as less than 5%, such as less than 3%, such as less than 1% of other stereoisomers of Compound 1. In some embodiments, Form I has an XRPD pattern substantially as depicted in FIG. 1. In some embodiments, Form I has a XRPD peak, in terms of 2-theta, at about 20.2 degrees. In some embodiments, Form I has XRPD peaks, in terms of 2-theta, at about 9.1, about 20.2 and about 24.9. In some embodiments, Form I has XRPD peaks, in terms of 2-theta, at about 9.1, about 11.2, about 20.2 and about 24.9. In some embodiments, Form I has XRPD peaks, in terms of 2-theta, at about 9.1, about 11.2, about 13.4, about 14.8, about 20.2, and about 29.4. In some embodiments, Form I has XRPD peaks, in terms of 2-theta, at about 9.1, about 11.2, about 13.4, about 14.8, about 18.3, about 18.6, about 20.2, about 23.6, about 24.9, and about 29.4.

In some embodiments, Form I has at least one, at least two or at least three XRPD peaks, in terms of 2-theta, selected from about 9.1, about 11.2, about 13.4, about 20.2, and about 24.9 degrees. In some embodiments, Form I has at least one, at least two or at least three XRPD peaks, in terms of 2-theta, selected from about 9.1, about 11.2, about 13.4, about 14.8, about 16.8, about 18.3, about 18.6, about 20.2, about 21.4, about 22.7, about 23.6, about 24.9, and about 29.4. In some embodiments, Form I has at least one, at least two or at least three XRPD peaks, in terms of 2-theta, selected from about 9.1, about 11.2, about 13.4, about 14.8, about 18.3, about 18.6, about 20.2, about 23.6, about 24.9, and about 29.4. In some embodiments, Form I has at least one, at least two or at least three XRPD peaks, in terms of 2-theta, selected from about 9.1, about 11.2, about 13.4, about 14.8, about 20.2, and about 29.4.

Figure 2:
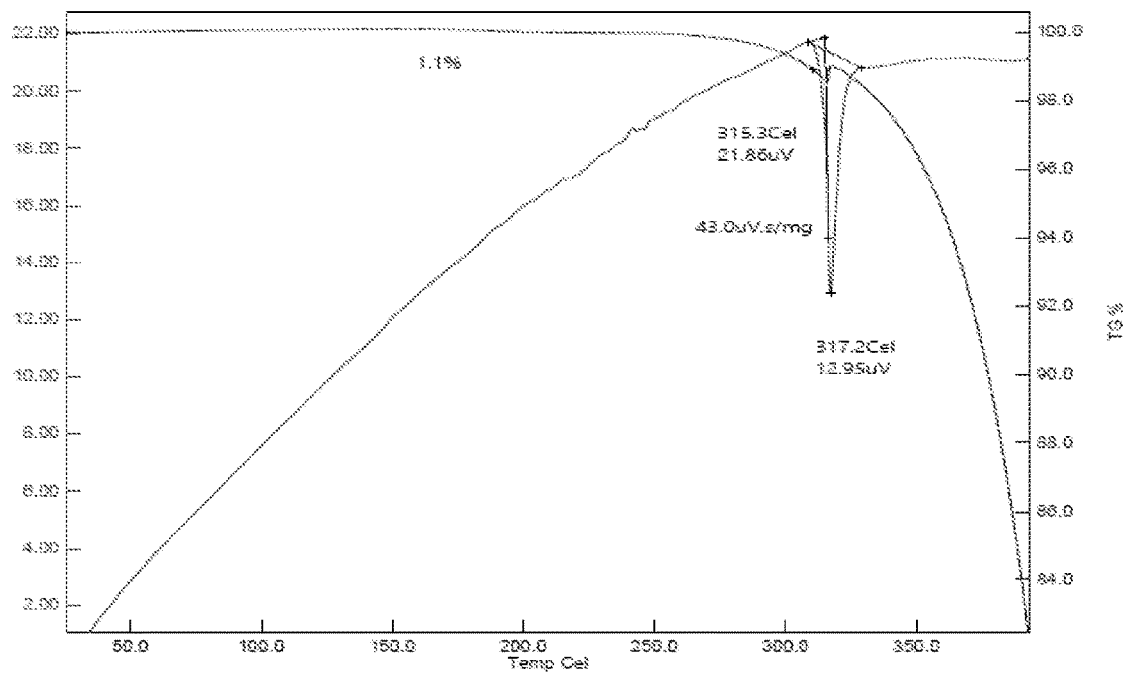
FIG. 2 is a TG/DTA thermogram of Compound 1 (Form I).
Figure 3:
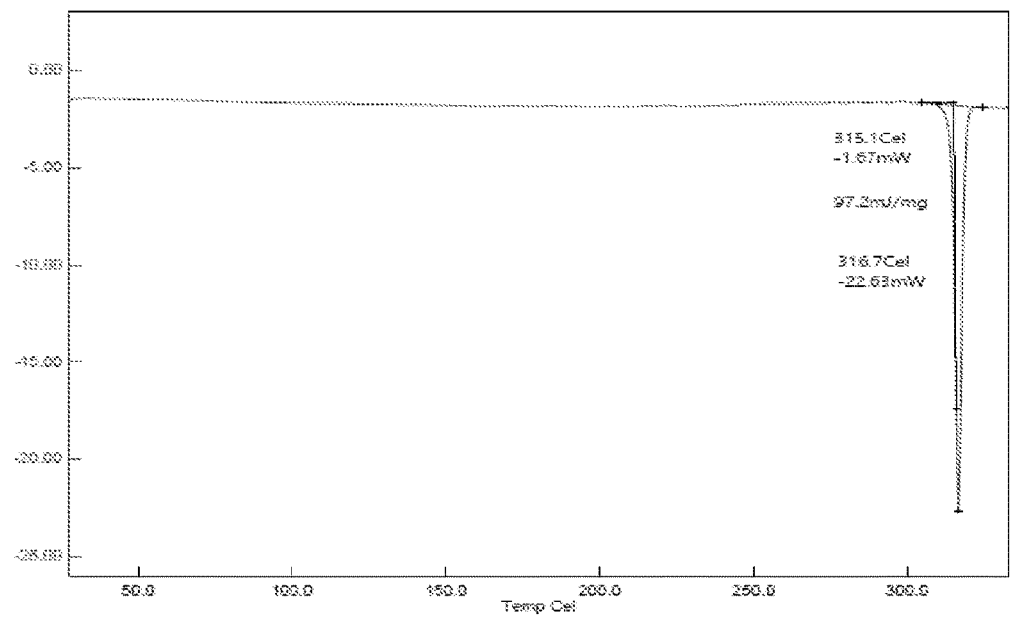
FIG. 3 is a DSC thermogram of Compound 1 (Form I).

In some embodiments, Form I has a DTA thermogram substantially as depicted in FIG. 2. In some embodiments, Form I has a DTA thermogram characterized by an endothermal event at about 317° C. In some embodiments, Form I has a DSC thermogram substantially as depicted in FIG. 3. In some embodiments, Form I has a DSC thermogram characterized by an endothermal event at about 317° C. In some aspects of the aforementioned embodiments, the endothermal event is a melting point. In some embodiments, Form I has a DSC thermogram characterized by an endothermal event at about 124° C. (e.g., at the second heating cycle). In some aspects of these embodiments, the endothermal event at about 124° C. is a glass transition temperature. Form I of Compound 1 is substantially anhydrous (Form I is not hydrated) and is substantially free of organic solvents (Form I is not solvated).

In some embodiments, Form I has hygroscopicity characterized by a mass uptake of about 0.3% at 90% RH as determined by GVS analysis. In other embodiments, Form I has hygroscopicity characterized by a mass uptake of about 0.7% at 90% RH as determined by DVS analysis. In some embodiments, Form I is substantially pure (e.g., the purity of the compound is at least about 90 wt. %, about 95 wt. %, about 98 wt. %, or about 99 wt. %). Purity values indicate the percentage of the amount of sample that is Form I. Purity values can be determined, for example, by HPLC/UV methods. In some embodiments, Form I is substantially free of impurities, such as organic impurities (e.g., process intermediates), inorganic impurities, and/or residual solvents.

In some embodiments, the crystalline form of Compound 1 exhibits the following single crystal X-ray crystallographic parameters at 120K:

| Crystal system | orthorhombic |
| --- | --- |
| Space group | $P2_12_12_1$ |
| a/Å | 6.91792(3) |
| b/Å | 13.74742(3) |
| c/Å | 19.22580(5) |
| α/° | 90.00 |
| β/° | 90.00 |
| γ/° | 90.00 |
| Volume/Å³ | 1828.442(10) |
| Z, Z' | 4 |
| ρcalc g/cm³ | 1.382 |

Figure 10:
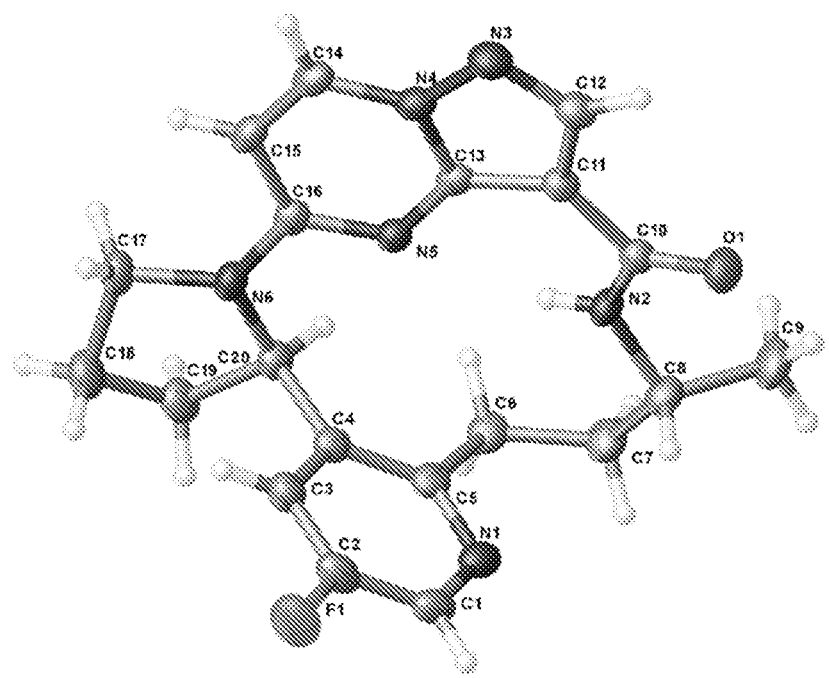
FIG. 10 is an image showing a 3-D view of Compound 1 (Form I) with atom labels.
Figure 11:
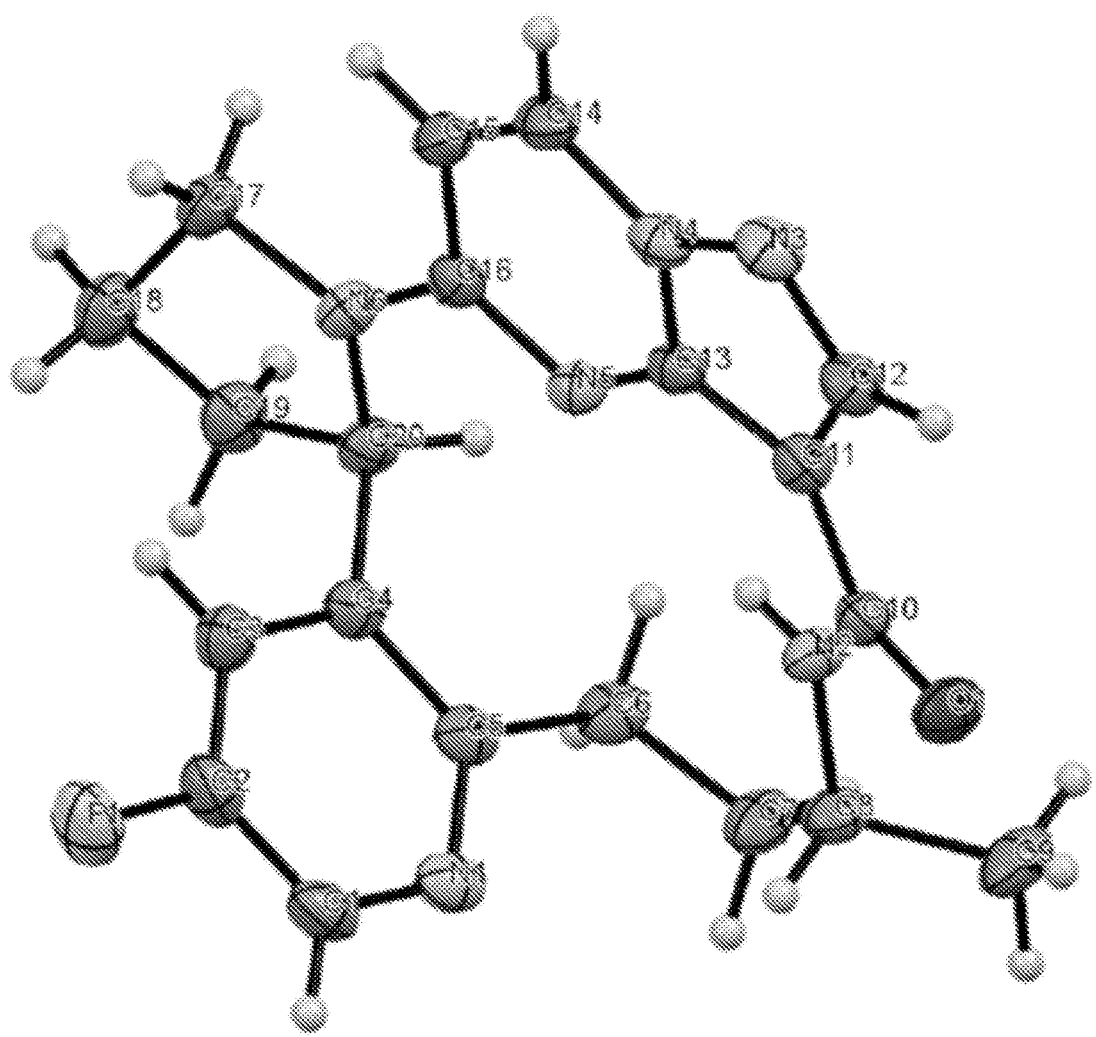
FIG. 11 is an image showing a ORTEP view of Compound 1 (Form I) with atom labels.

In some embodiments, the crystalline form of Compound 1 is substantially as shown in FIGS. 10 and 11.

In some embodiments, Compound 1 forms a solvate with acetonitrile solvent. In some embodiments, the acetonitrile solvate of Compound 1 is crystalline. In some embodiments, the crystalline form of acetonitrile solvate of Compound 1 exhibits the following single crystal X-ray crystallographic parameters at 120K:

| Crystal system | orthorhombic |
| --- | --- |
| Space group | $P2_12_12_1$ |
| a/Å | 6.03307(4) |
| b/Å | 16.10794(9) |
| c/Å | 23.72624(13) |
| α/° | 90.00 |
| β/° | 90.00 |
| γ/° | 90.00 |
| Volume /Å³ | 2305.73(2) |
| Z, Z' | 4 |
| ρcalc g/cm³ | 1.332 |

Figure 12:
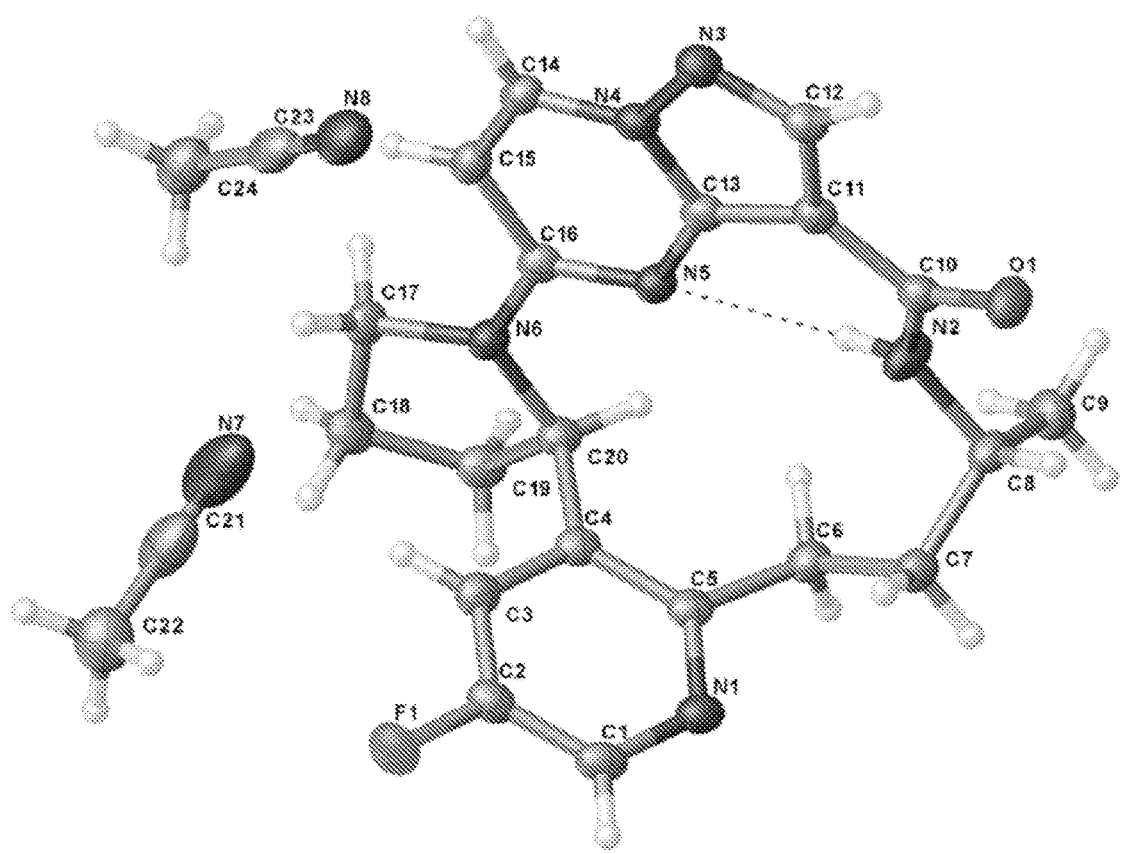
FIG. 12 is an image showing a 3-D view of Compound 1, acetonitrile solvate with atom labels.
Figure 13:
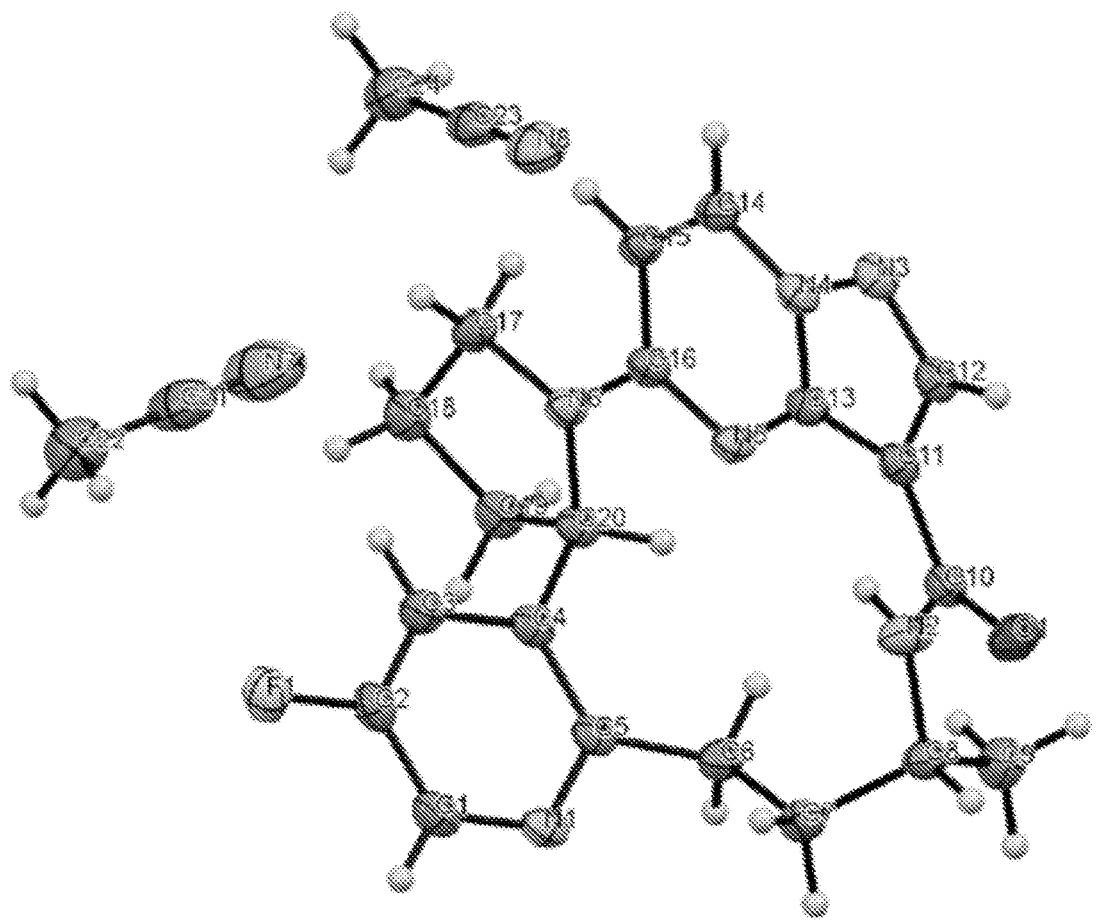
FIG. 13 is an image showing a ORTEP view of Compound 1, acetonitrile solvate with atom labels.

In some embodiments, the crystalline form of acetonitrile solvate is substantially as shown in FIGS. 12 and 13. In some embodiments, the crystalline form of acetonitrile solvate readily desolvates at room temperature to yield the crystalline Form I of Compound 1.

In some embodiments, the present disclosure provides crystalline Form I of Compound 1 prepared as disclosed herein. In one example, the disclosure provides the Form I of Compound 1 prepared by precipitating the solid crystalline form of Compound 1 from a saturated solution of Compound 1 in 1-propanol at about 2° C.

Compound 1 Benzenesulfonic Acid Salt

In some embodiments, provided herein is Compound 1 besylate. In some embodiments, Compound 1 besylate is at least 50%, at least 60%, at least 70%, at least 80%, at least 90%, or at least 99% crystalline solid. In some embodiments, crystalline Compound 1 besylate is substantially free of other forms of Compound 1 besylate. In some embodiments, crystalline Compound 1 besylate contains less than 10%, such as less than 5%, such as less than 3% of other forms of Compound 1 besylate. In some embodiments, the crystalline Compound 1 besylate is substantially free of the amorphous form of Compound 1 besylate. In some embodiments, the crystalline Compound 1 besylate contains less than 10%, less than 5%, or less than 3% of the amorphous form of Compound 1 besylate.

In some embodiments, the molar ratio of Compound 1 to the benzenesulfonic acid in the besylate is about 1:1. In some embodiments, Compound 1 besylate is a monobesylate.

Figure 17:
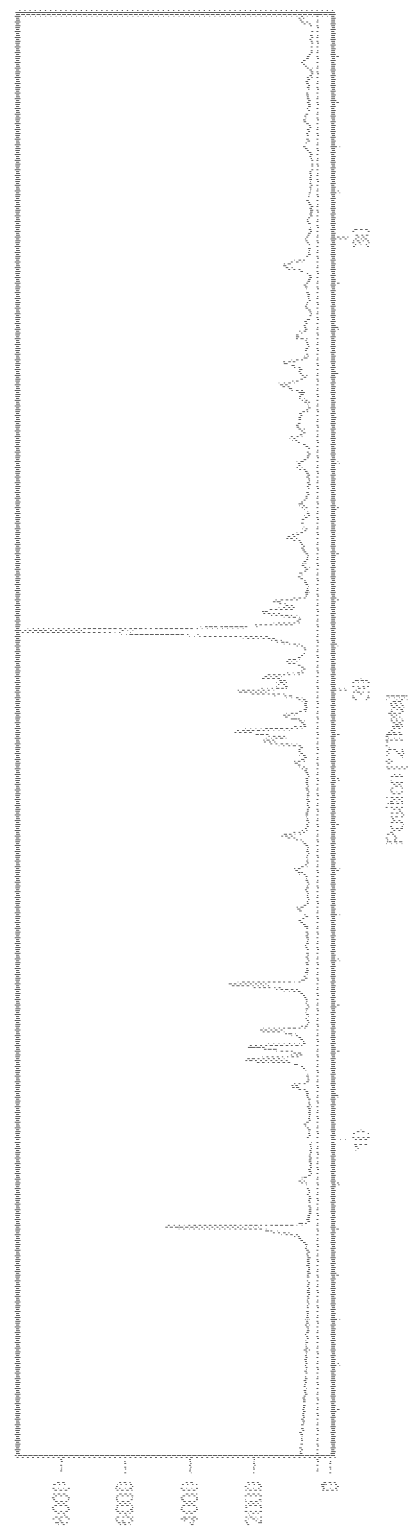
FIG. 17 is a XRPD diffractogram of Compound 1 besylate (pattern 1).
Figure 18:
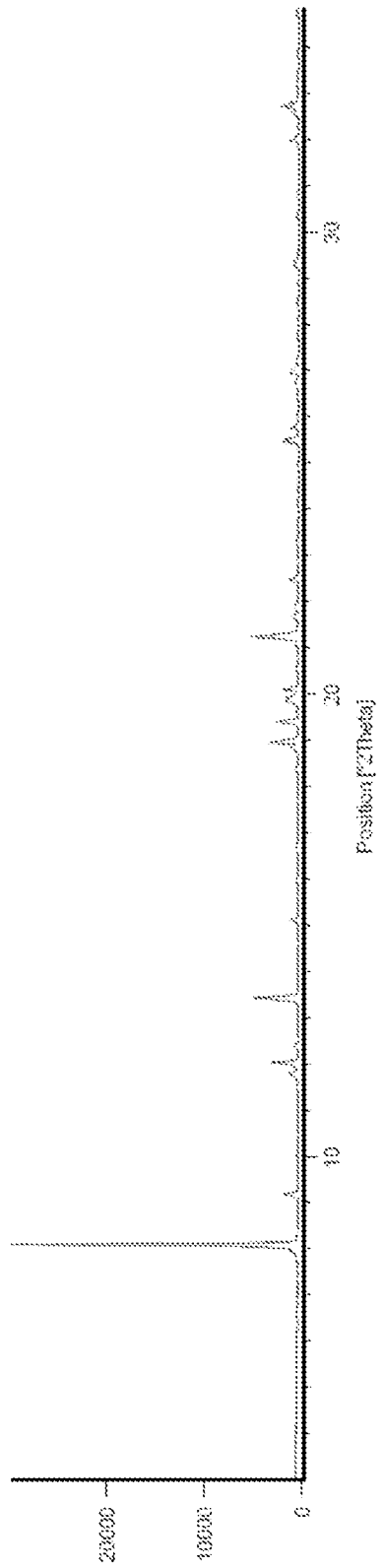
FIG. 18 is a XRPD diffractogram of Compound 1 besylate (pattern 2).

In some embodiments, the crystalline Compound 1 besylate has an XRPD pattern substantially as depicted in FIG. 17. In other embodiments, the crystalline Compound 1 besylate has an XRPD pattern substantially as depicted in FIG. 18.

In some embodiments, the crystalline Compound 1 besylate has a XRPD peak, in terms of 2-theta, at about 8.1 degrees. In some embodiments, the crystalline Compound 1 besylate has XRPD peaks, in terms of 2-theta, at about 8.1, about 13.4, and about 21.2. In some embodiments, the crystalline Compound 1 besylate has XRPD peaks, in terms of 2-theta, at about 8.1, about 12.0, about 13.4, about 19.0, about 19.4, and about 21.2. In some embodiments, the crystalline Compound 1 besylate has XRPD peaks, in terms of 2-theta, at about 8.1, about 12.0, about 13.4, about 19.0, about 19.4, about 19.9, about 20.1, about 21.2, about 25.5, and about 32.7.

In some embodiments, the crystalline Compound 1 besylate has a XRPD peak, in terms of 2-theta, at about 8.1, about 13.4, or about 21.2. In some embodiments, the crystalline Compound 1 besylate has at least one, at least two, or at least three XRPD peaks, in terms of 2-theta, selected from about 8.1, about 9.2, about 12.0, about 13.4, about 19.0, about 19.4, about 19.9, about 20.1, about 21.2, about 25.5, about 27.0, about 32.0, and about 32.7. In some embodiments, the crystalline Compound 1 besylate has at least one, at least two, or at least three XRPD peaks, in terms of 2-theta, selected from about 8.1, about 12.0, about 13.4, about 19.0, about 19.4, and about 21.2. In some embodiments, the crystalline Compound 1 besylate has at least one, at least two, or at least three XRPD peaks, in terms of 2-theta, selected from about 8.1, about 12.0, about 13.4, about 19.0, about 19.4, about 19.9, about 20.1, about 21.2, about 25.5, and about 32.7.

Figure 37:
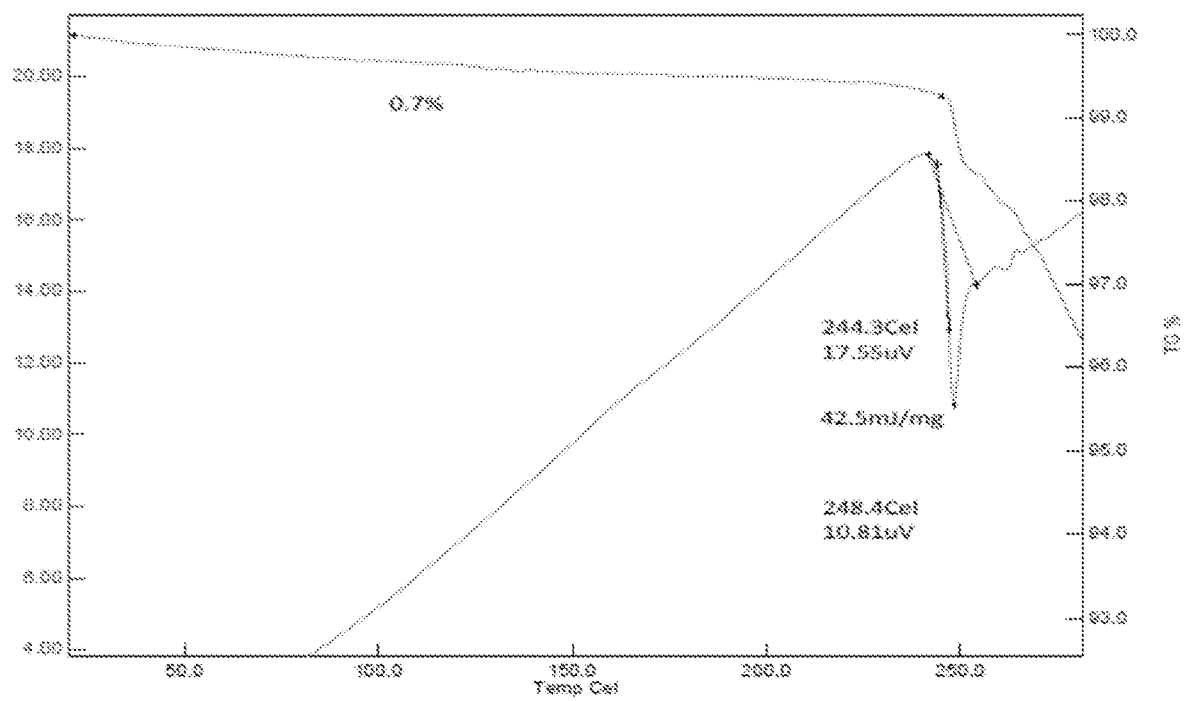
FIG. 37 is a TG/DTA thermogram of Compound 1 besylate.
Figure 38:
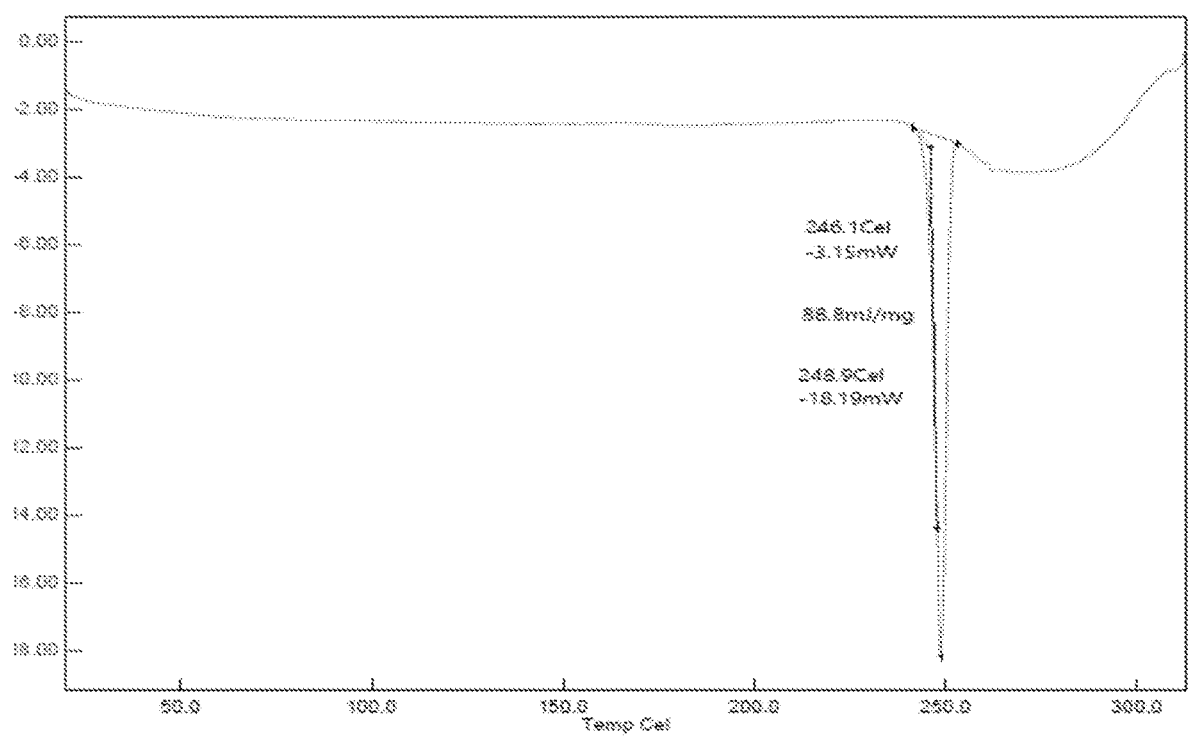
FIG. 38 is a DSC thermogram of Compound 1 besylate.

In some embodiments, the crystalline Compound 1 besylate has a DTA thermogram substantially as depicted in FIG. 37. In some embodiments, the crystalline Compound 1 besylate has a DTA thermogram characterized by an endothermal event at about 248° C. In some aspects of these embodiments, the endothermal event is a melting point. In some embodiments, the crystalline Compound 1 besylate has a DSC thermogram substantially as depicted in FIG. 38. In some embodiments, the crystalline Compound 1 besylate has a DSC thermogram characterized by an endothermal event at about 249° C.

In some embodiments, the crystalline Compound 1 besylate has hygroscopicity characterized by a mass uptake of about 0.7% at 90% RH as determined by DVS analysis. The crystalline Compound 1 besylate is substantially anhydrous (the crystalline form of the besylate is not hydrated) and is substantially free of organic solvents (the crystalline form of the besylate is not solvated).

In some embodiments, the crystalline Compound 1 besylate is substantially pure (e.g., free of organic, inorganic or other impurities). In some embodiments, the purity of the crystalline Compound 1 besylate is 90 wt. % or more, 95 wt. % or more, or 99 wt. % or more. In some embodiments, the crystalline Compound 1 besylate is substantially free of other crystalline forms of Compound 1 besylate.

In some embodiments, the benzenesulfonic acid salt of Compound 1 may form a hydrate. In some aspects of these embodiments, the hydrate is crystalline.

In some embodiments, the present disclosure provides a crystalline Compound 1 besylate prepared as disclosed herein. In one example, the application provides the crystalline Compound 1 besylate prepared by precipitating the solid crystalline form of Compound 1 besylate from a mixture of Compound 1 besylate with THF (e.g., a solution of Compound 1 besylate in THF). In another example, the application provides the crystalline Compound 1 besylate prepared by precipitating the crystalline form of Compound 1 besylate from a mixture of Compound 1 besylate with ethanol (e.g., a solution of Compound 1 besylate in ethanol).

Compound 1 Citric Acid Salt

In some embodiments, provided herein is Compound 1 citrate. In some embodiments, Compound 1 citrate is at least 50%, at least 60%, at least 70%, at least 80%, at least 90%, or at least 99% crystalline solid. In some embodiments, crystalline Compound 1 citrate is substantially free of other forms of Compound 1 citrate. In some embodiments, crystalline Compound 1 citrate contains less than 10%, such as less than 5%, such as less than 3% of other forms of Compound 1 citrate. In some embodiments, the crystalline form of Compound 1 citrate is substantially free of the amorphous form of Compound 1 citrate. In some embodiments, the crystalline form of Compound 1 citrate contains less than 10%, less than 5%, or less than 3% of the amorphous form of compound 1 citrate.

Figure 21:
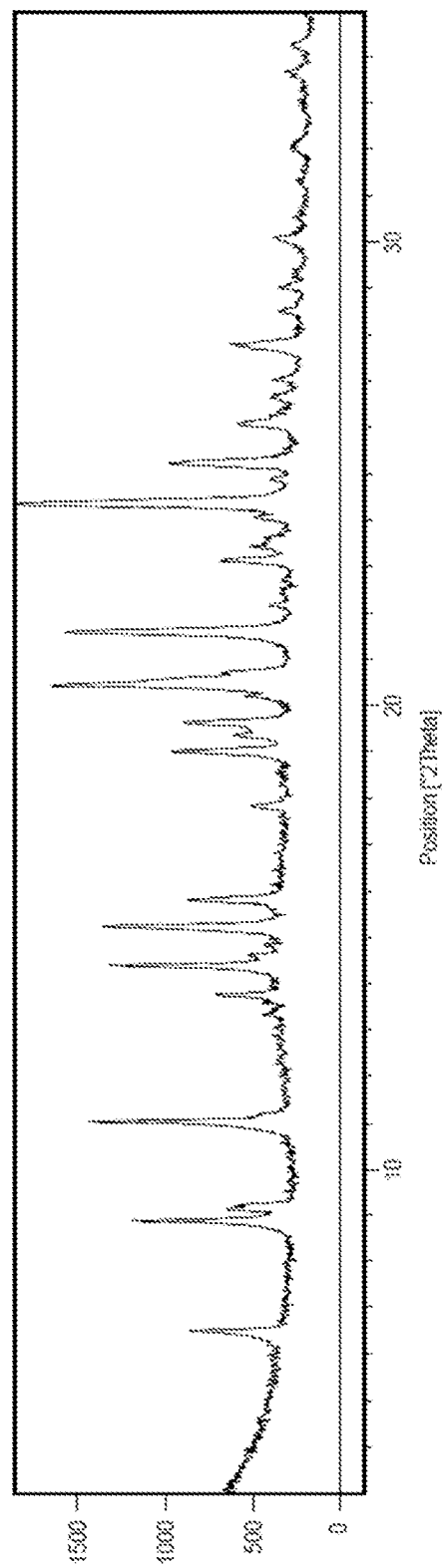
FIG. 21 is a XRPD diffractogram of Compound 1 citrate (Form A).

In some embodiments, the molar ratio of Compound 1 to the citric acid in the citrate is about 1:1. In some embodiments, Compound 1 citrate is a monocitrate. In some embodiments, crystalline Compound 1 citrate has Form A, which is described below in the Examples. In some embodiments, the Compound 1 citrate Form A has an XRPD pattern substantially as depicted in FIG. 21.

In some embodiments, the Compound 1 citrate Form A has a XRPD peak, in terms of 2-theta, at about 20.7 degrees. In some embodiments, Compound 1 citrate Form A has XRPD peaks, in terms of 2-theta, at about 20.7, about 21.6, and about 24.8. In some embodiments, Compound 1 citrate Form A has XRPD peaks, in terms of 2-theta, at about 8.9, about 11.1, about 14.4, about 15.4, about 20.7, about 21.6, and about 24.8. In some embodiments, Compound 1 citrate Form A has XRPD peaks, in terms of 2-theta, at about 8.9, about 11.1, about 13.9, about 14.4, about 15.4, about 19.2, about 20.7, about 21.6, about 24.8, and about 25.6.

In some embodiments, Compound 1 citrate Form A has at least one, at least two, or at least three XRPD peaks, in terms of 2-theta, selected from about 6.5, about 8.9, about 9.2, about 11.1, about 13.9, about 14.4, about 15.4, about 15.9, about 18.0, about 19.2, about 19.6, about 20.7, about 21.6, about 22.7, about 23.3, about 23.7, about 24.2, about 24.8, about 25.6, about 26.3, about 26.5, about 26.8, about 27.9, about 28.9, about 29.1, about 30.2, about 32.5, and about 33.7. In some embodiments, Compound 1 citrate Form A has at least one, at least two, or at least three XRPD peaks, in terms of 2-theta, selected from about 6.5, about 8.9, about 9.2, about 11.1, about 13.9, about 14.4, about 15.4, about 15.9, about 18.0, about 19.2, about 19.6, about 20.7, about 21.6, about 23.3, about 23.7, about 24.2, about 24.8, about 25.6, about 26.5, and about 27.9. In some embodiments, Compound 1 citrate Form A has at least one, at least two, or at least three XRPD peaks, in terms of 2-theta, selected from about 8.9, about 11.1, about 14.4, about 15.4, about 19.2, about 20.7, about 21.6, about 24.8, and about 25.6.

In some embodiments, Compound 1 citrate Form A has at least one, at least two, or at least three XRPD peaks, in terms of 2-theta, selected from about 6.5, about 8.9, about 9.2, about 11.1, about 13.9, about 14.4, about 15.4, about 15.9, about 18.0, about 19.2, about 19.6, about 20.7, about 21.6, about 22.3, about 22.7, about 23.3, about 23.7, about 24.2, about 24.8, about 25.6, about 26.3, about 26.5, about 26.8, about 27.9, about 28.9, about 29.1, about 30.2, about 30.6, about 31.8, about 32.5, about 33.1, about 33.7, about 34.3, and about 34.5.

Figure 43:
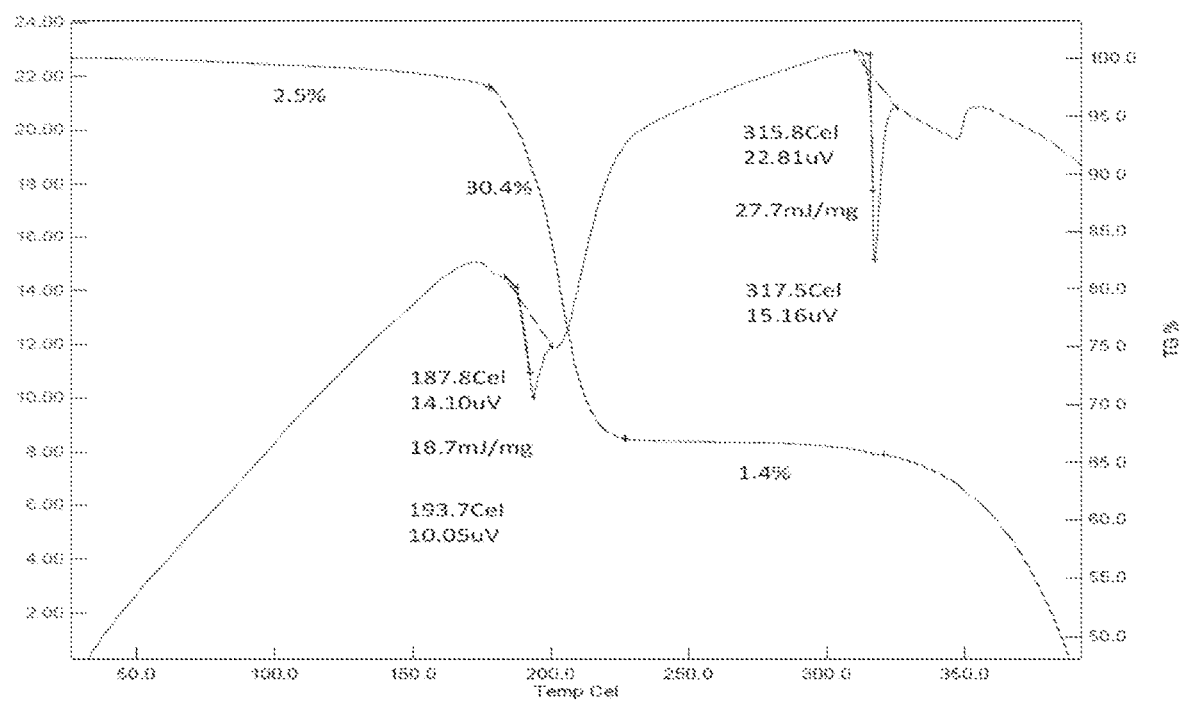
FIG. 43 is a TG/DTA thermogram of Compound 1 citrate (Form A).
Figure 44:
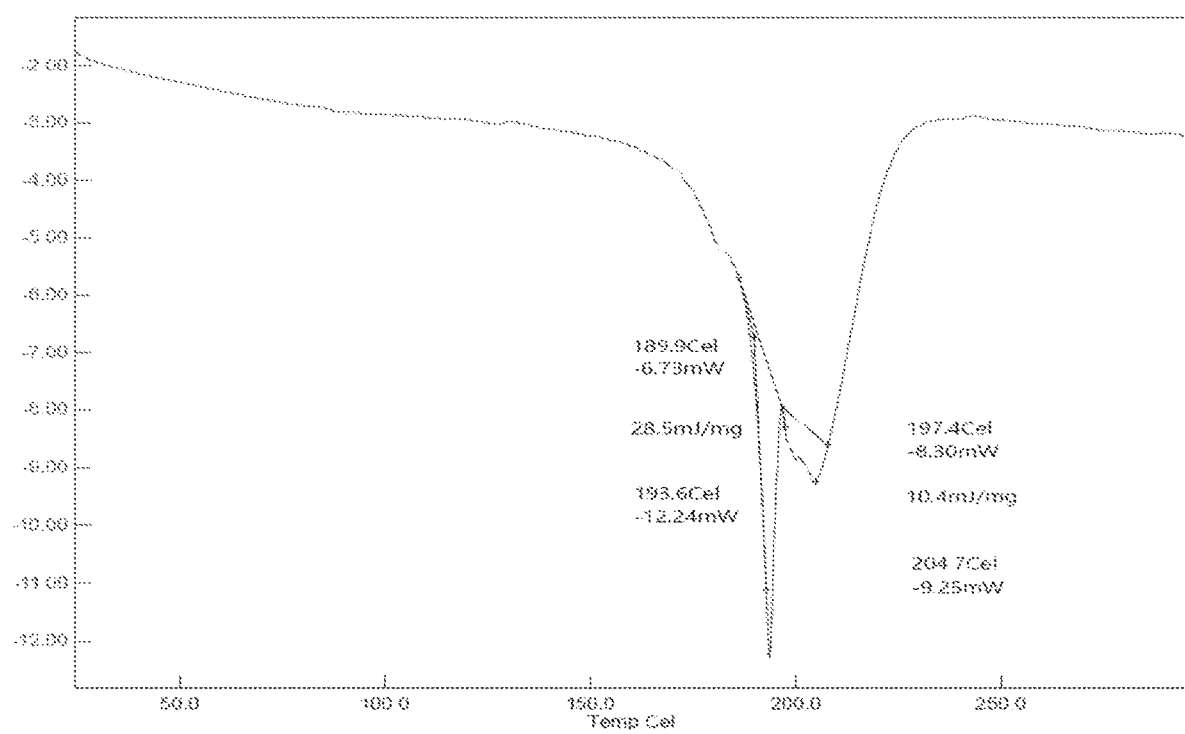
FIG. 44 is a DSC thermogram of Compound 1 citrate (Form A).

In some embodiments, Compound 1 citrate Form A has a DTA thermogram substantially as depicted in FIG. 43. In some embodiments, Compound 1 citrate Form A has a DTA thermogram characterized by an endothermal event at about 194° C. In some embodiments, Compound 1 citrate Form A has a DTA thermogram characterized by an endothermal event at about 318° C. In some embodiments, Compound 1 citrate Form A has a DTA thermogram characterized by an endothermal event at about 194° C. and an endothermal event at about 318° C. In some embodiments, Compound 1 citrate Form A has a DSC thermogram substantially as depicted in FIG. 44. In some embodiments, Compound 1 citrate Form A has a DSC thermogram characterized by an endothermal event at about 205° C. In some embodiments, Compound 1 citrate Form A has a DSC thermogram characterized by an endothermal event at about 194° C. and an endothermal event at about 205° C. In some aspects of these embodiments, the endothermal events are overlapping.

In some embodiments, Compound 1 citrate Form A has hygroscopicity characterized by a mass uptake of around 1.8% at 90% RH as determined by DVS analysis. Compound 1 citrate Form A is substantially anhydrous (Form A is not hydrated) and is substantially free of organic solvents (Form A is not solvated).

In some embodiments, Compound 1 citrate Form A is substantially pure (e.g., free of organic, inorganic or other impurities). In some embodiments, the purity of Compound 1 citrate Form A is 90 wt. % or more, 95 wt. % or more, or 99 wt. % or more. In some embodiments, Compound 1 citrate Form A is substantially free of other crystalline forms of Compound 1 citrate. For example, Compound 1 citrate Form A is substantially free of Compound 1 citrate Form B.

In some embodiments, the citric acid salt of Compound 1 may form a hydrate. In some aspects of these embodiments, the hydrate is crystalline.

Figure 49:
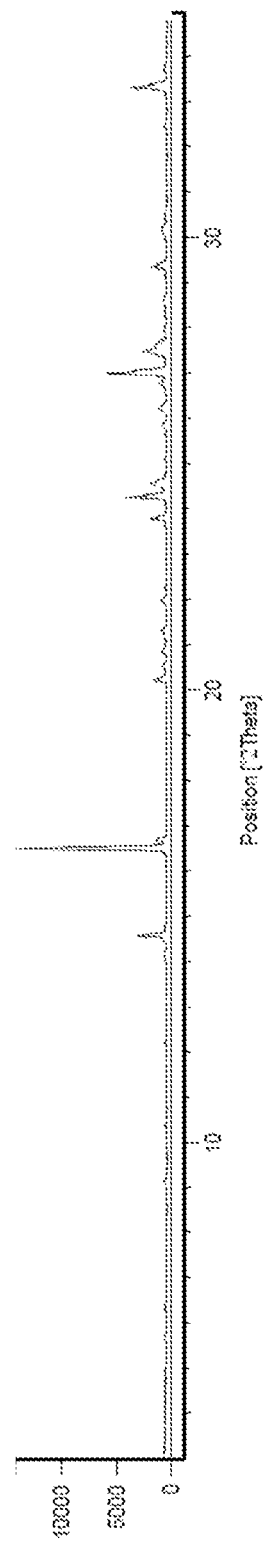
FIG. 49 is a XRPD diffractogram of a Compound 1 citrate (Form B).

In some embodiments, the crystalline Compound 1 citrate has Form B, which has an XRPD pattern substantially as depicted in FIG. 49.

In some embodiments, the present disclosure provides a crystalline form of Compound 1 citrate prepared as disclosed herein. In one example, the present application provides Compound 1 citrate Form A prepared by precipitating Form A from a mixture of Compound 1 citrate with acetone (e.g., a solution of Compound 1 in acetone).

Compound 1 Methanesulfonic Acid Salt

In some embodiments, provided herein is Compound 1 mesylate. In some embodiments, the Compound 1 mesylate is at least 50%, at least 60%, at least 70%, at least 80%, at least 90%, or at least 99% crystalline solid. In some embodiments, the crystalline form of Compound 1 mesylate is substantially free of the amorphous form of Compound 1 mesylate. In some embodiments, the crystalline form of Compound 1 mesylate contains less than 10%, less than 5%, or less than 3% of the amorphous form of compound 1 mesylate.

In some embodiments, the molar ratio of the Compound 1 to the methanesulfonic acid in the mesylate is about 1:1. In some embodiments, the Compound 1 mesylate is a monomesylate.

Figure 16:
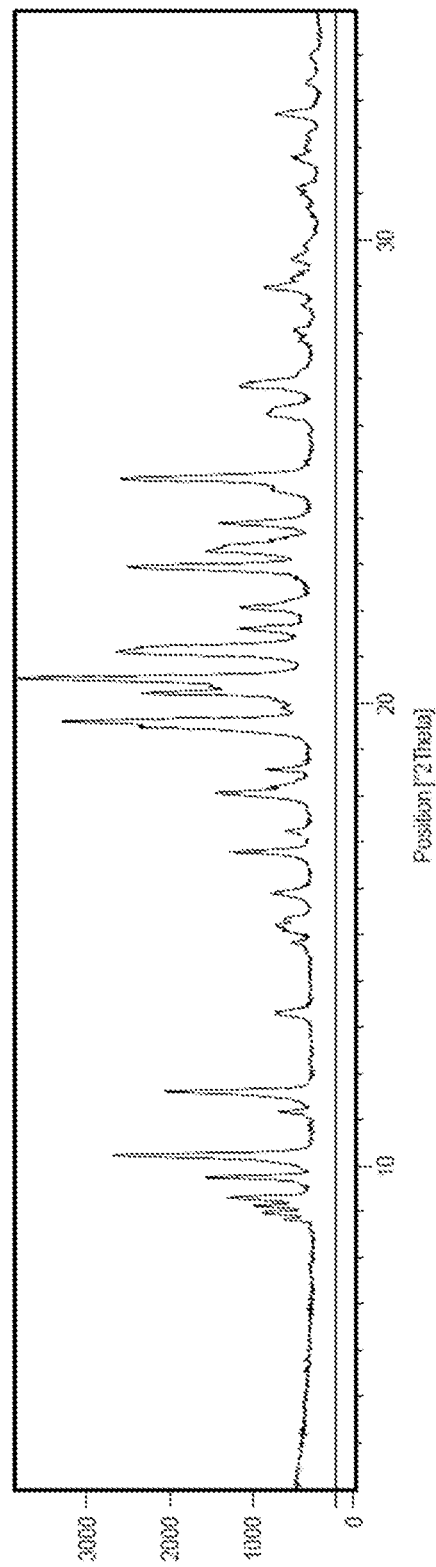
FIG. 16 is a XRPD diffractogram of Compound 1 mesylate.
Figure 25:
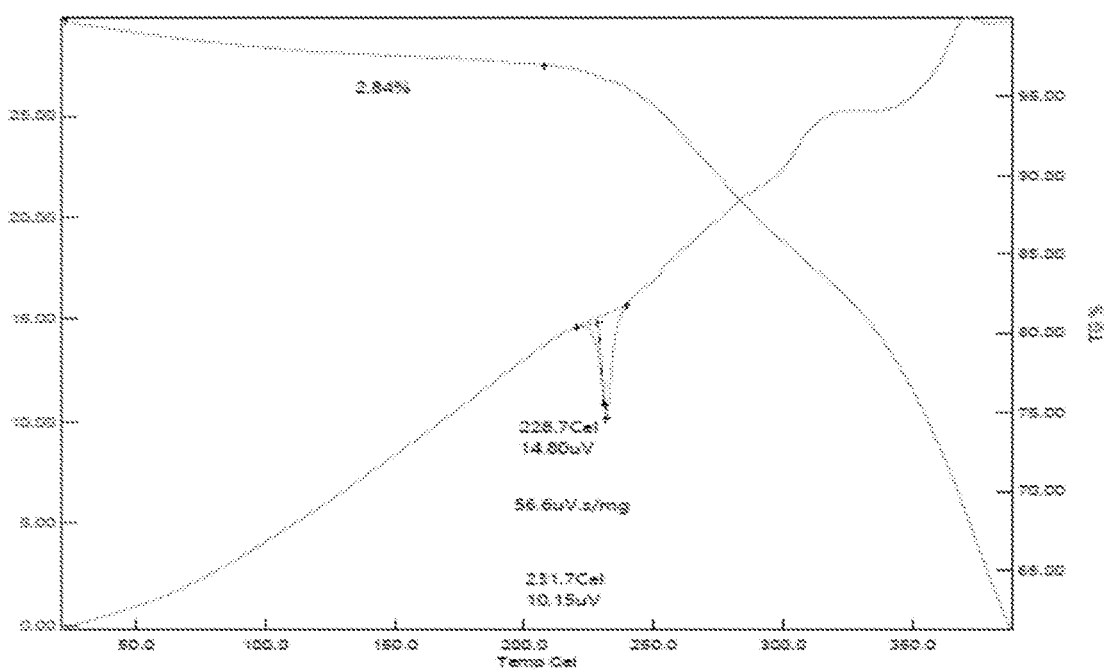
FIG. 25 is a TG/DTA thermogram of Compound 1 mesylate.
Figure 32:
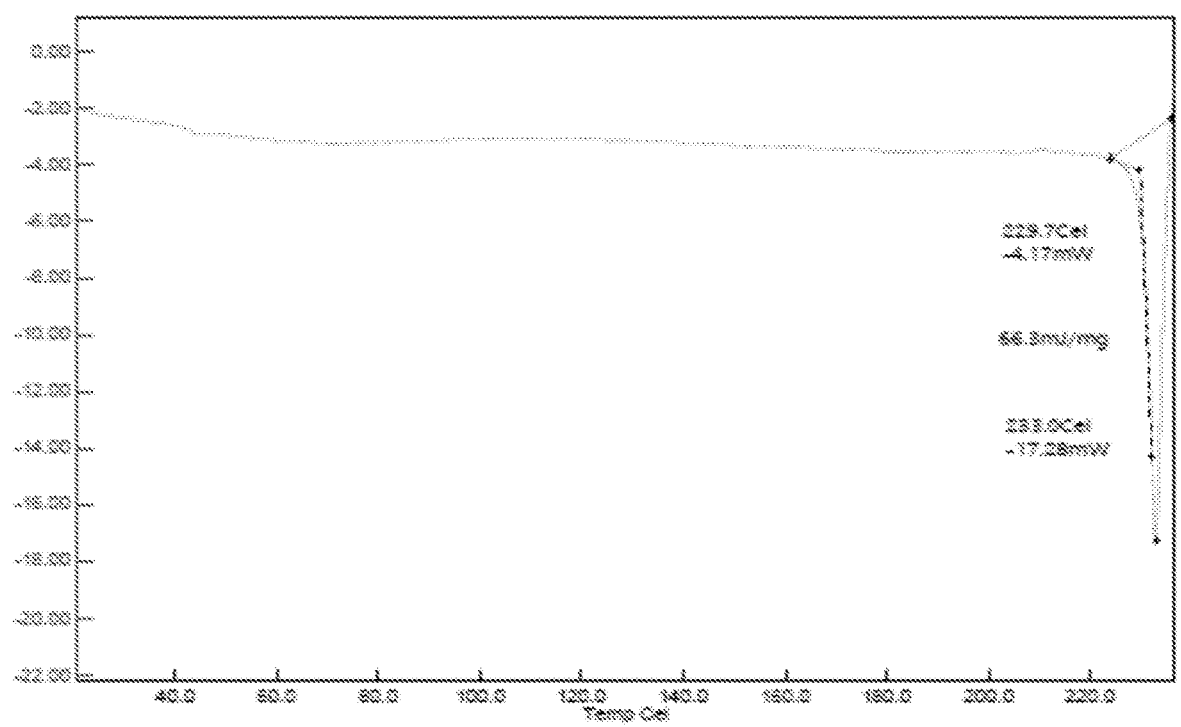
FIG. 32 is a DSC thermogram of Compound 1 mesylate.

In some embodiments, the crystalline form of Compound 1 mesylate has an XRPD pattern substantially as depicted in FIG. 16. In some embodiments, the crystalline solid of the Compound 1 mesylate has a DTA thermogram substantially as depicted in FIG. 25. In some embodiments, the crystalline solid of the Compound 1 mesylate has a DTA thermogram characterized by an endothermal event at about 232° C. (e.g., a melting point of the mesylate). In some embodiments, the crystalline Compound 1 mesylate has a DSC thermogram substantially as depicted in FIG. 32. In some embodiments, the crystalline Compound 1 mesylate has a DSC thermogram characterized by an endothermal event at about 233° C. The crystalline form of the mesylate is substantially anhydrous (the crystalline form is not hydrated) and is substantially free of organic solvents (the crystalline form is not solvated). In some embodiments, the crystalline form of the mesylate is substantially pure (e.g., purity is 90 wt. % or more, 95 wt. % or more, or 99 wt. % or more). In some embodiments, the crystalline form of Compound 1 mesylate is substantially free of other crystalline forms of Compound 1 mesylate.

Figure 30:
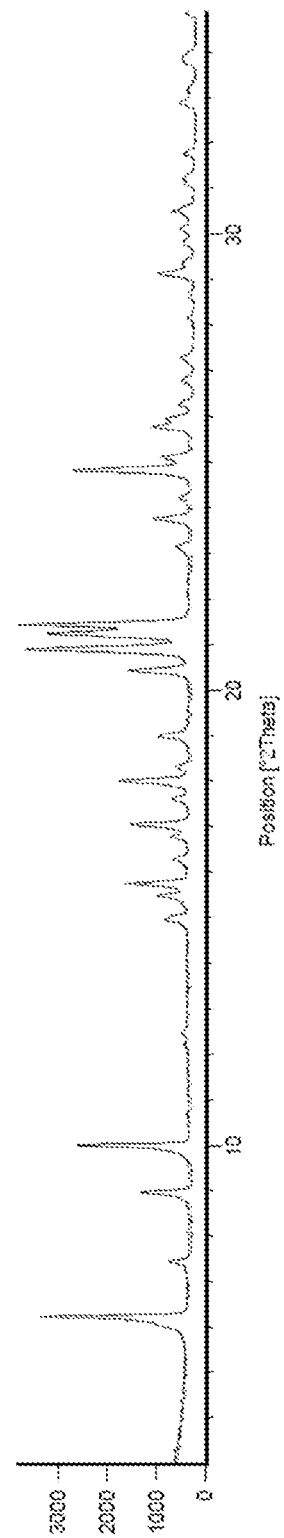
FIG. 30 is a XRPD diffractogram of Compound 1 mesylate acetone solvate.
Figure 31:
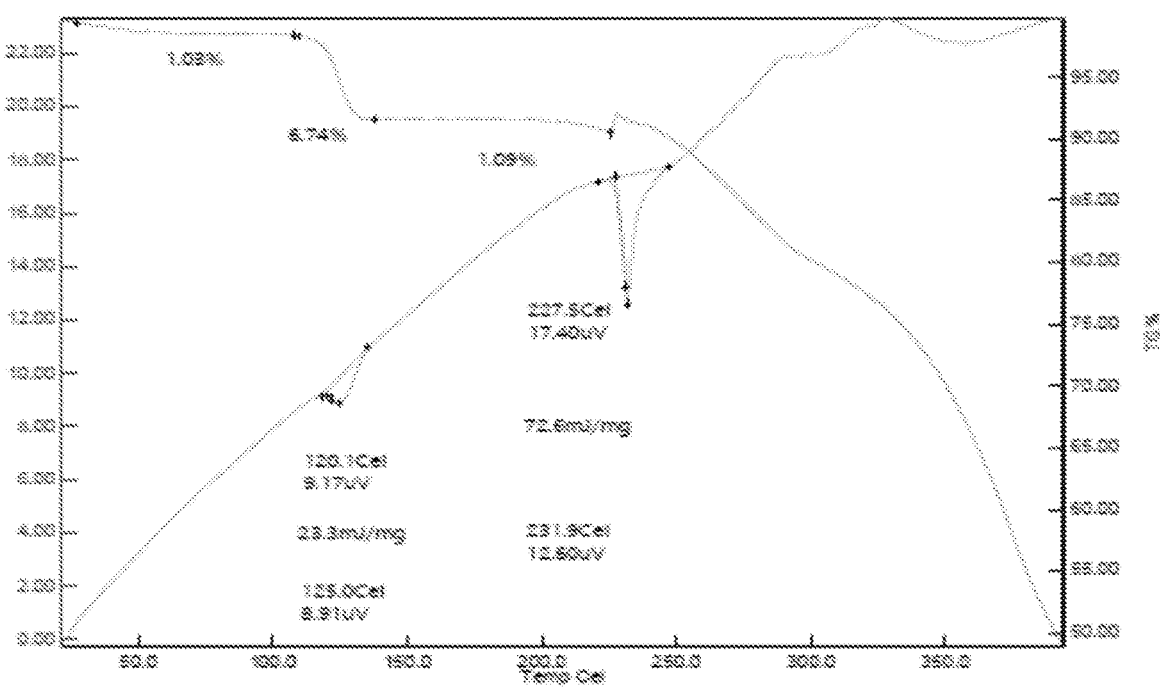
FIG. 31 is a TG/DTA thermogram of Compound 1 mesylate acetone solvate.

Compound 1 mesylate can be prepared as an acetone solvate. In some embodiments, the acetone solvate of the mesylate is a solid form (e.g., an amorphous solid, a crystalline solid, or a mixture thereof). In some embodiments, the acetone solvate of the mesylate is crystalline. In some embodiments, the crystalline form of the acetone solvate of the mesylate salt of Compound 1 is has an XRPD pattern substantially as depicted in FIG. 30. In some embodiments, the crystalline acetone solvate has a DTA thermogram substantially as depicted in FIG. 31. In some embodiments, the crystalline acetone solvate has a DTA thermogram characterized by an endothermal event at about 125° C. and an endothermal event at about 232° C. (melting point). The endothermal event at about 125° C. is likely associated with the desolvation of the material. In some embodiments, the crystalline acetone solvate has a DSC thermogram characterized by an endothermal event at about 233° C. at the first heating cycle, a solidification event at about 181° C. at the first cooling cycle, and an endothermal event at about 229° C. at the second heating cycle. In some embodiments, the acetone solvate readily desolvates upon heating to produce crystalline form of the Compound 1 mesylate.

In some embodiments, the present disclosure provides a crystalline form of Compound 1 mesylate prepared as disclosed herein. In one example, the application provides the crystalline form of Compound 1 mesylate prepared by precipitating the solid crystalline form of Compound 1 mesylate from a mixture of Compound 1 mesylate in 2-propanol (e.g., a solution of Compound 1 in isopropanol).

Other Salts

In some embodiments provided herein is a salt of Compound 1 which is Compound 1 edisylate, Compound 1 tosylate, Compound 1 oxalate, Compound 1 fumarate, Compound 1 L-malate or Compound 1 succinate. In some embodiments, each of Compound 1 edisylate, Compound 1 tosylate, Compound 1 oxalate, Compound 1 fumarate, Compound 1 L-malate and or Compound 1 succinate can be prepared as a solid form, e.g., as an amorphous solid, as a crystalline solid, or as a mixture thereof. In some aspects of these embodiments, any of the aforementioned salts of Compound 1 is at least 50%, at least 60%, at least 70%, at least 80%, at least 90%, or at least 99% crystalline solid. In other aspects of these embodiments, the crystalline salt of Compound 1 is substantially free of the amorphous form of the salt. For example, Compound 1 salt contains less than 10%, less than 5%, or less than 3% of the amorphous form of the salt.

In some embodiments, the present disclosure provides crystalline forms of Compound 1 edisylate, Compound 1 tosylate, Compound 1 oxalate, Compound 1 fumarate, Compound 1 L-malate or Compound 1 succinate prepared as disclosed herein.

Figure 14:
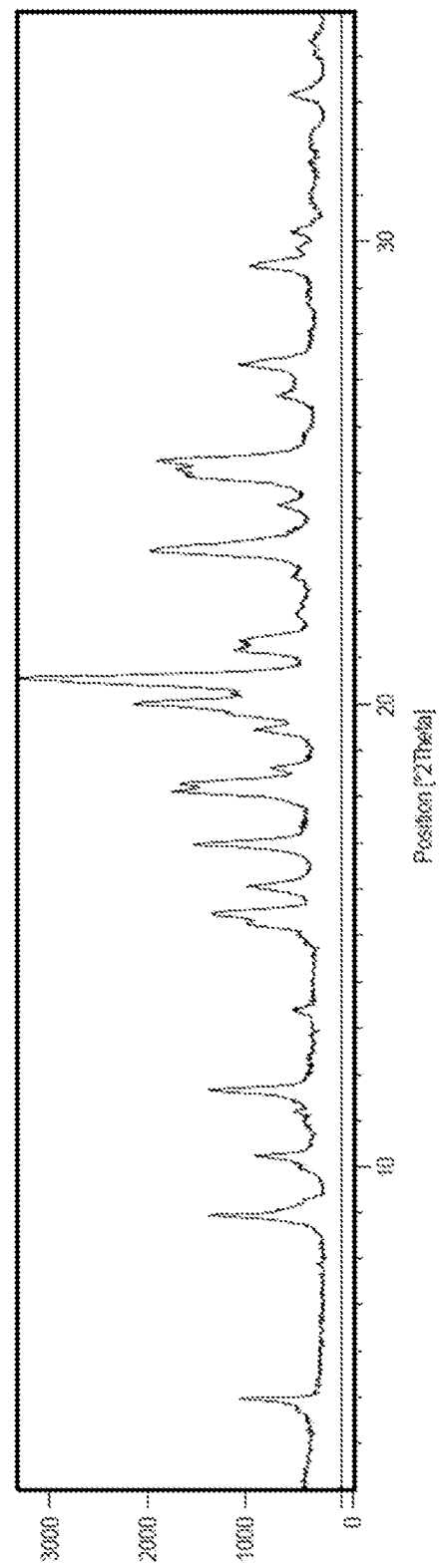
FIG. 14 is a XRPD diffractogram of Compound 1 edisylate.

In some embodiments, the crystalline Compound 1 edisylate has an XRPD pattern substantially as depicted in FIG. 14.

In some embodiments, the crystalline Compound 1 edisylate has XRPD peaks, in terms of 2-theta, at about 20.0, about 20.6, and about 23.3. In some embodiments, the crystalline Compound 1 edisylate has XRPD peaks, in terms of 2-theta, at about 18.1, about 18.3, about 20.0, about 20.6, about 23.3, and about 25.3. In some embodiments, the crystalline Compound 1 edisylate has XRPD peaks, in terms of 2-theta, at about 11.6, about 15.5, about 17.0, about 18.1, about 18.3, about 20.0, about 20.6, about 23.3, about 24.9, and about 25.3.

Figure 15:
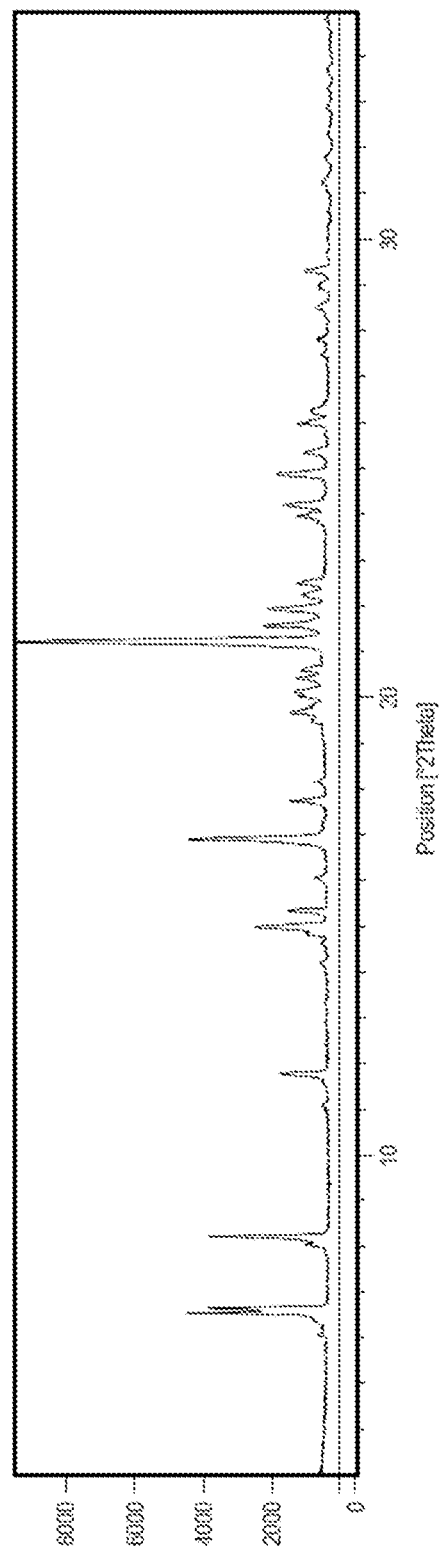
FIG. 15 is a XRPD diffractogram of Compound 1 tosylate.

In some embodiments, the crystalline Compound 1 tosylate has an XRPD pattern substantially as depicted in FIG. 15.

In some embodiments, the crystalline Compound 1 tosylate has XRPD peaks, in terms of 2-theta, at about 6.6, about 16.9, and about 21.2. In some embodiments, the crystalline Compound 1 tosylate has XRPD peaks, in terms of 2-theta, at about 6.6, about 8.2, about 15.0, about 16.9, about 21.2, and about 21.6. In some embodiments, the crystalline Compound 1 tosylate has XRPD peaks, in terms of 2-theta, at about 6.6, about 8.2, about 11.8, about 15.0, about 16.9, about 21.2, about 21.6, about 21.9, about 24.2 and about 24.9.

Figure 24:
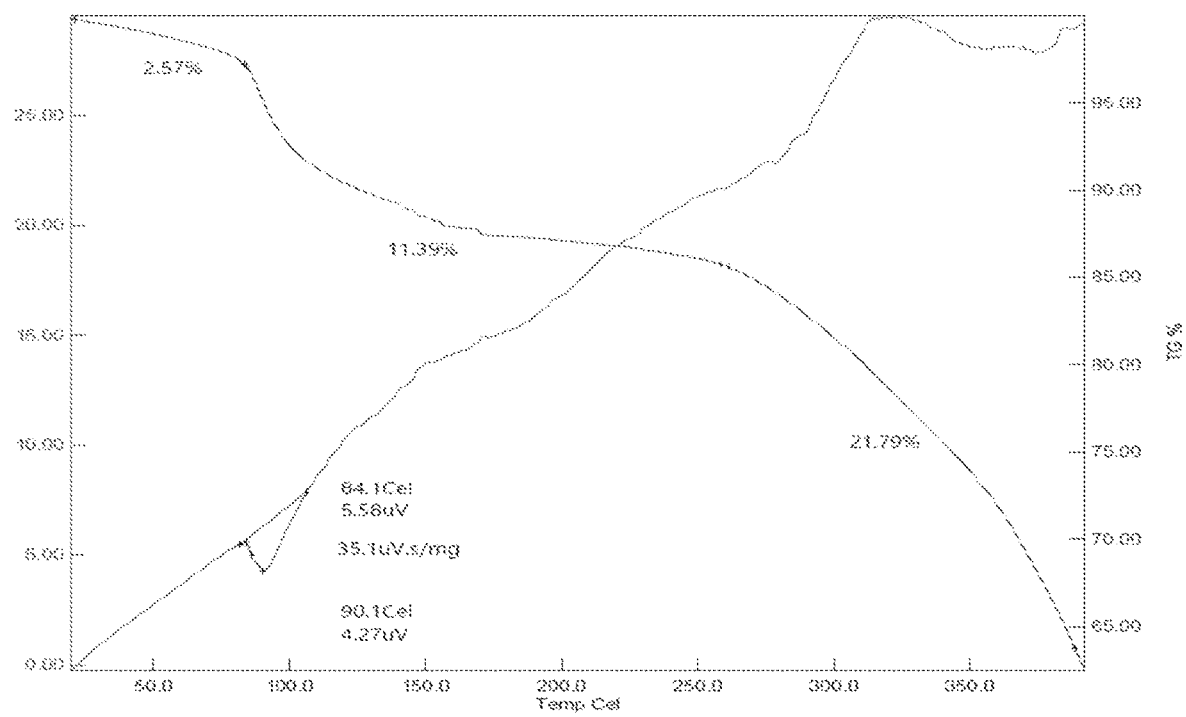
FIG. 24 is a TG/DTA thermogram of Compound 1 tosylate.

In some embodiments, the crystalline Compound 1 tosylate has a DTA thermogram substantially as depicted in FIG. 24. In some embodiments, the crystalline Compound 1 tosylate has a DTA thermogram characterized by an endothermal event at about 90° C.

Figure 19:
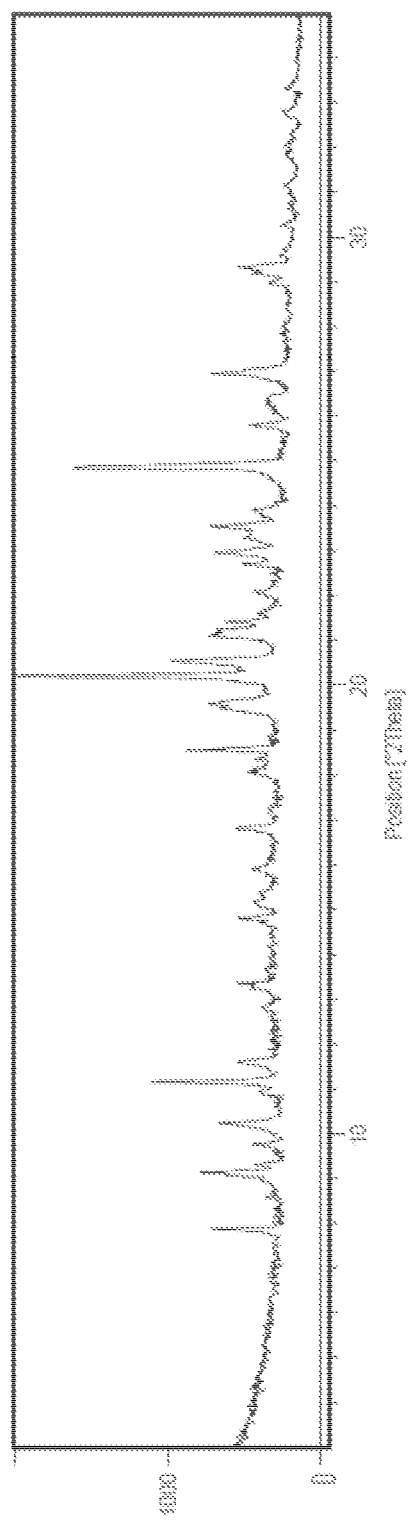
FIG. 19 is a XRPD diffractogram of Compound 1 oxalate.

In some embodiments, the crystalline Compound 1 oxalate has an XRPD pattern substantially as depicted in FIG. 19.

In some embodiments, the crystalline Compound 1 oxalate has XRPD peaks, in terms of 2-theta, at about 20.2, about 20.5, and about 24.9. In some embodiments, the crystalline Compound 1 oxalate has XRPD peaks, in terms of 2-theta, at about 11.2, about 18.6, about 20.2, about 20.5, about 23.5, and about 24.9. In some embodiments, the crystalline Compound 1 oxalate has XRPD peaks, in terms of 2-theta, at about 11.2, about 18.6, about 20.0, about 20.2, about 20.5, about 21.1, about 22.9, about 23.5, about 24.9, and about 27.0.

Figure 26:
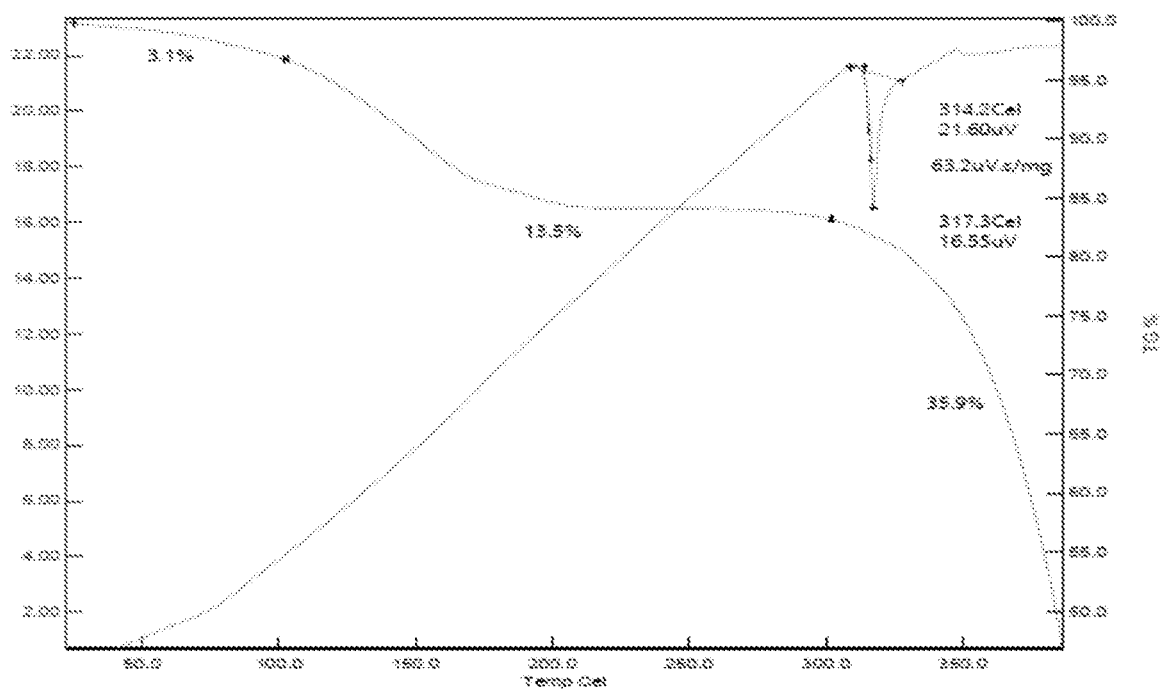
FIG. 26 is a TG/DTA thermogram of Compound 1 oxalate.

In some embodiments, the crystalline Compound 1 oxalate has a DTA thermogram substantially as depicted in FIG. 26. In some embodiments, the crystalline Compound 1 oxalate has a DTA thermogram characterized by an endothermal event at about 317° C. (a melting point).

Figure 20:
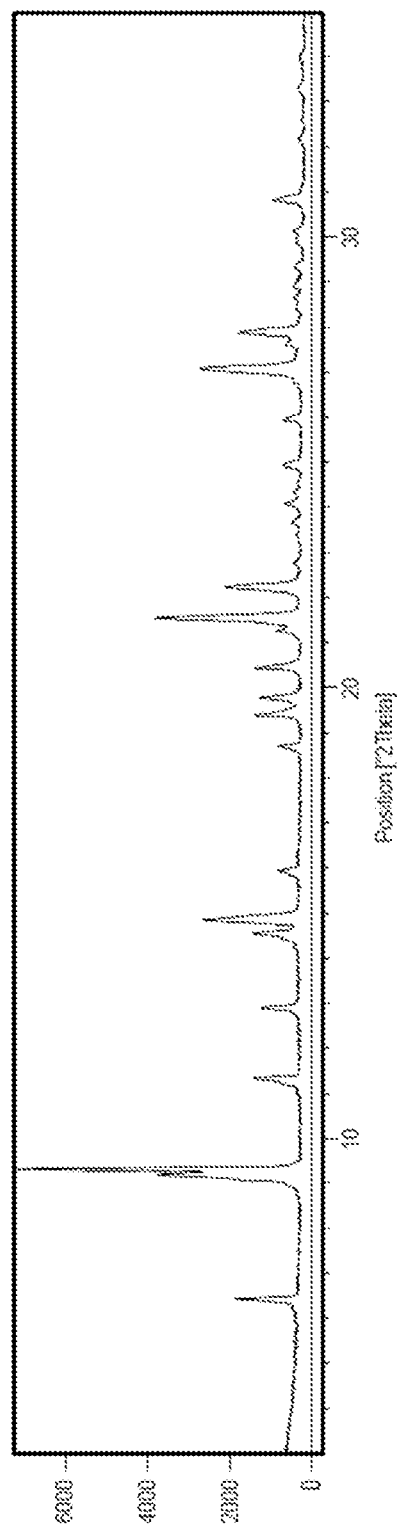
FIG. 20 is a XRPD diffractogram of Compound 1 fumarate.

In some embodiments, the crystalline Compound 1 fumarate has an XRPD pattern substantially as depicted in FIG. 20.

In some embodiments, the crystalline Compound 1 fumarate has XRPD peaks, in terms of 2-theta, at about 9.3, about 21.6, and about 27.1. In some embodiments, the crystalline Compound 1 fumarate has XRPD peaks, in terms of 2-theta, at about 9.3, about 14.8, about 21.6, about 22.2, about 27.1, and about 27.9. In some embodiments, the crystalline Compound 1 fumarate has XRPD peaks, in terms of 2-theta, at about 6.4, about 9.3, about 14.8, about 19.4, about 19.8, about 20.4, about 21.6, about 22.2, about 27.1, and about 27.9.

Figure 27:
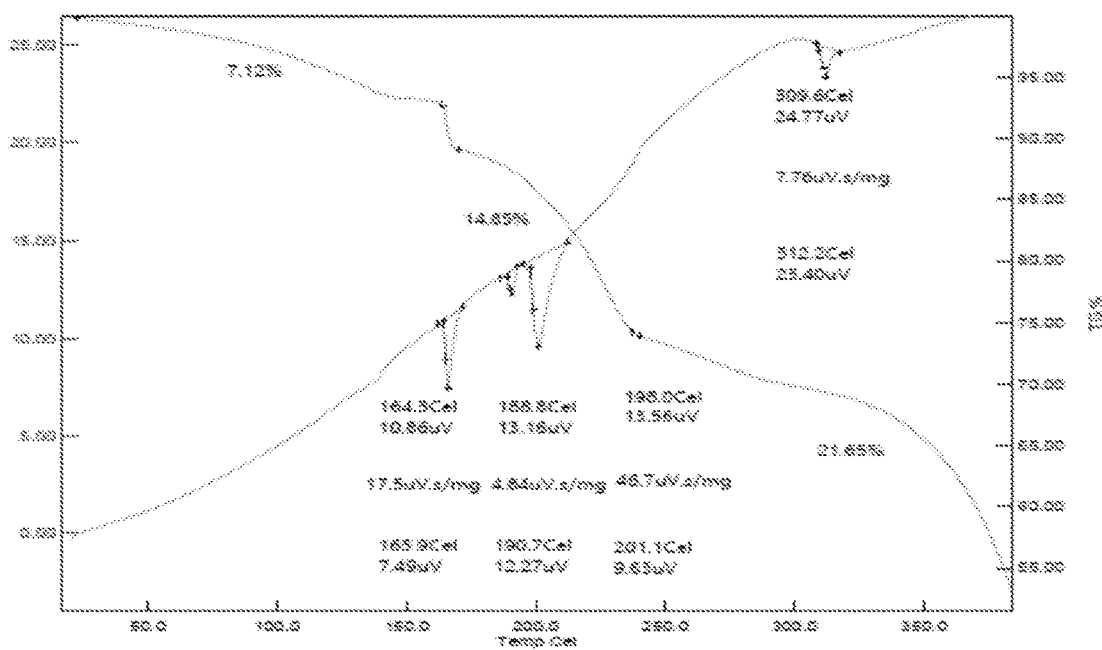
FIG. 27 is a TG/DTA thermogram of Compound 1 fumarate.

In some embodiments, the crystalline Compound 1 fumarate has a DTA thermogram substantially as depicted in FIG. 27. In some embodiments, the crystalline Compound 1 fumarate has a DTA thermogram characterized by an endothermal event at about 166° C. In some embodiments, the crystalline Compound 1 fumarate has a DTA thermogram characterized by an endothermal event at about 191° C. In some embodiments, the crystalline Compound 1 fumarate has a DTA thermogram characterized by an endothermal event at about 201° C. In some embodiments, the crystalline Compound 1 fumarate has a DTA thermogram characterized by an endothermal event at about 312° C. In some embodiments, the crystalline Compound 1 fumarate has a DTA thermogram characterized by an endothermal event at about 166° C., an endothermal event at about 191° C., an endothermal event at about 201° C., and an endothermal event at about 312° C.

Figure 22:
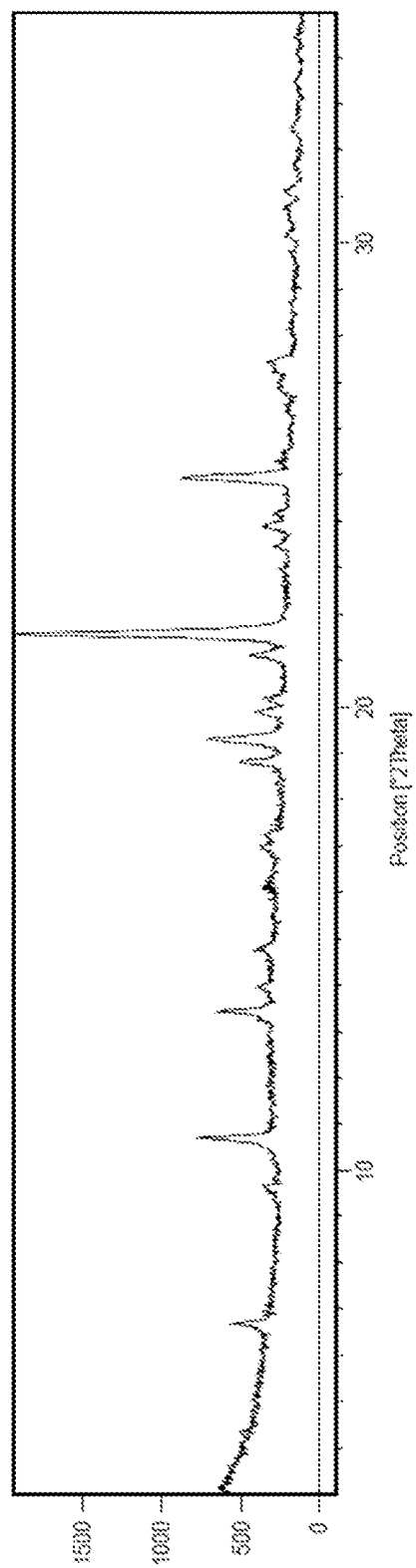
FIG. 22 is a XRPD diffractogram of Compound 1 L-malate.

In some embodiments, the crystalline Compound 1 L-malate has an XRPD pattern substantially as depicted in FIG. 22.

In some embodiments, the crystalline Compound 1 malate has XRPD peaks, in terms of 2-theta, at about 19.3, about 21.6, and about 24.9. In some embodiments, the crystalline Compound 1 malate has XRPD peaks, in terms of 2-theta, at about 10.7, about 13.4, about 18.8, about 19.3, about 21.6, and about 24.9. In some embodiments, the crystalline Compound 1 malate has XRPD peaks, in terms of 2-theta, at about 6.7, about 10.7, about 13.4, about 18.8, about 19.3, about 19.9, about 21.1, about 21.6, about 23.9, and about 24.9.

Figure 23:
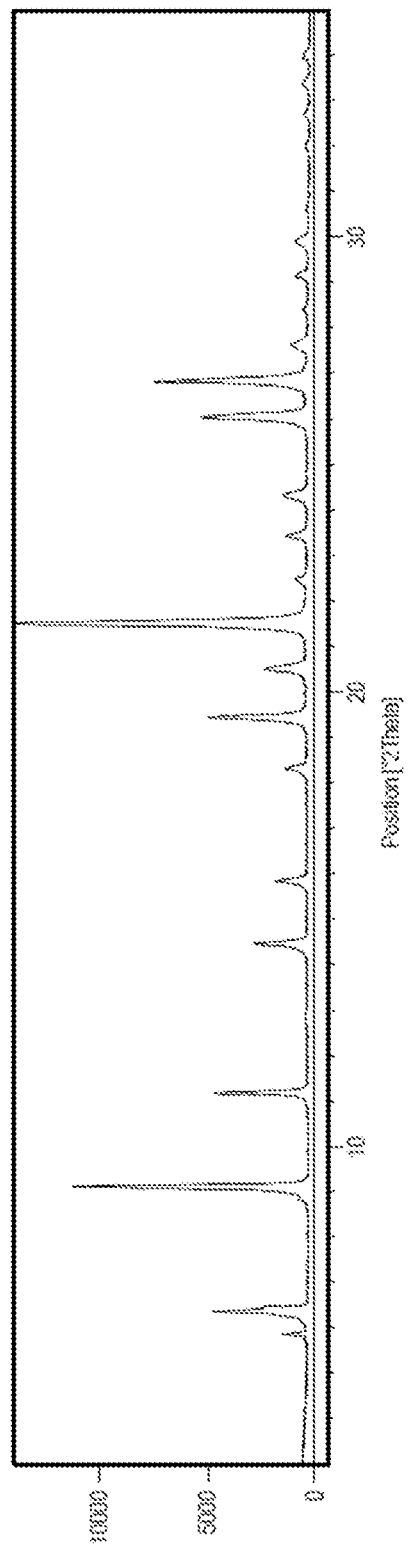
FIG. 23 is a XRPD diffractogram of Compound 1 succinate.
Figure 28:
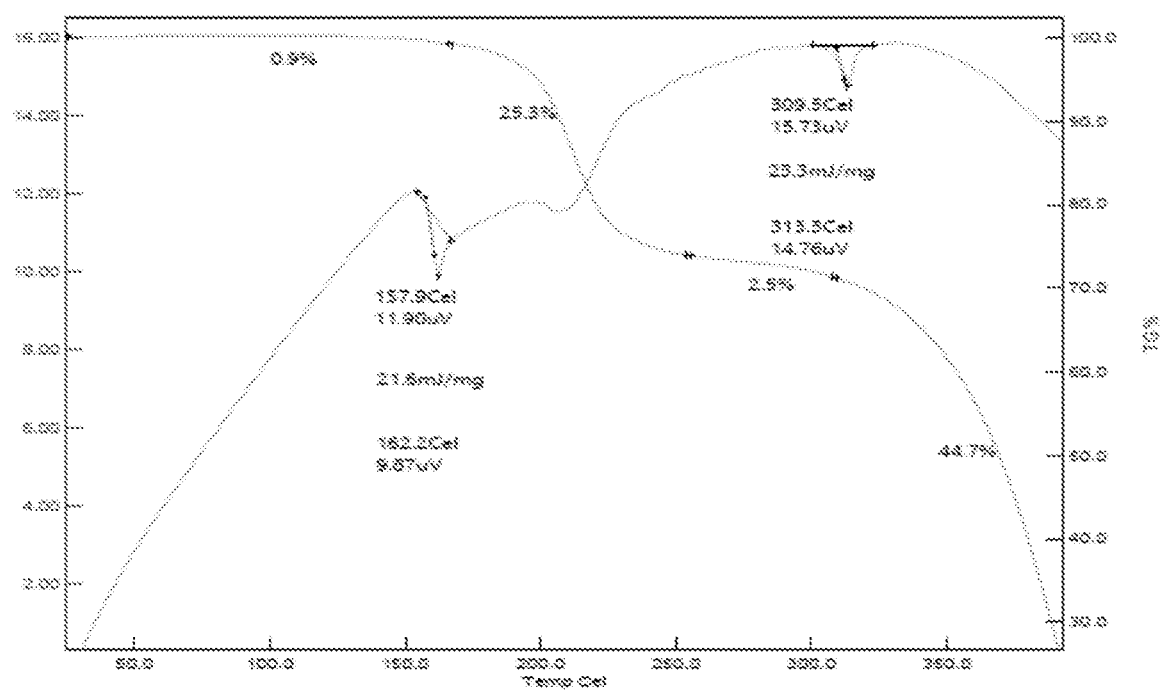
FIG. 28 is a TG/DTA thermogram of Compound 1 L-malate.

In some embodiments, the crystalline Compound 1 L-malate has a DTA thermogram substantially as depicted in FIG. 28. In some embodiments, the crystalline Compound 1 L-malate has a DTA thermogram characterized by an endothermal event at about 162° C. In some embodiments, the crystalline Compound 1 L-malate has a DTA thermogram characterized by an endothermal event at about 313° C. In some embodiments, the crystalline Compound 1 L-malate has a DTA thermogram characterized by an endothermal event at about 162° C. and an endothermal event at about 313° C. In some embodiments, the crystalline form of Compound 1 succinate has pattern 1. In some embodiments, the crystalline Compound 1 succinate has an XRPD pattern substantially as depicted in FIG. 23.

In some embodiments, the crystalline Compound 1 succinate has XRPD peaks, in terms of 2-theta, at about 9.1, about 21.5, and about 26.8. In some embodiments, the crystalline Compound 1 succinate has XRPD peaks, in terms of 2-theta, at about 9.1, about 11.2, about 19.4, about 21.5, about 26.0, and about 26.8. In some embodiments, the crystalline Compound 1 succinate has XRPD peaks, in terms of 2-theta, at about 6.4, about 9.1, about 11.2, about 14.5, about 15.8, about 19.4, about 20.5, about 21.5, about 26.0, about 26.8.

Figure 29:
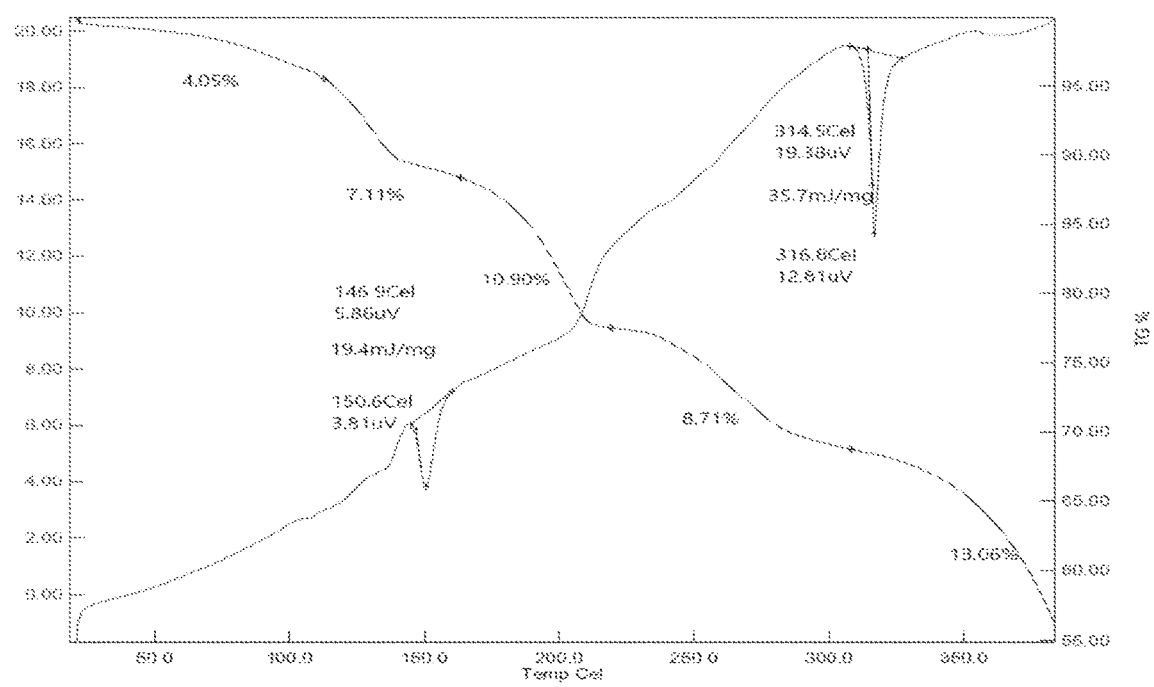
FIG. 29 is a TG/DTA thermogram of Compound 1 succinate.

In some embodiments, the crystalline Compound 1 succinate has a DTA thermogram substantially as depicted in FIG. 29. In some embodiments, the crystalline Compound 1 oxalate has a DTA thermogram characterized by an endothermal event at about 151° C. In some embodiments, the crystalline Compound 1 oxalate has a DTA thermogram characterized by an endothermal event at about 315° C. In some embodiments, the crystalline Compound 1 oxalate has a DTA thermogram characterized by an endothermal event at about 151° C. and an endothermal event at about 315° C. Compound 1 hydrochloride, Compound 1 sulfate, Compound 1 2-naphthalenesulfonate, Compound 1 isethionate, Compound 1 L-aspartate, Compound 1 maleate, Compound 1 phosphate, Compound 1 esylate, Compound 1 glutamate, Compound 1 L-tartrate, Compound 1 D-glucuronate, Compound 1 hippurate, Compound 1 D-gluconate, Compound 1 lactate, Compound 1 L-ascorbate, Compound 1 benzoate are provided herein and each of these salts can be prepared by treating Compound 1 with the corresponding acid.

Synthetic Preparations

Compound 1 and its forms

In some embodiments, Compound 1 (free base) may be prepared as described as disclosed herein. The crystalline form of Compound 1 (e.g., Form I as described herein) may be prepared by the method comprising precipitating the crystalline form from a mixture comprising Compound 1 (free base). In some embodiments, the mixture further comprises a solvent. In some embodiments, the method comprises obtaining a mixture of Compound 1 with a solvent. In some embodiments, the mixture is a solution of Compound 1 in a solvent. In some embodiments, the solution is saturated. The solvent may be selected from acetone, acetonitrile, 2-butanone, cyclopropylmethyl ether, 1,2-dimethoxyethane, 1,4-dioxane, ethanol, ethyl acetate, 2-ethoxy ethanol, isobutyl acetate, isopropyl acetate, methanol, MIBK, 2-propanol, 1-propanol and THF.

In some embodiments, the precipitating is carried out at a temperature above 0° C. (e.g., 5° C., 10° C., 20° C., or 30° C.). In some embodiments, the precipitating is carried out below room temperature. In some aspects of these embodiments, the precipitating is carried out below 10° C. In some embodiments, the precipitating is carried out at about 2° C. In some aspects of these embodiments, the solution comprises 2-propanol (e.g., Compound 1 is precipitated from the solution in 2-propanol).

In some embodiments, the precipitating is carried out at a temperature below 0° C. (e.g., −5° C., −10° C., −20° C., or −30° C.). In some aspects of these embodiments, the precipitating is carried out at about −18° C. In other aspects of these embodiments, the solution comprises a solvent selected from 1-butanol, ethanol, 2-propanol and 1-propanol. For example, the Form I of Compound 1 may be precipitated by cooling a saturated solution of Compound 1 in, e.g., 1-butanol, and further collecting the resultant solid.

In some embodiments, the precipitating is carried out for a time period from about 24 hours to about 72 hours (e.g., cooled solution of Compound 1 may be stored at the specified temperature for 24-72 hours).

In some embodiments, the precipitating comprises adding an anti-solvent to the solution of Compound 1. In some aspects of these embodiments, the anti-solvent is miscible with the solvent in which Compound 1 is dissolved. For example, the anti-solvent may be selected from heptane and t-butylmethyl ether (herein also referred to as TBME). In some embodiments, the precipitating is carried out at or above room temperature. In some aspects of these embodiments, the solvent may be acetone, acetonitrile, 2-butanone, 1,2-dimethoxyethane, 1,4-dioxane and ethanol. For instance, a MTBE may be added to the solution of Compound 1 in acetone at room temperature, followed by collection of the precipitated Form I. In other aspects of these embodiments, the precipitating is carried out below room temperature (e.g., at 0° C., 5° C., or 10° C.). In one example, the precipitating is carried out at about 2° C. In some aspects of these embodiments, the solvent may be selected from acetone, acetonitrile, 1-butanol, 2-butanone, 1,2-dimethoxyethane, 1,4-dioxane, ethanol, ethyl acetate, MIBK, 1-propanol and THF. For instance, a heptane may be added to the solution of Compound 1 in ethyl acetate at about 2° C., followed by collection of the precipitated Form I.

In some embodiments, the precipitating may be carried out by evaporating the solvent. In some aspects of these embodiments, the evaporating may be carried out at about room temperature. In other aspects of these embodiments, the solvent is selected from acetone, acetonitrile, 2-butanone, cyclopropylmethyl ether, 1,2-dimethoxyethane, 1,4-dioxane, ethanol, ethyl acetate, 2-ethoxy ethanol, isobutyl acetate, isopropyl acetate, methanol, MIBK, 2-propanol, 1-propanol and THF.

Compound 1 Salts and Crystalline Forms

Generally, the salts of the Compound 1 can be prepared by combining (6R,15R)-9-fluoro-15-methyl-2,11,16,20,21,24-hexaazapentacyclo[16.5.2.0$^{2,6}$.0$^{7,12}$.0$^{21,25}$]pentacosa-1(24),7,9,11,18(25),19,22-heptaen-17-one (Compound 1 free base) with an acid. That is, any one of the salts of Compound 1 described herein may be prepared by combining the Compound 1 with a benzenesulfonic acid, a citric acid, a methanesulfonic acid, a 1,2-ethane disulfonic acid, a p-toluene sulfonic acid, an oxalic acid, a fumaric acid, a L-malic acid, a hydrochloric acid, a sulfuric acid, a naphthalene-2-sulfonic acid, a 2-hydroxy ethanesulfonic acid, a L-aspartic acid, a maleic acid, a phosphoric acid, a ethanesulfonic acid, a L-glutamic acid, a L-tartaric acid, a D-glucuronic acid, a hippuric acid, a D-gluconic acid, a DL-lactic acid, a L-ascorbic acid, or a benzoic acid. In some embodiments, the combining may be carried out in the presence of a solvent, such as, for example, acetone, ethanol, methanol, 2-propanol, TBME or THF. In some embodiments, Compound 1 is combined with a solvent to obtain the first solution, an acid is separately combined with a solvent to obtain the second solution, and the salt of Compound 1 is obtained by combining the first solution with the second solution. In some embodiments, the combining is carried out with the acid in molar excess with respect to the Compound 1 free base. In some aspects of these embodiments, the molar ratio of the acid to the Compound 1 is from about 1:1 to about 1.1:1 (e.g., about 1.05:1). In some embodiments, the combining is carried out from about room temperature to about 40° C. (e.g., the combining is carried out by cycling the temperature between ambient and 40° C. in 4 hour cycles). In some embodiments, the combining is carried out for a time period from 24 hours to 72 hours.

Generally, any one of the crystalline forms of the salts of Compound 1 may be obtained by precipitating the crystalline form from a mixture of the salt with a solvent (e.g., precipitating the crystalline compound from a mixture, such as precipitating the crystalline compound from a solution). In some embodiments, the precipitating is carried out by temperature cycling the reaction mixture from about room temperature to about 40° C. (e.g., 4 hour cycles between room temperature and 40° C.). In some embodiments, the precipitating is carried out by evaporating the solvent from the mixture (e.g., by evaporating the solvent from the solution of Compound 1). In some embodiments, the precipitating is carried out by adding an anti-solvent (e.g., heptane of MTBE) to the solution of Compound 1 in a solvent.

In some embodiments, crystalline Compound 1 besylate may be obtained by precipitating the crystalline form from a mixture of Compound 1 besylate with a solvent selected from THF and t-BME. In some aspects of these embodiments, the mixture is a solution of Compound 1 besylate in THF or t-BME.

In some embodiments, crystalline Compound 1 besylate may be prepared by precipitating the crystalline form from a mixture of Compound 1 besylate with ethanol. In some aspects of these embodiments, the mixture is a solution of Compound 1 besylate in ethanol.

In some embodiments, crystalline Compound 1 citrate Form A may be prepared by precipitating Form A from a mixture of Compound 1 citrate with a solvent selected from acetone and t-BME. In some aspects of these embodiments, the mixture is a solution of Compound 1 citrate in acetone or t-BME.

In some embodiments, crystalline form of Compound 1 mesylate may be prepared by precipitating the crystalline form from a mixture of Compound 1 mesylate with a solvent selected from acetone, methanol and 2-propanol. In some aspects of these embodiments, the mixture is a solution of Compound 1 mesylate in acetone, methanol or 2-propanol.

In some embodiments, crystalline form of Compound 1 edisylate may be prepared by precipitating the crystalline form from a mixture of Compound 1 edisylate with 2-propanol. In some aspects of these embodiments, the mixture is a solution of Compound 1 edisylate in 2-propanol.

In some embodiments, crystalline form of Compound 1 tosylate may be prepared by precipitating the crystalline form from a mixture of Compound 1 tosylate with a solvent selected from acetone and THF. In some aspects of these embodiments, the mixture is a solution of Compound 1 tosylate in acetone or THF.

In some embodiments, crystalline form of Compound 1 oxalate may be prepared by precipitating the crystalline form from a mixture of Compound 1 oxalate with a solvent selected from ethanol and methanol. In some aspects of these embodiments, the mixture is a solution of Compound 1 oxalate in ethanol or methanol.

In some embodiments, a crystalline form of Compound 1 fumarate may be prepared by precipitating the crystalline form from a mixture of Compound 1 fumarate with acetone. In some aspects of these embodiments, the mixture is a solution of Compound 1 fumarate in ethanol or methanol.

In some embodiments, crystalline form of Compound 1 L-malate may be prepared by precipitating the crystalline form from a mixture of Compound 1 L-malate with TBME. In some aspects of these embodiments, the mixture is a solution of Compound 1 L-malate in TBME.

In some embodiments, crystalline form of Compound 1 succinate may be prepared by precipitating the crystalline form from a mixture of Compound 1 succinate with acetone. In some aspects of these embodiments, the mixture is a solution of Compound 1 succinate in acetone.

Methods of Use

Certain compounds which are inhibitors of TrkA and/or TrkB may be useful in the treatment of multiple types of pain including inflammatory pain, neuropathic pain, and pain associated with cancer, surgery, and bone fracture.

In one embodiment, Compound 1 or its solid forms, crystalline forms, solvates or hydrates, or the salts of Compound 1 or their solid forms, crystalline forms, solvates and hydrates as described herein, are useful for treating pain, including chronic and acute pain, in a mammal.

Acute pain, as defined by the International Association for the Study of Pain, results from disease, inflammation, or injury to tissues. This type of pain generally comes on suddenly, for example, after trauma or surgery, and may be accompanied by anxiety or stress. The cause can usually be diagnosed and treated, and the pain is confined to a given period of time and severity. In some rare instances, it can become chronic.

Chronic pain, as defined by the International Association for the Study of Pain, is widely believed to represent disease itself. It can be made much worse by environmental and psychological factors. Chronic pain persists over a longer period than acute pain and is resistant to most medical treatments, generally over 3 months or more. It can and often does cause severe problems for patients.

Compound 1 or its solid forms, crystalline forms, solvates or hydrates, or the salts of Compound 1 or their solid forms, crystalline forms, solvates and hydrates as described herein, are also useful for treating cancer in a mammal. Particular examples include neuroblastoma, ovarian, pancreatic, colorectal and prostate cancer.

Compound 1 or its solid forms, crystalline forms, solvates or hydrates, or the salts of Compound 1 or their solid forms, crystalline forms, solvates and hydrates as described herein, are also useful for treating inflammation in a mammal.

Compound 1 or its solid forms, crystalline forms, solvates or hydrates, or the salts of Compound 1 or their solid forms, crystalline forms, solvates and hydrates as described herein, are also useful for treating certain infectious diseases in a mammal, such as Trypanosoma cruzi infection.

Compound 1 or its solid forms, crystalline forms, solvates or hydrates, or the salts of Compound 1 or their solid forms, crystalline forms, solvates and hydrates as described herein, may also be used to treat neurodegenerative diseases in a mammal. Examples of neurodegenerative disease include demyelination and dysmyelination. Additional examples of neurodegenerative diseases include multiple sclerosis, Parkinson's disease and Alzheimer's disease.

In addition, Compound 1 or its solid forms, crystalline forms, solvates or hydrates, or the salts of Compound 1 or their solid forms, crystalline forms, solvates and hydrates as described herein, may also be used to treat interstitial cystitis (IC), painful bladder syndrome (PBS), urinary incontinence, asthma, anorexia, atopic dermatitis, and psoriasis in a subject (e.g., a mammal such as a human).

Accordingly, another embodiment of the present application provides a method of treating or preventing pain in a subject (e.g., mammal), comprising administering to said mammal Compound 1 or a solid form thereof, crystalline form thereof, or solvate or hydrate thereof, or a salt of Compound 1 or solid form thereof, crystalline form thereof, or solvate or hydrate thereof, as described herein, in an amount effective to treat or prevent said pain. In one embodiment, the pain is chronic pain. In one embodiment, the pain is acute pain. In one embodiment, the pain is inflammatory pain. In one embodiment, the pain is neuropathic pain. In one embodiment, the pain is pain associated with cancer. In one embodiment, the pain is pain associated with surgery. In one embodiment, the pain is pain associated with bone fracture. In one embodiment, the method comprises a method of treating said pain in a mammal. In one embodiment, the method comprises a method of preventing said pain in a mammal.

Another embodiment of the present disclosure provides a method of treating or preventing inflammation in a subject (e.g., mammal), comprising administering to said mammal Compound 1 or a solid form thereof, crystalline form thereof, or solvate or hydrate thereof, or a salt of Compound 1 or solid form thereof, crystalline form thereof, or solvate or hydrate thereof, as described herein, in an amount effective to treat or prevent the inflammation. In one embodiment, the method comprises treating the inflammation in a subject. In one embodiment, the method comprises preventing the inflammation in a subject.

Another embodiment of the present application provides a method of treating or preventing a neurodegenerative disease in a mammal, comprising administering to said mammal Compound 1 or a solid form thereof, crystalline form thereof, or solvate or hydrate thereof, or a salt of Compound 1 or solid form thereof, crystalline form thereof, or solvate or hydrate thereof, as described herein, in an amount effective to treat or prevent said neurodegenerative disease. In one embodiment, the neurodegenerative disease is demyelination. In one embodiment, the neurodegenerative disease is dysmyelination. In one embodiment, the neurodegenerative disease is multiple sclerosis. In one embodiment, the neurodegenerative disease is Parkinson's disease. In one embodiment, the neurodegenerative disease is Alzheimer's disease.

Another embodiment of the present disclosure provides a method of treating or preventing an infectious disease in a subject, comprising administering to the subject Compound 1 or a solid form thereof, crystalline form thereof, or solvate or hydrate thereof, or a salt of Compound 1 or solid form thereof, crystalline form thereof, or solvate or hydrate thereof, as described herein, in an amount effective to treat or prevent said infectious disease. In one embodiment, the infectious disease is Trypanosoma cruzi infection. In one embodiment, the method comprises treating the neurodegenerative disease in a subject. In one embodiment, the method comprises preventing the neurodegenerative disease in a subject.

Another embodiment of the present disclosure provides a method of treating or preventing cancer in a mammal, comprising administering to said mammal Compound 1 or a solid form thereof, crystalline form thereof, or solvate or hydrate thereof, or a salt of Compound 1 or solid form thereof, crystalline form thereof, or solvate or hydrate thereof, as described herein, in an amount effective to treat or prevent the cancer. In one embodiment, the cancer is neuroblastoma. In one embodiment, the cancer is ovarian cancer. In one embodiment, the cancer is pancreatic cancer. In one embodiment, the cancer is colorectal cancer. In one embodiment, the cancer is prostate cancer. In one embodiment, the method comprises treating the cancer in a subject. In one embodiment, the method comprises preventing the cancer in a subject.

Compound 1 or a solid form thereof, crystalline form thereof, or solvate or hydrate thereof, or a salt of Compound 1 or solid form thereof, crystalline form thereof, or solvate or hydrate thereof, as described herein, may be administered alone as a sole therapy or can be administered in addition with one or more other substances and/or treatments that work by the same or a different mechanism of action. Examples include anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), and chemotherapeutic agents. These agents may be administered with Compound 1 or a solid form thereof, crystalline form thereof, or solvate or hydrate thereof, or a salt of Compound 1 or solid form thereof, crystalline form thereof, or solvate or hydrate thereof, as described herein, as part of the same or separate dosage forms, via the same or different routes of administration, and on the same or different administration schedules according to standard pharmaceutical practice known to one skilled in the art.

In the field of medical oncology, it is normal practice to use a combination of different forms of treatment to treat each patient with cancer. In medical oncology the other component(s) of such conjoint treatment in addition to compositions of the present disclosure may be, for example, surgery, radiotherapy, chemotherapy, signal transduction inhibitors and/or immunotherapy (e.g., monoclonal antibodies).

Accordingly, Compound 1 or a solid form thereof, crystalline form thereof, or solvate or hydrate thereof, or a salt of Compound 1 or solid form thereof, crystalline form thereof, or solvate or hydrate thereof, as described herein, may be administered in combination with one or more agents selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, cytostatic agents anti-androgens, targeted antibodies, HMG-CoA reductase inhibitors, and prenyl-protein transferase inhibitors. These agents may be administered with one or more Compound 1, its solid form, crystalline form, solvate or hydrate, or a salt of Compound 1, or solid form, crystalline form, solvate or hydrate of the salt as described herein, as part of the same or separate dosage forms, via the same or different routes of administration, and on the same or different administration schedules according to standard pharmaceutical practice known to one skilled in the art.

The term "TRK-associated cancer" as used herein refers to cancers associated with or having a dysregulation of a TRK gene, a TRK protein, or expression or activity, or level of any of the same. Exemplary TRK-associated cancers are provided herein.

The phrase "dysregulation of a TRK gene, a TRK kinase, or the expression or activity or level of any of the same" refers to a genetic mutation (e.g., a TRK gene translocation that results in the expression of a fusion protein, a deletion in a TRK gene that results in the expression of a TRK protein that includes a deletion of at least one amino acid as compared to the wild-type TRK protein, a mutation in a TRK gene that results in the expression of a TRK protein with one or more point mutations, or an alternative spliced version of a TRK mRNA that results in a TRK protein having a deletion of at least one amino acid in the TRK protein as compared to the wild-type TRK protein) or a TRK gene amplification that results in overexpression of a TRK protein or an autocrine activity resulting from the overexpression of a TRK gene in a cell that results in a pathogenic increase in the activity of a kinase domain of a TRK protein (e.g., a constitutively active kinase domain of a TRK protein) in a cell. As another example, a dysregulation of a TRK gene, a TRK protein, or expression or activity, or level of any of the same, can be a mutation in a TRK gene that encodes a TRK protein that is constitutively active or has increased activity as compared to a protein encoded by a TRK gene that does not include the mutation. For example, a dysregulation of a TRK gene, a TRK protein, or expression or activity, or level of any of the same, can be the result of a gene or chromosome translocation which results in the expression of a fusion protein that contains a first portion of TRK that includes a functional kinase domain, and a second portion of a partner protein that is not TRK. In some examples, dysregulation of a TRK gene, a TRK protein, or expression or activity or level of any of the same can be a result of a gene translocation of one TRK gene with another non-TRK gene. Non-limiting examples of fusion proteins are described in Tables 1-3. Additional examples of TRK kinase protein mutations (e.g., point mutations) are TRK inhibitor resistance mutations.

The term "wildtype" or "wild-type" when referring to a TRK nucleic acid or protein describes a nucleic acid (e.g., a TRK gene or a TRK mRNA) or protein (e.g., a TRK protein) that is found in a subject that does not have a TRK-associated disease, e.g., a TRK-associated cancer (and optionally also does not have an increased risk of developing a TRK-associated disease and/or is not suspected of having a TRK-associated disease), or is found in a cell or tissue from a subject that does not have a TRK-associated disease, e.g., a TRK-associated cancer (and optionally also does not have an increased risk of developing a TRK-associated disease and/or is not suspected of having a TRK-associated disease).

In some embodiments, the dysregulation of a TRK gene, a TRK kinase protein, or expression or activity or level of any of the same, includes one or more chromosome translocations or inversions resulting in a TRK gene fusion. In some embodiments, the dysregulation of a TRK gene, a TRK kinase protein, or expression or activity or level of any of the same, is a result of genetic translocations in which the expressed protein is a fusion protein containing residues from a non-TRK partner protein, and includes a minimum of a functional TRK kinase domain. See, for example, Tables 1-3.

TABLE 1

Exemplary TrkA Fusion Proteins and Cancers

| Fusion Protein | Non-TrkA Fusion Partner | Non-limiting Exemplary Trk- and Synonyms of Associated Cancer(s) |
|---|---|---|
| TP53-TrkA[1, 11] | Tumor Protein P53 | Spitzoid Melanoma, Spitz tumors |
| LMNA-TrkA[1, 12] | Lamin A/C | Spitzoid Melanoma, Spitz tumors, Undifferentiated Sarcoma, Adult Soft Tissue Sarcoma (e.g., Soft Tissue Sarcoma Metastatic to Lung), Soft Tissue Fibrosarcoma, Spindle Cell Sarcoma[G], Congenital Infantile Fibrosarcoma[H], Pediatric haemangiopericytoma-like sarcoma[I], Colorectal Cancer[K], Pediatric soft tissue tumor[M] |
| CD74-TrkA[2] | MHC class II invariant chain | Non-Small Cell Lung Cancer (NSCLC) Lung adenocarcimona |
| TFG-TrkA (TRK-T3)[3] | TRK-Fused Gene | Papillary Thyroid Carcinoma (PTC), Soft Tissue Solitary Fibrous Tumor |
| TPM3-TrkA[3] | Tropomyosin 3 | Lung Cancer, Papillary Thyroid Carcinoma (PTC), Acute Myeloid Leukemia (AML), Sarcoma, Pediatric Gliomas, Colorectal Cancer (CRC), Soft Tissue Schwannoma, Spitzoid melanocytic tumors[J] |
| NFASC-TrkA[4] | Neurofascin | Gliobastoma multiforme (GBM); Glioblastoma |
| BCAN-TrkA[4] | Brevican | Glioblastoma multiforme (GBM) |
| MPRIP-TrkA[5, E] | Myosin Phosphatase Rho Interacting Protein or Rho Interacting Protein 3 | Non-small cell lung cancer (NSCLC), Lung adenocarcinoma |
| TPR-TrkA (TRK-T1 or TRK-T2)[3] | Translocated Promoter Region, Nuclear Basket Protein | Papillary Thyroid Carcinoma (PTC), Colorectal Cancer (CRC)[A], Non-small cell lung cancer (NSCLC) |
| RFWD2-TrkA[6] | Ring Finger and WD Repeat Domain 2 | Large Cell Neuroendrocine Cancer (LCNEC); NSCLC |
| IRF2BP2-TrkA[7] | Interferon Regulatory Factor 2 Binding Protein 2 | Thyroid Cancer; Thyroid Gland Carcinoma |
| SQSTM1-TrkA[7] | Sequestosome 1 | Thyroid Cancer (e.g., Papillary Thyroid Cancer), Thyroid Gland Carcinoma, Soft TissueFibrosarcoma, Non-small-cell lung cancer[L] |
| SSBP2-TrkA[7] | Single-Stranded DNA Binding Protein 2 | Thyroid Cancer (e.g., Papillary Thyroid Cancer); Thyroid Gland Carcinoma |
| RABGAP1L-TrkA[8] | RAB GTPase Activating Protein 1-Like | Intrahepatic Cholangicarcinoma (ICC) |
| C18ORF8-TrkA[9] | Chromosome 18 Open Reading Frame 8 | Non-Small Cell Lung Cancer (NSCLC) |
| RNF213-TrkA[9] | Ring Finger Protein 213 | Non-Small Cell Lung Cancer (NSCLC) |
| TBC1D22A-TrkA[9] | TBC1 Domain Family, Member 22A | Non-Small Cell Lung Cancer (NSCLC) |
| C20ORF112-TrkA[9] | Chromosome 20 Open Reading Frame 112 | Non-Small Cell Lung Cancer (NSCLC) |
| DNER-TrkA[9] | Delta/Notch-Like EGF Repeat Containing | Non-Small Cell Lung Cancer (NSCLC) |
| ARHGEF2-TrkA[13] | Rho Guanine Nucleotide Exchange Factor 2 | Glioblastoma |
| CHTOP-TrkA[13] | Chromatin Target of PRMT1 | Glioblastoma |
| PPL-TrkA[13] | Periplakin | Thyroid Carcinoma |
| PLEKHA6-TrkA | Pleckstrin Homology Domain-Containing Family A Member 6 | |
| PEAR1-TrkA | Platelet Endothelial Aggregation Receptor 1 | |
| MRPL24-TrkA | 39S Ribosomal Protein L24, Mitochondrial | |
| MDM4-TrkA | Human Homolg of Mouse Double Minute 4 | |
| LRRC71-TrkA | Leucine Rich Repeat Containing 71 | |

TABLE 1-continued

Exemplary TrkA Fusion Proteins and Cancers

| Fusion Protein | Non-TrkA Fusion Partner | Non-limiting Exemplary Trk- and Synonyms of Associated Cancer(s) |
|---|---|---|
| GRIPAP1-TrkA | GRIP1 Associated Protein 1 | |
| EPS15-TrkA | Epidermal Growth Factor Receptor Substrate 15 | |
| DYNC2H1-TrkA[B] | Dynein, Cytoplasmic 2, Heavy Chain 1 | Sarcoma |
| CEL-TrkA | Carboxyl Ester Lipase | Pancreatic adenocarcinoma sample[D] |
| EPHB2-TrkA[B] | EPH Receptor B2 | Lower Grade Glioma |
| TGF-TrkA[C] | Transforming Growth Factor | Papillary Thyroid Cancer |
| NELL1-TrkA[F] | Cytoplasmic Protein That Contains Epidermal Growth Factor (Egf)-Like Repeats | Non-Small Cell Lung Cancer (NSCLC) |
| EPL4-TrkA[F] | EPH-Related Receptor Tyrosine Kinase Ligand 4/ Ephrin-A4 Protein | Non-Small Cell Lung Cancer (NSCLC) |
| CTNND2-TrkA[F] | Catenin (Cadherin-Associated Protein), Delta 2 | Non-Small Cell Lung Cancer (NSCLC) |
| TCEANC2-TrkA[F] | Transcription Elongation Factor A (SII) N-Terminal And Central Domain | Non-Small Cell Lung Cancer (NSCLC) |
| SCYL3-TrkA[N] | SCY1 Like Pseudokinase 3 | Colorectal Cancer |

[A]Créancier et al., *Cancer Lett.* 365(1): 107-111, 2015. J
[B]U.S. patent application Pub. No. 2015/0315657.
[C]U.S. patent application Pub. No. 2015/0283132.
[D]Egren et al., *Cancer Res.* 75(15 Supplement): 4793, 2015.
[E]U.S. patent application Pub. No. 2015/0073036.
[F]P.C.T. Patent Application Publication No. WO2015184443A1.
[G]Haller et al., The Journal of pathology 238.5 (2016): 700-710.
[H]Wong et al., *J Natl Cancer Inst* 2016; 108: djv307.
[I]Haller et al., J. Pathol. 238(5): 700-10.
[J]Wu et al., Mod Pathol. 2016 April; 29(4): 359-69.
[K]Konicek et al., *Cancer research*, Vol. 76, No. 14, Supp. Supplement. Abstract Number: 2647; 107th Annual Meeting of the American Association for Cancer Research, AACR 2016. New Orleans, LA; 16-20 Apr. 2016.
[L]Drilon et al., *Cancer research*, Vol. 76, No. 14, Supp. Supplement. Abstract Number: CT007; 107th Annual Meeting of the American Association for Cancer Research, AACR 2016. New Orleans, LA; 16-20 Apr. 2016.
[M]Kohsaka et al., *Hum. Pathol.*, August 26. pii: S0046-8177(17)30299-X. doi: 10.1016/j.humpath.2017.08.017, 2017.
[N]Milione et al., *Oncotarget*, July 24; 8(33): 55353-55360. doi: 10.18632/oncotarget.19512, 2017.

TABLE 2

Exemplary TrkB Fusion Proteins and Cancers

| Fusion Protein | Non-TrkB Fusion Partner | Non-limiting Exemplary Trk- and Synonyms of Associated Cancer(s) |
|---|---|---|
| NACC2-TrkB[10] | NACC Family Member 2, BEN and BTB (POZ) Domain Containing | Pilocytic Astrocytoma |
| QKI-TrkB[10] | QKI, KH Domain Containing, RNA Binding | Pilocytic Astrocytoma |
| AFAP1-TrkB[7] | Actin Filament Associated Protein 1 | Lower-grade Glioma, In vitro (murine Ba/F3 cells)[B], Pilocytic astrocytoma with anaplasia (PAA)[E] |
| PAN3-TrkB[7] | PAN3 Poly(A) Specific Ribonuclease Subunit | Head and Neck Squamous Cell Carcinoma |
| SQSTM1-TrkB[7] | Sequestosome 1 | Lower-Grade Glioma |
| TRIM24-TrkB[7] | Tripartite Motif Containing 24 | Lung adenocarcinoma |
| VCL-TrkB[11] | Vinculin | Pediatric gliomas |
| AGBL4-TrkB[11] | ATP/GTP Binding Protein-Like 4 | Pediatric gliomas |
| DAB2IP-TrkB | Disabled Homolog 2-Interacting Protein | |
| NTRK2-TERT[A] | Telomerase Reverse Transcriptase | Thyroid Cancer |
| TEL-TrkB[C] (ETV6) | ETS Variant 6 | In vitro (murine Ba/F3 cells) |

TABLE 2-continued

Exemplary TrkB Fusion Proteins and Cancers

| Fusion Protein | Non-TrkB Fusion Partner | Non-limiting Exemplary Trk- and Synonyms of Associated Cancer(s) |
|---|---|---|
| QKI-TrkB[D] | Protein Quaking | Astrocytoma |
| NOS1AP-TrkB [F] | | Anaplastic Astrocytoma |
| GKAP1-TrkB [F] | | Glioblastoma |
| KCTD8-TrkB [F] | | Glioblastoma |
| TBC1D2-TrkB [F] | | Glioblastoma |
| SOSTM1-TrkB [F] | | Glioblastoma |
| VCAN-TrkB [F] | | Grade II Astrocytoma |
| SLMAP-TrkB[G] | | Ganglioma |

[A]PCT Patent Application Publication No. WO 2015/183836A1
[B]Drilon et al., *Ann Oncol.* 2016 May; 27(5): 920-6.
[C]Yuzugullu et al., *Cell Discov.* 2: 16030, 2016.
[D]Ni et al., *Neuro Oncol.* 2017 January; 19(1): 22-30.
[E]Lin et al., *Neuro-Oncol*, Vol. 18, Supp. Supplement 3, pp. iii58, Abstract Number: HG-48; 17th International Symposium on Pediatric Neuro-Oncology, ISPNO 2016. Liverpool, UK, 12 Jun. 2016-15 Jun. 2016.
[F]Subramaniam et al., *J. Clin. Onc.*, Vol. 35, No. 15, Supp. 1, 2017 Annual Meeting of the American Society of Clinical Oncology, ASCO. Chicago, IL, United States, 2017.
[G]Ellison et al., *Neuropathology and Applied Neurobiology.*, Vol. 42, Supp. 1, pp. 18. Abstract Number: O13, 117th Meeting of the British Neuropathological Society, Royal College of Physicians. London, United Kingdom, 2017.

TABLE 3

Exemplary TrkC Fusion Proteins and Cancers

| Fusion Protein | Non-TrkB Fusion Partner | Non-limiting Exemplary Trk- and Synonyms of Associated Cancer(s) |
|---|---|---|
| ETV6-TrkC[11] (TEL; or chromosomal translocation t(12; 15) (p13; q25))[J] | ETS Variant 6 | Salivary Gland Cancer, Secretory Breast Carcinoma, Acute Myeloid Leukemia, Fibrosarcoma, Nephroma, Melanoma, Colorectal Cancer (CRC), Breast Cancer, Pediatric Gliomas, Thyroid Cancer (e.g., Papillary Thyroid Cancer), Infantile Fibrosarcoma, Soft Tissue Hemangioma, Gastrointestinal Stromal Tumor (GIST) (e.g., c-kit-negative GIST), Mammary Carcinoma (e.g., Mammary Analogue Secretory Carcinoma, Secretory Breast Carcinoma (SBSC))[K], Congenital Fibrosarcoma, Acute Myelogenous Leukemia, Polymorphous low-grade adenocarcinoma[D], ALK-negative inflammatory myofibroblastic tumors (IMT)[E], Infantile Fibrosarcoma (IFS)[F,M], Acinic cell carcinoma (AcCC)[G], Cellular mesoblastic nephroma[H], Promyelocytic leukemia[I], Burkitt Lymphoma[I], B-cell lymphoma[I], multiple myeloma[I], medulloblastoma[I], neuroblastoma[I], ovarian cancer[I], intestinal cancer[I], acute lymphblastic leukemia[K], Sinonasal Low-grade Non-intestinal-type Adenocarcinoma[N] |
| BTBD1-TrkC[11] | BTB (POZ) Domain Containing 1 | Pediatric Gliomas |
| LYN-TrkC[7] | V-Yes-1 Yamaguchi Sarcoma Viral Related Oncogene Homolog (also known as Lck/Yes-Related Novel Protein Tyrosine Kinase) | Head and Neck Squamous Cell Carcinoma |
| RBPMS-TrkC[7] | RNA Binding Protein with Multiple Splicing | Thyroid Cancer (e.g., Papillary Thyroid Cancer) |
| EML4-TrkC[4] | Echinoderm Microtubule-Associated Protein-Like 4 | Fibrosarcoma (e.g., Pediatric Fibrosarcoma[L]), Glioblastoma[P], Colon Cancer[R] |

TABLE 3-continued

Exemplary TrkC Fusion Proteins and Cancers

| Fusion Protein | Non-TrkB Fusion Partner | Non-limiting Exemplary Trk- and Synonyms of Associated Cancer(s) |
|---|---|---|
| HOMER2-TrkC | Homer Protein Homolog 2 | Soft Tissue Sarcoma |
| TFG-TrkC | TRK-Fused Gene | Soft Tissue Solitary Fibrous Tumor |
| FAT1-TrkC | FAT Atypical Cadherin 1 | Cervical Squamous Cell Carcinoma[B] |
| MYO5A-TrkC | Myosin VA | Spitz tumor[C] |
| MYH9-TrkC | Myosin Heavy Chain 9 | Spitz tumor[C] |
| KANK1-TrkC[N] | KANK1 | Renal Metanephric Adenoma (MA) |
| SQSTM1-TrkC[O] | Sequestosome 1 | Papillary Thyroid Carcinoma |

[A]Tannenbaum et al., *Cold Spring Harb. Mol.* Case Stud. 1: a000471, 2015.
[B]U.S. patent application Pub. No. 2015/0315657.
[C]Yeh et al., *J Pathol.* 240(3): 282-90, 2016
[D]Montalli et al., *J Oral Pathol Med.* doi: 10.1111/jop.12491, 2016
[E]Alassiri et al., *Am J Surg Pathol.*, August; 40(8): 1051-61, 2016.
[F]Nagasubramanian et al., *Pediatr Blood Cancer.*, August; 63(8): 1468-70, 2016.
[G]Chintakuntlawar et al., *Oral Surg Oral Med Oral Pathol Oral Radiol.* 2016 May; 121(5): 542-549. e1.
[H]U.S. Pat. No. US9511050B2.
[I]U.S Pat. No. US9447135B2.
[J]Skalova et al., *Modern Pathology* 30, S27-S43, 2017.
[K]Hyrcza et al., Vol. 469, Supp. Supplement 1, pp. S17. Abstract Number: OFP-1997-7; 31$^{st}$ International Congress of the International Academy of Pathology and the 28$^{th}$ Congress of the European Society of Pathology, Cologne, Germany. 25-29 Sep. 2016.
[L]Sims et al., *Journal of Immunotherapy of Cancer*, Vol. 4, Supp. Supplement 1; Abstract Number: P280; 31$^{st}$ Annual Meeting and Associated Programs of the Society for Immunotherapy of Cancer, SITC 2016. National Harbor, MD; 9-13 Nov. 2016.
[K]Roberts et al., Blood, Vol. 128, No. 22. Abstract Number: 278, 58th Annual Meeting of the American Society of Hematology, ASH 2016. San Diego, CA, United States. 3 Dec. 2016-6 Dec. 2016.
[M]Pavlick et al., *Pediatr Blood Cancer*, doi: 10.1002/pbc.26433, 2017.
[M]Andreasen et al., *Am J Surg Pathol.*, November; 41(11): 1552-1560, 2017.
[N]Catic et al., *Cancer Genet.*, August; 214-215: 9-15, doi: 10.1016/j.cancergen.2017.03.001, 2017.
[O]Lu et al., *Oncotarget*, , July 11; 8(28): 45784-45792. doi: 10.18632/oncotarget.17412, 2017.
[P]Schram et al., *Cancer Research*, Vol. 77, No. 13, Supp. Supplement 1. Abstract Number: LB-302, American Association for Cancer Research Annual Meeting, Washington, DC, United States, 2017.
[R]Coebergh et al., *Cancer Research*, Vol. 77, No. 13, Supp. Supplement 1. Abstract Number: 490, American Association for Cancer Research Annual Meeting, Washington, DC, United States, 2017.

In some embodiments, the dysregulation of a TRK gene, a TRK kinase, or expression or activity or level of any of the same, includes at least one point mutation in a TRK gene that results in the production of a TRK kinase that has one or more amino acid substitutions, insertions, or deletions as compared to the wild-type TRK kinase.

In some embodiments, a TRK-associated cancer has been identified as having one or more TRK inhibitor resistance mutations (that result in an increased resistance to a TRK inhibitor.

In one embodiment, Compound 1 or a solid form thereof, crystalline form thereof, or solvate or hydrate thereof, or a salt of Compound 1 or solid form thereof, crystalline form thereof, or solvate or hydrate thereof, as described herein, is useful for treating diseases and disorders which can be treated with a TRK inhibitor. Non-limiting examples of cancer (e.g., a Trk-associated cancer) include adenocarcinoma, adrenal gland cortical carcinoma, adrenal gland neuroblastoma, anus squamous cell carcinoma, appendix adenocarcinoma, bladder urothelial carcinoma, bile duct adenocarcinoma, bladder carcinoma, bladder urothelial carcinoma, bone chordoma, bone marrow leukemia lymphocytic chronic, bone marrow leukemia non-lymphocytic acute myelocytic, bone marrow lymph proliferative disease, bone marrow multiple myeloma, bone sarcoma, brain astrocytoma, brain glioblastoma, brain medulloblastoma, brain meningioma, brain oligodendroglioma, breast adenoid cystic carcinoma, breast carcinoma, breast ductal carcinoma in situ, breast invasive ductal carcinoma, breast invasive lobular carcinoma, breast metaplastic carcinoma, cervix neuroendocrine carcinoma, cervix squamous cell carcinoma, colon adenocarcinoma, colon carcinoid tumor, duodenum adenocarcinoma, endometrioid tumor, esophagus adenocarcinoma, eye intraocular melanoma, eye intraocular squamous cell carcinoma, eye lacrimal duct carcinoma, fallopian tube serous carcinoma, gallbladder adenocarcinoma, gallbladder *glomus* tumor, gastroesophageal junction adenocarcinoma, head and neck adenoid cystic carcinoma, head and neck carcinoma, head and neck neuroblastoma, head and neck squamous cell carcinoma, kidney chromophore carcinoma, kidney medullary carcinoma, kidney renal cell carcinoma, kidney renal papillary carcinoma, kidney sarcomatoid carcinoma, kidney urothelial carcinoma, leukemia lymphocytic, liver cholangiocarcinoma, liver hepatocellular carcinoma, lung adenocarcinoma, lung adenosquamous carcinoma, lung atypical carcinoid, lung carcinosarcoma, lung large cell neuroendocrine carcinoma, lung non-small cell lung carcinoma, lung sarcoma, lung sarcomatoid carcinoma, lung small cell carcinoma, lung small cell undifferentiated carcinoma, lung squamous cell carcinoma, lymph node lymphoma diffuse large B cell, lymph node lymphoma follicular lymphoma, lymph node lymphoma mediastinal B-cell, lymph node lymphoma plasmablastic lung adenocarcinoma, lymphoma follicular lymphoma, lymphoma, non-Hodgkin's lymphoma, nasopharynx and paranasal sinuses undifferentiated carcinoma, ovary carcinoma, ovary carcinosarcoma, ovary clear cell carcinoma, ovary epithelial carcinoma, ovary granulosa cell tumor, ovary serous carcinoma, pancreas carcinoma, pancreas ductal adenocarcinoma, pancreas neuroendocrine carcinoma, peritoneum mesothelioma, peritoneum serous carcinoma, placenta choriocarcinoma, pleura mesothelioma, prostate acinar adenocarcinoma, prostate carcinoma, rectum adenocarcinoma, rectum squamous cell carcinoma, skin adnexal carcinoma, skin basal cell carcinoma, skin melanoma, skin Merkel cell carcinoma, skin squamous cell carcinoma, small intestine adenocarcinoma, small intestine gastrointestinal stromal tumors (GISTs), soft tissue angiosarcoma, soft tissue Ewing sarcoma, soft tissue hemangioendothelioma, soft tissue inflammatory myofibroblastic tumor, soft tissue leiomyosarcoma, soft tissue liposarcoma, soft tissue neuroblastoma, soft tissue paraganglioma, soft tissue perivascular epitheliod cell tumor, soft tissue sarcoma, soft tissue synovial sarcoma, stomach adenocarcinoma, stomach adenocarcinoma diffuse-type, stomach adenocarcinoma intestinal type, stomach adenocarcinoma intestinal type, stomach leiomyosarcoma, thymus carcinoma, thymus thymoma lymphocytic, thyroid papillary carcinoma, unknown primary adenocarcinoma, unknown primary carcinoma, unknown primary malignant neoplasm, unknown primary melanoma, unknown primary sarcomatoid carcinoma, unknown primary squamous cell carcinoma, unknown undifferentiated neuroendocrine carcinoma, unknown primary undifferentiated small cell carcinoma, uterus carcinosarcoma, uterus endometrial adenocarcinoma, uterus endometrial adenocarcinoma endometrioid, uterus endometrial adenocarcinoma papillary serous, and uterus leiomyosarcoma.

Additional examples of cancers (e.g., Trk inhibitor-resistant cancer) include: adrenocortical carcinoma, anal cancer, appendix cancer, atypical teratoid/rhabdoid tumor (e.g., central nervous system atypical teratoid/rhabdoid tumor), B-cell cancer, bile duct cancer, bladder cancer, bone cancer (e.g., osteosarcoma and malignant fibrous histiocytoma), brain cancer (e.g., brain and spinal cord tumor, brain stem glioma, central nervous system embryonal tumors, central nervous system germ cell tumors, craniopharyngioma, and ependymoma), breast cancer, bronchogenic carcinoma, bronchus cancer, cancer of hematological tissues, cancer of the oral cavity or pharynx, carcinoid tumor, cervical cancer, childhood cancers, chordoma, chronic lymphocytic leukemia, chronic myeloproliferative neoplasms, colon cancer, colorectal cancer, cutaneous T-cell lymphoma, ductal carcinoma in situ, embryonal tumor, endometrial cancer, esophageal cancer, esthesioneuroblastoma, extracranial germ cell tumor, extragonadal germ cell tumor, extrahepatic bile duct cancer, eye cancer (e.g., retinoblastoma), fallopian tube cancer, fibrosarcoma, fibrous histiocytoma of bone, gallbladder cancer, gastric cancer, gastrointestinal carcinoid tumor, germ cell tumor, gestational trophoblastic disease, glioblastoma multiforme, glioma (e.g., lower-grade glioma), head and neck cancer, heart cancer, histiocytosis, hypopharyngeal cancer, inflammatory myofibroblastic tumors, intrahepatic cholangiocarcinoma, islet cell tumor, kidney cancer (e.g., renal cell cancer), Langerhans cell histiocytosis, large cell neuroendocrine cancer, laryngeal cancer, leukemia (e.g., acute lymphoblastic leukemia, acute myeloid leukemia, chronic myelogenous leukemia, and hairy cell leukemia), lip cancer, liver cancer, lung cancer, Burkitt lymphoma, Hodgkin's lymphoma, and primary central nervous system lymphoma), medulloblastoma, mesothelioma, mouth cancer, multiple myeloma, myelodysplastic syndromes, nasal cavity and paranasal sinus cancer, nasopharyngeal cancer, neoplasm (e.g., a melanocystic neoplasm), nephroma, neuroblastoma, non-small cell lung cancer, oral cancer, oropharyngeal cancer, ovarian cancer, pancreatic cancer, paraganglioma, parathyroid cancer, pediatric glioma, penile cancer, pharyngeal cancer, pheochromocytoma, pilocytic astrocytoma, pituitary tumor, plasma cell neoplasm, primary peritoneal cancer, prostate cancer, rectum carcinoma, salivary gland cancer, sarcoma (e.g., Ewing sarcoma, rhabdomyosarcoma, uterine sarcoma, and undifferentiated sarcoma), secretory breast carcinoma, Sezary syndrome, skin cancer, small bowel cancer, small cell lung cancer, small intestine cancer, Spitz nevi, Spitz tumors, spitzoid melanoma, stomach cancer, squamous cell carcinoma, squamous neck cancer, testicular cancer, throat cancer, thymoma and thymic carcinoma, thyroid carcinoma, urethral cancer, uterine cancer, urinary bladder cancer, vaginal cancer, vulvar cancer, and Wilms tumor.

In some embodiments, the cancer is a pediatric cancer. In some embodiments, the pediatric cancer is a mesenchymal cancer. For example, the mesenchymal cancer can be selected from the group consisting of: pediatric nephroma, congenital fibrosarcoma (CFS), pediatric high-grade glioma (HGG), mesenchymal cancers (infant fibrosarcoma (IF), congenital mesoblastic nephroma, congenital infantile fibrosarcoma (CIFS); pilocytic astrocytoma, brain tumors, pediatic acute leukemia, Ph-like acute lymphoblastic leukemia, cellular congenital mesoblastic nephroma (CMN); infantile fibrosarcoma, pediatric high-grade glioma (HGG), diffuse intrinsic pontine gliomas (DIPGs), non-brainstem HGGs (NBS-HGGs), anaplastic large cell lymphoma (ALCL), non-Hodgkin's lymphoma (NHL), pediatric papillary thyroid carcinoma, soft tissue sarcoma, spitzoid melanoma, pediatric hemangiopericytoma-like sarcoma, spindle cell sarcoma, NOS with myo/haemangiopericytic growth pattern, lung cancer, advanced pediatric solid tumors, neuroectodermal-derived tumors, pediatric colorectal cancer, adrenal neuroblastoma, and central nervous system tumors.

In some embodiments, the pediatric cancer is a fibrosarcoma such as infantile fibrosarcoma.

In some embodiments, the pediatric cancer is a glioma. For example, the pediatric cancer is selected from the group consisting of: pediatric high-grade glioma (HGG), diffuse intrinsic pontine gliomas (DIPGs), and on-brainstem HGGs (NB S-HGGs).

Provided herein are methods of treating a subject having a cancer (e.g., any of the cancers described herein) that include identifying a subject having a cancer cell that has at least one point mutation in a NTRK gene that results in the expression of a Trk protein including a mutation at one or more of the amino acid positions shown in Tables 4, 5, 6 or 7, and administering to the identified subject Compound 1 or a solid form thereof, crystalline form thereof, or solvate or hydrate thereof, or a salt of Compound 1 or solid form thereof, crystalline form thereof, or solvate or hydrate thereof, as described herein.

Also provided herein are methods of treating a subject that include administering a therapeutically effective amount of Compound 1 or a solid form thereof, crystalline form thereof, or solvate or hydrate thereof, or a salt of Compound 1 or solid form thereof, crystalline form thereof, or solvate or hydrate thereof, as described herein, to a subject having a clinical record that indicates that the subject has a cancer cell that has at least one point mutation in a NTRK gene that results in the expression of a Trk protein including a mutation at one or more amino acid positions (e.g., a mutation at one or more of the amino acid positions shown in Tables 4, 5, 6 or 7).

Also provided herein are methods of treating a subject having a cancer (e.g., any of the cancers described herein or known in the art) that include: identifying a subject having a cancer cell that has at least one point mutation in a NTRK gene that results in the expression of a Trk protein including a mutation at one or more amino acid positions (e.g., a mutation at one or more of the amino acid positions shown in Tables 4, 5, 6 or 7); and administering to the identified subject Compound 1 or a solid form thereof, crystalline form thereof, or solvate or hydrate thereof, or a salt of Compound 1 or solid form thereof, crystalline form thereof, or solvate or hydrate thereof, as described herein.

Also provided herein are methods of treating a subject having a cancer (e.g., any of the cancers described herein or known in the art) that include: identifying a subject having a cancer cell that has at least one point mutation in a NTRK gene that results in the expression of a Trk protein including a mutation at one or more amino acid positions (e.g., a mutation at one or more of the amino acid positions shown in Tables 4, 5, 6 or 7); and administering to the identified subject Compound 1 or a solid form thereof, crystalline form thereof, or solvate or hydrate thereof, or a salt of Compound 1 or solid form thereof, crystalline form thereof, or solvate or hydrate thereof, as described herein, and another anticancer agent (e.g., any one or more of the anticancer agents described herein) or anticancer therapy (e.g., any one or more of the anticancer therapies provided herein.

Also provided herein are methods of treating a subject that include administering a therapeutically effective amount of Compound 1 or a solid form thereof, crystalline form thereof, or solvate or hydrate thereof, or a salt of Compound 1 or solid form thereof, crystalline form thereof, or solvate or hydrate thereof, as described herein, to a subject having a clinical record that indicates that the subject has a cancer cell that has at least one point mutation in a NTRK gene that results in the expression of a Trk protein including a mutation at one or more amino acid positions (e.g., a mutation at one or more of the amino acid positions shown in Tables 4, 5, 6 or 7).

Also provided herein are methods of treating a subject that include administering a therapeutically effective amount of Compound 1 or a solid form thereof, crystalline form thereof, or solvate or hydrate thereof, or a salt of Compound 1 or solid form thereof, crystalline form thereof, or solvate or hydrate thereof, as described herein, and another anticancer agent (e.g., any one or more of the anticancer agents described herein) or anticancer therapies (e.g., any one or more of the anticancer therapies described herein), to a subject having a clinical record that indicates that the subject has a cancer cell that has at least one point mutation in a NTRK gene that results in the expression of a Trk protein including a mutation at one or more amino acid positions (e.g., a mutation at one or more of the amino acid positions shown in Tables 4, 5, 6 or 7).

In some embodiments, the dysregulation of a NTRK gene, a Trk protein, or expression or activity, or level of the same, includes one or more deletions, insertions, or point mutation(s) in a Trk protein. In some embodiments, the dysregulation of a NTRK gene, a Trk protein, or expression or activity, or level of the same, includes a deletion of one or more residues from the TrkA protein, resulting in constitutive activity of the Trk kinase domain. In some embodiments, the dysregulation of a NTRK gene, a Trk protein, or expression or activity, or level of the same, includes at least one point mutation in a NTRK1 gene that results in the production of a TrkA protein that has one or more amino acid substitutions as compared to the wildtype TrkA protein (see, for example, the point mutations listed in Tables 4 and 5). An exemplary wildtype TrkA polypeptide is SEQ ID NO: 1, an exemplary wildtype TrkB polypeptide is SEQ ID NO: 2, and an exemplary TrkC polypeptide is SEQ ID NO: 3.

TABLE 4

Activating TrkA Point Mutations

| Mutation | | Pediatric Cancer | Reference |
|---|---|---|---|
| C6773T, C7232T, C7301T | TrkA | neuroblastoma | Scaruffi et al., Int. J. Oncol. 14: 935-938, 1999 |

TABLE 5

Activating TrkA Point Mutations[A]

| Point Mutation | Rationale | Exemplary Isoform in which Mutation is Present (if known) |
|---|---|---|
| R6W[I] | | |
| R33W[B] | | NP_001007793.1[F] |
| A336E | Near NGF Binding Site | Reference TrkA sequence |
| A337T | Near NGF Binding Site | Reference TrkA sequence |
| R324Q or R324W | Near NGF Binding Site | Unknown |
| V420M | Close to Membrane | Reference TrkA sequence |
| R444Q or R444W | Close to Membrane | Reference TrkA sequence |
| G517R or G517V | P-Loop | Reference TrkA sequence |
| K538A | Activating | Reference TrkA sequence |
| V573M[E] | | Reference TrkA sequence |
| R583H[I] | | |
| F589L[E] | | Reference TrkA sequence |
| G595R or G667C[D] | Catalytic Domain | Reference TrkA sequence |
| F598L[E] | | Unknown |
| R649W or R649L | Arginine may stabilize auto-inhibited conformation. | Reference TrkA sequence |
| R682S | Activation Loop | Reference TrkA sequence |
| V683G | Activation Loop | Reference TrkA sequence |
| I699V[H] | | |
| Q627X[C], Q597X[C], Q633X[C] | | NP_001012331.1[G], NP_001007793.1[F], and Reference TrkA sequence, respectively |
| R702C | Exposed, may form face-to-face disulfide linked dimer | Reference TrkA sequence |
| R744H[I] | | |

[A]Reference TrkA sequence is UniProtKB/Swiss-Prot: P04629.4, and can be found at URL: www.ncbi-nlm.nih.gov/protein/94730402?report=genbank&log$=protalign&blast_rank=0&RID=0 (SEQ ID NO: 1)
[B]Zhang et al., Blood 124(21): 1682, 2014. Mutation found in T-cell prolymphocytic leukemia.
[C]Park et al., Proc. Natl. Acad. Sci. U.S.A. 112(40): 12492-12497, 2015. Mutation found in colorectal cancer.
[D]Russo et al., Cancer Discov. January; 6(1): 36-44, 2016.
[E]PCT Application No. WO2016196141A1.
[F]www.ncbi.nlm.nih.gov/protein/56118210?report=genbank&log$=protalign&blast_rank=3&RID=0
[G]www.ncbi.nlm.nih.gov/protein/59889558
[H]Deihimi et al., Oncotarget. June 20; 8(25): 39945-39962. doi: 10.18632/oncotarget.18098, 2017.
[I]Iniguez-Ariza et al., Journal of Clinical Oncology, (20 Jun. 2017) Vol. 35, No. 15, Supp. 1, 2017 Annual Meeting of the American Society of Clinical Oncology, ASCO, 2017.

In some embodiments, the dysregulation of a NTRK gene, a Trk protein, or expression or activity, or level of the same, includes a splice variation in a TrkA mRNA which results in an expressed protein that is an alternatively spliced variant of TrkA having at least one residue deleted (as compared to a wild-type TrkA protein) resulting in constitutive activity of the TrkA kinase domain. In some embodiments, an alternatively spliced form of TrkA with constitutive activity has deletions of exons 8, 9, and 11 resulting in an expressed protein missing residues 192-284 and 393-398 relative to TrkA Isoform 2, has a deletion of exon 10 in TrkA, or has a deletion in a NTRK1 gene that encodes a TrkA protein with a 75 amino acid deletion in the transmembrane domain (Reuther et al., Mol. Cell Biol. 20:8655-8666, 2000).

In some embodiments, the dysregulation of a NTRK gene, a Trk protein, or expression or activity, or level of the same, includes at least one point mutation in a NTRK1 gene that results in the production of a TrkB protein that has one or more amino acid substitutions as compared to the wildtype TrkB protein (see, for example, the point mutations listed in Table 6.

TABLE 6

Activating TrkB Point Mutations[A]

| Point Mutation | Rationale | Exemplary Isoform in which Mutation is Present (if known) |
|---|---|---|
| A13T[C] | | Reference TrkB sequence |
| E142K[C] | | Reference TrkB sequence |
| R136H[C] | | Reference TrkB sequence |
| S167Y[F] | | |
| V619M[B] | | Unknown |
| F633L[B] | | NP_006171.2[D] (Corresponding to position 617 of Reference TrkB sequence) |
| G639R[B] | | NP_006171.2[D] (Corresponding to position 623 of Reference TrkB sequence) |
| G709C or G709A or G709S[B] | | NP_006171.2[D] (Corresponding to position 693 of Reference TrkB sequence) |
| P716S[E] | | |

[A]Reference TrkB sequence is UniProtKB/Swiss-Prot: Q16620.1, and can be found at URL: www.ncbi.nlm.nih.gov/protein/2497560?report=genbank&log$=protalign&blast_rank=0&RID=0 (SEQ ID NO: 2)
[B]PCT Application No. WO2016196141A1.
[C]Bonanno et al., *Journal of Thoracic Oncology*, Vol. 11, No. 4, Supp. Suppl. 1, pp S67. Abstract Number: 28P; 6th European Lung Cancer Conference, ELCC 2016, Geneva, Switzerland.
[D]www.ncbi.nlm.nih.gov/protein/NP_006171.2
[E]Deihimi et al., *Oncotarget*. Jun. 20; 8(25): 39945-39962. doi: 10.18632/oncotarget.18098, 2017.
[F]Iniguez-Ariza et al., *Journal of Clinical Oncology*, (20 Jun. 2017) Vol. 35, No. 15, Supp. 1, 2017 Annual Meeting of the American Society of Clinical Oncology, ASCO, 2017.

In some embodiments, the dysregulation of a NTRK gene, a Trk protein, or expression or activity, or level of the same, includes at least one point mutation in a NTRK1 gene that results in the production of a TrkC protein that has one or more amino acid substitutions as compared to the wildtype TrkC protein (see, for example, the point mutations listed in Table 7.

TABLE 7

Activating TrkC Point Mutations[A]

| Point Mutation | Rationale | Exemplary Isoform in which Mutation is Present (if known) |
|---|---|---|
| V603M[C] | | NP_001007157.1[D] |
| F617L[C] | | Reference TrkC sequence |
| G623R[B,C] | Steric Hinderance | Reference TrkC sequence |
| G696C or G696A or G696S[C] | | Reference TrkC sequence |
| R745L[E] | | |
| I749M[F] | | |

[A]Reference TrkC sequence is UniProtKB/Swiss-Prot: Q16288.2, and can be found at URL: www.ncbi.nlm.nih.gov/protein/134035335?report=genbank&log$=protalign&blast_rank=0&RID=0 (SEQ ID NO: 3)
[B]Drilon et al., Ann Oncol. 2016 May; 27(5): 920-6. doi: 10.1093/annonc/mdw042. Epub 2016 Feb. 15.
[C]PCT Application No. WO2016196141A1.
[D]www.ncbi.nlm.nih.gov/protein/NP_001007157
[E]Deihimi et al., *Oncotarget*. June 20; 8(25): 39945-39962. doi: 10.18632/oncotarget.18098, 2017.
[F]Iniguez-Ariza et al., *Journal of Clinical Oncology*, (20 Jun. 2017) Vol. 35, No. 15, Supp. 1, 2017 Annual Meeting of the American Society of Clinical Oncology, ASCO, 2017.

ORIGINAL LIST OF REFERENCES (BELIEVED TO BE APPLICABLE TO ALL TABLES)

[1] Wiesner et al., *Nature Comm.* 5:3116, 2014.
[2] Vaishnavi et al., *Nature Med.* 19:1469-1472, 2013.
[3] Greco et al., *Mol. Cell. Endocrinol.* 28:321, 2010.
[4] Kim et al., *PloS ONE* 9(3): e91940, 2014.
[5] Vaishnavi et al., *Nature Med.* 19:1469-1472, 2013.
[6] Fernandez-Cuesta et al., "Cross-entity mutation analysis of lung neuroendocrine tumors sheds light into their molecular origin and identifies new therapeutic targets," AACR Annual Meeting 2014, Abstract, April 2014.
[7] Stransky et al., *Nature Comm.* 5:4846, 2014.
[8] Ross et al., *Oncologist* 19:235-242, 2014.
[9] Doebele et al., *J. Clin. Oncol.* 32:5s, 2014.
[10] Jones et al., *Nature Genetics* 45:927-932, 2013.
[11] Wu et al., *Nature Genetics* 46:444-450, 2014.
[12] WO 2013/059740
[13] Zheng et al., "Anchored multiplex PCR for targeted next-generation sequencing," *Nature Med.*, published online on Nov. 10, 2014.
[14] Caria et al., *Cancer Genet. Cytogenet.* 203:21-29, 2010.
[15] Frattini et al., *Nature Genet.* 45:1141-1149, 2013.
[16] Martin-Zanca et al., *Nature* 319:743, 1986.
[17] Meyer et al., *Leukemia* 21: 2171-2180, 2007.
[18] Reuther et al., *Mol. Cell. Biol.* 20:8655-8666, 2000.
[19] Marchetti et al., *Human Mutation* 29(5):609-616, 2008.
[20] Tacconelli et al., *Cancer Cell* 6:347, 2004.
[21] Walch et al., *Clin. Exp. Metastasis* 17: 307-314, 1999.
[22] Papatsoris et al., *Expert Opin. Invest. Drugs* 16(3):303-309, 2007.
[23] Van Noesel et al., *Gene* 325: 1-15, 2004.
[24] Zhang et al., *Oncology Reports* 14: 161-171, 2005.
[25] Truzzi et al., *J. Invest. Dermatol.* 128(8):2031, 2008.
[26] Kolokythas et al., *J. Oral Maxillofacial Surgery* 68(6): 1290-1295, 2010.
[27] Ni et al., *Asian Pacific Journal of Cancer Prevention* 13:1511, 2012.

In some embodiments, a TRK-associated cancer has been identified as having one or more TRK inhibitor resistance mutations (that result in an increased resistance to a TRK inhibitor. Non-limiting examples of TRK inhibitor resistance mutations are listed in Tables 8-10.

TABLE 8

Exemplary TrkA Resistance Mutations

Amino acid position 517 (e.g., G517R)
Amino acid position 542 (e.g., A542V)
Amino acid position 564 (e.g., L564SH[2])
Amino acid position 568 (e.g., Q568x)
Amino acid position 573 (e.g., V573M)
Amino acid position 589 (e.g., F589L, F589C)
Amino acid position 595 (e.g., G595S, G595R[1], G595L[2])
Amino acid position 599 (e.g., D596V)
Amino acid position 600 (e.g., F600L)
Amino acid position 602 (e.g., R602x)
Amino acid position 646 (e.g., F646V, F646I[2])
Amino acid position 656 (e.g., C656Y, C656F)
Amino acid position 657 (e.g., L657V)
Amino acid position 667 (e.g., G667C[1], G667S)
Amino acid position 676 (e.g., Y676S)
Amino acid position 679 (e.g., D679G[2])

[1]Russo et al., Acquired Resistance to the TRK Inhibitor Entrectinib in Colorectal Cancer, *Cancer Discov.*, January; 6(I): 36-44, 2016.
[2]Fuse et al., Mechanisms of Resistance to NTRK Inhibitors and Therapeutic Strategies in NTRK1-Rearranged Cancers, *Mol. Cancer Ther.*, . January; 6(1): 36-44, 2016.

TABLE 9

Exemplary TrkB Resistance Mutations

Amino acid position 545 (e.g., G545R)
Amino acid position 570 (e.g., A570V)
Amino acid position 596 (e.g., Q596E, Q596P)
Amino acid position 601 (e.g., V601G)
Amino acid position 617 (e.g., F617L, F617C, F617I)
Amino acid position 623 (e.g., G623S, G623R)
Amino acid position 624 (e.g., D624V)
Amino acid position 628 (e.g., F628x)
Amino acid position 630 (e.g., R630K)
Amino acid position 639 (e.g., G639R)[1]
Amino acid position 672 (e.g., F672x)
Amino acid position 682 (e.g., C682Y, C682F)
Amino acid position 683 (e.g., L683V)
Amino acid position 693 (e.g., G693S)
Amino acid position 702 (e.g., Y702x)

[1]PCT Application No. WO2017155018A1.

TABLE 9

Exemplary TrkC Resistance Mutations

Amino acid position 545 (e.g., G545R)
Amino acid position 570 (e.g., A570V)
Amino acid position 596 (e.g., Q596x)
Amino acid position 601 (e.g., V601)
Amino acid position 617 (e.g., F617x, F617L)
Amino acid position 623 (e.g., G623R[1])
Amino acid position 624 (e.g., D624V)
Amino acid position 628 (e.g., F628x)
Amino acid position 630 (e.g., R630x)
Amino acid position 675 (e.g., F675x)
Amino acid position 685 (e.g., C685Y, C684F)
Amino acid position 686 (e.g., L686V)
Amino acid position 696 (e.g., G696x, G696A)
Amino acid position 705 (e.g., Y705x)

[1]Drilon et al., What hides behind the MASC: clinical response and acquired resistance to entrectinib after ETV6-NTRK3 identification in a mammary analogue secretory carcinoma (MASC), Ann Oncol. 2016 May; 27(5): 920-6. doi: 10.1093/annonc/mdw042. Epub 2016 Feb. 15.

The letter "x" when used to describe a mutation of an amino acid at a specific amino acid position means (i) a substitution of the amino acid present at the same amino acid position in the corresponding wildtype protein with a different naturally-occurring amino acid, or (ii) a deletion of the amino acid present at the same amino acid position in the corresponding wildtype protein.

Pharmaceutical Compositions, Formulations, Routes of Administration

In some embodiments, provided herein is a process for preparing a pharmaceutical composition comprising mixing (i) a compound of any one of formulae described herein or salt thereof prepared according to any of the processes described herein, and (ii) a pharmaceutically acceptable carrier. Pharmaceutical compositions containing the compound of any one of formulae described herein or a salt thereof as the active ingredient can be prepared by intimately mixing the compound of any one of formulae described herein or a salt thereof with a pharmaceutical carrier according to conventional pharmaceutical compounding techniques. The carrier can take a wide variety of forms depending upon the desired route of administration (e.g., oral, parenteral). Thus, for liquid oral preparations such as suspensions, elixirs and solutions, suitable carriers and additives include water, glycols, oils, alcohols, flavoring agents, preservatives, stabilizers, coloring agents, and the like; for solid oral preparations, such as powders, capsules and tablets, suitable carriers and additives include starches, sugars, diluents, granulating agents, lubricants, binders, disintegrating agents, and the like. Solid oral preparations can also be coated with substances such as sugars or be enteric-coated so as to modulate major site of absorption. For parenteral administration, the carrier will usually consist of sterile water, and other ingredients can be added to increase solubility or preservation. Injectable suspensions or solutions can also be prepared utilizing aqueous carriers along with appropriate additives.

The pharmaceutical compositions herein contain, per unit dosage unit, e.g., tablet, capsule, suspension, solution, sachet for reconstitution, powder, injection, I.V., suppository, sublingual/buccal film, teaspoonful, and the like, of from about 0.1-1000 mg or any range therein, and may be given at a dosage of from about 0.01-300 mg/kg/day, or any range therein, preferably from about 0.5-50 mg/kg/day, or any range therein. In some embodiments, the pharmaceutical compositions provided herein contain, per unit dosage unit, about 25 mg to about 500 mg of a compound provided herein (for example, about 25 mg to about 400 mg, about 25 mg to about 300 mg, about 25 mg to about 250 mg, about 25 mg to about 200 mg, about 25 mg to about 150 mg, about 25 mg to about 100 mg, about 25 mg to about 75 mg, about 25 mg to a about 50 mg, about 50 mg to about 500 mg, about 100 mg to about 500 mg, about 150 mg to about 500 mg, about 200 mg to about 500 mg, about 250 mg to about 500 mg, about 300 mg to about 500 mg, about 400 mg to about 500 mg, about 50 to about 200 mg, about 100 to about 250 mg, about 50 to about 150 mg). In some embodiments, the pharmaceutical compositions provided herein contain, per unit dosage unit, about 25 mg, about 50 mg, about 100 mg, about 150 mg, about 200 mg, about 250 mg, about 300 mg, about 400 mg, or about 500 mg of Compound 1 or any one of crystalline forms, solid forms, solvates, hydrates or salts described herein. The dosages, however, can be varied depending upon the requirement of the patient, the severity of the condition being treated, and/or (if applicable) the crystalline form, solid form, solvate, hydrate or salt being employed. In some embodiments, the dosages are administered once daily (QD) or twice daily (BID). Preferably, these compositions are in unit dosage forms, such as sterile solutions or suspensions for oral administration.

To prepare the pharmaceutical compositions provided herein, the compound of any one of formulae described herein or a salt thereof as the active ingredient is intimately admixed with a pharmaceutical carrier according to conventional pharmaceutical compounding techniques. The carrier can take a wide variety of forms depending on the form of preparation desired for administration (e.g., oral or parenteral). Any one of crystalline forms, solid forms, solvates, hydrates or salts described herein can be administered by any convenient route, e.g., into the gastrointestinal tract (e.g., rectally or orally), the nose, lungs, musculature or vasculature, or transdermally or dermally. Any one of crystalline forms, solid forms, solvates, hydrates or salts described herein can be administered in any convenient administrative form, e.g., tablets, powders, capsules, solutions, dispersions, suspensions, syrups, sprays, suppositories, gels, emulsions, patches, etc. Such compositions can contain components that are conventional in pharmaceutical preparations, e.g., diluents, carriers, pH modifiers, sweeteners, bulking agents, and further active agents. If parenteral administration is desired, the compositions will be sterile and in a solution or suspension form suitable for injection or infusion. Such compositions form a further aspect of the present disclosure.

In preparing the compositions in oral dosage form, any of the usual pharmaceutical media can be employed. Thus, for liquid oral preparations, such as, for example, suspensions, elixirs, and solutions, suitable carriers and additives include water, glycols, glycerols, oils, cyclodextrins, alcohols, e.g., ethanol, flavoring agents, preservatives, coloring agents, and the like; for solid oral preparations such as, for example, powders, capsules, caplets, gelcaps and tablets, suitable carriers and additives include starches, sugars, diluents, granulating agents, lubricants, binders, disintegrating agents, and the like. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride, and the like. Disintegrators include, without limitation, starch, methyl cellulose, agar, bentonite, xanthan gum and the like.

Because of their ease in administration, tablets and capsules represent the most advantageous oral dosage unit form, in which case solid pharmaceutical carriers are employed. If desired, tablets can be sugar coated or enteric coated by standard techniques. For parenteral formulations, the carrier will usually comprise sterile water, through other ingredients, for example, for purposes such as aiding solubility or for preservation, can be included. In some embodiments, the carrier is 0.8% saline or a 5% dextrose. Injectable suspensions can also be prepared, in which case appropriate liquid carriers, suspending agents, and the like can be employed. The pharmaceutical compositions herein can contain, per dosage unit, e.g., tablet, capsule, powder, injection, teaspoonful, and the like, an amount of the active ingredient necessary to deliver an effective dose as described above.

In some embodiments, the dosages are administered once daily (QD) or twice daily (BID). Alternatively, the composition can be presented in a form suitable for once-weekly or once-monthly administration. For preparing solid compositions such as tablets, any one of crystalline forms, solid forms, solvates, hydrates or salts described herein is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid composition containing any one of crystalline forms, solid forms, solvates, hydrates or salts described herein. When referring to these preformulation compositions as homogeneous, it is meant that the active ingredient is dispersed evenly throughout the composition so that the composition can be readily subdivided into equally effective dosage forms such as tablets, pills and capsules. This solid preformulation composition is then subdivided into unit dosage forms of the type described above containing from 0.1 to about 1000 mg, or any amount or range thereof, of the active ingredient provided herein. The tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol, and cellulose acetate.

The liquid forms in which the compositions provided herein can be incorporated for administration orally or by injection include aqueous solutions, cyclodextrins, suitably flavored syrups, aqueous or oil suspensions, and flavored emulsions with edible oils, such as cottonseed oil, sesame oil, coconut oil, or peanut oil, as well as elixirs and similar pharmaceutical vehicles. Suitable dispersing or suspending agents for aqueous suspensions include synthetic and natural gums, such as tragacanth, acacia, alginate, dextran, sodium carboxymethylcellulose, methylcellulose, polyvinyl-pyrrolidone, and gelatin. For parenteral administration, sterile suspensions and solutions are desired. Isotonic preparations which generally contain suitable preservatives are employed when intravenous administration is desired.

Any one of crystalline forms, solid forms, solvates, hydrates or salts described herein can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications, such as *Pharmaceutical Dosage Forms: Tablets, Second Edition, Revised and Expanded*, Volumes 1-3, edited by Lieberman et al.; *Pharmaceutical Dosage Forms: Parenteral Medications*, Volumes 1-2, edited by Avis et al.; and *Pharmaceutical Dosage Forms: Disperse Systems*, Volumes 1-2, edited by Lieberman et al.; published by Marcel Dekker, Inc.

Compounds provided herein can be administered in any of the foregoing compositions and according to dosage regimens established in the art whenever treatment of cancer, pain, inflammation, neurodegenerative disease or Trypanosoma cruzi infection is required.

The daily dosage of the compound of any one of formulae described herein or a salt thereof can be varied over a wide range from 1.0 to 10,000 mg per adult human per day, or higher, or any range therein. For oral administration, the compositions are preferably provided in the form of tablets containing 0.01, 0.05, 0.1, 0.5, 1.0, 2.5, 5.0, 10.0, 15.0, 25.0, 50.0, 100, 150, 200, 250 or 500 milligrams of the active ingredient for the symptomatic adjustment of the dosage to the patient to be treated. An effective amount of the drug is ordinarily supplied at a dosage level of from about 0.1 mg/kg to about 1000 mg/kg of body weight per day, or any range therein. Preferably, the range is from about 0.5 to about 500 mg/kg of body weight per day, or any range therein. More preferably, from about 1.0 to about 250 mg/kg of body weight per day, or any range therein. More preferably, from about 0.1 to about 100 mg/kg of body weight per day, or any range therein. In an example, the range can be from about 0.1 to about 50.0 mg/kg of body weight per day, or any amount or range therein. In another example, the range can be from about 0.1 to about 15.0 mg/kg of body weight per day, or any range therein. In yet another example, the range can be from about 0.5 to about 7.5 mg/kg of body weight per day, or any amount to range therein. The compound of any one of formulae described herein or a salt thereof can be administered on a regimen of 1 to 4 times per day or in a single daily dose.

Optimal dosages to be administered can be readily determined by those skilled in the art, and can vary with the mode of administration, the strength of the preparation, the mode of administration, and the advancement of the disease condition. In addition, factors associated with the particular patient being treated, including patient age, weight, diet, and time of administration, can result in the need to adjust dosages.

EXAMPLES

Materials and methods for the preparation of compounds, crystalline forms, solid forms, solvates, hydrates, and salts thereof.

Example A

1) Preparation of Compound 1 (the Compound of Formula I)

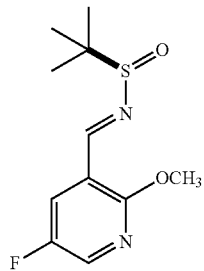

2

(R,E)-N-((5-fluoro-2-methoxypyridin-3-yl) methylene)-2-methylpropane-2-sulfinamide (2): A flask (equipped with a nitrogen inlet, overhead stirring, and thermocouple) was charged with DCM (3 L, 10 vol). The mixture was agitated, and the mixture was deoxygenated with subsurface nitrogen for 1 h. Next 5-fluoro-2-methoxynicotinaldehyde (1) (300 g, 1934 mmol) and (R)-2-methylpropane-2-sulfinamide (246 g, 2031 mmol) were charged. The Cs$_2$CO$_3$ (441 g, 1354 mmol) was charged in portions, with agitation, over several minutes. The reaction was agitated overnight at ambient temperature under nitrogen. The reaction was sampled and analyzed by HPLC for reaction completion. A 15 wt % solution of the citric acid (in water) was prepared (using 1.5 eq of citric acid based on the Cs$_2$CO$_3$ input). This solution was charged into the reactor with the reaction mixture, using an addition funnel. The charge was done in portions. The biphasic mixture was transferred to a separatory funnel, and the lower DCM layer was removed. The upper aqueous layer was removed and discarded. The DCM layer was transferred back into the separatory funnel, and washed with saturated brine (2 L). Again, the lower DCM layer was removed, and the upper aqueous layer was discarded. The DCM layer was concentrated under vacuum (rotovap) to give the desired product.

(S)—N—((S)-3-(1,3-dioxan-2-yl)-1-(5-fluoro-2-methoxypyridin-3-yl)propyl)-2-methylpropane-2-sulfinamide (5): A flask (equipped with a nitrogen inlet, overhead stirring, reflux condenser, thermocouple, and addition funnel) was charged with Mg turnings (565 g, 23.2 moles) followed by THF (24 L, 8 vol) under nitrogen. This mixture was agitated and warmed to ~30° C. When the internal temperature was 29.9° C., DIBAL (31.2 mL, 0.004 eq.) was added. A separate flask was charged with 2-(2-bromoethyl)-1,3-dioxane (4531 g, 23.2 moles) and THF (15.9 L, 5.3 vol). The mixture was agitated at ambient temperature to dissolve. The reaction flask with the Mg/Dibal-H mixture was slowly charged with the 2-(2-bromoethyl)-1,3-dioxane (3)/THF solution via an addition funnel. The charge was made in portions over ~5 h. The bromide solution was added so that the internal temperature did not rise above 50° C. The reaction mixture was then held for 45 minutes. After the 45-minute hold, the active Grignard mixture was cooled to −30 to −40° C. (dry ice/acetonitrile). A separate flask was charged with the (R,E)-N-((5-fluoro-2-methoxypyridin-3-yl)methylene)-2-methylpropane-2-sulfinamide (3000 g, 11.6 moles), followed by THF (5.1 L, 1.7 vol). Using an addition funnel, the starting material solution was portion-wise transferred at ambient temperature into the Grignard mixture over ~2 h and the internal temp was kept at −37.3 to −28.9° C. The reaction mixture was agitated at low temperature and analyzed by HPLC for reaction completion. To quench the reaction, a 15 wt % solution of citric acid (~11 vol) was charged into a round bottom flask and cooled with an ice bath to ~10° C. The reaction mixture was transferred into the citric acid solution in portions. When the transfer was complete, the mixture was allowed to stir for ~15 minutes. MTBE (9 L, 3 vol) was charged into the mixture and then the entire mixture was transferred to a separatory funnel. The reaction flask was rinsed with MTBE (3 L, 1 vol) and transferred to the separatory funnel. The biphasic mixture was agitated for 5 minutes and then the phases were allowed to settle. The layers were separated, and the bottom aqueous layer was back extracted with additional MTBE (16 L, ~5 vol). After mixing and settling, the layers were separated. The MTBE layers were combined and washed with sat. brine (15 L, 5 vol). After mixing and settling, the aqueous layer was discarded. The MTBE layer was concentrated under vacuum. MTBE (6 L, 2 vol) was charged, and the product was dissolved with agitation at ambient temperature. To the MTBE solution, heptane (30 L, 10 vol) was charged over ~1 h. The slurry was allowed to agitate at ambient temperature overnight, and then filtered through polypropylene filter cloth. The cake was rinsed with heptane (9 L, 3 vol), and the wet solid 5 was dried in trays under vacuum at ~50° C. to constant weight.

5

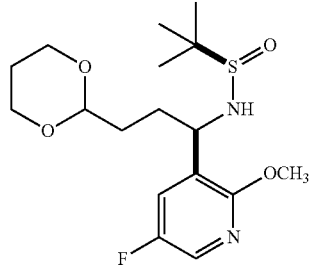

7

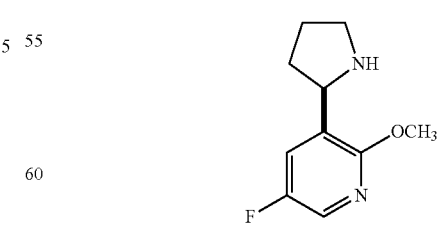

(R)-5-fluoro-2-methoxy-3-(pyrrolidin-2-yl) pyridine (7): A flask (equipped with mechanical stirring, N$_2$ inlet, condenser and J-Kem) was charged with 5 (1993 g, 5322 mmol) 2,2,2-trifluoroacetic acid (7971 mL) and water (1918 mL).

The reaction was sampled to monitor completion of the deprotection by HPLC. After the reaction was judged to be complete, the reaction was charged with triethylsilane (2550 mL, 16.0 moles) via addition funnel over ~1 h. The reaction mixture was stirred at ambient temperature overnight and the solvent was removed under vacuum with heating to 45-50° C. The resulting product was added to a 100 L separatory funnel and was diluted with MTBE (15 L) and water (15 L). The layers were agitated and the separated layers were dropped into tared carboys (Aq 1 and MTBE 1). The MTBE layer was added back to the separatory funnel and was back extracted with 6000 mL 1 M HCl. After mixing, the separated layers were dropped into tared carboys (Aq2 and MTBE 2). The aqueous layers were combined in the separatory funnel. To the aqueous layer was added DCM (16 L). To the mixture was added 50 wt % NaOH (~900 mL) to reach pH≥12. After mixing, the organic layer was dropped into a tared flask (DCM 1). The aqueous layer was extracted with DCM (16 L) and the organic layer was dropped into a tared flask. The aqueous layer was extracted a third time with DCM (8 L). The organic layer was dropped into a tared flask (DCM 3). The combined organic layers were transferred to the separatory funnel and washed with sat. brine (9 L). The layers were separated and the organic layers were dropped and then the solvent was removed under vacuum to isolated the product.

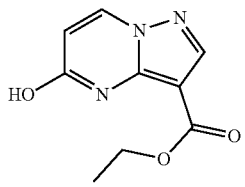

Ethyl 5-hydroxypyrazolo[1,5-a]pyrimidine-3-carboxylate: To a reactor was charged K₃PO₄ (4104 g granular, 19.3 moles), ethyl 3-amino-1H-pyrazole-4-carboxylate (2000 g, 12.9 moles), and DMF (18.8 kg) and the mixture was agitated. After 20 min, (E)-ethyl 3-ethoxyacrylate, (2230 g, 15.5 moles) was added and the mixture was heated to 110-115° C. internal temperature (IT). After the reaction was judged to be complete based on consumption of starting material, heating was ceased. The mixture was allowed to stir and cool overnight. Aqueous hydrochloric acid (3 M, 13 L) was added over ~2 h. DI water (6 L) was added and the mixture was allowed to stir overnight. The mixture was filtered through polypropylene filter cloth (PPFC) and the residue was washed with water (3×5 vol, 3×10 L). The solid was placed in trays and oven dried under vacuum at 55° C. for 3 days and then 45° C. for 4 days to constant weight of (2553 g 95.6%).

Ethyl 5-chloropyrazolo[1,5-a]pyrimidine-3-carboxylate (8): To a flask, under nitrogen, outfitted with mechanical stirring, J-Kem temperature probe, and condenser was added ethyl 5-hydroxypyrazolo[1,5-a]pyrimidine-3-carboxylate (2319 g, 11.2 moles), acetonitrile (9200 mL), and phosphoryl trichloride (1230 mL, 13.4 mmol). The reaction mixture was heated to ~74° C. (IT) until it was judged complete by HPLC. The reaction was cooled to ~30° C. While cooling, a separate flask was outfitted with mechanical stirring and a J-Kem temperature probe. Water (37 L) was added to this and the water was cooled to below 15° C. The reaction mixture was added portion-wise producing a mixture. The chlorination reactor was rinsed with 4:1 water/MeCN (2 L) and the rinse was added to the mixture. To the mixture was added MeCN (1 L) The transfer line was rinsed with 4:1 water/MeCN (2 L), and the rinse was added to the mixture. The mixture was cooled back to below 20° C. and a solution of tribasic phosphate (2312 g, 10.9 mol) in water (4.0 L) was added portion-wise at a rate to keep the IT below 25° C. The slurry was stirred at ambient temperature overnight. The slurry was filtered (PPFC) and rinsed with 4:1 water/MeCN (6 L). The cake was rinsed a second time with water (7.0 L). The solid was placed in trays and dried in a vacuum oven at 50° C. for 36-72 h to give 8.

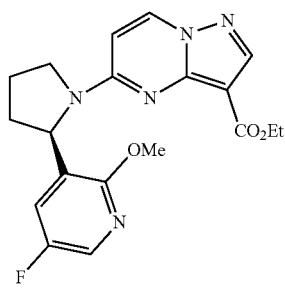

Ethyl (R)-5-(2-(5-fluoro-2-methoxypyridin-3-yl)pyrrolidin-1-yl)pyrazolo[1,5-a]pyrimidine-3-carboxylate (9): Combined triethylamine (1187 mL, 8518 mmol), (R)-5-fluoro-2-methoxy-3-(pyrrolidin-2-yl) pyridine (7) (889 g, 4259 mmol) in EtOH (200 proof, 5 mL/g, 4.4 L) and then ethyl 5-chloropyrazolo[1,5-a]pyrimidine-3-carboxylate (8) (1001 g, 4259 mmol) were added. The reaction was stirred overnight at ambient temp (19 h). The next day, water (10 mL/g, 8.9 L) was added and after stirring at room temperature for 2 h it was filtered through polypropylene filter cloth (PPFC), 23° C. and washed with 2:1 water:EtOH (2×1.8 L) then heptane (1.8 L). The product was placed in trays and dried under vacuum (with N₂ bleed) at 55° C. to give 9.

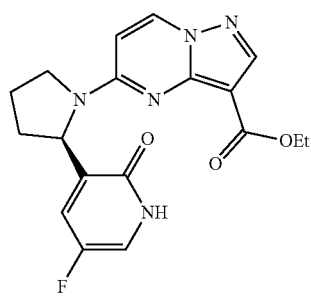

Ethyl (R)-5-(2-(5-fluoro-2-oxo-1,2-dihydropyridin-3-yl) pyrrolidin-1-yl)pyrazolo[1,5-a]pyrimidine-3-carboxylate (10): A solution of 4 M HCl in dioxane (1.0 L) was added to a flask containing (R)-ethyl 5-(2-(5-fluoro-2-methoxypyridin-3-yl) pyrrolidin-1-yl)pyrazolo[1,5-a]pyrimidine-3-carboxylate (9) (2500 g, 6486.9 mmol). The mixture was heated to 60° C. with an outlet at the top of the condenser (not under nitrogen). Once complete by HPLC, it was put under nitrogen and allowed to cool to room temperature with stirring overnight. The next day 20% $K_3PO_4$ (aq) (19 L, 7.5 mL/g—made by diluting 3800 g of $K_3PO_4$ to 19 kg total with water), was added. Once the temp was <35° C., EtOAc (12.5 L, 5 mL/g) was added and stirring continued for another 30 min. The mixture was pumped into a separatory vessel, and the aqueous layer dropped. The organic layer was concentrated under vacuum (rotovap) and the product was dried on vacuum pump at ambient temp to give 10.

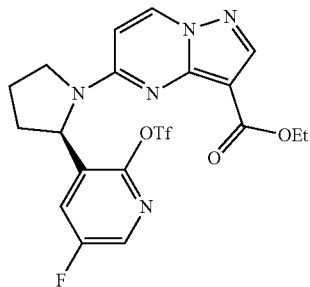

11 ethyl (R)-5-(2-(5-fluoro-2-(((trifluoromethyl) sulfonyl) oxy)pyridin-3-yl) pyrrolidin-1-yl) pyrazolo[1,5-a]pyrimidine-3-carboxylate (11): To a DCM solution of 10 was added triethylamine (1467 mL, 105.2 mol) and the mixture cooled to <5° C. Trifluoromethanesulfonic anhydride (1930 g, 684.0 mol) was added in portions maintaining temp <15° C. After 1 h reaction time sat. $NaHCO_3$ (5 mL/g, 11 L) was added The mixture was stirred for 1 h and was then transferred to a separatory vessel with DCM and the layers were separated. The organic layer was washed with $NaHCO_3$ (11 L). The organic layer was concentrated to minimum volume and solvent-swapped to MeOH (target MeOH volume about 10 L). The MeOH solution was added to a flask containing 1:1 MeOH:water (20 L), the suspension was stirred at room temperature for 2 h, filtered, and washed with 1:2 water:MeOH (2×2 mL/g). The solid was oven dried under vacuum at 55° C. until constant weight, to give 11.

N-Phenyl-bis(trifluoromethanesulfonimide) may be used instead of Trifluoromethanesulfonic anhydride to provide 11.

ethyl 5-((R)-2-(2-((R)-3-aminobut-1-yn-1-yl)-5-fluoropyridin-3-yl)pyrrolidin-1-yl)pyrazolo[1,5-a]pyrimidine-3-carboxylate (13): Toluene (16 L) was deoxygenated by $N_2$ bubbling for ~2 h. To a separate flask equipped with a heat source and reflux condenser were charged (R)-ethyl 5-(2-(5-fluoro-2-(((trifluoromethyl)sulfonyl)oxy)pyridin-3-yl) pyrrolidin-1-yl)pyrazolo[1,5-a]pyrimidine-3-carboxylate 11 (1440 g, 2860 mmol), copper(I) iodide (105 g, 551.3 mmol), Pd catalyst (398 g, 567.0 mmol), and the deoxygenated toluene. Diisopropylamine (810 ml, 5779 mmol) was added and the mixture was heated to 60° C. After ~1 h, the reaction temp was 60° C. and commercially available (R)-tert-butyl but-3-yn-2-ylcarbamate (12) (728 g, 4302 mmol) was added in three portions. After ~1 h, the mixture was cooled with an ice/water bath and then water (14 L) was added. When the reaction temp reaches ~35° C., it was filtered (PPFC) and washed with water (2×3.5 L). The filtrate was transferred to a separatory vessel and the aqueous layer was washed with toluene (2×3.5 L). The aqueous layer was transferred to a separate flask and added DCM (14 L) was added. The mixture was cooled to <15° C., then sat. $NH_4OH$ (2.4 L) was added. The solution was transferred to a separatory vessel and then washed with DCM (7 L). The DCM layers were allowed to stand at ambient temperature overnight and then they were combined and washed with brine (7 L). The organic layer was then concentrated, MeOH (5 L) was added and the mixture was concentrated to give 13.

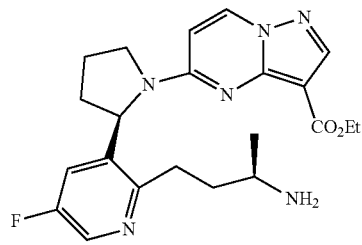

Ethyl 5-((R)-2-(2-((R)-3-aminobutyl)-5-fluoropyridin-3-yl) pyrrolidin-1-yl) pyrazolo[1,5-a] pyrimidine-3-carboxylate (14): Palladium on carbon (235 g, 104 mmol, 4.7 wt %), a 1285 g methanolic solution of ethyl 5-((R)-2-(2-((R)-3-aminobut-1-yn-1-yl)-5-fluoropyridin-3-yl)pyrrolidin-1-yl) pyrazolo[1,5-a]pyrimidine-3-carboxylate (13) (472 g, 1117 mmol) and MeOH (2.5 L~4 L total volume) were charged into a 8 L Parr reactor. The mixture was stirred at 50 psi $H_2$ until it was judged complete. The hydrogen atmosphere was replaced with nitrogen and the reaction mixture was allowed to stand overnight. The next day it was filtered through GF/F filter paper. The solution was concentrated to give 14.

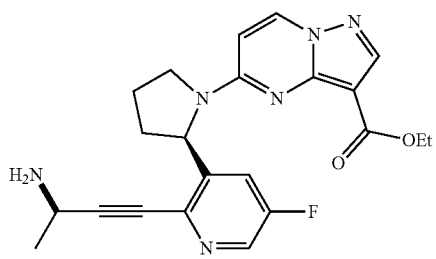

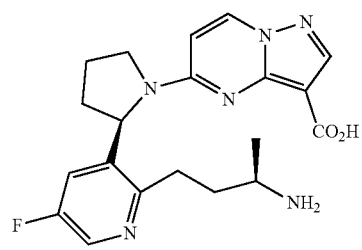

5-((R)-2-(2-((R)-3-aminobutyl)-5-fluoropyridin-3-yl) pyrrolidin-1-yl)pyrazolo[1,5-a]pyrimidine-3-carboxylic acid (15): A methanol solution of 14 (861 g, 2019 mmol) was combined with IPA (4 L) and then concentrated to 2.2 kg under vacuum. The concentrate was transferred to a reactor (with reflux condenser) with further dilution in IPA (10 L). The mixture was heated to 75° C. (IT). Sodium hydroxide (184 mL, 2631 mmol) was added and the reaction continues until it was judged complete by HPLC. The heat was removed and the mixture was allowed to cool to ambient temp overnight. Concentrated hydrochloric acid (214 mL, 2632 mmol) was added. The mixture was concentrated under vacuum with external heating to 45° C. to ~5 mL/g. Heptane (12 L) was added and the suspension was allowed to cool to ambient temp and then stirred for ~1 h. The suspension was filtered (PPFC) and washed with 3:1 heptane:IPA (2×1600 mL). The wet cake was placed in trays and dried under vacuum at 55° C. to constant weight to give 15.

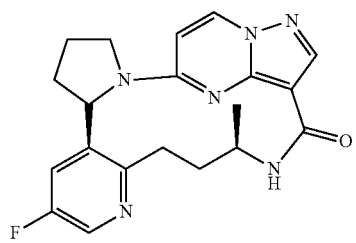

(13E,14E,22R,6R)-35-fluoro-6-methyl-7-aza-1(5,3)-pyrazolo[1,5-a]pyrimidina-3(3,2)-pyridina-2(1,2)-pyrrolidinacyclooctaphan-8-one(Compound 1): To a flask containing EDCI (157 g, 819 mmol) and DMAP (133 g, 1091 mmol) in DCM (50 mL/g, 125 mL) was added 5-((R)-2-(2-((R)-3-aminobutyl)-5-fluoropyridin-3-yl)pyrrolidin-1-yl)pyrazolo[1,5-a]pyrimidine-3-carboxylic acid (15) (302 g, 546 mmol) in 8 portions (37.8 g each). The portions were added ~60 min apart. The reaction mixture was stirred overnight at ambient temperature. The mixture was transferred to a separatory funnel with minimal DCM and washed with sat. NaHCO₃ (2×3 L), and 0.25 M citric acid (2×3 L, pH 5.5). The combined aqueous layers were washed with DCM (3 L, 10 mL/g) and then concentrated under vacuum (rotovap). The concentrate was dissolved in 3% MeOH in DCM and loaded onto a flash column (3 kg, SiO₂) and eluted with 3% MeOH in DCM (40 L total). The fractions containing the product were concentrated to give Compound 1 Combined lots of solid Compound 1 were triturated in IPAc (2.5 L, ca. 5 mL/g) at room temperature for 2 h. The mixture was heated to 40-45° C. for 10 minutes, then triturated at room temperature. The suspension was filtered and washed with IPAc (2×250 mL, ca. 2×0.5 mL/g) to give, after oven drying at 55° C., Compound 1.

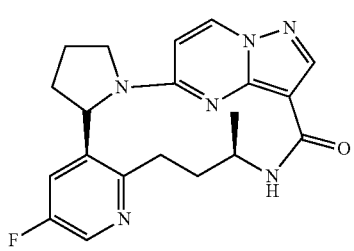

Compound 1

(13E,14E,22R,6R)-35-fluoro-6-methyl-7-aza-1(5,3)-pyrazolo[1,5-a]pyrimidina-3(3,2)-pyridina-2(1,2)-pyrrolidinacyclooctaphan-8-one(Compound 1) (alternative preparation): To a flask containing EDCI (1091 g, 5.7 mol, 1.7 eq) and DMAP (941 g, 7.71 mol, 2.3 eq) in DCM (38 L) were added the amino-acid 15 [5-((R)-2-(2-((R)-3-aminobutyl)-5-fluoropyridin-3-yl)pyrrolidin-1-yl)pyrazolo[1,5-a]pyrimidine-3-carboxylic acid] (1900 g, 3.35 mol) in 6 portions (added at least one hour apart), and the reaction was stirred at room temperature overnight. Once the reaction was complete it was transferred to a separatory funnel and washed with sat'd NaHCO₃ solution (2×19 L). The DCM layer was then washed with 0.25 M citric acid (38 L). The combined, citric acid aqueous layers were back-extracted with DCM (19 L), and the organic phases were added back to the 100 L round-bottomed flask. Charcoal (2.01 kg) and silica gel (2.01 kg) were added, and the suspension stirred at room temperature overnight. The next day, the suspension was filtered, and the charcoal cake was washed with DCM (3×19 L). The DCM filtrates were filtered a second time. The pale yellow solution was concentrated to minimum volume. Isopropyl acetate (28.5 L) was added and concentrated to 10 to 20 L. The suspension was heated overnight at 75° C., and the mixture was allowed to cool to room temperature. The solids were collected by filtration and washed with isopropyl acetate (2×1.9 L). The crude product was transferred to trays and dried in a vacuum oven 55° C. until constant mass was achieved.

To a flask was charged [(1³E,1⁴E, 2²R, 6R)-3⁵-fluoro-6-methyl-7-aza-1(5,3)-pyrazolo[1,5-a]pyrimidina-3(3,2)-pyridina-2(1,2)-pyrrolidinacyclooctaphan-8-one] followed by 2-butanone (6.3 L). The slurry was agitated at 75° C. for 2 days and then the product was collected by filtration, and the product cake was washed with 2-butanone (2×950 mL g). The product was transferred to trays and dried in a vacuum oven at 55° C. until constant mass was achieved to provide Compound 1.

The average purity of Compound 1 was 98.8% as determined by HPLC-UV. The structure of Compound 1 was confirmed using ¹H NMR.

2) Preparation of the Compound of Formula II

Compound of Formula II is prepared using methods and procedures similar to those used to prepare the compound of Formula I using tert-butyl prop-2-ynylcarbamate (compound 19) instead of tert-butyl (R)-but-3-yn-2-ylcarbamate (compound 12)

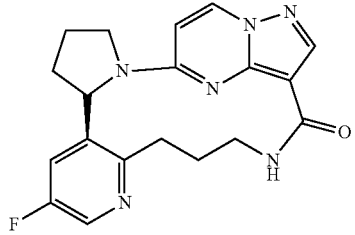

Formula II (6R)-9-fluoro-2,11,16,20,21,24-hexaazapentacyclo[16.5.2.0²,⁶.0⁷,¹².0²¹,²⁵]pentacosa-1(24),7,9,11,18(25),19,22-heptaen-17-one (Formula II)

MS (apci) m/z=367.3 (M+H).

3) Preparation of the Compound of Formula III

Compound of Formula III is prepared using methods and procedures similar to those used to prepare the compound of Formula I, using tert-butyl 2-methylbut-3-yn-2-ylcarbamate (compound 23) instead of tert-butyl (R)-but-3-yn-2-ylcarbamate (compound 12).

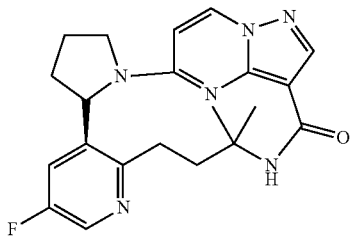

Formula III (6R)-9-fluoro-15,15-dimethyl-2,11,16,20,21,24-hexaazapentacyclo [16.5.2.0$^{2,6}$.0$^{7,12}$.0$^{21,25}$]pentacosa-1(24),7,9,11,18(25),19,22-heptaen-17-one (Formula III MS (apci) m/z=395.1 (M+H).

Preparation of Crystalline Forms and Salts of Compound 1

General methods for preparation and characterization of Compound 1 salts

Approximately 20 mg Compound 1 was weighed into 2 mL vials. Acid counterions were weighed into separate vials and stock solutions prepared for the liquid counterions (1.05 eq.). Table 11 shows acid weights and volumes.

TABLE 11

| | | | | | Neat Addition Amounts | |
|---|---|---|---|---|---|---|
| Acid | | pKa | | | By Weight | By Volume |
| No. | Acid | 1 | 2 | 3 | (mg) | (µL) |
| 1 | Hydrochloric acid 37 wt. % (12M) | −6.10 | | | 5.45 | 4.6 |
| 2 | Sulfuric acid | −3.00 | 1.92 | | 5.71 | 3.1 |
| 3 | 1-2-Ethane disulfonic acid | −2.10 | −1.50 | | 12.94 | |
| 4 | p-Toluene sulfonic acid | −1.34 | | | 10.84 | |
| 5 | Methane sulfonic acid | −1.20 | | | 5.31 | 3.6 |
| 6 | Naphthalene-2-sulfonic acid | 0.17 | | | 14.14 | |
| 7 | Benzene sulfonic acid | 0.70 | | | 8.92 | |
| 8 | Oxalic acid | 1.27 | 4.27 | | 5.08 | |
| 9 | 2-Hydroxy ethanesulfonic acid | 1.66 | | | 8.19 | |
| 10 | L-Aspartic acid | 1.88 | 3.65 | | 7.36 | |
| 11 | Maleic acid | 1.92 | 6.23 | | 6.48 | |
| 12 | Phosphoric acid | 1.96 | 7.12 | 12.32 | 5.42 | |
| 13 | Ethane sulfonic acid | −2.05 | | | 6.41 | 4.7 |
| 14 | L-Glutamic acid | 2.19 | 4.25 | | 8.13 | |
| 15 | L-Tartaric acid | 3.02 | 4.36 | | 8.34 | |
| 16 | Fumaric acid | 3.03 | 4.38 | | 6.48 | |
| 17 | Citric acid | 3.13 | 4.76 | 6.40 | 10.67 | |
| 18 | D-Glucuronic acid | 3.18 | | | 10.73 | |
| 19 | L-Malic acid | 3.46 | 5.10 | | 7.49 | |
| 20 | Hippuric acid | 3.55 | | | 10.1 | |
| 21 | D-Gluconic acid (50% in water) | 3.76 | | | 21.68 | 17.6 |
| 22 | DL-Lactic acid (85% aq. solution) | 3.86 | | | 5.86 | 4.8 |
| 23 | L-Ascorbic acid | 4.17 | 11.57 | | 9.73 | |
| 24 | Benzoic acid | 4.19 | | | 6.82 | |
| 25 | Succinic acid | 4.21 | 5.64 | | 6.59 | |

Preparation of samples of salts of these acids and the Compound 1 in selective solvents (acetone, ethanol, methanol, 2-propanol, TBME and THF) is described in the Examples. In the Examples 8-32, solids observed post-temperature cycling were collected and analyzed by XRPD. Samples in which solid was not observed had anti-solvent additions made to saturated solutions and the resultant solids were analyzed by XRPD.

Anti-Solvent Additions

Approximately 1 mL of anti-solvent (heptane or TBME depending on miscibility) was added dropwise to saturated salt solutions of Compound 1 free base. Any resulting solid was analyzed by XRPD.

Salt Stability Studies

Recovered salts were placed in an oven at 40° C./75% RH for 1 week, and the resultant materials were analyzed by XRPD to determine any changes to form or crystallinity.

Thermodynamic Solubility

Thermodynamic solubility studies were carried out as follows: 10 mg of prepared salts were suspended in pH 1, 4.5, 6.8 and un-buffered water (300 µL). The pH of the slurries was measured and adjusted accordingly using either 0.2M HCl solution or 0.2M sodium hydroxide solution. The slurries were agitated for 24 hours at ambient temperature using an incubator shaker. The resulting slurries were filtered, any solids recovered were analyzed by XRPD and filtrate pH measured and submitted for UPLC analysis. pH 1.0 Buffer: 67 mL 0.1M hydrochloric acid solution was added to 12.5 mL 0.2M potassium chloride solution and diluted to 100 mL using de-ionized water and adjusted accordingly. pH 4.5 Buffer: 7.0 mL 0.2M sodium hydroxide solution was added to 25 mL 0.2 potassium hydrogen phthalate solution and diluted to 100 mL using de-ionized water and adjusted accordingly. pH 6.8 Buffer: 11.2 mL 0.2M sodium hydroxide solution was added to 25 mL 0.2M potassium phosphate mono-basic and diluted to 100 mL using de-ionized water and adjusted accordingly.

Salt Disproportionation Studies

Salt disproportionation studies were carried out as follows: 20 mg of prepared salts were weighed into a vial and 0.5 mL of deionized water was added. The samples were then agitated for 24 h at ambient temperature. The pH of the samples was taken pre- and post-agitation. Any solids recovered were submitted for XRPD analysis to determine any changes to form.

Hydration Screen

Hydration screen was carried out as follows: 10 mg of prepared salts were suspended in several acetone/water mixtures of various water activities (low: aw=0.281, medium: aw=0.776 and high: aw=0.919) and agitated at ambient temperatures for 24 hr. Any recovered solids were submitted for XRPD analysis to determine any changes to form.

Analytical Methods

X-ray Powder Diffraction (XRPD)

XRPD analysis was carried out on a Panalytical X'pert pro, scanning the samples between 3 and 35° 2θ. The material was gently ground and loaded onto a multi-well plate with Kapton or mylar polymer film to support the sample. The multi well plate was then loaded into a Panalytical diffractometer running in transmission mode, using Cu K radiation, and analyzed. The experimental conditions are shown in Table 12.

TABLE 12

| Raw Data Origin: | XRD measurement |
|---|---|
| Scan Axis: | Gonio |
| Start Position [°2θ]: | 3.0066 |
| End Position [°2θ]: | 34.9866 |
| Step Size [°2θ]: | 0.0130 |
| Scan Step Time [s]: | 18.8700 |
| Scan Type: | Continuous |
| PSD Mode: | Scanning |
| PSD Length [°2θ]: | 3.35 |
| Offset [°2θ]: | 0.0000 |
| Divergence Slit Type: | Fixed |
| Divergence Slit Size [°]: | 1.0000 |
| Measurement Temperature | 25.00 |
| Anode Material: | Cu |
| K-Alpha 1 [Å]: | 1.54060 |
| K-Alpha2 [Å]: | 1.54443 |
| K-Beta [Å]: | 1.39225 |
| K-A2/K-A1 Ratio: | 0.50000 |
| Generator Settings: | 40 mA, 40 kV |
| Goniometer Radius [mm]: | 240.00 |
| Dist. Focus-Diverg. Slit [mm]: | 91.00 |
| Incident Beam Monochromator: | No |
| Spinning: | No |

Single Crystal X-ray Analysis (SXRD)

SXRD analysis was conducted on a Agilent Technologies (Dual Source) SuperNova diffractometer using monochromated Cu Kα (λ=1.54184 Å) radiation. The diffractometer was fitted with an Oxford Cryosystems low temperature device to enable data collection to be performed at 120(1) K and the crystal encased in a protective layer of Paratone oil. The data collected were corrected for absorption effects based on Gaussian integration over a multifaceted crystal model, implemented as a part of the CrysAlisPro software package (Agilent Technologies, 2014).

The structure was solved by direct methods (SHELXS97) (Sheldrick, G. M. *Acta Cryst. Sect. A* 2008, 64, 112.) and developed by full least squares refinement on F2 (SHELXL97) interfaced via the OLEX2 software package. Images were produced using OLEX2 (Dolomanov, O. V. et al. *J Appl. Cryst.* 2009, 42, 339-341).

Polarized Light Microscopy (PLM)

The presence of crystallinity (birefringence) was determined using an Olympus BX50 polarizing microscope, equipped with a Motic camera and image capture software (Motic Images Plus 2.0). All images were recorded using the 20× objective, unless otherwise stated.

Thermogravimetric Analysis (TGA)/Differential Thermal Analysis (DTA)

Approximately, 5 mg of material was weighed into an open aluminum pan and loaded into a simultaneous thermogravimetric/differential thermal analyzer (TG/DTA) and held at room temperature. The sample was then heated at a rate of 10° C./min from 20° C. to 400° C. during which time the change in sample weight was recorded along with any differential thermal events (DTA). Nitrogen was used as the purge gas, at a flow rate of 300 cm$^3$/min.

Differential Scanning Calorimetry (DSC)

Approximately, 5 mg of material was weighed into an aluminum DSC pan and sealed non-hermetically with a pierced aluminum lid. The sample pan was then loaded into a Seiko DSC6200 (equipped with a cooler) cooled and held at 20° C. Once a stable heat-flow response was obtained, the sample and reference were heated to 350° C. at scan rate of 10° C./min and the resulting heat flow response monitored.

Infrared Spectroscopy (IR)

Infrared spectroscopy was carried out on a Bruker ALPHA P spectrometer. Sufficient material was placed onto the center of the plate of the spectrometer and the spectra were obtained using parameters indicated in Table 13:

TABLE 13

| Resolution: | 4 cm$^{-1}$ |
|---|---|
| Background Scan Time: | 16 scans |
| Sample Scan Time: | 16 scans |
| Data Collection: | 4000 to 400 cm$^{-1}$ |
| Result Spectrum: | Transmittance |

Nuclear Magnetic Resonance (NMR)

NMR experiments were performed on a Bruker AVIIIHD spectrometer equipped with a DCH cryoprobe operating at 500.12 MHz for $^1$H channel Experiments were performed in deuterated DMSO and each sample was prepared to about 10 mM concentration.

Dynamic Vapor Sorption (DVS)

Approximately, 10 mg of sample was placed into a mesh vapor sorption balance pan and loaded into a DVS-1 dynamic vapor sorption balance by Surface Measurement Systems. The sample was subjected to a ramping profile from 40-90% relative humidity (RH) at 10% increments, maintaining the sample at each step until a stable weight had been achieved (99.5% step completion). After completion of the sorption cycle, the sample was dried using the same procedure to 0% RH and then a second sorption cycle back to 40% RH. The weight change during the sorption/desorption cycles were plotted, allowing for the hygroscopic nature of the sample to be determined. XRPD analysis was then carried out on any solid retained.

Gravimetric Vapor Sorption (GVS)

Approximately 10-20 mg of sample was placed into a mesh vapor sorption balance pan and loaded into an IGAS-orp Moisture Sorption Analyzer balance by Hiden Analytical. The sample was subjected to a ramping profile from 40-90% relative humidity (RH) at 10% increments, maintaining the sample at each step until a stable weight had been achieved (98% step completion). After completion of the sorption cycle, the sample was dried using the same procedure to 0% RH, and finally taken back to the starting point of 40% RH. The weight change during the sorption/desorption cycles were plotted, allowing for the hygroscopic nature of the sample to be determined.

High Performance Liquid Chromatography-Ultraviolet Detection (HPLC-UV)

HPLC experiments were performed on Agilent 1100 HPLC instrument with diode array detector (DAD) using parameters indicated in Table 14:

TABLE 14

| Column: | ACE3 C181-PFP 50 × 4.6 × 3 μm |
|---|---|
| Column Temperature: | 45.0° C. |
| Autosampler Temperature: | Ambient |
| UV wavelength: | 265 nm |
| Injection Volume: | 2.00 μL |
| Flow Rate: | 2 mL/min |
| Mobile Phase A: | 95.0% (0.1% TFA/DI-H2O) |
| Mobile Phase B: | 5.0% (0.1% TFA/MeCN) |

Gradient program is shown in Table 15:

TABLE 15

| Time (minutes) | Solvent B [%] |
|---|---|
| 0.00 | 5.0 |
| 2.50 | 60.0 |

TABLE 15-continued

| Time (minutes) | Solvent B [%] |
|---|---|
| 3.20 | 80.0 |
| 3.21 | 5.0 |
| 5.50 | 5.0 |

Example 1

Solubility of Compound 1 Free Base

A solid Compound 1 was obtained as follows. A 53 mL of solution containing about 330 mg of Compound 1 in warm 1,4-dioxane was divided between 33, 2 mL glass vials (1.5 mL in each). The solutions were frozen and freeze-dried by lyophilization overnight. The resulting material was then analyzed by XRPD to confirm mostly amorphous material.

Approximately 10 mg of amorphous Compound 1 was produced in 32×2 mL glass vials from freeze drying and 100 μL of the appropriate solvent system was added to the appropriate vial. Between each addition, the mixture was checked for dissolution and if no dissolution was apparent, the mixture was heated to about 40° C. and checked again. This procedure was continued until dissolution was observed or until 2 mL had been added (to the compound concentration of <5 mg/mL). The results of the solubility measurements are shown in Table 16.

TABLE 16

| Solvent | Approx. Solubility mg/mL |
|---|---|
| Acetone | 11.1 |
| Acetonitrile | 12.5 |
| Anisole | 11.1 |
| 1-Butanol | 17 |
| 2-Butanone | 11.1 |
| TBME | <5 |
| Cyclohexane | <5 |
| Cyclopentylmethyl ether | <5 |
| Dichloromethane | >100 |
| Diisopropyl ether | <5 |
| N,N-Dimethylacetamide | >100 |
| 1,2-Dimethoxyethane | 8.3 |
| Diglyme (bis(2-methoxyethyl ether) | 8.3 |
| 1,4-Dioxane | 8.3 |
| Dimethylformamide | >100 |
| Dimethylsulfoxide | 50 |
| Ethanol | 20 |
| Ethyl acetate | <5 |
| 2-Ethoxy ethanol | 50 |
| Heptane | <5 |
| Isobutyl acetate | <5 |
| Isopropyl acetate | <5 |
| Methanol | 50 |
| Methylisobutyl ketone | 6.25 |
| 2-Methyl THF | <5 |
| N-Methylpyrrolidone | >100 |
| 2-Propanol | 14.3 |
| 1-Propanol | >100 |
| Tetrahydrofuran | 20 |
| Toluene | <5 |
| TBME:Heptane (60:40 v/v) | <5 |
| Water | <5 |

Compound 1 showed low solubility in non-polar solvents such as toluene and 1,4-dioxane, medium solubility in polar aprotic solvents such as acetone, ethyl acetate and acetonitrile and high solubility in polar solvents such as DMSO, DMF and protic solvents such as methanol. In the remainder of cases and where "<" is present, solid was still present after the maximum volume of 2 mL was added. XRPD analysis of the recovered solids from the solvent solubility study returned the same crystalline form of free base in all cases (Form I), however, showing varying degrees of crystallinity and peak intensity (preferred orientation may have an effect on crystallinity of a sample). Insufficient solids were recovered from anisole, 1-butanol, diglyme, 2-ethoxy ethanol, MIBK and N-methylpyrrolidone.

Example 2

Preparation of Crystalline Compound 1 (Form I)

Solid Compound 1 was obtained as follows. A 212 mL of solution containing about 1.04 g of Compound 1 in warm 1,4-dioxane was divided between 26, 20 mL glass vials (approximately 8 mL in each). The solutions were frozen and freeze-dried by lyophilization overnight. The resulting material was then analyzed by XRPD to confirm mostly amorphous material.

The 25 vials each containing approximately 40 mg of amorphous freeze-dried Compound 1 were used. A solvent was added to each vial and Compound 1 was suspended in the solvent. The following 25 solvents were used: acetone, acetonitrile, anisole, 1-butanol, 2-butanone, TBME, cyclohexane, cyclopentylmethyl ether, 1,2-dimethoxyethane, 1,4-dioxane, ethanol, ethyl acetate, 2-ethoxy ethanol, heptane, isobutyl acetate, isopropyl acetate, methanol, methylisobutyl ketone, 2-methyl THF, 2-propanol, 1-propanol, tetrahydrofuran (THF), toluene, TBME:heptane (60:40 v/v), and water. The crystallization conditions consisted of maturation cycles, evaporation, cooling and anti-solvent addition techniques.

Temperature Cycling

Each of the 25 vials was temperature cycled between ambient temperature and 40° C. in 4 hour cycles over 72 h The resulting solids were isolated by centrifugation and analyzed by XRPD and PLM. Solids recovered from temperature cycling and analyzed by XRPD appeared to be the same as the input material (Form I) with varying degrees in crystallinity. No residual solid material was recovered from anisole, 1-butanol, 2-butanone, 2-ethoxy ethanol, 2-methyl THF, 1-propanol and THF.

A filtered saturated solution of Compound 1 in a specified solvent was divided into five vials and used to prepare crystalline forms of the compound according to the procedures described below:

Crash Cool (2° C.)

Saturated solutions of Compound 1 were stored at 2° C. for 24-72 h. At this time any material recovered was analyzed by XRPD. The crash cooling experiments at 2° C. recovered insufficient solids from all solvents for XRPD analysis except from 2-propanol which returned Compound 1 (Form I).

Crash Cool (−18° C.)

Saturated solutions of Compound 1 were stored at −18° C. for 24-72 h. At this time any material recovered was analyzed by XRPD. The crash cooling experiments at −18° C. recovered insufficient solids from all solvents for XRPD analysis except 1-butanol, ethanol, 2-propanol and 1-propanol. From the solids that were analyzed by XRPD analysis, all returned Compound 1 (Form I) with varying degrees of crystallinity.

Anti-Solvent Addition at Ambient Temperature

Approximately 1 mL of anti-solvent (heptane or TBME depending on miscibility) was added dropwise to saturated solutions of Compound 1 free base. Any resulting solid was analyzed by XRPD. The anti-solvent addition at ambient temperature experiments recovered insufficient solids from all solvents for XRPD analysis except acetone, acetonitrile, 2-butanone, 1,2-dimethoxyethane, 1,4-dioxane and ethanol. From the solids that were analyzed by XRPD analysis, all returned Compound 1 (Form I) with varying degrees of crystallinity.

Anti-Solvent Addition at 2° C.

Approximately 1 mL of anti-solvent (heptane or TBME depending on miscibility) was added dropwise to saturated solutions of Compound 1 free base. Any resulting solid was analyzed by XRPD. The anti-solvent addition at 2° C. experiments recovered insufficient solids from all solvents for XRPD analysis except acetone, acetonitrile, 1-butanol, 2-butanone, 1,2-dimethoxyethane, 1,4-dioxane, ethanol, ethyl acetate, MIBK, 1-propanol and THF. From the solids that were analyzed by XRPD, all returned Compound 1 (Form I) with varying degrees of crystallinity.

Evaporation

Saturated solutions of Compound 1 were transferred to 2 mL vials, these vials were then uncapped and allowed to evaporate at ambient temperature to recover material. Any material recovered was analyzed by XRPD. The evaporation experiments recovered insufficient solids from all solvents for XRPD analysis except acetone, acetonitrile, 2-butanone, cyclopropylmethyl ether, 1,2-dimethoxyethane, 1,4-dioxane, ethanol, ethyl acetate, 2-ethoxy ethanol, isobutyl acetate, isopropyl acetate, methanol, MIBK, 2-propanol, 1-propanol and THF. From the solids that were analyzed by)(RFD, all returned Compound 1 (Form I) with varying degrees of crystallinity.

Example 3

Characterization of Crystalline Compound 1 (Form I)

X-Ray Powder Diffraction (XRPD)

Form I of crystalline (6R,15R)-9-fluoro-15-methyl-2,11,16,20,21,24-hexaazapentacyclo[16.5.2.0$^{2,6}$.0$^{7,12}$.0$^{21,25}$]pentacosa-1(24),7,9,11,18(25),19,22-heptaen-17-one (Compound 1 free base) was characterized by XRPD. The XRPD pattern is shown in FIG. 1 and XRPD data is provided in Table 17.

TABLE 17

| 2-Theta (°) | Height | H % |
|---|---|---|
| 7.9 | 692 | 4.0 |
| 9.1 | 10133 | 58.1 |
| 11.2 | 6232 | 35.7 |
| 12.8 | 695 | 4.0 |
| 13.4 | 4471 | 25.6 |
| 14.8 | 2667 | 15.3 |
| 15.2 | 479 | 2.8 |
| 15.5 | 144 | 0.8 |
| 16.8 | 929 | 5.3 |
| 18.3 | 2049 | 11.8 |
| 18.6 | 2818 | 16.2 |
| 19.5 | 792 | 4.5 |
| 20.2 | 17437 | 100.0 |
| 21.4 | 1327 | 7.6 |
| 22.7 | 1668 | 9.6 |
| 23.2 | 210 | 1.2 |
| 23.6 | 1908 | 10.9 |
| 24.9 | 6322 | 36.3 |
| 25.8 | 783 | 4.5 |
| 26.1 | 447 | 2.6 |
| 26.5 | 537 | 3.1 |
| 27.0 | 1478 | 8.5 |
| 27.7 | 220 | 1.3 |

TABLE 17-continued

| 2-Theta (°) | Height | H % |
|---|---|---|
| 28.4 | 259 | 1.5 |
| 28.8 | 228 | 1.3 |
| 29.4 | 1795 | 10.3 |
| 30.0 | 142 | 0.8 |
| 30.3 | 358 | 2.1 |
| 31.2 | 197 | 1.1 |
| 32.1 | 359 | 2.1 |
| 32.3 | 357 | 2.1 |
| 33.3 | 248 | 1.4 |
| 34.4 | 70 | 0.4 |

As shown in FIG. 1, according to the XRPD analysis, the material is crystalline. PLM analysis showed birefringence with irregular morphology.

Thermogravimetric/differential Thermal Analysis (TG/DTA)

Form I of crystalline (6R,15R)-9-fluoro-15-methyl-2,11,16,20,21,24-hexaazapentacyclo[16.5.2.0$^{2,6}$.0$^{7,12}$.0$^{21,25}$]pentacosa-1(24),7,9,11,18(25),19,22-heptaen-17-one (Compound 1 free base) was characterized by TGA and DTA. TGA showed a weight loss of approximately 1.1% from outset up to 200° C., while DTA showed an endothermal "melting" event at onset about 315° C. (peak at 317° C.). The TG/DTA thermogram is shown in FIG. 2.

Differential Scanning Calorimetry (DSC)

Form I of crystalline (6R,15R)-9-fluoro-15-methyl-2,11,16,20,21,24-hexaazapentacyclo[16.5.2.0$^{2,6}$.0$^{7,12}$.0$^{21,25}$]pentacosa-1(24),7,9,11,18(25),19,22-heptaen-17-one (Compound 1 free base) was characterized by DSC. DSC analysis in the first heat showed a sharp endothermal event at onset 315° C. (peak at 317° C.) which is consistent with TG/DTA. No thermal events were seen in the cooling cycle. The second heating cycle showed a small endothermal event at onset around 118° C. (peak at 124° C.) which is highly likely to be a glass transition ($T_g$). The DSC thermograms are shown in FIG. 3

In sum, Compound 1 exists as one crystalline form (Form I) with favorable thermal properties with a melting point of 315° C. and low hygroscopicity with a mass uptake of 0.3% at 90% RH and no changes to form or crystallinity after exposure to GVS humidity conditions.

Example 4

Recrystallization of Compound 1 and Characterization of the Recrystallized Material Compound 1 was recrystallized from 1-propanol as follows. 500 mg of Compound 1 was weighed into a 20 mL vial. To this vial, 20 mL of 1-propanol was added gradually over 3 hours. The sample was placed in a 95° C. heated block to aid dissolution. The sample was slow to dissolve but a clear solution was achieved. The sample was cooled to 10° C. at 5° C./min. Once the cooling cycle had reached 10° C. the sample remained at 10° C. for a further 24 hours to recover material. The solids were then recovered and dried using a vacuum oven at ambient temperature.

XRPD analysis of the recrystallized solid showed no changes in crystalline form, and PLM analysis showed the material to be birefringent with irregular morphology. TGA showed a weight loss of approximately 0.7% from the outset up to 250° C., whilst DTA showed an endothermal 'melting' event at onset approximately at 314° C. (peak at about 318° C.).

Figure 9:
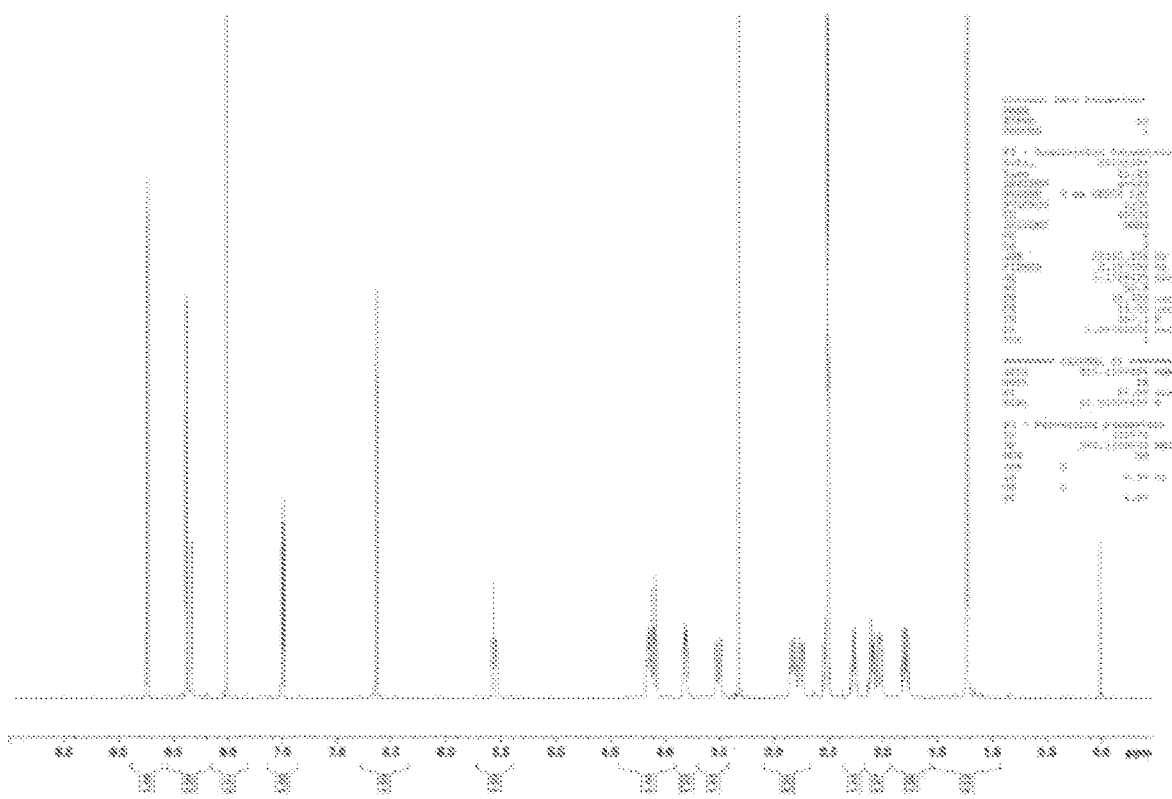
FIG. 9 is a $^1$H NMR spectrum of Compound 1 (Form I).

Purity of recrystallized solid is 99.2% as determined by HPLC-UV. $^1$H-NMR analysis shows that the spectrum is consistent with the structure and shows little if any obvious residual process solvents. $^1$H NMR spectrum is shown in FIG. 9.

Differential Scanning Calorimetry (DSC)

DSC analysis in the first heating cycle showed a sharp endothermal event at onset approximately 316° C. (peak at 317° C.). This endothermal event is consistent with TG/DTA. In the first cooling cycle of the DSC analysis, a slow broad recrystallization is observed with a peak at about 284° C. shows the thermogram of the first cooling cycle. DSC analysis in the second heating cycle showed a series of exothermic events which could be potential recrystallizations which were followed by a sharp endothermal event at onset about 313° C. (peak at about 316° C.). shows the thermogram of the second heating cycle of the recrystallized Compound 1 free base.

Infra-Red Analysis (IR)

Figure 8:
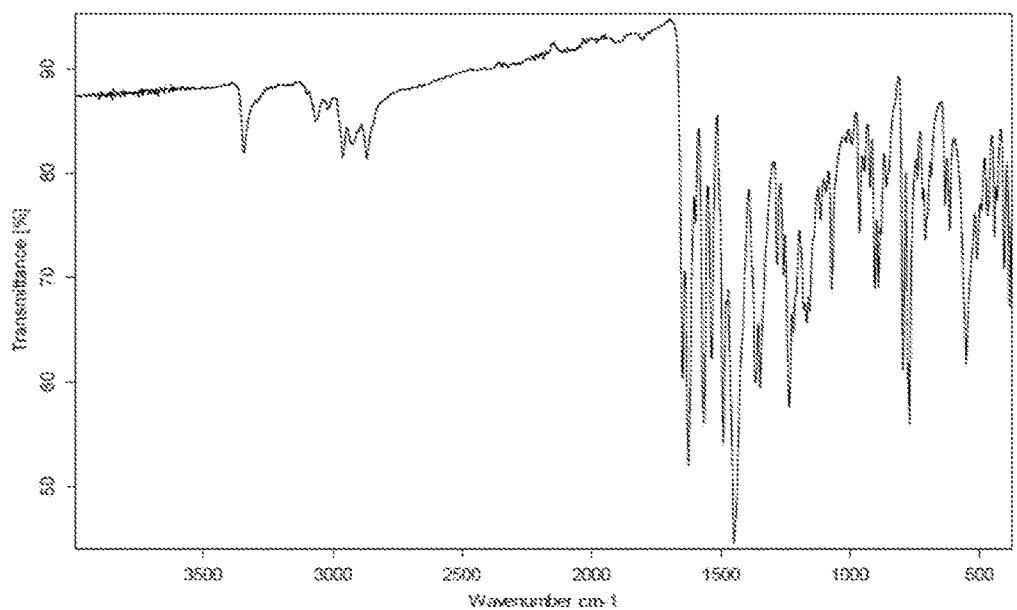
FIG. 8 is an IR spectrum Compound 1 (Form I).

Recrystallized Form I of crystalline Compound 1 was characterized by IR. FIG. 8 shows IR spectrum and the peaks are listed in Table 18.

TABLE 18

| Wave Number | Abs. Intensity | Rel. Intensity | Width |
|---|---|---|---|
| 3344.4 | 0.8 | 0.1 | 27.8 |
| 3066.3 | 0.9 | 0.0 | 31.6 |
| 3019.9 | 0.9 | 0.0 | 15.3 |
| 2962.0 | 0.8 | 0.0 | 18.7 |
| 2929.8 | 0.8 | 0.0 | 25.5 |
| 2870.4 | 0.8 | 0.1 | 143.0 |
| 1649.6 | 0.6 | 0.1 | 2538.9 |
| 1625.8 | 0.5 | 0.4 | 43.1 |
| 1599.0 | 0.8 | 0.0 | 61.5 |
| 1566.9 | 0.6 | 0.3 | 17.6 |
| 1537.4 | 0.6 | 0.2 | 13.5 |
| 1492.1 | 0.5 | 0.2 | 2106.0 |
| 1450.6 | 0.4 | 0.5 | 63.7 |
| 1365.4 | 0.6 | 0.1 | 1743.6 |
| 1346.7 | 0.6 | 0.2 | 44.5 |
| 1281.8 | 0.7 | 0.1 | 8.5 |
| 1257.5 | 0.7 | 0.1 | 8.0 |
| 1234.4 | 0.6 | 0.2 | 40.6 |
| 1219.2 | 0.6 | 0.0 | 5.5 |
| 1167.6 | 0.7 | 0.1 | 35.4 |
| 1156.0 | 0.7 | 0.0 | 5.6 |
| 1114.8 | 0.8 | 0.0 | 9.4 |
| 1093.2 | 0.8 | 0.0 | 9.7 |
| 1070.8 | 0.7 | 0.1 | 10.7 |
| 992.3 | 0.8 | 0.0 | 318.0 |
| 964.0 | 0.7 | 0.1 | 13.0 |
| 945.2 | 0.8 | 0.0 | 132.0 |
| 923.0 | 0.8 | 0.1 | 6.9 |
| 903.6 | 0.7 | 0.1 | 7.3 |
| 890.8 | 0.7 | 0.2 | 35.4 |
| 859.2 | 0.8 | 0.0 | 175.9 |
| 796.2 | 0.6 | 0.2 | 11.5 |
| 777.7 | 0.6 | 0.0 | 0.1 |
| 770.5 | 0.6 | 0.3 | 19.5 |
| 740.5 | 0.8 | 0.0 | 147.4 |
| 719.7 | 0.8 | 0.0 | 694.4 |
| 709.6 | 0.7 | 0.1 | 25.8 |
| 686.7 | 0.8 | 0.0 | 170.0 |
| 633.0 | 0.8 | 0.1 | 7.9 |
| 616.0 | 0.7 | 0.1 | 11.2 |
| 552.4 | 0.6 | 0.2 | 43.9 |
| 509.5 | 0.7 | 0.0 | 9.3 |
| 468.8 | 0.8 | 0.1 | 13.6 |
| 442.2 | 0.7 | 0.0 | 16.7 |
| 432.1 | 0.8 | 0.0 | 91.7 |
| 405.0 | 0.7 | 0.1 | 10.1 |

In sum, Compound 1 recrystallized from 1-propanol exhibited the same properties as the compound prior to recrystallization, with an increased purity of >99%. As shown in Example 5, the material showed no change to form or purity after exposure to stability stress conditions and no change to form after an aqueous solubility assessment.

Example 5

Stability of Compound 1 (Form I)

Compound 1 (Form I) was subjected to various different environmental conditions to assess stability.

Vapor Sorption—before Recrystallization

Figure 4:
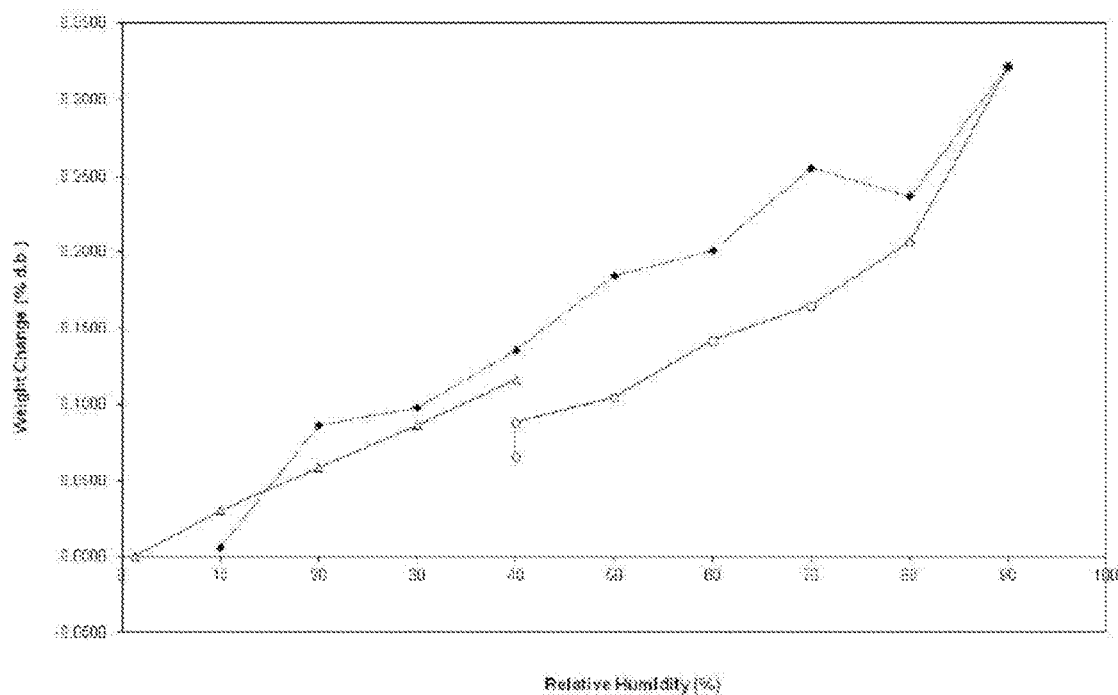
FIG. 4 is a GVS isotherm plot of Compound 1 (Form I).
Figure 5:
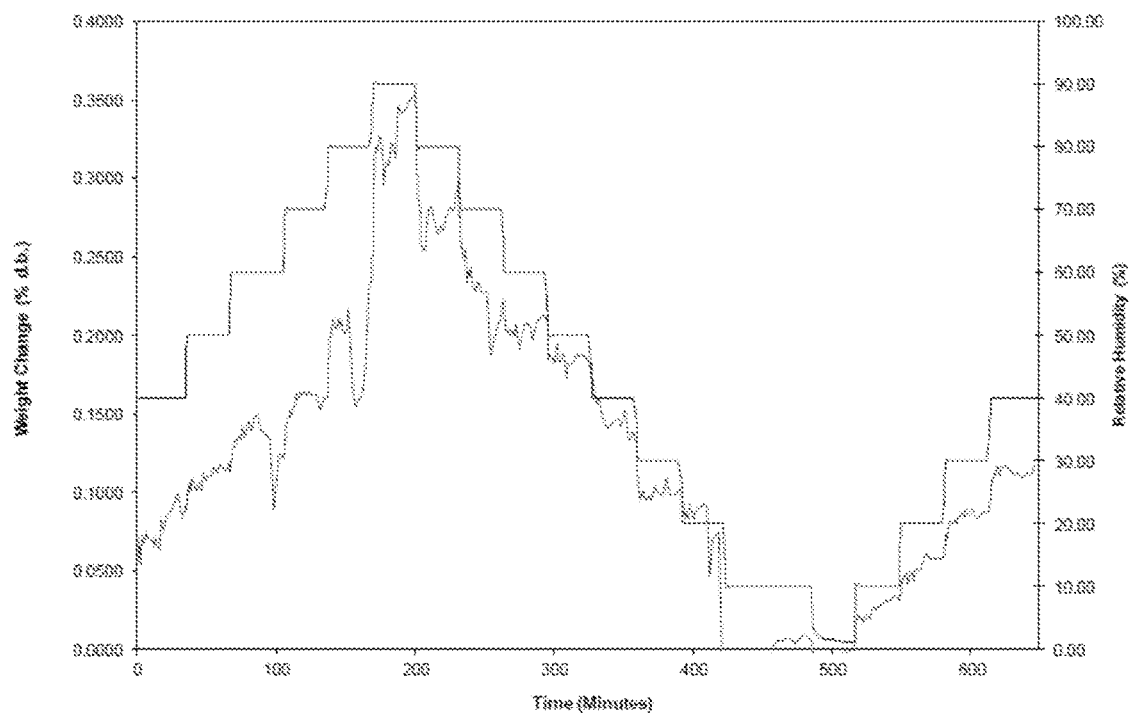
FIG. 5 is a GVS kinetic plot of Compound 1 (Form I).

Gravimetric vapor sorption (GVS) showed that Compound 1 exhibits slight hygroscopicity with a mass uptake of approximately 0.3% at 90% RH. FIG. 4 shows GVS isotherm plot and FIG. 5 shows GVS kinetic plot. Post-XRPD analysis showed no changes in crystalline form upon exposure to GVS conditions.

Vapor Sorption—Recrystallized Solid

Figure 6:
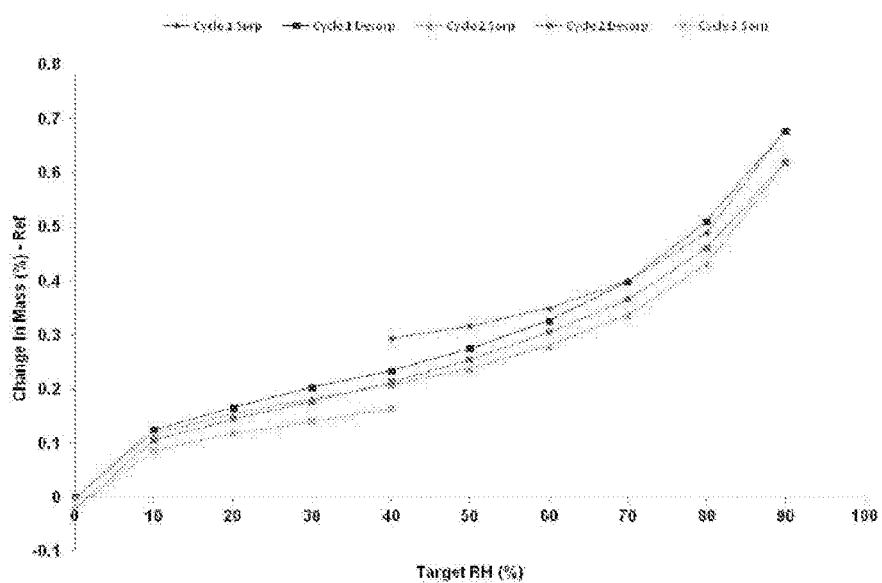
FIG. 6 is a DVS isotherm plot of Compound 1 (Form I).
Figure 7:
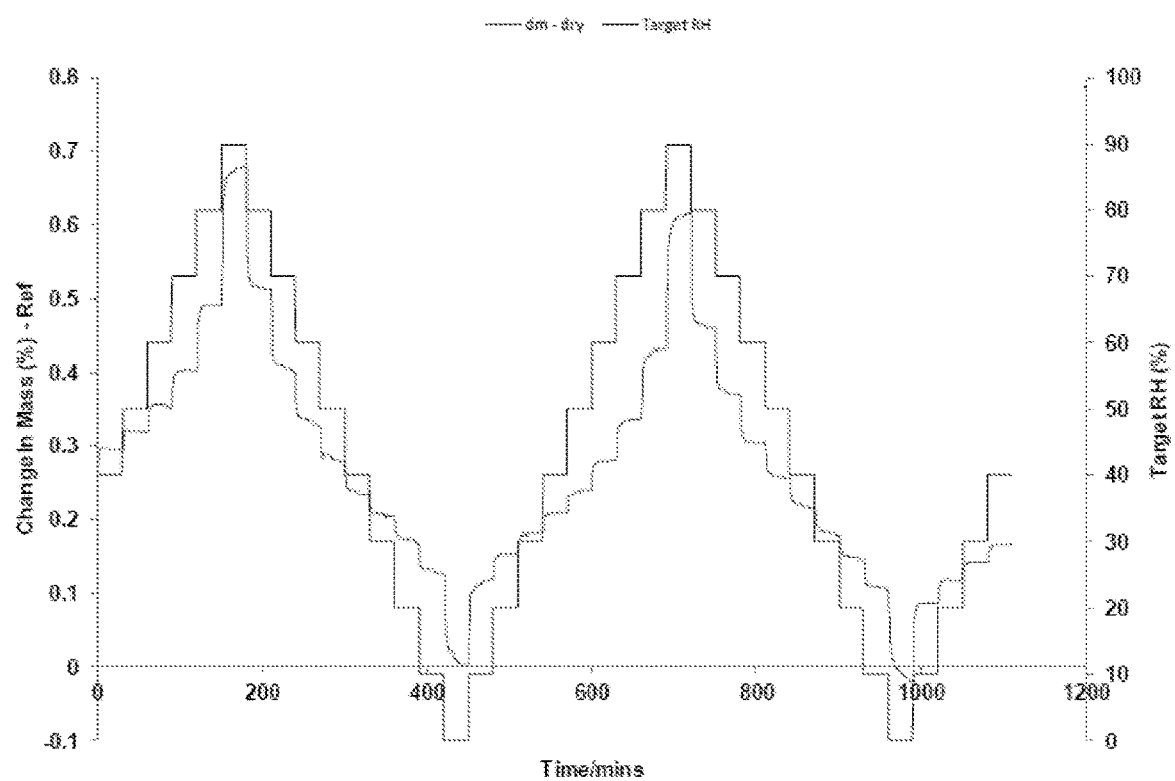
FIG. 7 is a DVS change in mass plot of Compound 1 (Form I).

Dynamic vapor sorption (DVS) analysis of the recrystallized compound shows the material to exhibit slight hygroscopicity with a mass uptake of about 0.7% at 90% RH. FIG. 6 shows DVS analysis of the recrystallized compound. FIG. 7 shows DVS kinetic plot of the recrystallized solid. Post-DVS XRPD analysis shows no change in crystalline form upon exposure to DVS humidity conditions.

Humidity, temperature, Ambient Light—Recrystallized Solid 1-week stability tests on recrystallized solid showed no change to form after exposure to 40° C./75% RH, 80° C. and under ambient light. UPLC analysis showed no change in purity of the samples after exposure to stability stress conditions (average purity 99.2 for relative humidity and ambient light tests, and 99.3% for 80° C. test).

Example 6

Single Crystal X-ray Analysis of Compound 1 (Form I)

Crystals of Compound 1 (Form 1) were prepared as follows. Compound 1 (2 mg) was dissolved in methanol (500 µL) in a 1.75 clear glass vial then capped with a pierced lid. The solution was left to stand at ambient for several days without agitation to allow for large rod-like crystals to grow that were suitable for interrogation by single crystal X-ray diffraction.

The highest residual Fourier peak was found to be 0.16 e. Å$^{-3}$ approx 0.72 Å from C(4), and the deepest Fourier hole was found to be −0.22 e. Å$^{-3}$ approx 0.75 Å from C(10). Crystal Data for $C_{20}H_{21}FN_6O$ (M=380.43 g/mol): orthorhombic, space group $P2_12_12_1$ (no. 19), a=6.91792(3) Å, b=13.74742(3) Å, c=19.22580(5) Å, V=1828.442(10) Å$^3$, Z=4, T=207(120) K, µ(CuKα)=0.799 mm-1, Dcalc=1.382 g/cm$^3$, 169333 reflections measured (7.9°≤2Θ≤152.76°), 3833 unique (Rint=0.0639, Rsigma=0.0180) which were used in all calculations. The final R$^1$ was 0.0338 (>2sigma (I)) and wR$_2$ was 0.0908 (all data). Crystallographic parameters and refinement indicators of Compound 1 (Form I) are shown in Table 19.

TABLE 19

| | |
|---|---|
| Empirical formula | $C_{20}H_{21}FN_6O$ |
| Formula weight | 380.43 |
| Temperature/K | 120(1) |
| Crystal system | Orthorhombic |

TABLE 19-continued

| | |
|---|---|
| Space group | P2$_1$2$_1$2$_1$ |
| a/Å | 6.91792(3) |
| b/Å | 13.74742(3) |
| c/Å | 19.22580(5) |
| α/° | 90.00 |
| β/° | 90.00 |
| γ/° | 90.00 |
| Volume/Å$^3$ | 1828.442(10) |
| Z, Z' | 4 |
| ρcalc g/cm$^3$ | 1.382 |
| μ/mm$^{-1}$ | 0.799 |
| F(000) | 800.0 |
| Crystal size/mm$^3$ | 0.47 × 0.117 × 0.105 |
| Radiation | CuKα (λ = 1.54178) |
| 2Θ range for data collection/° | 7.9 to 152.76 |
| Index ranges | −8 ≤ h ≤ 7, −17 ≤ k ≤ 17, −24 ≤ l ≤ 24 |
| Reflections collected | 169333 |
| Independent reflections | 3833 [R$_{int}$ = 0.0639, R$_{sigma}$ = 0.0180] |
| Data/restraints/parameters | 3833/0/258 |
| S | 1.060 |
| Final R indexes [F$^2$ > 2σ (F$^2$)] | R$_1$ = 0.0338, wR$_2$ = 0.0907 |
| Final R indexes [all data] | R$_1$ = 0.0340, wR$_2$ = 0.0908 |
| Δρmax, Δρmin/e Å$^{-3}$ | 0.16/−0.22 |
| Flack parameter | −0.01(15) |

FIG. 10 shows 3-D view of Compound 1 (Form I) with atom labels. FIG. 11 shows ORTEP view of Compound 1 (Form I) with atom labels. All non-hydrogen atoms are shown with thermal ellipsoids set at the 50% probability level.

Example 7

Single Crystal X-ray Analysis of Compound 1, Acetonitrile Solvate

Crystals of Compound 1, acetonitrile solvate were prepared vas follows. Compound 1 (2 mg) was dissolved in acetonitrile (500 μl) in a 1.75 clear glass vial then capped with a pierced lid. This solution was left to stand at ambient for several days without agitation to allow for large rod-like crystals to grow that were suitable for interrogation by single crystal X-ray diffraction.

The highest residual Fourier peak was found to be 0.19 e. Å$^{-3}$ approx 0.67 Å from C(11), and the deepest Fourier hole was found to be −0.21 e. Å$^{-3}$ approx 0.81 Å from N(4). Crystal Data for C$_{24}$H$_{27}$FN$_8$O (M=462.54 g/mol): orthorhombic, space group P2$_1$2$_1$2$_1$ (no. 19), a=6.03307(4) Å, b=16.10794(9) Å, c=23.72624(13) Å, V=2305.73(2) Å$^3$, Z=4, T=294.01(10) K, μ(CuKα)=0.757 mm-1, Dcalc=1.332 g/cm$^3$, 110019 reflections measured (6.64°≤2Θ≤152.4°), 4840 unique (Rint=0.0983, Rsigma=0.0211) which were used in all calculations. The final R$^1$ was 0.0339 (>2sigma (I)) and wR$_2$ was 0.0891 (all data). Crystallographic parameters and refinement indicators of Compound 1 (Form I) are shown in Table 20.

TABLE 20

| | |
|---|---|
| Empirical formula | C$_{24}$H$_{27}$FN$_8$O |
| Formula weight | 462.54 |
| Temperature/K | 120(1) |
| Crystal system | orthorhombic |
| Space group | P2$_1$2$_1$2$_1$ |
| a/Å | 6.03307(4) |

TABLE 20-continued

| | |
|---|---|
| b/Å | 16.10794(9) |
| c/Å | 23.72624(13) |
| α/° | 90.00 |
| β/° | 90.00 |
| γ/° | 90.00 |
| Volume/Å$^3$ | 2305.73(2) |
| Z, Z' | 4 |
| ρcalc g/cm$^3$ | 1.332 |
| μ/mm$^{-1}$ | 0.757 |
| F(000) | 976.0 |
| Crystal size/mm$^3$ | 0.564 × 0.082 × 0.033 |
| Radiation | CuKα (λ = 1.54184) |
| 2Θ range for data collection/° | 6.64 to 152.4 |
| Index ranges | 7 ≤ h ≤ 6, −20 ≤ k ≤ 20, −29 ≤ l ≤ 29 |
| Reflections collected | 110019 |
| Independent reflections | 4840 [R$_{int}$ = 0.0983, R$_{sigma}$ = 0.0211] |
| Data/restraints/parameters | 4840/0/310 |
| S | 1.096 |
| Final R indexes [F$^2$ > 2σ (F$^2$)] | R$_1$ = 0.0339, wR$_2$ = 0.0887 |
| Final R indexes [all data] | R$_1$ = 0.0345, wR$_2$ = 0.0891 |
| Δρmax, Δρmin/e Å$^{-3}$ | 0.19/−0.21 |
| Flack parameter | −0.02(14) |

FIG. 12 shows 3-D view of Compound 1 bis-acetonitrile solvate with atom labels. FIG. 13 shows ORTEP view of Compound 1 bis-acetonitrile solvate asymmetric unit with atom labels. All non-hydrogen atoms are shown with thermal ellipsoids set at the 50% probability level.

Example 8

Preparation and Characterization of Compound 1 Benzenesulfonic Acid Salt

250 μL of the appropriate solvent was added to the vials containing 20 mg of compound 1. In a separate vial, 250 μL of the appropriate solvent was added to the vial containing benzenesulfonic acid (8.92 mg). The solutions/slurries were then added to the solvent/compound 1 solution (1.05 eq. of acid to free base). The samples were then temperature cycled between ambient and 40° C. in 4 hour cycles over 24 hrs.

Scale-Up Preparation from Ethanol

About 300 mg of Compound 1 was weighed into a vial and 133 mg of benzenesulfonic acid was weighed into a separate vial. To both vials, 3.75 mL of ethanol was added and the two mixtures combined. The resulting slurry was then temperature cycled for 24 hours (ambient to 40° C. in 4 hours cycles) (1.05 eq. of acid to free base). The resulting slurry was then allowed to evaporate at ambient temperatures to remove excess ethanol.

Observations from the treatment of Compound 1 with benzenesulfonic acid are shown in Table 21 below:

TABLE 21

| Time-point | Solvent | | | | | |
|---|---|---|---|---|---|---|
| | Acetone | Ethanol | Methanol | 2-propanol | TBME | THF |
| Pre-Cycling | Slurry | Slurry | Slurry | Slurry | Slurry | Slurry |
| Post-Cycling | Solid | Clear Solution | Gum | Slurry | Slurry | Solid |

To the samples which were recovered as clear solutions, 2-3 mg of Compound 1 was added to produce a mobile slurry and the sample temperature cycled for a further 2-3 hours. XRPD analysis of benzenesulfonic acid experiments recovered 5 crystalline hits, free base (Form I) recovered from acetone and 2-propanol, pattern 1 was recovered from THF and t-BME (FIG. 17) and pattern 2 recovered from ethanol (FIG. 18). Insufficient solids were recovered from ethanol to determine form.

XRPD data for Compound 1 besylate is provided in Table 22.

TABLE 22

| 2-Theta (°) | Height | H % |
|---|---|---|
| 8.1 | 15179 | 100.0 |
| 9.2 | 864 | 5.7 |
| 10.0 | 85 | 0.6 |
| 11.7 | 591 | 3.9 |
| 12.0 | 1879 | 12.4 |
| 12.4 | 394 | 2.6 |
| 13.4 | 3923 | 25.9 |
| 15.1 | 548 | 3.6 |
| 16.0 | 196 | 1.3 |
| 16.7 | 156 | 1.0 |
| 18.4 | 302 | 2.0 |
| 19.0 | 2184 | 14.4 |
| 19.4 | 1644 | 10.8 |
| 19.9 | 1220 | 8.0 |
| 20.1 | 959 | 6.3 |
| 20.6 | 226 | 1.5 |
| 21.2 | 3809 | 25.1 |
| 21.7 | 587 | 3.9 |
| 21.9 | 362 | 2.4 |
| 22.5 | 749 | 4.9 |
| 23.3 | 165 | 1.1 |
| 23.7 | 114 | 0.8 |
| 24.1 | 80 | 0.5 |
| 25.5 | 1263 | 8.3 |
| 25.8 | 545 | 3.6 |
| 26.0 | 183 | 1.2 |
| 26.4 | 159 | 1.1 |
| 26.7 | 420 | 2.8 |
| 27.0 | 768 | 5.1 |
| 27.8 | 126 | 0.8 |
| 28.1 | 66 | 0.4 |
| 28.5 | 153 | 1.0 |
| 28.9 | 39 | 0.3 |
| 29.3 | 478 | 3.2 |
| 30.3 | 127 | 0.8 |
| 30.8 | 50 | 0.3 |
| 32.0 | 806 | 5.3 |
| 32.7 | 1080 | 7.1 |
| 33.2 | 155 | 1.0 |
| 33.4 | 177 | 1.2 |
| 33.8 | 153 | 1.0 |
| 34.7 | 260 | 1.7 |

TG/DT Analysis

TGA of besylate pattern 1 from tBME showed a total weight loss of approximately 13% from the outset to about 150° C. DTA showed an endothermal event at onset about 241° C. (peak at about 247° C.). TGA of besylate pattern 1 from ethanol showed a total weight loss of approximately 0.4% from the outset to about 250° C. DTA showed an endothermal event at onset about 244° C. (peak at about 248° C.).

Result of Stability Studies

XRPD analysis of post-stability besylate pattern 1 recovered from THF showed an increase to crystallinity but no changes to form after exposure to stability conditions. XRPD analysis of post-stability besylate pattern 1 recovered from TBME showed preferred orientation but no changes to form after exposure to stability conditions. XRPD analysis of post-stability besylate pattern 1 recovered from ethanol showed a decrease in crystallinity after exposure to stability conditions.

Secondary Salt Scale Up

XRPD analysis of besylate scale up showed successful formation of besylate pattern 2 from ethanol seen in the salt screen, a large amount of preferred orientation is seen in the sample.

TGA (FIG. 37) showed a weight loss of approximately 0.7% from the outset up to around 250° C. whilst DTA showed an endothermal "melting" event at onset around 244° C. (peak at around 248° C.).

Figure 39:
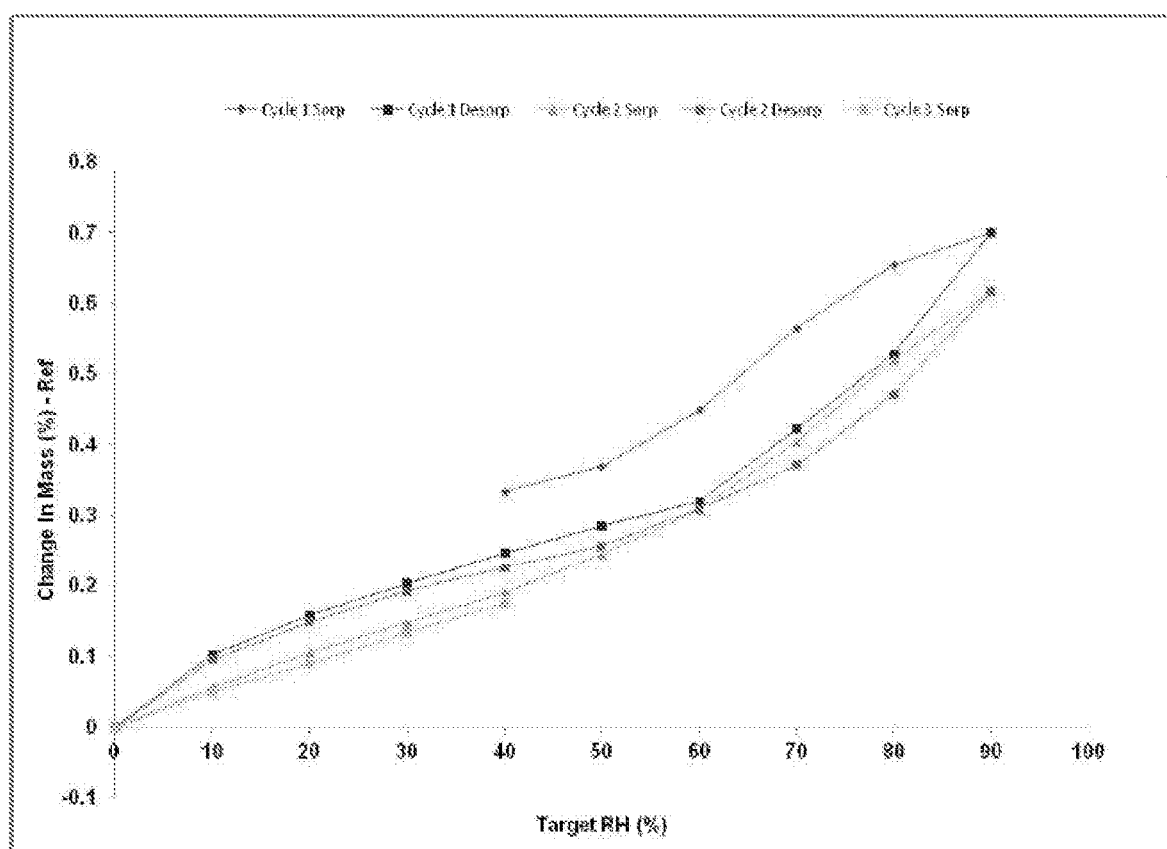
FIG. 39 is a DVS isotherm of Compound 1 besylate.
Figure 40:
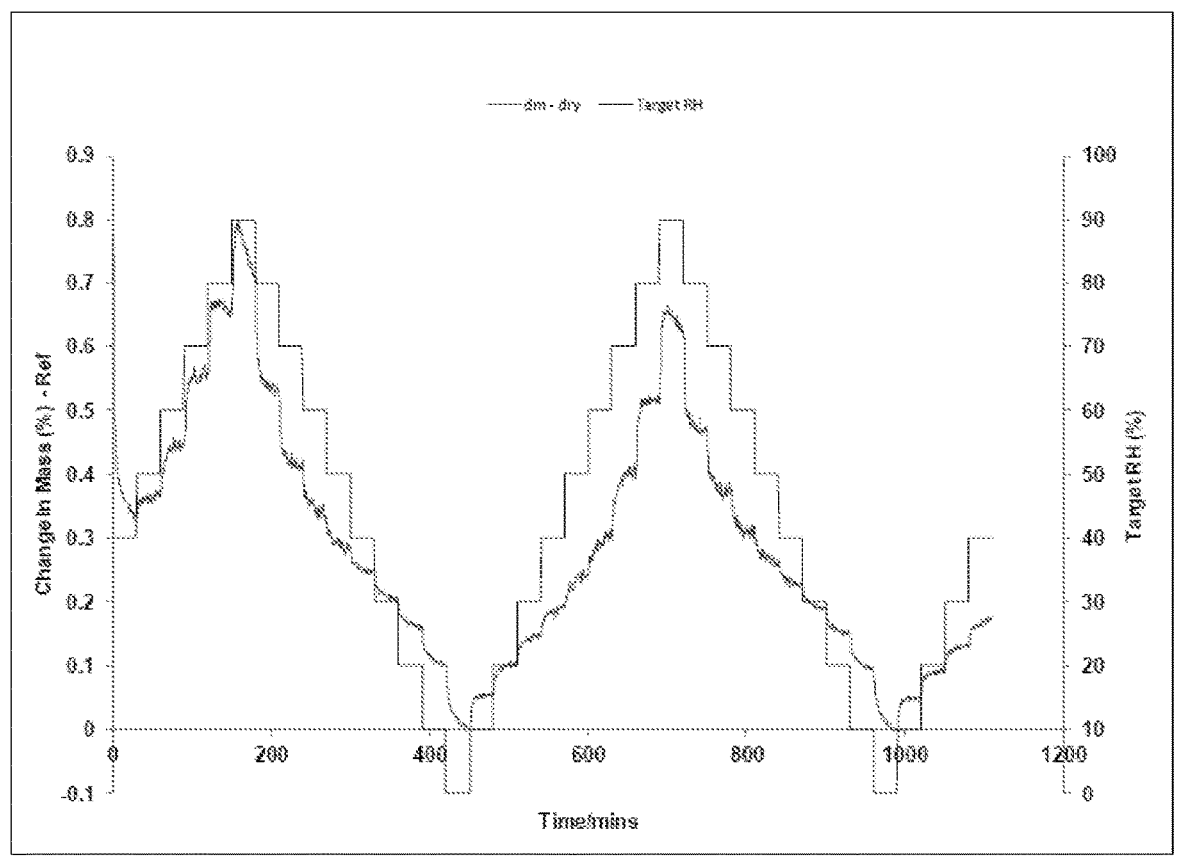
FIG. 40 is a DVS kinetic plot of Compound 1 besylate.

DSC analysis (FIG. 38) in the first heating cycle showed a sharp endothermal event at onset around 246° C. (peak at 249° C.). This endothermal event is consistent with TG/DTA and no thermal events were seen in the cooling or second heating cycle. Compound 1 besylate exhibits low hygroscopicity when exposed by DVS conditions with a mass uptake of about 0.7% at 90% RH (FIGS. 39 and 40). Post-DVS XRPD analysis shows no changes in crystalline form after exposure, a large amount of preferred orientation is seen in the sample. The hysteresis observed is most likely caused by a small amount of amorphous content which appears to crystallize at 90% RH.

Figure 41:
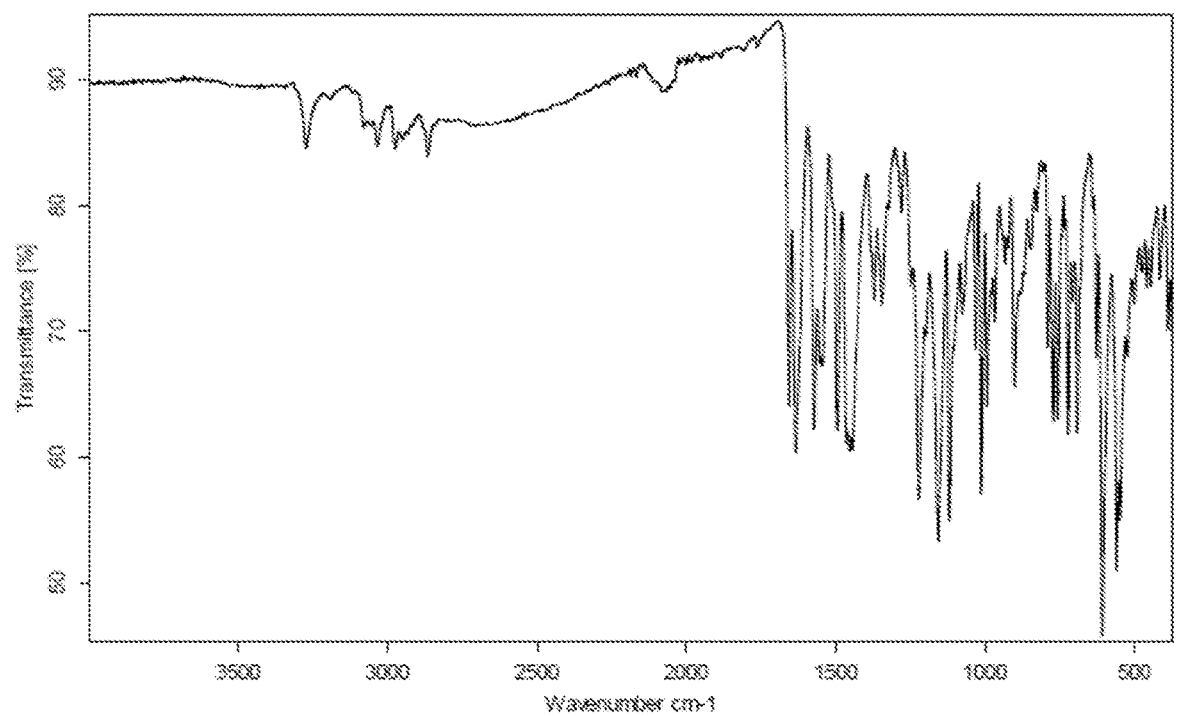
FIG. 41 is an IR spectrum of Compound 1 besylate.

An IR spectrum of Compound 1 besylate was taken for reference which can be found in FIG. 41 with peak lists in Table 23.

TABLE 23

| Wave number |
|---|
| 3271 |
| 3033 |
| 2974 |
| 2864 |
| 2069 |
| 1657 |
| 1634 |
| 1573 |
| 1544 |
| 1496 |
| 1464 |
| 1456 |
| 1446 |
| 1371 |
| 1343 |
| 1279 |
| 1248 |
| 1222 |

TABLE 23-continued

| Wave number |
|---|
| 1197 |
| 1157 |
| 1119 |
| 1077 |
| 1032 |
| 1018 |
| 994 |
| 968 |
| 933 |
| 923 |
| 902 |
| 846 |
| 828 |
| 791 |
| 772 |
| 757 |
| 734 |
| 723 |
| 708 |
| 692 |
| 640 |
| 628 |
| 609 |
| 561 |
| 549 |
| 526 |
| 503 |
| 476 |
| 459 |
| 445 |
| 415 |

Figure 42:
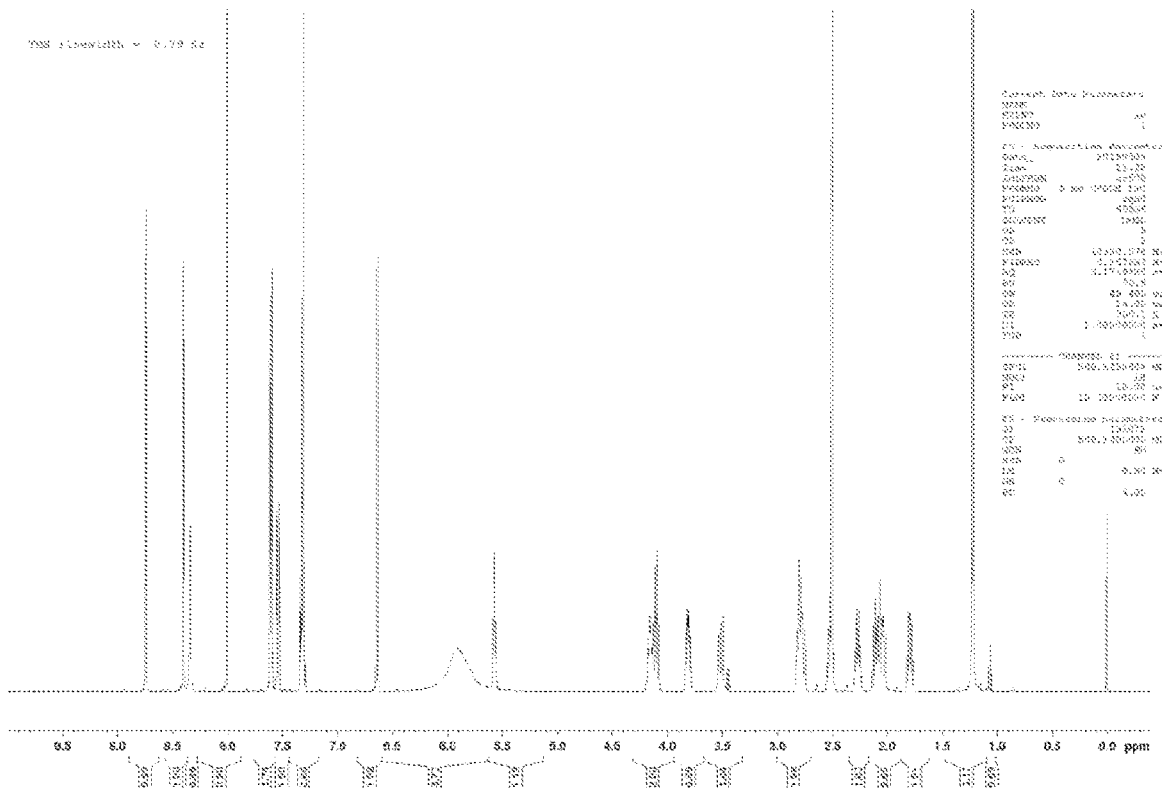
FIG. 42 is $^1$H NMR spectrum of Compound 1 besylate.

$^1$H-NMR spectrum shown in FIG. 42 shows 0.88 eq. benzenesulfonic acid, and 0.028 eq. EtOH. UPLC analysis of Compound 1 besylate gave an average purity of 99.4%.

1 week stability tests at 80° C. and under ambient light showed no change to form after exposure and no change to purity. However, by XRPD analysis, the sample held at 40° C./75% RH appears to be a mixture of besylate salt and something else.

Thermodynamic solubility studies of Compound 1 besylate show the salt is highly soluble in pH 1, moderately soluble in 4.5 and unbuffered water. The sample shows low solubility in pH 6.8. pH and concentration values can be found in Table 24.

TABLE 24

| Sample ID | Concentration (mg/mL) |
|---|---|
| pH 1 | 30.8 |
| pH 4.5 | 12.7 |
| pH 6.8 | 1.9 |
| Un-buffered Water | 17.9 |

XRPD analysis showed insufficient solids were recovered from pH 1, an unknown form was recovered from pH 4.5 and poorly crystalline free base was recovered from pH 6.8 and unbuffered water. Salt disproportionation studies of Compound 1 besylate showed the recovered material to be poorly crystalline free base by XRPD analysis.

Hydration studies of Compound 1 besylate found insufficient solids were recovered from medium water activity and poorly crystalline besylate salt recovered from low and high water activities, by the poor crystallinity of the recovered material and a peak at around 21 degrees indicate the potential of a hydrate formation.

Example 9

Preparation and Characterization of Compound 1 Citric acid Salt

250 μL of the appropriate solvent was added to the vials containing 20 mg of compound 1. In a separate vial, 250 μL of the appropriate solvent was added to the vial containing citric acid (10.67 mg). The solutions/slurries were then added to the solvent/compound 1 solution (1.05 eq. of acid to free base). The samples were then temperature cycled between ambient and 40° C. in 4 hour cycles over 24 hrs.

Scale-Up Preparation from Acetone

About 300 mg of compound 1 was weighed into a vial and 160 mg of citric acid was weighed into a separate vial. To both vials, 3.75 mL of acetone was added and the two mixtures combined. The resulting slurry was then temperature cycled for 24 hours (ambient to 40° C. in 4 hours cycles). The resulting slurry was then allowed to evaporate at ambient temperature to remove excess acetone (1.05 eq. of acid to free base). Observations from the treatment of Compound 1 with citric acid are shown in Table 25 below:

TABLE 25

| | Solvent | | | | | |
|---|---|---|---|---|---|---|
| Time-point | Acetone | Ethanol | Methanol | 2-propanol | TBME | THF |
| Pre-Cycling | Slurry | Slurry | Slurry | Slurry | Slurry | Slurry |
| Post-Cycling | Slurry | Slurry | Slurry | Slurry | Slurry | Slurry |

XRPD analysis of citric acid experiments recovered 6 crystalline hits, free base (Form I) recovered from ethanol, methanol, 2-propanol, and THF and Form I recovered from acetone and TBME (FIG. 21).

XRPD data for Form I is provided in Table 26.

TABLE 26

| 2-Theta (°) | Height | H % |
|---|---|---|
| 6.5 | 1116 | 17.6 |
| 8.9 | 4365 | 68.8 |
| 9.2 | 1294 | 20.4 |
| 11.1 | 2946 | 46.5 |
| 13.9 | 1576 | 24.9 |
| 14.4 | 2604 | 41.1 |
| 15.4 | 2495 | 39.3 |
| 15.9 | 1182 | 18.6 |
| 18.0 | 755 | 11.9 |
| 19.2 | 2335 | 36.8 |
| 19.6 | 1370 | 21.6 |
| 20.7 | 6342 | 100.0 |
| 21.6 | 4090 | 64.5 |
| 22.3 | 274 | 4.3 |
| 22.7 | 348 | 5.5 |
| 23.3 | 1387 | 21.9 |

TABLE 26-continued

| 2-Theta (°) | Height | H % |
|---|---|---|
| 23.7 | 962 | 15.2 |
| 24.2 | 737 | 11.6 |
| 24.8 | 4022 | 63.4 |
| 25.6 | 2421 | 38.2 |
| 26.3 | 533 | 8.4 |
| 26.5 | 788 | 12.4 |
| 26.8 | 581 | 9.2 |
| 27.9 | 927 | 14.6 |
| 28.9 | 378 | 6.0 |
| 29.1 | 350 | 5.5 |
| 30.2 | 533 | 8.4 |
| 30.6 | 180 | 2.9 |
| 31.8 | 205 | 3.2 |
| 32.5 | 365 | 5.8 |
| 33.1 | 137 | 2.2 |
| 33.7 | 347 | 5.5 |
| 34.3 | 151 | 2.4 |
| 34.5 | 138 | 2.2 |

TG/DT Analysis

TGA of citrate Form A showed a total weight loss of approximately 1% from the outset up to about 175° C. DTA showed several endothermal events; first event at onset about 187° C. (peak at about 194° C.) and the second event at onset about 316° C. (peak at about 318° C.).

Result of Stability studies

XRPD analysis of post-stability citrate Form A recovered from acetone showed a decrease to crystallinity but no change to form after exposure to stability conditions. XRPD analysis of post-stability citrate Form A recovered from TBME showed a decrease to crystallinity but no change to form after exposure to stability conditions.

Secondary Salt Scale Up

XRPD analysis of the scaled up citrate salt shows successful formation of citrate Form A from acetone seen in the salt screen.

TGA (FIG. 43) showed a total weight loss of approximately 3% from the outset up to 175° C. DTA showed several endothermal events, the first event at onset around 188° C. (peak at around 194° C.) and the second event at onset around 316° C. (peak at around 318° C.).

DSC analysis in the first heating cycle (FIG. 44) showed a potential overlap of two endothermal events (peaks at 194 and 205° C.). No thermal events were seen in the cooling or second heating cycle.

Figure 45:
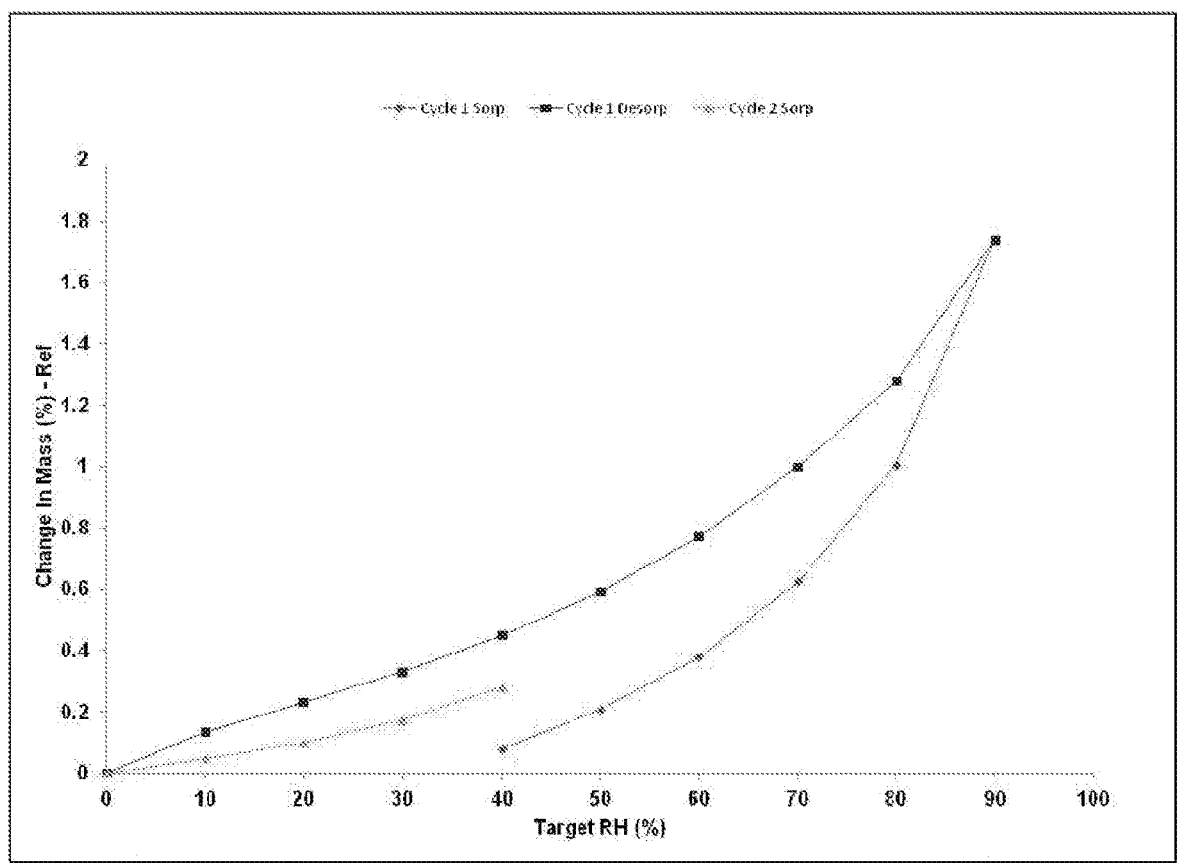
FIG. 45 is a DVS isotherm of Compound 1 citrate (Form A).
Figure 46:
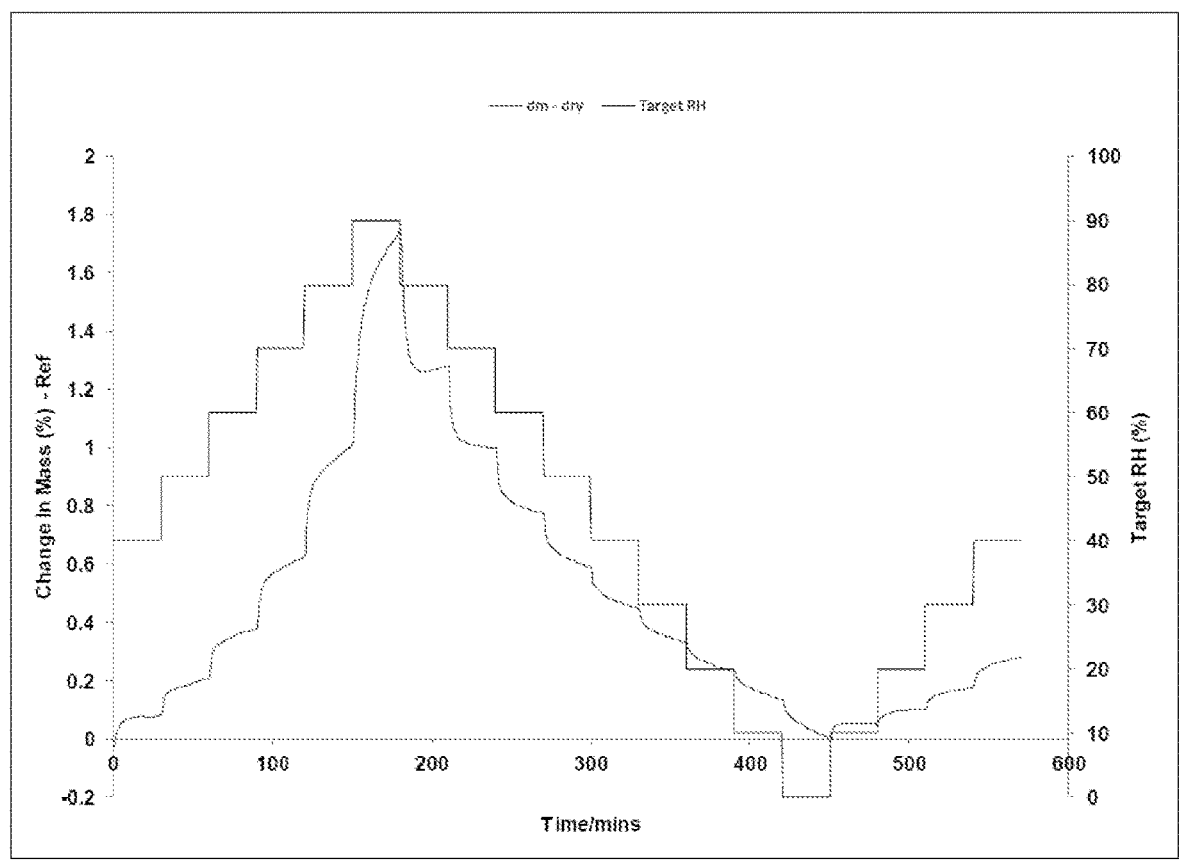
FIG. 46 is a DVS kinetic plot of Compound 1 citrate (Form A).

Compound 1 citrate exhibits low hygroscopicity by DVS analysis (FIG. 45) with a mass uptake of around 1.8% at 90% RH. Post-DVS XRPD analysis of the material showed no changes in crystalline form upon exposure to DVS conditions.

Figure 47:
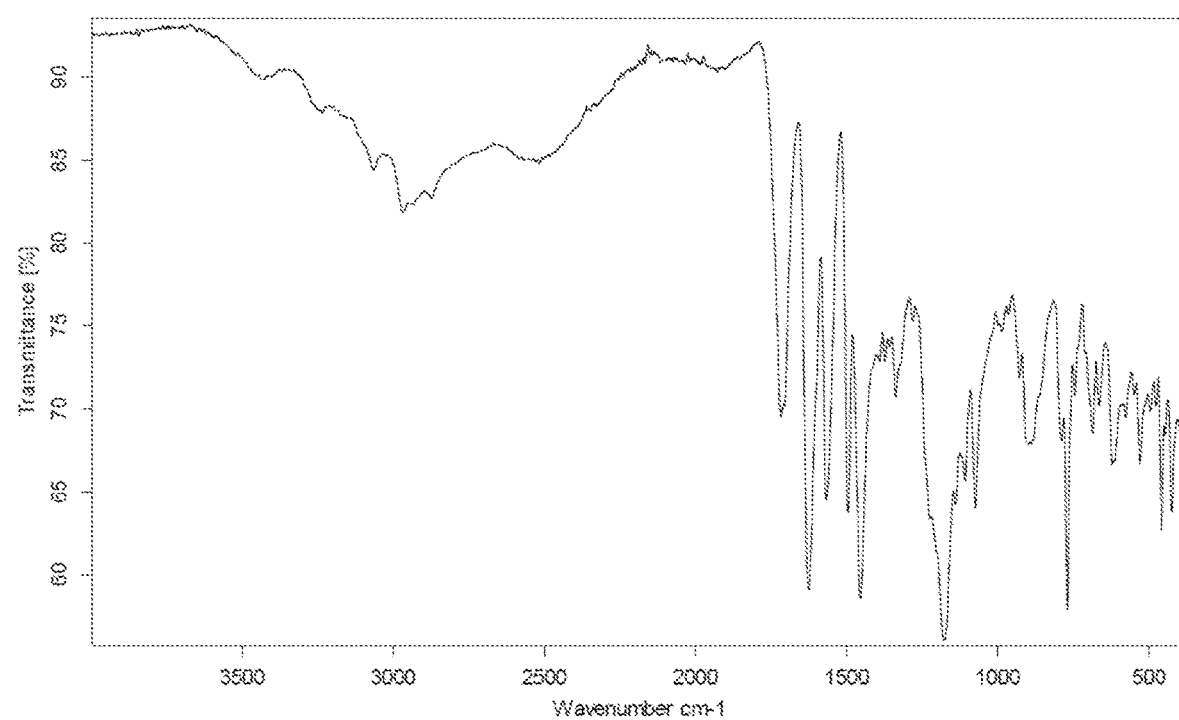
FIG. 47 is an IR spectrum of Compound 1 citrate (Form A).

An IR spectrum of Compound 1 citrate was taken for reference which can be found in FIG. 47 with peak lists in Table 27.

TABLE 27

| Wave Number |
|---|
| 3430 |
| 3066 |
| 2967 |
| 2518 |
| 2033 |
| 1929 |
| 1718 |
| 1626 |
| 1568 |
| 1497 |

TABLE 27-continued

| Wave Number |
|---|
| 1456 |
| 1373 |
| 1338 |
| 1281 |
| 1178 |
| 1141 |
| 1109 |
| 1074 |
| 987 |
| 929 |
| 899 |
| 790 |
| 771 |
| 747 |
| 687 |
| 667 |
| 623 |
| 578 |
| 550 |
| 532 |
| 497 |
| 478 |
| 459 |
| 446 |
| 425 |

Figure 48:
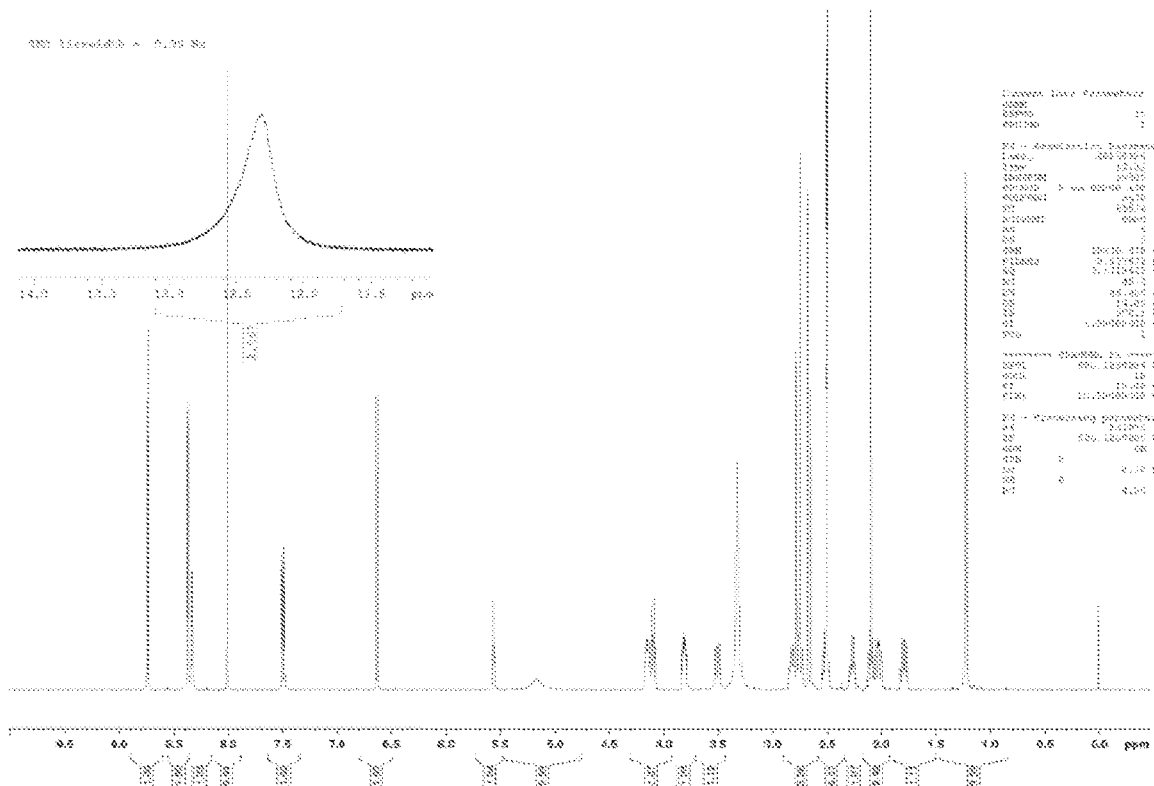
FIG. 48 is a $^1$H NMR spectrum of Compound 1 citrate (Form A).

$^1$H-NMR spectrum shown in FIG. 48 shows 0.97 eq. citric acid and 0.24 eq. acetone. UPLC analysis of Compound 1 citrate gave an average purity of 99.4%. 1 week stability tests at 40° C./75% RH, 80° C. and under ambient light showed no change to form after exposure and no change to purity. Thermodynamic solubility studies of Compound 1 citrate show the salt is highly soluble in un-buffered water and has high solubility at pH 1 with a lower solubility at 4.5 and 6.8. pH and concentration values can be found in Table 28.

TABLE 28

| Sample ID | Concentration (mg/mL) |
|---|---|
| pH 1 | 18.6 |
| pH 4.5 | 0.3 |
| pH 6.8 | 0.9 |
| Un-Buffered Water | 21.0 |

XRPD analysis showed poorly crystalline solids were recovered from pH 1, Compound 1 citrate was recovered from pH 4.5 and un-buffered water and poorly crystalline free base was recovered from pH 6.8. Salt disproportionation studies of Compound 1 citrate showed the recovered material to be poorly crystalline citrate salt by XRPD analysis.

Hydration studies of Compound 1 citrate found poorly crystalline citrate salt recovered from high and low water activities and unknown form, referred to here as Form B, recovered from medium water activity. XRPD diffractogram of the Compound I citrate Form B is shown in FIG. 49.

Example 10

Preparation and Characterization of Compound 1 Methanesulfonic Acid Salt

A stock solution of methanesulfonic acid was prepared in water (36 µL of methane sulfuric acid in 964 µL H$_2$O). 400 µL of the appropriate solvent was added to the vial containing the weighed compound 1, 100 µL of the methanesulfonic acid stock solution was then added to the solvent/compound 1 slurry (1.05 eq. of acid to free base). The samples were then temperature cycled between ambient and 40° C. in 4 hour cycles over 24 hrs.

Scale-Up Preparation from Acetone

About 300 mg of Compound 1 was weighed into a vial and a stock solution of methanesulfonic acid was prepared in water (538 µL of acid in 10 mL of water). To the weighed compound 1, 6 mL of acetone was added which was then followed by 1.5 mL of the acid stock solution, this slurry was then temperature cycled for 24 hours (ambient to 40° C. in 4 hour cycles) (1.05 eq. of acid to free base). The resulting clear solution was allowed to evaporate to recover solids; to which a crystal/oil mixture was recovered. To this mixture, acetone was added and the vial sonicated to produce solids. These solids were then filtered and dried for 72 hours under vacuum at ambient temperature. Observations from the treatment of Compound 1 with methanesulfonic acid are shown in a Table 29 below:

TABLE 29

| Time-point | Solvent | | | | | |
|---|---|---|---|---|---|---|
|  | Acetone | Ethanol | Methanol | 2-propanol | TBME | THF |
| Pre-Cycling | Slurry | Slurry | Slurry | Slurry | Slurry | Slurry |
| Post-Cycling | Slurry | Clear Solution | Slurry | Clear Solution | Slurry | Clear Solution |

To the samples which were recovered as clear solutions, 2-3 mg of Compound 1 was added to produce a mobile slurry and the sample temperature cycled for a further 2-3 hours. XRPD analysis of methanesulfonic acid experiments recovered 4 crystalline hits, free base (Form I) recovered from THF and pattern 1 from acetone, methanol and 2-propanol (FIG. 16). Insufficient solids were recovered from ethanol and TBME.

TG/DT Analysis

TGA of crystalline mesylate (FIG. 25) showed a total weight loss of approximately 3% from the outset up to about 200° C. DTA showed an endothermal event at onset about 229° C. (peak at about 232° C.).

Result of Stability Studies

XRPD analysis of post-stability crystalline mesylate recovered from acetone showed no changes to crystallinity or form after exposure to stability conditions. XRPD analysis of post-stability crystalline mesylate recovered from methanol showed a decrease in crystallinity but no changes to form after exposure to stability conditions. XRPD analysis of post-stability crystalline mesylate recovered from isopropanol showed a slight increase in crystallinity but no changes to form after exposure to stability conditions.

Secondary Salt Scale Up

XRPD analysis of the scaled up mesylate from acetone (shown in FIG. 30) showed a different form than seen previously.

TGA showed a series of weight losses with a total of around 9% up to 228° C. (FIG. 31). The weight loss seen at around 120° C. indicates the material to be an acetone solvate. DTA (FIG. 31) showed a small endothermal event at onset around 120° C. (peak at around 125° C.). This event is likely associated with the 6.74% weight loss, which would equate to about 0.59 equivalents of acetone. A larger endothermal "melting" event at onset about 228° C. (peak at about 232° C.). This event is consistent with the earlier collected mesylate TG/DTA.

DSC Analysis in the first heating cycle (FIG. 32) showed a sharp endothermal event at onset around 230° C. (peak at 233° C.). This endothermal event shown is consistent with TG/DTA. At this point, the material had already believed to have been desolvated otherwise there should have been an endothermal event relating to the weight loss.

A broad recrystallization event can be seen in the first cooling cycle with an onset of around 193° C. (peak at around 181° C.) and in the second heating cycle showed an endothermal event at onset around 223° C. (peak at 229° C.).

Figure 33:
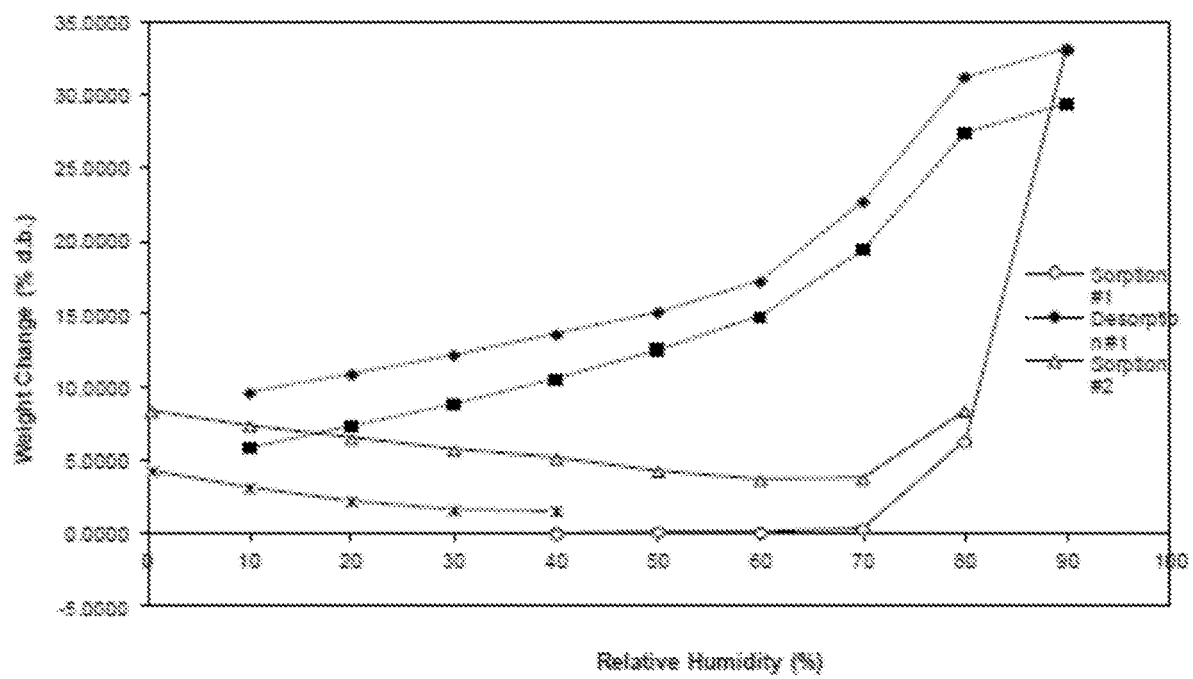
FIG. 33 is a GVS isotherm of Compound 1 mesylate acetone solvate.
Figure 34:
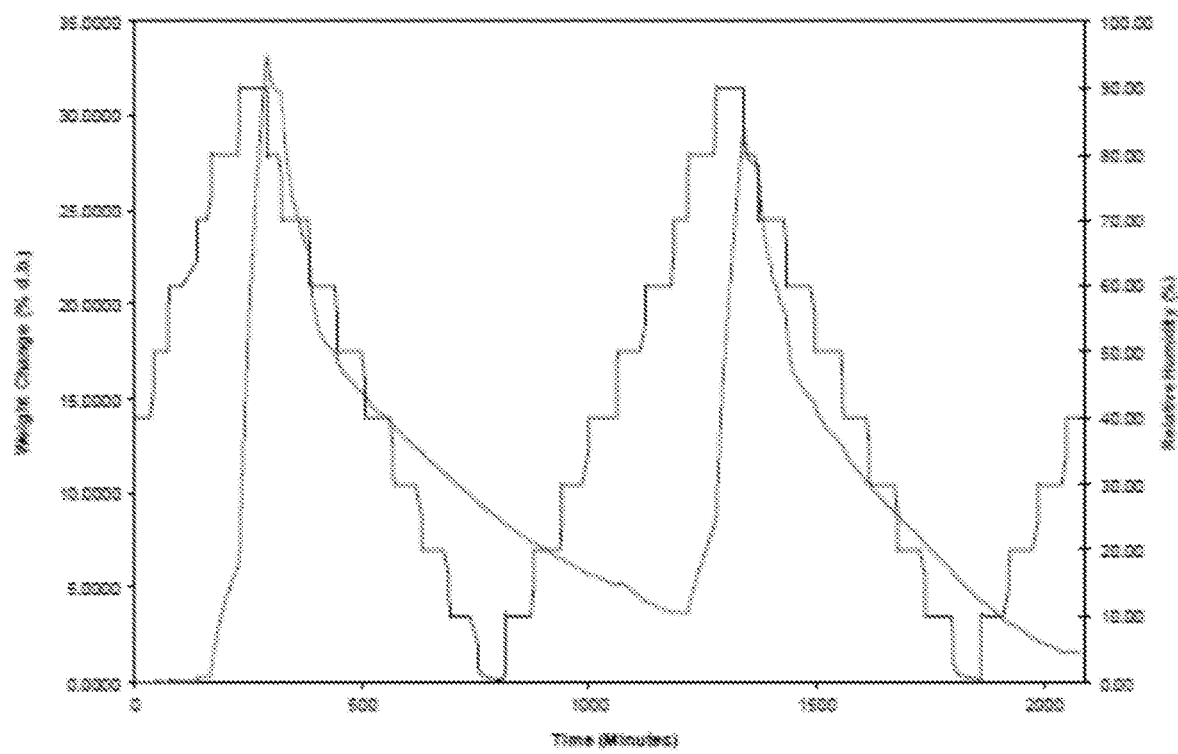
FIG. 34 is a GVS kinetic plot of Compound 1 mesylate acetone solvate.

Compound 1 mesylate salt exhibits high hygroscopicity by upon exposure to GVS humidity conditions (FIGS. 33 and 34); mass uptake of about 32% at 90% RH. Post-GVS XRPD analysis of the mesylate salt shows the material to desolvate and become the mesylate form seen in the salt screen. At 30% RH the material deliquesced and upon drying crystallized to the same form seen in the primary salt screen.

Figure 35:
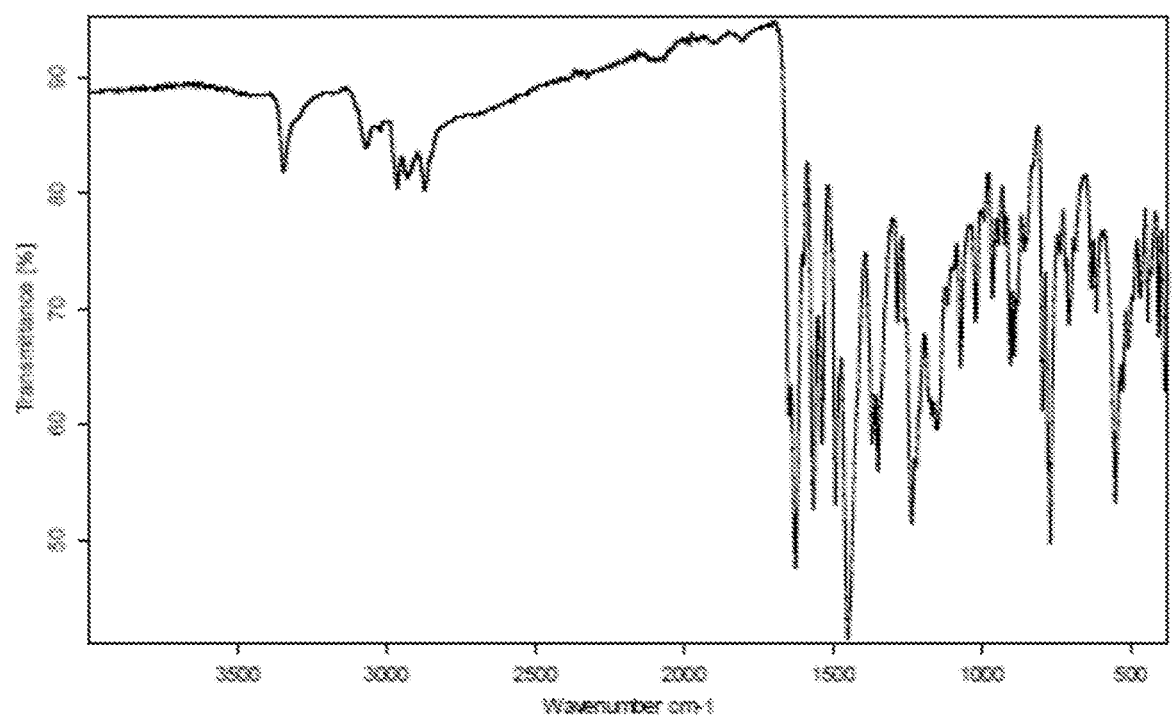
FIG. 35 is an IR spectrum of Compound 1 mesylate acetone solvate.

An IR spectrum of Compound 1 mesylate salt was taken for reference which can be found in FIG. 35 and peak listings in Table 30.

TABLE 30

| Wave Number |
|---|
| 3344 |
| 3068 |
| 3020 |
| 2963 |
| 2930 |
| 2870 |
| 1805 |
| 1649 |
| 1626 |
| 1600 |
| 1566 |
| 1538 |
| 1492 |
| 1451 |
| 1367 |
| 1347 |
| 1282 |
| 1235 |
| 1167 |
| 1153 |
| 1115 |
| 1071 |
| 1020 |
| 991 |
| 964 |
| 944 |
| 923 |
| 904 |
| 891 |
| 859 |
| 796 |
| 770 |
| 740 |
| 720 |
| 708 |
| 687 |
| 633 |
| 616 |
| 552 |
| 528 |
| 509 |
| 469 |
| 442 |
| 405 |

Figure 36:
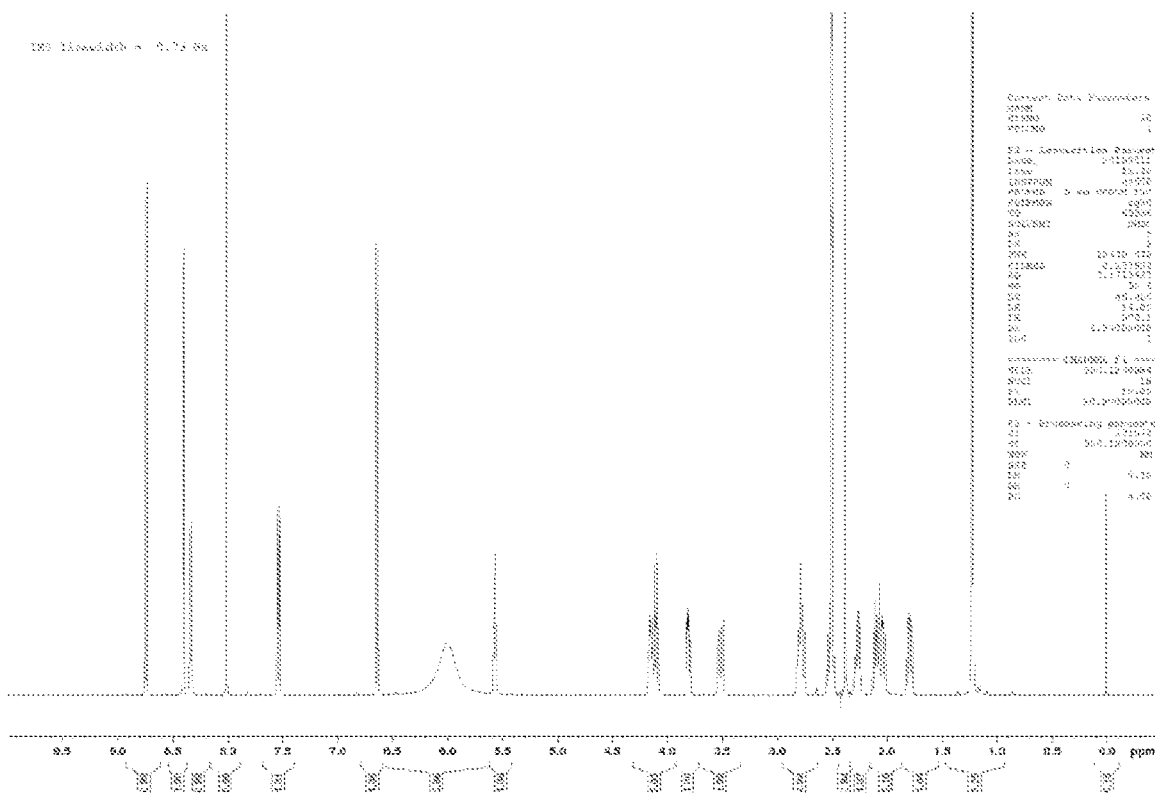
FIG. 36 is a $^1$H NMR spectrum of Compound 1 mesylate acetone solvate.

¹H NMR Spectrum shown in FIG. 36 shows about 1 eq. of sulfonic acid. It is not possible to accurately quantify any residual acetone from this data due to spectral overlap but the levels, if there are any, are considered low.

to free base). The samples were then temperature cycled between ambient and 40° C. in 4 hour cycles over 24 hrs.

Observations from the treatment of Compound 1 with 1,2-ethane disulfonic acid are shown in Table 32 below:

TABLE 32

| Time-point | Solvent | | | | | |
| --- | --- | --- | --- | --- | --- | --- |
| | Acetone | Ethanol | Methanol | 2-propanol | TBME | THF |
| Pre-Cycling | Slurry | Slurry | Slurry | Slurry | Slurry | Slurry |
| Post-Cycling | Yellow solution/ dark solids | Clear solution | Slurry | Slurry | Slurry | Slurry |

UPLC analysis of Compound 1 mesylate gave an average purity of 99.4%.

1 Week stability tests at 40° C./75% RH, 80° C. and under ambient light showed change to form after exposure by XRPD. However, changes to the mesylate form seen previously in the salt screen and no change to purity.

Thermodynamic solubility studies of Compound 1 mesylate show the salt is moderately soluble in pH 1, 4.5 and unbuffered water. The sample shows low solubility in pH 6.8. pH and concentration values can be found in Table 31.

TABLE 31

| Sample ID | Concentration (mg/mL) |
| --- | --- |
| pH 1 | 14.3 |
| pH 4.5 | 9.3 |
| pH 6.8 | 1.5 |
| Unbuffered Water | 9.6 |

XRPD analysis showed insufficient solids were recovered from pH 1, mesylate salt was recovered from pH 4.5 and free base was recovered from pH 6.8 and un-buffered water. Salt disproportionation studies of Compound 1 mesylate showed no change to form by XRPD analysis but crystallinity reduced. Hydration studies of Compound 1 mesylate showed mesylate salt recovered from medium water activities, a mixture of free base and salt recovered from low water activities and free base recovered from high water activities.

Example 11

Preparation and Characterization of Compound 1 1,2-Ethane Disulfonic Acid Salt

250 µL of the appropriate solvent was added to the vials containing 20 mg of compound 1. In a separate vial, 250 µL of the appropriate solvent was added to the vial containing 1,2-ethane disulfonic acid (12.94 mg). The solutions/slurries were then added to the solvent/API solution (1.05 eq. of acid to free base). The samples were then temperature cycled between ambient and 40° C. in 4 hour cycles over 24 hrs.

To the samples which were recovered as clear solutions, 2-3 mg of Compound 1 was added to produce a mobile slurry and the sample temperature cycled for a further 2-3 hours. XRPD analysis of 1,2-ethane disulfonic acid experiments recovered 4 crystalline hits, free base (Form I) recovered from acetone, THF and TBME and pattern 1 from 2-propanol (FIG. 14). Insufficient solids were recovered from ethanol and methanol.

Result of Stability studies

XRPD analysis of post-stability edisylate recovered from isopropanol showed the material to become amorphous after exposure to stability conditions.

Example 12

Preparation and Characterization of Compound 1 p-Toluene Sulfonic Acid Salt

250 µL of the appropriate solvent was added to the vials containing 20 mg of compound 1. In a separate vial, 250 µL of the appropriate solvent was added to the vial containing p-toluene sulfonic acid (10.84 mg). The solutions/slurries were then added to the solvent/compound 1 solution (1.05 eq. of acid to free base). The samples were then temperature cycled between ambient and 40° C. in 4 hour cycles over 24 hrs.

Observations from the treatment of compound 1 with p-toluene sulfonic acid are shown in Table 33 below:

TABLE 33

| Time-point | Solvent | | | | | |
| --- | --- | --- | --- | --- | --- | --- |
| | Acetone | Ethanol | Methanol | 2-propanol | TBME | THF |
| Pre-Cycling | Slurry | Slurry | Slurry | Slurry | Slurry | Slurry |
| Post-Cycling | Solid | Clear Solution | Slurry | Slurry | Slurry | Solid |

To the samples which were recovered as clear solutions, 2-3 mg of Compound 1 was added to produce a mobile slurry and the sample temperature cycled for a further 2-3 hours. XRPD analysis of p-toluene sulfonic acid experiments recovered 4 crystalline hits, free base (Form I) recovered from 2-propanol and TBME and pattern 1 from acetone and THF (FIG. 15). Insufficient solids were recovered from ethanol and methanol.

TG/DT Analysis

TGA of p-toluene sulfonate (FIG. 24) showed a total weight loss of approximately 14% from the outset up to about 250° C. DTA showed an endothermal event at onset about 84° C. (peak at about 90° C.).

Result of Stability Studies

XRPD analysis of post-stability p-toluene sulfonate recovered from acetone showed the material to become amorphous after exposure to stability conditions.

Example 13

Preparation and Characterization of Compound 1 Oxalic Acid Salt

250 μL of the appropriate solvent was added to the vials containing 20 mg of compound 1. In a separate vial, 250 μL of the appropriate solvent was added to the vial containing oxalic acid (5.08 mg). The solutions/slurries were then added to the solvent/compound 1 solution (1.05 eq. of acid to free base). The samples were then temperature cycled between ambient and 40° C. in 4 hour cycles over 24 hrs.

Observations from the treatment of Compound 1 with oxalic acid are shown in Table 34 below:

TABLE 34

| | Solvent | | | | | |
|---|---|---|---|---|---|---|
| Time-point | Acetone | Ethanol | Methanol | 2-propanol | TBME | THF |
| Pre-Cycling | Slurry | Slurry | Slurry | Slurry | Slurry | Slurry |
| Post-Cycling | Slurry | Slurry | Solid | Slurry | Slurry | Slurry |

XRPD analysis of oxalic acid experiments recovered 6 crystalline hits, free base (Form I) recovered from acetone (which was mostly amorphous), 2-propanol, THF and TBME and pattern 1 recovered from ethanol and methanol (FIG. 19).

TG/DT Analysis

TGA of oxalate (FIG. 26) showed a total weight loss of approximately 17% from the outset up to about 300° C. DTA showed a small endothermal event at onset about 314° C. (peak at about 317° C.).

Result of Stability Studies

XRPD analysis of post-stability oxalate recovered from ethanol showed a change in crystallinity and form after exposure to stability conditions. XRPD analysis of post-stability oxalate recovered from methanol showed no change to crystallinity however, changes to form were seen after exposure to stability conditions.

Example 14

Preparation and Characterization of Compound 1 Fumaric Acid Salt

250 μL of the appropriate solvent was added to the vials containing 20 mg of compound 1. In a separate vial, 250 μL of the appropriate solvent was added to the vial containing fumaric acid (6.48 mg). The solutions/slurries were then added to the solvent/compound 1 solution (1.05 eq. of acid to free base). The samples were then temperature cycled between ambient and 40° C. in 4 hour cycles over 24 hrs.

Observations from the treatment of Compound 1 with fumaric acid are shown in Table 35 below

TABLE 35

| | Solvent | | | | | |
|---|---|---|---|---|---|---|
| Time-point | Acetone | Ethanol | Methanol | 2-propanol | TBME | THF |
| Pre-Cycling | Slurry | Slurry | Slurry | Slurry | Slurry | Slurry |
| Post-Cycling | Slurry | Slurry | Slurry | Slurry | Slurry | Slurry |

XRPD analysis of fumaric acid experiments recovered 6 crystalline hits, free base (Form I) recovered from ethanol, methanol, 2-propanol, THF and TBME and pattern 1 recovered from acetone (FIG. 20).

TG/DT Analysis

TGA of crystalline fumarate (FIG. 27) showed a total weight loss of approximately 22% from the outset up to about 250° C. DTA showed several endothermal events; first event at onset about 164° C. (peak at about 166° C.), second event at onset about 189° C. (peak at about 191° C.), third event at onset of about 198° C. (peak at about 201° C.) and forth event at onset about 310° C. (peak at about 312° C.).

Result of Stability Studies

XRPD analysis of post-stability crystalline fumarate recovered from acetone showed a slight decrease to crystallinity however, no change to form after exposure to stability conditions.

Example 15

Preparation and Characterization of Compound 1 L-Malic Acid Salt

250 μL of the appropriate solvent was added to the vials containing 20 mg of compound 1. In a separate vial, 250 μL of the appropriate solvent was added to the vial containing L-malic acid (7.49 mg). The solutions/slurries were then added to the solvent/compound 1 solution (1.05 eq. of acid to free base). The samples were then temperature cycled between ambient and 40° C. in 4 hour cycles over 24 hrs.

Observations from the treatment of Compound 1 with L-malic acid are shown in Table 36 below:

TABLE 36

| Time-point | Solvent | | | | | |
|---|---|---|---|---|---|---|
| | Acetone | Ethanol | Methanol | 2-propanol | TBME | THF |
| Pre-Cycling | Slurry | Slurry | Slurry | Slurry | Slurry | Slurry |
| Post-Cycling | Slurry | Slurry | Slurry | Slurry | Slurry | Solid |

XRPD analysis of L-malic acid experiments recovered 6 crystalline hits, free base (Form I) recovered from acetone (with a large amount of preferred orientation), ethanol, methanol, 2-propanol, and THF and pattern 1 recovered from TBME (FIG. 22).

TG/DT Analysis

TGA of crystalline L-malate (FIG. 28) showed a total weight loss of approximately 26% from the outset up to about 250° C. DTA showed several endothermal events; first event at onset about 158° C. (peak at about 162° C.) and the second event at onset about 310° C. (peak at about 313° C.).

Result of Stability Studies

XRPD analysis of post-stability crystalline L-malate prepared from TBME showed no change to crystallinity and form after exposure to stability conditions.

Example 16

Preparation and Characterization of Compound 1 Succinic Acid Salt

250 µL of the appropriate solvent was added to the vials containing 20 mg of compound 1. In a separate vial, 250 µL of the appropriate solvent was added to the vial containing succinic acid (6.59 mg). The solutions/slurries were then added to the solvent/compound 1 solution (1.05 eq. of acid to free base). The samples were then temperature cycled between ambient and 40° C. in 4 hour cycles over 24 hrs.

Observations from the treatment of Compound 1 with succinic acid are shown in Table 37 below:

TABLE 37

| Time-point | Solvent | | | | | |
|---|---|---|---|---|---|---|
| | Acetone | Ethanol | Methanol | 2-propanol | TBME | THF |
| Pre-Cycling | Slurry | Slurry | Slurry | Slurry | Slurry | Slurry |
| Post-Cycling | Slurry | Slurry | Slurry | Slurry | Slurry | Slurry |

XRPD analysis of succinic acid experiments recovered 6 crystalline hits, free base (Form I) recovered from ethanol, methanol, 2-propanol, THF and TBME and pattern 1 recovered from acetone (FIG. 23).

TG/DT Analysis

TGA of succinate FIG. 29) showed a total weight loss of approximately 22% from the outset about 210° C. DTA showed several endothermal events; first event at onset about 147° C. (peak at about 151° C.) and the second event at onset about 315° C. (peak at about 315° C.).

Result of Stability Studies

XRPD analysis of post-stability crystalline succinate recovered from acetone showed a decrease in crystallinity but no change to form after exposure to stability conditions.

Example 17

Preparation and Characterization of Compound 1 Hydrochloric Acid Salt

A stock solution of HCl was prepared in water (46 µL of HCl in 954 µL H$_2$O). 400 µL of the appropriate solvent was added to the vial containing the weighed compound 1, 100 µL of the HCl stock solution was then added to the solvent/compound 1 slurry (1.05 eq. of acid to free base). The samples were then temperature cycled between ambient and 40° C. in 4 hour cycles over 24 hrs.

Observations from the treatment of Compound 1 with HCl are shown in Table 38 below:

TABLE 38

| Time-point | Solvent | | | | | |
|---|---|---|---|---|---|---|
| | Acetone | Ethanol | Methanol | 2-Propanol | TBME | THF |
| Pre-Cycling | Slurry | Slurry | Slurry | Slurry | Slurry | Slurry |
| Post-Cycling | Slurry | Clear Solution | Clear Solution | Clear Solution | Clear Solution | Slurry |

To the samples which were recovered as clear solutions, 2-3 mg of compound 1 was added to produce a mobile slurry and the sample temperature cycled for a further 2-3 hours. Further solids were recovered from ethanol, methanol, 2-propanol, TBME and THF through anti-solvent additions described in Materials and methods section. XRPD analysis of HCl experiments recovered 6 crystalline hits. Freebase (Form I) was recovered from all solvent systems analyzed.

Example 18

Preparation and Characterization of Compound 1 Sulfuric Acid Salt

A stock solution of sulfuric acid was prepared in water (31 µL of sulfuric acid in 969 µL $H_2O$). 400 µL of the appropriate solvent was added to the vial containing the weighed compound 1, 100 µL of the sulfuric acid stock solution was then added to the solvent/compound 1 slurry (1.05 eq. of acid to free base). The samples were then temperature cycled between ambient and 40° C. in 4 hour cycles over 24 hrs.

Observations from the treatment of Compound 1 with sulfuric acid are shown in Table 39 below:

TABLE 39

| Time-point | Solvent | | | | | |
|---|---|---|---|---|---|---|
| | Acetone | Ethanol | Methanol | 2-propanol | TBME | THF |
| Pre-Cycling | Slurry | Slurry | Slurry | Slurry | Slurry | Slurry |
| Post-Cycling | Clear solution | Clear solution | Clear solution | Clear solution | Clear solution | Clear solution |

To the samples which were recovered as clear solutions, 2-3 mg of Compound 1 was added to produce a mobile slurry and the sample temperature cycled for a further 2-3 hours. Further solids were recovered from ethanol, methanol, 2-propanol, TBME and THF through anti-solvent additions described. XRPD analysis of sulfuric acid experiments recovered 6 amorphous hits from all solvent systems analyzed.

Example 19

Preparation and characterization of Compound 1 Naphthalene-2-Sulfonic Acid Salt

250 µL of the appropriate solvent was added to the vials containing 20 mg of compound 1. In a separate vial, 250 µL of the appropriate solvent was added to the vial containing naphthalene-2-sulfonic acid (14.14 mg). The solutions/slurries were then added to the solvent/compound 1 solution (1.05 eq. of acid to free base). The samples were then temperature cycled between ambient and 40° C. in 4 hour cycles over 24 hrs.

Observations from the treatment of Compound 1 with naphthalene-2-sulfonic acid are shown in Table 40 below.

TABLE 40

| Time-point | Solvent | | | | | |
|---|---|---|---|---|---|---|
| | Acetone | Ethanol | Methanol | 2-propanol | TBME | THF |
| Pre-Cycling | Slurry | Slurry | Slurry | Slurry | Slurry | Slurry |
| Post-Cycling | Clear Solution | Clear Solution | Clear Solution | Clear Solution | Slurry | Solid |

To the samples which were recovered as clear solutions, 2-3 mg of Compound 1 was added to produce a mobile slurry and the sample temperature cycled for a further 2-3 hours. XRPD analysis of naphthalene-2-sulfonic acid experiments recovered 3 crystalline hits, free base (Form I) recovered from ethanol, THF and TBME. Insufficient solids were recovered from acetone, methanol and 2-propanol.

Example 20

Preparation and Characterization of Compound 1 2-Hydroxy Ethanesulfonic Acid Salt 250 µL of the appropriate solvent was added to the vials containing 20 mg of compound 1. In a separate vial, 250 µL of the appropriate solvent was added to the vial containing 2-hydroxy ethanesulfonic acid (8.19 mg). The solutions/slurries were then added to the solvent/compound 1 solution. The samples were then temperature cycled between ambient and 40° C. in 4 hour cycles over 24 hrs.

Observations from the treatment of Compound 1 with 2-hydroxy-ethanesulfonic acid are shown in Table 41 below:

TABLE 41

| Time-point | Solvent | | | | | |
|---|---|---|---|---|---|---|
| | Acetone | Ethanol | Methanol | 2-propanol | TBME | THF |
| Pre-Cycling | Slurry | Slurry | Slurry | Slurry | Slurry | Slurry |
| Post-Cycling | Slurry | Slurry | Solid | Slurry | Slurry | Slurry |

XRPD analysis of 2-hydroxy ethanesulfonic acid experiments recovered 6 crystalline hits, free base (Form I) recovered from all solvent systems analyzed.

Example 21

Preparation and characterization of Compound 1 L-Aspartic Acid Salt

250 µL of the appropriate solvent was added to the vials containing 20 mg of compound 1. In a separate vial, 250 µL of the appropriate solvent was added to the vial containing L-aspartic acid (7.36 mg). The solutions/slurries were then added to the solvent/compound 1 solution (1.05 eq. of acid to free base). The samples were then temperature cycled between ambient and 40° C. in 4 hour cycles over 24 hrs.

Observations from the treatment of Compound 1 with L-aspartic acid are shown in Table 42 below:

TABLE 42

| Time-point | Solvent | | | | | |
|---|---|---|---|---|---|---|
| | Acetone | Ethanol | Methanol | 2-propanol | TBME | THF |
| Pre-Cycling | Slurry | Slurry | Slurry | Slurry | Slurry | Slurry |
| Post-Cycling | Slurry | Slurry | Slurry | Slurry | Slurry | Slurry |

XRPD analysis of L-aspartic acid experiments recovered 6 crystalline hits, free base (Form I) recovered from all solvent systems analyzed.

Example 22

Preparation and Characterization of Compound 1 Maleic Acid Salt

250 µL of the appropriate solvent was added to the vials containing 20 mg of compound 1. In a separate vial, 250 µL of the appropriate solvent was added to the vial containing maleic acid (6.48 mg). The solutions/slurries were then added to the solvent/compound 1 solution (1.05 eq. of acid to free base). The samples were then temperature cycled between ambient and 40° C. in 4 hour cycles over 24 hrs.

Observations from the treatment of Compound 1 with maleic acid are shown in Table 43 below:

TABLE 43

| Time-point | Solvent | | | | | |
|---|---|---|---|---|---|---|
| | Acetone | Ethanol | Methanol | 2-propanol | TBME | THF |
| Pre-Cycling | Slurry | Slurry | Slurry | Slurry | Slurry | Slurry |
| Post-Cycling | Solid | Slurry | Gum | Slurry | Slurry | Slurry |

XRPD analysis of maleic acid experiments recovered 6 crystalline hits, free base (Form I) recovered from all solvent systems analyzed.

Example 23

Preparation and Characterization of Compound 1 Phosphoric Acid Salt

250 µL of the appropriate solvent was added to the vials containing 20 mg of compound 1. In a separate vial, 250 µL of the appropriate solvent was added to the vial containing phosphoric acid (5.42 mg). The solutions/slurries were then added to the solvent/compound 1 solution (1.05 eq. of acid to free base). The samples were then temperature cycled between ambient and 40° C. in 4 hour cycles over 24 hrs.

Observations from the treatment of Compound 1 with phosphoric acid are shown in Table 44 below:

TABLE 44

| Time-point | Solvent | | | | | |
|---|---|---|---|---|---|---|
| | Acetone | Ethanol | Methanol | 2-propanol | TBME | THF |
| Pre-Cycling | Slurry | Slurry | Slurry | Slurry | Slurry | Slurry |
| Post-Cycling | Solid | Clear Solution | Clear Solution | Slurry | Slurry | Slurry |

To the samples which were recovered as clear solutions, 2-3 mg of Compound 1 was added to produce a mobile slurry and the sample temperature cycled for a further 2-3 hours. XRPD analysis of phosphoric acid experiments recovered 3 crystalline hits, free base (Form I) recovered from all solvent systems analyzed.

Example 24

Preparation and Characterization of Compound 1 Ethanesulfonic Acid Salt

A stock solution of ethane sulfonic acid was prepared in water (47 µL of sulfuric acid in 953 µL H$_2$O). 400 µL of the appropriate solvent was added to the vial containing the weighed compound 1, 100 µL of the ethane sulfonic acid stock solution was then added to the solvent/compound 1 slurry (1.05 eq. of acid to free base). The samples were then temperature cycled between ambient and 40° C. in 4 hour cycles over 24 hrs.

Observations from the treatment of Compound 1 with ethanesulfonic acid are shown Table 45 below:

TABLE 45

| | Solvent | | | | | |
|---|---|---|---|---|---|---|
| Time-point | Acetone | Ethanol | Methanol | 2-propanol | TBME | THF |
| Pre-Cycling | Slurry | Slurry | Slurry | Slurry | Slurry | Slurry |
| Post-Cycling | Clear Solution | Clear Solution | Clear Solution | Clear Solution | Clear Solution | Slurry |

To the samples which were recovered as clear solutions, 2-3 mg of Compound 1 was added to produce a mobile slurry and the sample temperature cycled for a further 2-3 hours. XRPD analysis of ethanesulfonic acid experiments recovered 4 crystalline hits, free base (Form I) recovered from acetone, THF and TBME. Insufficient solids were recovered from methanol, ethanol and 2-propanol.

Example 25

Preparation and characterization of Compound 1 L-Glutamic Acid Salt

250 µL of the appropriate solvent was added to the vials containing 20 mg of compound 1. In a separate vial, 250 µL of the appropriate solvent was added to the vial containing L-glutamic acid (8.13 mg). The solutions/slurries were then added to the solvent/compound 1 solution (1.05 eq. of acid to free base). The samples were then temperature cycled between ambient and 40° C. in 4 hour cycles over 24 hrs.

Observations from the treatment of Compound 1 with L-glutamic acid are shown in Table 46 below:

TABLE 46

| | Solvent | | | | | |
|---|---|---|---|---|---|---|
| Time-point | Acetone | Ethanol | Methanol | 2-propanol | TBME | THF |
| Pre-Cycling | Slurry | Slurry | Slurry | Slurry | Slurry | Slurry |
| Post-Cycling | Slurry | Slurry | Slurry | Slurry | Slurry | Slurry |

XRPD analysis of L-glutamic acid experiments recovered 6 crystalline hits, free base (Form I) recovered from all solvent systems analyzed.

Example 26

Preparation and Characterization of Compound 1 L-Tartaric Acid Salt

250 μL of the appropriate solvent was added to the vials containing 20 mg of compound 1. In a separate vial, 250 μL of the appropriate solvent was added to the vial containing L-tartaric acid (8.34 mg). The solutions/slurries were then added to the solvent/compound 1 solution. The samples were then temperature cycled between ambient and 40° C. in 4 hour cycles over 24 hrs.

Observations from the treatment of Compound 1 with L-tartaric acid are shown in Table 47 below:

TABLE 47

| Time-point | Solvent | | | | | |
| --- | --- | --- | --- | --- | --- | --- |
| | Acetone | Ethanol | Methanol | 2-propanol | TBME | THF |
| Pre-Cycling | Slurry | Slurry | Slurry | Slurry | Slurry | Slurry |
| Post-Cycling | Slurry | Slurry | Slurry | Slurry | Slurry | Slurry |

XRPD analysis of L-tartaric acid experiments recovered 6 crystalline hits, free base (Form I) recovered from all solvent systems analyzed.

Example 27

Preparation and Characterization of Compound 1 D-Glucuronic Acid salt

250 μL of the appropriate solvent was added to the vials containing 20 mg of compound 1. In a separate vial, 250 μL of the appropriate solvent was added to the vial containing D-glucuronic acid (10.73 mg). The solutions/slurries were then added to the solvent/compound 1 solution (1.05 eq. of acid to free base). The samples were then temperature cycled between ambient and 40° C. in 4 hour cycles over 24 hrs.

Observations from the treatment of Compound 1 with D-glucuronic acid are shown in Table 48 below:

TABLE 48

| Time-point | Solvent | | | | | |
| --- | --- | --- | --- | --- | --- | --- |
| | Acetone | Ethanol | Methanol | 2-propanol | TBME | THF |
| Pre-Cycling | Slurry | Slurry | Slurry | Slurry | Slurry | Slurry |
| Post-Cycling | Slurry | Slurry | Slurry | Slurry | Slurry | Slurry |

XRPD analysis of D-glucuronic acid experiments recovered 6 crystalline hits, free base (Form I) recovered from all solvent systems analyzed.

Example 28

Preparation and Characterization of Compound 1 Hippuric Acid Salt

250 μL of the appropriate solvent was added to the vials containing 20 mg of compound 1. In a separate vial, 250 μL of the appropriate solvent was added to the vial containing hippuric acid (10.1 mg). The solutions/slurries were then added to the solvent/compound 1 solution (1.05 eq. of acid to free base). The samples were then temperature cycled between ambient and 40° C. in 4 hour cycles over 24 hrs.

Observations from the treatment of Compound 1 with hippuric acid are shown in Table 49 below:

TABLE 49

| Time-point | Solvent | | | | | |
|---|---|---|---|---|---|---|
| | Acetone | Ethanol | Methanol | 2-propanol | TBME | THF |
| Pre-Cycling | Slurry | Slurry | Slurry | Slurry | Slurry | Slurry |
| Post-Cycling | Slurry | Slurry | Slurry | Slurry | Slurry | Slurry |

XRPD analysis of hippuric acid experiments recovered 6 crystalline hits, free base (Form I) recovered from all solvent systems analyzed.

Example 29

Preparation and Characterization of Compound 1 D-Gluconic Acid Salt

A stock solution of D-gluconic acid was prepared in water (176 μL of D-gluconic acid in 824 μL H$_2$O). 400 μL of the appropriate solvent was added to the vial containing the weighed compound 1, 100 μL of the D-gluconic stock solution was then added to the solvent/compound 1 slurry (1.05 eq. of acid to free base). The samples were then temperature cycled between ambient and 40° C. in 4 hour cycles over 24 hrs.

Observations from the treatment of Compound 1 with D-gluconic acid are shown in Table 50 below:

TABLE 50

| Time-point | Solvent | | | | | |
|---|---|---|---|---|---|---|
| | Acetone | Ethanol | Methanol | 2-propanol | TBME | THF |
| Pre-Cycling | Slurry | Slurry | Slurry | Slurry | Slurry | Slurry |
| Post-Cycling | Clear Solution | Clear Solution | Clear Solution | Clear Solution | Clear Solution | Slurry |

To the samples which were recovered as clear solutions, 2-3 mg of Compound 1 was added to produce a mobile slurry and the sample temperature cycled for a further 2-3 hours. XRPD analysis of D-gluconic acid experiments recovered 1 crystalline hit, free base (Form I) recovered from TBME and insufficient solids recovered from acetone, ethanol, methanol, 2-propanol and THF.

Example 30

Preparation and Characterization of Compound 1 DL-Lactic Acid Salt

A stock solution of DL-lactic acid was prepared in water (48 μL of DL-lactic acid in 952 μL H$_2$O). 400 μL of the appropriate solvent was added to the vial containing the weighed compound 1, 100 μL of the DL-lactic acid stock solution was then added to the solvent/compound 1 slurry (1.05 eq. of acid to free base). The samples were then temperature cycled between ambient and 40° C. in 4 hour cycles over 24 hrs.

Observations from the treatment of Compound 1 with DL-lactic acid are shown in Table 51 below:

TABLE 51

| Time-point | Solvent | | | | | |
|---|---|---|---|---|---|---|
| | Acetone | Ethanol | Methanol | 2-propanol | TBME | THF |
| Pre-Cycling | Slurry | Slurry | Slurry | Slurry | Slurry | Slurry |
| Post-Cycling | Clear Solution | Clear Solution | Clear Solution | Clear Solution | Gum | Slurry |

To the samples which were recovered as clear solutions, 2-3 mg of Compound 1 was added to produce a mobile slurry and the sample temperature cycled for a further 2-3 hours. XRPD analysis of DL-lactic acid experiments recovered 5 crystalline hits, free base (Form I) recovered from acetone, ethanol, methanol, THF and TBME. Insufficient solids recovered from 2-propanol.

Example 31

Preparation and Characterization of Compound 1 L-Ascorbic Acid Salt

250 µL of the appropriate solvent was added to the vials containing 20 mg of Compound 1. In a separate vial, 250 µL of the appropriate solvent was added to the vial containing L-ascorbic acid (9.73 mg). The solutions/slurries were then added to the solvent/compound 1 solution (1.05 eq. of acid to free base). The samples were then temperature cycled between ambient and 40° C. in 4 hour cycles over 24 hrs.

Observations from the treatment of Compound 1 with L-ascorbic acid are shown in Table 52 below:

TABLE 52

| Time-point | Solvent | | | | | |
| --- | --- | --- | --- | --- | --- | --- |
| | Acetone | Ethanol | Methanol | 2-propanol | TBME | THF |
| Pre-Cycling | Slurry | Slurry | Slurry | Slurry | Slurry | Slurry |
| Post-Cycling | Slurry | Slurry | Slurry | Slurry | Slurry | Slurry |

XRPD analysis of L-ascorbic acid experiments recovered 6 crystalline hits, free base (Form I) recovered from all solvent systems analyzed.

Example 32

Preparation and Characterization of Compound 1 Benzoic Acid Salt

250 µL of the appropriate solvent was added to the vials containing 20 mg of compound 1. In a separate vial, 250 µL of the appropriate solvent was added to the vial containing benzoic acid (6.82 mg). The solutions/slurries were then added to the solvent/compound 1 solution (1.05 eq. of acid to free base). The samples were then temperature cycled between ambient and 40° C. in 4 hour cycles over 24 hrs.

Observations from the treatment of Compound 1 with benzoic acid are shown in Table 53 below:

TABLE 53

| Time-point | Solvent | | | | | |
| --- | --- | --- | --- | --- | --- | --- |
| | Acetone | Ethanol | Methanol | 2-propanol | TBME | THF |
| Pre-Cycling | Slurry | Slurry | Slurry | Slurry | Slurry | Slurry |
| Post-Cycling | Slurry | Slurry | Slurry | Slurry | Slurry | Slurry |

XRPD analysis of benzoic acid experiments recovered 6 crystalline hits, free base (Form I) recovered from all solvent systems analyzed.

Example 33

Solubility Measurements

General method to measure the thermodynamic aqueous solubility of a crystalline, organic solid.

Preparation of Reagents:
1. Aqueous Phosphate Buffer Solution (PBS): pH 7.4, 30 mM 1 Liter of 0.05 M (50 mM) Phosphate Buffer (25° C.) at pH 7.4 was prepared as follows: 11.2 mL of 1 M potassium phosphate (monobasic) was mixed with 38.8 mL of 1 M potassium phosphate (dibasic) and diluted to one liter with water.

To make a 0.03 M (30 mM) Phosphate Buffer (25° C.) at pH 7.4, the above recipe was adjusted as follows: 6.72 mL of 1 M potassium phosphate (monobasic) were mixed with 23.28 mL of 1 M potassium phosphate (dibasic) and diluted to one liter with water. The pH was adjusted with HCl or NaOH. Alternatively, 0.9144 g ($6.72 \times 10^{-3}$ mol) of potassium phosphate monobasic were mixed with 4.0908 g ($23.28 \times 10^{-3}$ mol) of potassium phosphate dibasic and diluted to 1 L with water to get a 30 mM solution of Phosphate Buffer (25° C.).

2. Aqueous phosphate buffer, 30 mM, adjusted to pH 6.5
3. Aqueous 0.1N HCl with 0.2% NaCl, adjusted to pH 1.2
4. If necessary, phosphate buffers of other pHs or other strengths could be made by adjusting the recipe above.
5. Suitable organic solvents (ACN, methanol, etc.) were used for preparation of stock and standards.

Instrumentation Used:
1. Balance
2. Agitator for mixing
3. Pipets
4. Filters or centrifuge
5. HPLC w/UV and MS detection (Waters Acquity UPLC with PDA and ZQ MS)

Standards:
1. ~0.5 mg of compound were dissolved in 2.5% DMSO/MeOH (or other organic) to a final concentration of 250 µg/mL stock
2. 50 uL of stock were accurately pipetted into 96 Shallow well plate containing 200 uL methanol for high standard concentration of 50 ug/mL.
3. 50 uL of 50 µg/mL high standard were accurately pipetted into adjacent well containing 200 uL methanol for medium standard concentration of 10 ug/mL.
4. 50 uL of 10 µg/mL medium standard were accurately pipetted into adjacent well containing 200 uL methanol for low standard concentration of 2 ug/mL.

Sample Preparation:
1. ≥0.5 mg of compound were accurately weighed into a 4-mL vial for each pH to be tested.

2. The appropriate amount of desired buffer was added to the appropriate vials to get a resulting concentration of 1.02 mg/mL.
3. Vials were capped and shaken at 350 rpm for 24 hours at room temperature.
4. ~450 µL of sample solutions were pipetted from 4-mL vials into 96 DWP.
5. The plate was centrifuged at 3500 rpm for 10 minutes at 20° C. and 250 µL of supernatant were transferred to catch plate.
6. 125 µL of supernatant were pipetted into 96 shallow well plate containing 125 µL of methanol and mixed to get a 2× dilution of the sample.
7. 50 µL of 2× dilution were pipetted into 96 shallow well plate containing 200 µL of methanol and mixed to obtain a 10× dilution of sample.
8. 50 µL of 10× dilution were pipetted into 96 shallow well plate containing 200 µL of methanol and mixed to obtain a 50× dilution of sample.

Analysis:
Data Collection:
1. Each standard (2, 10, 50 µg/mL) and sample (2×, 10×, 50× dilution) was injected in triplicate using a 3 µL injection volume on the UPLC, starting with the lowest concentrations and going to the highest. A standard, linear, rapid gradient method and 220 nm and 254 nm UV detection were used with the appropriate mobile phase and column.
2. The UV peak areas of the analyte were integrated and recorded for each chromatogram. If MS data was available, the mass of the parent peak was confirmed for each sample.
3. The responses for the standards were fitted using a y=mx linear model (through zero).
4. The model was used to quantify the amount of compound in the aqueous solutions. The values of the lowest dilution sample that fit within the standard curve was reported.

Note: Adjustments could be made to the above instructions if appropriate for a given compound.

Example 34

In Vitro Metabolic Stability of the Compound of Formula I (Compound 1) and the Compound for formula I'

Abbreviation Description
° C. Degrees centigrade
$CL_h$ Predicted hepatic clearance
$CL_{int}$ Predicted intrinsic clearance
DMEM Dulbecco's modified Eagle's medium
DMPKCP Drug Metabolism, Pharmacokinetics and Clinical Pharmacology
DMSO Dimethyl sulfoxide
ESI+ Electrospray ionization positive mode
ELN Electronic Laboratory Notebook
ER Extraction ratio
$f_u$ Unbound fraction of compound
g Gravity
HCl Hydrochloride
HPLC High performance liquid chromatography
IPA Isopropyl alcohol
IS Internal standard
$K_2HPO_4$ Potassium phosphate, dibasic
$KH_2PO_4$ Potassium phosphate, monobasic
$k_m$ Rate of loss of test compound
KPB Potassium phosphate buffer
$MgCl_2$ Magnesium chloride
NADP+ Nicotinamide adenine dinucleotide phosphate
NADPH Nicotinamide adenine dinucleotide phosphate reduce
NaOH Sodium hydroxide
NRS NADPH-regenerating solution
LC-MS/MS Liquid chromatography with tandem mass spectrometric detection
m/z Mass to charge ratio
µL Microliter
µM Micromolar
mM Millimolar
MRM Multiple reaction monitoring
n Number considered for assessment
PAR Peak area ratio
% REM Percent remaining
Abbreviation Description
rpm Revolutions per minute
$t_{1/2}$ Half-life In vitro metabolic stabilities were studied at a concentration of 1 µM in the presence of liver microsomes and isolated hepatocytes.

Materials

The following reagents were required for experimentation: acetonitrile (HPLC grade, Burdick & Jackson, Madison, Wis.), potassium phosphate (KH2PO4 and K2HPO4, anhydrous, Sigma-Aldrich, Co., St. Louis, Mo.), magnesium chloride (MgCl2, Sigma-Aldrich), water (HPLC grade, JT Baker, Phillipsburg, N.J.), isopropanol (IPA, reagent grade, EMD Chemicals, Gibbstown, N.J.), formic acid (reagent grade, Sigma-Aldrich), and dimethyl sulfoxide (DMSO; reagent grade, EM Science, Gibbstown, N.J.). Labetalol (Sigma-Aldrich) was used as an internal standard (IS) for analytical purposes. Human liver microsomes were purchased from Corning Life Sciences (Tewksbury Mass.), lot BD38289 (150-donor mixed gender pool, human). Liver microsomes from Sprague Dawley rat were purchased from XenoTech, LLC (Lenexa, Kans.). Lot numbers were XT1110042 and XT1310214. Cryopreserved human hepatocytes were either purchased from Invitrogen/CellzDirect (Pittsboro, N.C.) and lot number HUP50 or purchased from In Vitro ADMET Laboratories, LLC (Malden, Mass.) and lot number PHS9001 was used (10-donor mixed gender pool, human). Rat cryopreserved hepatocytes were purchased from Bioreclamation/In Vitro Technologies (Baltimore, Md.) and were from pooled male donors unless otherwise noted. Lots OGN, PZG and MSO were used for this study. All other reagents, control compounds, and solvents were of the highest analytical grade supplied by Sigma (St. Louis, Mo.).

Methods
Liver Microsomal Incubations

A 100 mM potassium phosphate assay buffer solution (KPB) was prepared as follows. Both KH2PO4 and K2HPO4 were dissolved separately in reagent grade water resulting in final concentrations 100 mM. A 75:25 mixture v/v of K2HPO4:KH2PO4 was prepared and the pH of the solution was adjusted to 7.4 using diluted HCl or diluted NaOH solutions. A stock solution of test compound was prepared at 10 mM (active compound) in DMSO. The stock solution was diluted immediately before use to 2.5 µM using the KPB solution to create the working standard. All test compounds were completely soluble in DMSO by visual inspection at room temperature. The NADPH-regenerating solution (NRS) was prepared on the day of analysis by diluting one volume of 17 mg/mL NADP+ with one volume of 78 mg/mL glucose-6-phosphate (both prepared in KPB, pH 7.4) and 7.9 volumes of 20 mM MgCl2. The final concentrations of NADP+ and glucose-6-phosphate were 1.7 mg/mL and 7.8 mg/mL, respectively. Immediately prior to use, the NRS was activated by the addition of 10 μL of glucose-6-phosphate dehydrogenase (150 Units/mL in KPB, pH 7.4) per mL of NRS stock solution. Liver microsomes were diluted to 2.5 mg protein/mL using KPB.

For the compound of formula I or the compound of formula I' or each positive control (i.e., dextromethorphan, diazepam, diltiazem, phenacetin, tolbutamide, and verapamil), 20 μL of 2.5 μM working standard solution of test compound and 20 μL of microsomes (2.5 mg protein/mL) were added to each well of a 96-well polypropylene plate (Costar, VWR, West Chester, Pa.) in duplicate. The plates were placed in an incubator at 37° C. for 5 minutes before adding the start solution. A 10-μL aliquot of the NRS solution was added to each original well to initiate metabolism. The concentration of the test compound at the beginning of the incubation was 1 μM. One incubation plate was prepared for each time point (i.e., 0 and 20 minutes). Incubations were conducted at 37° C. and 100% relative humidity. At each time point, the appropriate incubation plate was removed from the incubator and a solution containing internal standard (150 μL, 0.25 μM labetalol in 60% acetonitrile) was added to each well. The plate was immediately spun in a centrifuge at 2,095×g for 7 minutes at room temperature using an Allegra benchtop centrifuge (Beckman Coulter, Fullerton, Calif.). A 200-μL aliquot of the supernatant was transferred from each well to a 96-well shallow plate (Costar). The plates were sealed using disposable plate mats.

Hepatocyte Incubations

A stock solution of the test compound was prepared at 10 mM (active compound) in DMSO. The in vitro stability of the test compound (1 μM) was assessed in the presence of hepatocytes as follows. Cryopreserved hepatocytes were thawed, isolated from shipping media and diluted to a density of 1×106 viable cells/mL, according to the supplier's guidelines, using Dulbecco's Modified Eagle Medium, 1×, high glucose (DMEM, Invitrogen, Carlsbad, Calif.). Viability was determined by trypan blue exclusion using a hemocytometer (3500 Hausser, VWR, West Chester, Pa.). The 10 mM stock solution of test compound was diluted to 2 μM using supplemented DMEM to create the working standard. A 20-μL aliquot of test compound or control (i.e., antipyrine, diazepam, diltiazem, lorazepam, propranolol, verapamil, and 7-ethyl-10-hydroxycamptothecin (SN-38)) was added to each test well of a 96-well polypropylene plate (Costar, VWR, West Chester, Pa.) immediately followed by the addition of 20 μL of the hepatocyte suspension. One incubation plate was prepared for each time point (i.e., 0, 60 and 120 minutes) with samples being prepared in duplicate. Incubations were conducted at 37° C. and 100% relative humidity. At each time point, the appropriate incubation plate was removed from the incubator and a solution containing IS (200 μL, 0.2 μM labetalol in 60% acetonitrile) was added to each well. The plate was mixed at 600 rpm for 2 minute on a plate shaker (IKA MTS 2/4 Digital Microtiter Shaker, VWR) and immediately spun in a centrifuge at 2,095×g for 10 minutes at room temperature using an Allegra benchtop centrifuge (Beckman Coulter, Fullerton, Calif.). A 200-μL aliquot of the supernatant was transferred from each well to a 96-well shallow plate (Costar). The plates were sealed using disposable plate mats.

Analytical Quantitation

The LC-MS/MS system was comprised of an HTS-PAL autosampler (Leap Technologies, Carrboro, N.C.), an HP1200 HPLC (Agilent, Palo Alto, Calif.), and an API4000 triple quadrupole mass spectrometer (PE Sciex, a division of Applied Biosystems, Foster City, Calif.). Chromatographic separation of the analyte and internal standard was achieved at room temperature using a C18 column (Kinetex®, 30×3.0 mm, 2.6 μm particle size, Phenomenex, Torrance, Calif.) in conjunction with gradient conditions using mobile phases A (aqueous 0.1% formic acid with 1% isopropyl alcohol) and B (0.1% formic acid in acetonitrile). The total run time, including re-equilibration, for a single injection was 2 minutes. Mass spectrometric detection of the analytes was accomplished using the ESI+ ionization mode. Ion current was optimized during infusion of a stock solution of test compound. Analyte responses were measured by multiple reaction monitoring (MRM) of transitions unique to each compound.

Data were acquired and peak areas were calculated for test compounds and the internal standard using Analyst 1.6.1 software (Sciex). For the liver microsomal and hepatocyte stability assessments, peak area tables were exported to BioAssay Enterprise (CambridgeSoft, Cambridge, Mass.), where the average analyte-to-internal standard peak area ratios were used to calculate percent remaining (% REM), half-life (t½), predicted hepatic clearance (CLh) and predicted hepatic extraction ratio (ER).

Calculations

All calculations were performed using BioAssay Enterprise. The mean peak area ratios were calculated by averaging the peak area ratios (n=2) of test compound and the internal standard for each sample. Percent remaining was calculated by determining the ratio of the peak area ratio at each time point to the peak area ratio of the time-zero samples. The rate of loss of test compound (km) was determined by linear regression of—ln(f(t)) versus time. The regression used the form "y=mx", therefore the model forced an intercept of 100% remaining and assumed that the metabolism followed first order kinetics. The t½ was determined dividing ln(2) by km. The predicted intrinsic clearance (CLint) was calculated by scaling the in vitro half-life for stability of test compound using physical and physiological scaling factors listed in Table 5.1 and employed in the following equation:

$$CL_{int} = \frac{\ln 2}{t_{1/2}}\left(\frac{D \cdot w}{C}\right)$$

where D is the number of hepatocytes per mass of liver for a particular species. W is the average mass of liver present per weight of animal, and C is the number of hepatocytes present during the incubations per unit volume. The $CL_h$ was calculated using the following equation:

$$CL_h = \frac{CL_{int} \cdot Q}{CL_{int} + Q}$$

where Q is the species-dependent hepatic blood flow. No adjustment was made for the unbound fraction of the test compound (fu). The ER was determined by calculating the ratio of the $CL_h$ to Q:

$$ER = \frac{CL_h}{Q}$$

In Vitro Stability in Liver Microsomes

Test compounds were incubated with liver microsomes from Sprague Dawley rats and humans. Control compounds (i.e., dextromethorphan, diazepam, diltiazem, phenacetin, tolbutamide, and verapamil) performed within expected limits with respect to the fraction remaining after incubation in each liver microsomal system. The percentage of the compound of formula I and of the compound of formula I' remaining after 20 minutes, calculated t½ values, the predicted clearance values, and the predicted hepatic ERs were determined.

In Vitro Stability in Hepatocytes

Test compounds were incubated with hepatocytes from Sprague Dawley rats and humans. Control compounds (i.e., antipyrine, diazepam, diltiazem, lorazepam, propranolol, verapamil, and 7-ethyl-10-hydroxycamptothecin) performed within expected limits with respect to the fraction remaining after incubation in each hepatocyte system. The percentage of the compound of formula I and of the compound of formula I' remaining after 2 hours, calculated t½ values, the predicted clearance values, and the predicted hepatic extraction ratios as determined in hepatocyte incubations for each species were determined.

Example 35

MDR1 LLC-PK1 Cell Culture and Experimental Conditions

Both LLC-PK1 and MDR1 transfected LLC-PK1 cells were cultured and plated according to manufacturer's recommendations with the exception that the passage media contained only 2% fetal bovine serum so as to extend passage time out to seven days.

Both positive and negative controls were used to assess functionality of P-gp efflux in the assay. Stock solutions for assay controls and the test article were prepared in DMSO for a final test concentrations of 10 µM. Final organic concentration in the assay was 1%. All dosing solutions contained 10 µM lucifer yellow to monitor LLC-PK1 cell monolayer integrity.

For the apical to basolateral determination (A to B), 75 µL of the test article in transport buffer were added to the apical side of the individual transwells and 250 µL of basolateral media, without compound or lucifer yellow, were added to each well. For the basolateral to apical determination (B to A), 250 µL of test article in transport buffer were added to each well and 75 transport buffer, without compound or lucifer yellow, were added to each transwell. All tests were performed in triplicate, and each compound was tested for both apical to basolateral and basolateral to apical transport. The plates were incubated for 2 hours on a Lab-Line Instruments Titer Orbital Shaker (VWR, West Chester, Pa.) at 50 rpm and 37° C. with 5% $CO_2$. All culture plates were removed from the incubator and 50 µL of media were removed from the apical and basolateral portion of each well and added to 150 µL of 1 µM labetalol in 2:1 acetonitrile (ACN): $H_2O$, v/v. The plates were read using a Molecular Devices (Sunnyvale, Calif.) Gemini Fluorometer to evaluate the lucifer yellow concentrations at excitation/emission wavelengths of 425/535 nm. These values were accepted when found to be below 5% for apical to basolateral and basolateral to apical flux across the MDR1 transfected LLC-PK1 cell monolayers. The plates were sealed and the contents of each well analyzed by LC-MS/MS. The compound concentrations were determined from the ratio of the peak areas of the compound to the internal standard (labetalol) in comparison to the dosing solution.

LC-MS Analysis

The LC-MS/MS system was comprised of an HTS-PAL autosampler (Leap Technologies, Carrboro, N.C.), an HP1200 HPLC (Agilent, Palo Alto, Calif.), and a MDS Sciex 4000 Q Trap system (Applied Biosystems, Foster City, Calif.). Chromatographic separation of the analyte and internal standard was achieved at room temperature using a C18 column (Kinetics®, 30×3 mm, 2.6 µm particle size, Phenomenex, Torrance, Calif.) in conjunction with gradient conditions using mobile phases A (water containing 1% isopropyl alcohol and 0.1% formic acid) and B (0.1% formic acid in ACN). The total run time, including re-equilibration time, for a single injection was 1.2 minutes. Mass spectrometric detection of the analytes was accomplished using the ion spray positive mode. Analyte responses were measured by multiple reaction monitoring (MRM) of transitions unique to each compound (the protonated precursor ion and selected product ions for each test article and m/z 329 to m/z 162 for labetalol, the internal standard).

Determination of Apparent Permeability ($P_{app}$)

Permeability ($P_{app}$) was calculated in BioAssay v. 9.0 (Cambridge Soft, Cambridge, Mass.) using the following equation:

$$P_{app}(\times 10^{-6} \text{ cm}/s) = \frac{(C_d \cdot V \cdot (1 \times 10_5^6))}{(t \cdot 0.12 \text{ cm}^2 \cdot C)}$$

where $C_d$, V, t and $C_0$ are the detected concentration (µM), the volume on the dosing side (mL), the incubation time (s) and the initial dosing concentration (µM), respectively. The calculations for $P_{app}$ were made for each replicate and then averaged.

Other Embodiments

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

We claim:

1. A crystalline form of (6R,15R)-9-fluoro-15-methyl-2,11,16,20,21,24-hexaazapentacyclo[16.5.2.0$^{2,6}$.0$^{7,12}$.0$^{21,25}$]pentacosa-1(24),7,9,11,18(25),19,22-heptaen-17-one having the following structure:

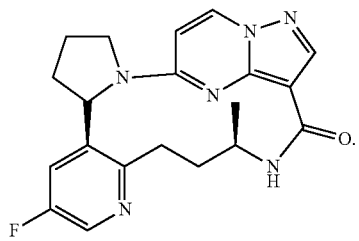

2. The crystalline form of claim 1, wherein the crystalline form is characterized by XRPD peaks, in terms of 2-theta, at 9.1, 20.2, and 24.9.

3. The crystalline form of claim 2, having one or more additional XRPD peaks, at 11.2, 13.4, 14.8, 18.3, 18.6, 23.6, and 29.4.

4. The crystalline form of claim 2, having hygroscopicity characterized by a mass uptake of about 0.3% at 90% relative humidity as determined by dynamic vapor sorption analysis.

5. The crystalline form of claim 2, which is substantially free of an amorphous form.

6. A process for making a pharmaceutical composition comprising mixing a salt or crystalline form according to any one of claim 1 and a pharmaceutically acceptable carrier.

7. A method of treating a cancer mediated by a Trk kinase in a subject in need thereof, comprising administering the crystalline form according to claim 1 to the subject.

8. The method according to claim 7, wherein the cancer is selected from the group consisting of adenocarcinoma, adrenal gland cortical carcinoma, adrenal gland neuroblastoma, anus squamous cell carcinoma, appendix adenocarcinoma, bladder urothelial carcinoma, bile duct adenocarcinoma, bladder carcinoma, bladder urothelial carcinoma, bone chordoma, bone marrow leukemia lymphocytic chronic, bone marrow leukemia non-lymphocytic acute myelocytic, bone marrow lymph proliferative disease, bone marrow multiple myeloma, bone sarcoma, brain astrocytoma, brain glioblastoma, brain medulloblastoma, brain meningioma, brain oligodendroglioma, breast adenoid cystic carcinoma, breast carcinoma, breast ductal carcinoma in situ, breast invasive ductal carcinoma, breast invasive lobular carcinoma, breast metaplastic carcinoma, cervix neuroendocrine carcinoma, cervix squamous cell carcinoma, colon adenocarcinoma, colon carcinoid tumor, duodenum adenocarcinoma, endometrioid tumor, esophagus adenocarcinoma, eye intraocular melanoma, eye intraocular squamous cell carcinoma, eye lacrimal duct carcinoma, fallopian tube serous carcinoma, gallbladder adenocarcinoma, gallbladder *glomus* tumor, gastroesophageal junction adenocarcinoma, head and neck adenoid cystic carcinoma, head and neck carcinoma, head and neck neuroblastoma, head and neck squamous cell carcinoma, kidney chromophore carcinoma, kidney medullary carcinoma, kidney renal cell carcinoma, kidney renal papillary carcinoma, kidney sarcomatoid carcinoma, kidney urothelial carcinoma, leukemia lymphocytic, liver cholangiocarcinoma, liver hepatocellular carcinoma, lung adenocarcinoma, lung adenosquamous carcinoma, lung atypical carcinoid, lung carcinosarcoma, lung large cell neuroendocrine carcinoma, lung non-small cell lung carcinoma, lung sarcoma, lung sarcomatoid carcinoma, lung small cell carcinoma, lung small cell undifferentiated carcinoma, lung squamous cell carcinoma, lymph node lymphoma diffuse large B cell, lymph node lymphoma follicular lymphoma, lymph node lymphoma mediastinal B-cell, lymph node lymphoma plasmablastic lung adenocarcinoma, lymphoma follicular lymphoma, lymphoma, non-Hodgkin's lymphoma, nasopharynx and paranasal sinuses undifferentiated carcinoma, ovary carcinoma, ovary carcinosarcoma, ovary clear cell carcinoma, ovary epithelial carcinoma, ovary granulosa cell tumor, ovary serous carcinoma, pancreas carcinoma, pancreas ductal adenocarcinoma, pancreas neuroendocrine carcinoma, peritoneum mesothelioma, peritoneum serous carcinoma, placenta choriocarcinoma, pleura mesothelioma, prostate acinar adenocarcinoma, prostate carcinoma, rectum adenocarcinoma, rectum squamous cell carcinoma, skin adnexal carcinoma, skin basal cell carcinoma, skin melanoma, skin Merkel cell carcinoma, skin squamous cell carcinoma, small intestine adenocarcinoma, small intestine gastrointestinal stromal tumors (GISTs), soft tissue angiosarcoma, soft tissue Ewing sarcoma, soft tissue hemangioendothelioma, soft tissue inflammatory myofibroblastic tumor, soft tissue leiomyosarcoma, soft tissue liposarcoma, soft tissue neuroblastoma, soft tissue paraganglioma, soft tissue perivascular epithelioid cell tumor, soft tissue sarcoma, soft tissue synovial sarcoma, stomach adenocarcinoma, stomach adenocarcinoma diffuse-type, stomach adenocarcinoma intestinal type, stomach adenocarcinoma intestinal type, stomach leiomyosarcoma, thymus carcinoma, thymus thymoma lymphocytic, thyroid papillary carcinoma, unknown primary adenocarcinoma, unknown primary carcinoma, unknown primary malignant neoplasm, unknown primary melanoma, unknown primary sarcomatoid carcinoma, unknown primary squamous cell carcinoma, unknown undifferentiated neuroendocrine carcinoma, unknown primary undifferentiated small cell carcinoma, uterus carcinosarcoma, uterus endometrial adenocarcinoma, uterus endometrial adenocarcinoma endometrioid, uterus endometrial adenocarcinoma papillary serous, and uterus leiomyosarcoma.

9. The crystalline form of claim 1, wherein the crystalline form is characterized by a DTA thermogram characterized by an endothermal event at about 317° C.

10. The crystalline form of claim 1, wherein the crystalline form is characterized by a DSC thermogram characterized by an endothermal event at about 317° C.

11. The crystalline form of claim 1, wherein the crystalline form is characterized by a hygroscopicity characterized by a mass uptake of about 0.7% at 90% relative humidity as determined by dynamic vapor sorption analysis.

* * * * *

SEQUENCE LISTING

```
<160> NUMBER OF SEQ ID NOS: 3

<210> SEQ ID NO 1
<211> LENGTH: 796
<212> TYPE: PRT
<213> ORGANISM: Homo sapiens

<400> SEQUENCE: 1
```

-continued

```
Met Leu Arg Gly Gly Arg Arg Gly Gln Leu Gly Trp His Ser Trp Ala
1               5                   10                  15

Ala Gly Pro Gly Ser Leu Leu Ala Trp Leu Ile Leu Ala Ser Ala Gly
            20                  25                  30

Ala Ala Pro Cys Pro Asp Ala Cys Cys Pro His Gly Ser Ser Gly Leu
        35                  40                  45

Arg Cys Thr Arg Asp Gly Ala Leu Asp Ser Leu His His Leu Pro Gly
    50                  55                  60

Ala Glu Asn Leu Thr Glu Leu Tyr Ile Glu Asn Gln Gln His Leu Gln
65                  70                  75                  80

His Leu Glu Leu Arg Asp Leu Arg Gly Leu Gly Glu Leu Arg Asn Leu
                85                  90                  95

Thr Ile Val Lys Ser Gly Leu Arg Phe Val Ala Pro Asp Ala Phe His
            100                 105                 110

Phe Thr Pro Arg Leu Ser Arg Leu Asn Leu Ser Phe Asn Ala Leu Glu
        115                 120                 125

Ser Leu Ser Trp Lys Thr Val Gln Gly Leu Ser Leu Gln Glu Leu Val
    130                 135                 140

Leu Ser Gly Asn Pro Leu His Cys Ser Cys Ala Leu Arg Trp Leu Gln
145                 150                 155                 160

Arg Trp Glu Glu Glu Gly Leu Gly Gly Val Pro Glu Gln Lys Leu Gln
                165                 170                 175

Cys His Gly Gln Gly Pro Leu Ala His Met Pro Asn Ala Ser Cys Gly
            180                 185                 190

Val Pro Thr Leu Lys Val Gln Val Pro Asn Ala Ser Val Asp Val Gly
        195                 200                 205

Asp Asp Val Leu Leu Arg Cys Gln Val Glu Gly Arg Gly Leu Glu Gln
210                 215                 220

Ala Gly Trp Ile Leu Thr Glu Leu Glu Gln Ser Ala Thr Val Met Lys
225                 230                 235                 240

Ser Gly Gly Leu Pro Ser Leu Gly Leu Thr Leu Ala Asn Val Thr Ser
                245                 250                 255

Asp Leu Asn Arg Lys Asn Val Thr Cys Trp Ala Glu Asn Asp Val Gly
            260                 265                 270

Arg Ala Glu Val Ser Val Gln Val Asn Val Ser Phe Pro Ala Ser Val
        275                 280                 285

Gln Leu His Thr Ala Val Glu Met His His Trp Cys Ile Pro Phe Ser
    290                 295                 300

Val Asp Gly Gln Pro Ala Pro Ser Leu Arg Trp Leu Phe Asn Gly Ser
305                 310                 315                 320

Val Leu Asn Glu Thr Ser Phe Ile Phe Thr Glu Phe Leu Glu Pro Ala
                325                 330                 335

Ala Asn Glu Thr Val Arg His Gly Cys Leu Arg Leu Asn Gln Pro Thr
            340                 345                 350

His Val Asn Asn Gly Asn Tyr Thr Leu Leu Ala Ala Asn Pro Phe Gly
        355                 360                 365

Gln Ala Ser Ala Ser Ile Met Ala Ala Phe Met Asp Asn Pro Phe Glu
    370                 375                 380

Phe Asn Pro Glu Asp Pro Ile Pro Val Ser Phe Ser Pro Val Asp Thr
385                 390                 395                 400

Asn Ser Thr Ser Gly Asp Pro Val Glu Lys Lys Asp Glu Thr Pro Phe
                405                 410                 415
```

```
Gly Val Ser Val Ala Val Gly Leu Ala Val Phe Ala Cys Leu Phe Leu
            420                 425                 430

Ser Thr Leu Leu Leu Val Leu Asn Lys Cys Gly Arg Arg Asn Lys Phe
        435                 440                 445

Gly Ile Asn Arg Pro Ala Val Leu Ala Pro Glu Asp Gly Leu Ala Met
    450                 455                 460

Ser Leu His Phe Met Thr Leu Gly Gly Ser Ser Leu Ser Pro Thr Glu
465                 470                 475                 480

Gly Lys Gly Ser Gly Leu Gln Gly His Ile Ile Glu Asn Pro Gln Tyr
                485                 490                 495

Phe Ser Asp Ala Cys Val His His Ile Lys Arg Arg Asp Ile Val Leu
            500                 505                 510

Lys Trp Glu Leu Gly Glu Gly Ala Phe Gly Lys Val Phe Leu Ala Glu
        515                 520                 525

Cys His Asn Leu Leu Pro Glu Gln Asp Lys Met Leu Val Ala Val Lys
    530                 535                 540

Ala Leu Lys Glu Ala Ser Glu Ser Ala Arg Gln Asp Phe Gln Arg Glu
545                 550                 555                 560

Ala Glu Leu Leu Thr Met Leu Gln His Gln His Ile Val Arg Phe Phe
                565                 570                 575

Gly Val Cys Thr Glu Gly Arg Pro Leu Leu Met Val Phe Glu Tyr Met
            580                 585                 590

Arg His Gly Asp Leu Asn Arg Phe Leu Arg Ser His Gly Pro Asp Ala
        595                 600                 605

Lys Leu Leu Ala Gly Gly Glu Asp Val Ala Pro Gly Pro Leu Gly Leu
    610                 615                 620

Gly Gln Leu Leu Ala Val Ala Ser Gln Val Ala Ala Gly Met Val Tyr
625                 630                 635                 640

Leu Ala Gly Leu His Phe Val His Arg Asp Leu Ala Thr Arg Asn Cys
                645                 650                 655

Leu Val Gly Gln Gly Leu Val Val Lys Ile Gly Asp Phe Gly Met Ser
            660                 665                 670

Arg Asp Ile Tyr Ser Thr Asp Tyr Tyr Arg Val Gly Gly Arg Thr Met
        675                 680                 685

Leu Pro Ile Arg Trp Met Pro Pro Glu Ser Ile Leu Tyr Arg Lys Phe
    690                 695                 700

Thr Thr Glu Ser Asp Val Trp Ser Phe Gly Val Val Leu Trp Glu Ile
705                 710                 715                 720

Phe Thr Tyr Gly Lys Gln Pro Trp Tyr Gln Leu Ser Asn Thr Glu Ala
                725                 730                 735

Ile Asp Cys Ile Thr Gln Gly Arg Glu Leu Glu Arg Pro Arg Ala Cys
            740                 745                 750

Pro Pro Glu Val Tyr Ala Ile Met Arg Gly Cys Trp Gln Arg Glu Pro
        755                 760                 765

Gln Gln Arg His Ser Ile Lys Asp Val His Ala Arg Leu Gln Ala Leu
    770                 775                 780

Ala Gln Ala Pro Pro Val Tyr Leu Asp Val Leu Gly
785                 790                 795
```

<210> SEQ ID NO 2
<211> LENGTH: 822
<212> TYPE: PRT
<213> ORGANISM: Homo sapiens

<400> SEQUENCE: 2

```
Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
    290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
        355                 360                 365

Lys Asp Glu Lys Gln Ile Ser Ala His Phe Met Gly Trp Pro Gly Ile
    370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415
```

-continued

```
Ile Pro Ser Thr Asp Val Thr Asp Lys Thr Gly Arg Glu His Leu Ser
            420                 425                 430

Val Tyr Ala Val Val Ile Ala Ser Val Val Gly Phe Cys Leu Leu
        435                 440                 445

Val Met Leu Phe Leu Leu Lys Leu Ala Arg His Ser Lys Phe Gly Met
450                 455                 460

Lys Gly Pro Ala Ser Val Ile Ser Asn Asp Asp Ser Ala Ser Pro
465                 470                 475                 480

Leu His His Ile Ser Asn Gly Ser Asn Thr Pro Ser Ser Ser Glu Gly
                485                 490                 495

Gly Pro Asp Ala Val Ile Ile Gly Met Thr Lys Ile Pro Val Ile Glu
            500                 505                 510

Asn Pro Gln Tyr Phe Gly Ile Thr Asn Ser Gln Leu Lys Pro Asp Thr
            515                 520                 525

Phe Val Gln His Ile Lys Arg His Asn Ile Val Leu Lys Arg Glu Leu
        530                 535                 540

Gly Glu Gly Ala Phe Gly Lys Val Phe Leu Ala Glu Cys Tyr Asn Leu
545                 550                 555                 560

Cys Pro Glu Gln Asp Lys Ile Leu Val Ala Val Lys Thr Leu Lys Asp
            565                 570                 575

Ala Ser Asp Asn Ala Arg Lys Asp Phe His Arg Glu Ala Glu Leu Leu
            580                 585                 590

Thr Asn Leu Gln His Glu His Ile Val Lys Phe Tyr Gly Val Cys Val
        595                 600                 605

Glu Gly Asp Pro Leu Ile Met Val Phe Glu Tyr Met Lys His Gly Asp
610                 615                 620

Leu Asn Lys Phe Leu Arg Ala His Gly Pro Asp Ala Val Leu Met Ala
625                 630                 635                 640

Glu Gly Asn Pro Pro Thr Glu Leu Thr Gln Ser Gln Met Leu His Ile
            645                 650                 655

Ala Gln Gln Ile Ala Ala Gly Met Val Tyr Leu Ala Ser Gln His Phe
            660                 665                 670

Val His Arg Asp Leu Ala Thr Arg Asn Cys Leu Val Gly Glu Asn Leu
        675                 680                 685

Leu Val Lys Ile Gly Asp Phe Gly Met Ser Arg Asp Val Tyr Ser Thr
690                 695                 700

Asp Tyr Tyr Arg Val Gly Gly His Thr Met Leu Pro Ile Arg Trp Met
705                 710                 715                 720

Pro Pro Glu Ser Ile Met Tyr Arg Lys Phe Thr Thr Glu Ser Asp Val
            725                 730                 735

Trp Ser Leu Gly Val Val Leu Trp Glu Ile Phe Thr Tyr Gly Lys Gln
            740                 745                 750

Pro Trp Tyr Gln Leu Ser Asn Asn Glu Val Ile Glu Cys Ile Thr Gln
        755                 760                 765

Gly Arg Val Leu Gln Arg Pro Arg Thr Cys Pro Gln Glu Val Tyr Glu
        770                 775                 780

Leu Met Leu Gly Cys Trp Gln Arg Glu Pro His Met Arg Lys Asn Ile
785                 790                 795                 800

Lys Gly Ile His Thr Leu Leu Gln Asn Leu Ala Lys Ala Ser Pro Val
                805                 810                 815

Tyr Leu Asp Ile Leu Gly
                820
```

<210> SEQ ID NO 3
<211> LENGTH: 839
<212> TYPE: PRT
<213> ORGANISM: Homo sapiens

<400> SEQUENCE: 3

```
Met Asp Val Ser Leu Cys Pro Ala Lys Cys Ser Phe Trp Arg Ile Phe
1               5                   10                  15

Leu Leu Gly Ser Val Trp Leu Asp Tyr Val Gly Ser Val Leu Ala Cys
            20                  25                  30

Pro Ala Asn Cys Val Cys Ser Lys Thr Glu Ile Asn Cys Arg Arg Pro
        35                  40                  45

Asp Asp Gly Asn Leu Phe Pro Leu Leu Glu Gly Gln Asp Ser Gly Asn
    50                  55                  60

Ser Asn Gly Asn Ala Ser Ile Asn Ile Thr Asp Ile Ser Arg Asn Ile
65                  70                  75                  80

Thr Ser Ile His Ile Glu Asn Trp Arg Ser Leu His Thr Leu Asn Ala
                85                  90                  95

Val Asp Met Glu Leu Tyr Thr Gly Leu Gln Lys Leu Thr Ile Lys Asn
            100                 105                 110

Ser Gly Leu Arg Ser Ile Gln Pro Arg Ala Phe Ala Lys Asn Pro His
        115                 120                 125

Leu Arg Tyr Ile Asn Leu Ser Ser Asn Arg Leu Thr Thr Leu Ser Trp
    130                 135                 140

Gln Leu Phe Gln Thr Leu Ser Leu Arg Glu Leu Gln Leu Glu Gln Asn
145                 150                 155                 160

Phe Phe Asn Cys Ser Cys Asp Ile Arg Trp Met Gln Leu Trp Gln Glu
                165                 170                 175

Gln Gly Glu Ala Lys Leu Asn Ser Gln Asn Leu Tyr Cys Ile Asn Ala
            180                 185                 190

Asp Gly Ser Gln Leu Pro Leu Phe Arg Met Asn Ile Ser Gln Cys Asp
        195                 200                 205

Leu Pro Glu Ile Ser Val Ser His Val Asn Leu Thr Val Arg Glu Gly
    210                 215                 220

Asp Asn Ala Val Ile Thr Cys Asn Gly Ser Gly Ser Pro Leu Pro Asp
225                 230                 235                 240

Val Asp Trp Ile Val Thr Gly Leu Gln Ser Ile Asn Thr His Gln Thr
                245                 250                 255

Asn Leu Asn Trp Thr Asn Val His Ala Ile Asn Leu Thr Leu Val Asn
            260                 265                 270

Val Thr Ser Glu Asp Asn Gly Phe Thr Leu Thr Cys Ile Ala Glu Asn
        275                 280                 285

Val Val Gly Met Ser Asn Ala Ser Val Ala Leu Thr Val Tyr Tyr Pro
    290                 295                 300

Pro Arg Val Val Ser Leu Glu Glu Pro Glu Leu Arg Leu Glu His Cys
305                 310                 315                 320

Ile Glu Phe Val Val Arg Gly Asn Pro Pro Thr Leu His Trp Leu
                325                 330                 335

His Asn Gly Gln Pro Leu Arg Glu Ser Lys Ile Ile His Val Glu Tyr
            340                 345                 350

Tyr Gln Glu Gly Glu Ile Ser Glu Gly Cys Leu Leu Phe Asn Lys Pro
        355                 360                 365

Thr His Tyr Asn Asn Gly Asn Tyr Thr Leu Ile Ala Lys Asn Pro Leu
    370                 375                 380
```

```
Gly Thr Ala Asn Gln Thr Ile Asn Gly His Phe Leu Lys Glu Pro Phe
385                 390                 395                 400

Pro Glu Ser Thr Asp Asn Phe Ile Leu Phe Asp Glu Val Ser Pro Thr
            405                 410                 415

Pro Pro Ile Thr Val Thr His Lys Pro Glu Glu Asp Thr Phe Gly Val
            420                 425                 430

Ser Ile Ala Val Gly Leu Ala Ala Phe Ala Cys Val Leu Leu Val Val
            435                 440                 445

Leu Phe Val Met Ile Asn Lys Tyr Gly Arg Arg Ser Lys Phe Gly Met
    450                 455                 460

Lys Gly Pro Val Ala Val Ile Ser Gly Glu Glu Asp Ser Ala Ser Pro
465                 470                 475                 480

Leu His His Ile Asn His Gly Ile Thr Thr Pro Ser Ser Leu Asp Ala
                485                 490                 495

Gly Pro Asp Thr Val Val Ile Gly Met Thr Arg Ile Pro Val Ile Glu
                500                 505                 510

Asn Pro Gln Tyr Phe Arg Gln Gly His Asn Cys His Lys Pro Asp Thr
            515                 520                 525

Tyr Val Gln His Ile Lys Arg Arg Asp Ile Val Leu Lys Arg Glu Leu
            530                 535                 540

Gly Glu Gly Ala Phe Gly Lys Val Phe Leu Ala Glu Cys Tyr Asn Leu
545                 550                 555                 560

Ser Pro Thr Lys Asp Lys Met Leu Val Ala Val Lys Ala Leu Lys Asp
                565                 570                 575

Pro Thr Leu Ala Ala Arg Lys Asp Phe Gln Arg Glu Ala Glu Leu Leu
            580                 585                 590

Thr Asn Leu Gln His Glu His Ile Val Lys Phe Tyr Gly Val Cys Gly
            595                 600                 605

Asp Gly Asp Pro Leu Ile Met Val Phe Glu Tyr Met Lys His Gly Asp
610                 615                 620

Leu Asn Lys Phe Leu Arg Ala His Gly Pro Asp Ala Met Ile Leu Val
625                 630                 635                 640

Asp Gly Gln Pro Arg Gln Ala Lys Gly Glu Leu Gly Leu Ser Gln Met
                645                 650                 655

Leu His Ile Ala Ser Gln Ile Ala Ser Gly Met Val Tyr Leu Ala Ser
        660                 665                 670

Gln His Phe Val His Arg Asp Leu Ala Thr Arg Asn Cys Leu Val Gly
            675                 680                 685

Ala Asn Leu Leu Val Lys Ile Gly Asp Phe Gly Met Ser Arg Asp Val
690                 695                 700

Tyr Ser Thr Asp Tyr Tyr Arg Leu Phe Asn Pro Ser Gly Asn Asp Phe
705                 710                 715                 720

Cys Ile Trp Cys Glu Val Gly Gly His Thr Met Leu Pro Ile Arg Trp
                725                 730                 735

Met Pro Pro Glu Ser Ile Met Tyr Arg Lys Phe Thr Thr Glu Ser Asp
            740                 745                 750

Val Trp Ser Phe Gly Val Ile Leu Trp Glu Ile Phe Thr Tyr Gly Lys
            755                 760                 765

Gln Pro Trp Phe Gln Leu Ser Asn Thr Glu Val Ile Glu Cys Ile Thr
        770                 775                 780

Gln Gly Arg Val Leu Glu Arg Pro Arg Val Cys Pro Lys Glu Val Tyr
785                 790                 795                 800

Asp Val Met Leu Gly Cys Trp Gln Arg Glu Pro Gln Gln Arg Leu Asn
```

```
                805             810                 815
Ile Lys Glu Ile Tyr Lys Ile Leu His Ala Leu Gly Lys Ala Thr Pro
            820             825                 830

Ile Tyr Leu Asp Ile Leu Gly
        835
```